United States Patent
Mcguire et al.

(10) Patent No.: US 9,623,014 B2
(45) Date of Patent: Apr. 18, 2017

(54) β-LACTAMASE INHIBITOR COMPOUNDS

(71) Applicant: Entasis Therapeutics Limited, London (GB)

(72) Inventors: Helen Mcguire, Watertown, MA (US); Shanta Bist, Nashua, NH (US); Neil Bifulco, Sudbury, MA (US); Liang Zhao, Lexington, MA (US); Ye Wu, Waltham, MA (US); Hoan Huynh, Waltham, MA (US); Hui Xiong, Chesterbrook, PA (US); Janelle Comita-Prevoir, Northborough, MA (US); Daemian Dussault, Lowell, MA (US); Bolin Geng, Andover, MA (US); Brendan Chen, Sudbury, MA (US); Thomas Francois Durand-Reville, Belmont, MA (US); Satenig Guler, Waltham, MA (US)

(73) Assignee: Entasis Therapeutics Limited, London (GB)

( * ) Notice: Subject to any disclaimer, the term of this patent is extended or adjusted under 35 U.S.C. 154(b) by 0 days.

(21) Appl. No.: 15/056,090

(22) Filed: Feb. 29, 2016

(65) Prior Publication Data
US 2016/0175290 A1 Jun. 23, 2016

Related U.S. Application Data

(63) Continuation of application No. 14/389,854, filed as application No. PCT/GB2013/050869 on Apr. 2, 2013, now Pat. No. 9,309,245.

(60) Provisional application No. 61/618,993, filed on Apr. 2, 2012.

(51) Int. Cl.
| | |
|---|---|
| *A61K 31/407* | (2006.01) |
| *A61K 31/439* | (2006.01) |
| *C07D 471/08* | (2006.01) |
| *A61K 31/427* | (2006.01) |
| *A61K 31/43* | (2006.01) |
| *A61K 31/444* | (2006.01) |
| *A61K 31/4545* | (2006.01) |
| *A61K 31/496* | (2006.01) |
| *A61K 31/546* | (2006.01) |
| *A61K 31/675* | (2006.01) |

(52) U.S. Cl.
CPC .......... *A61K 31/439* (2013.01); *A61K 31/407* (2013.01); *A61K 31/427* (2013.01); *A61K 31/43* (2013.01); *A61K 31/444* (2013.01); *A61K 31/4545* (2013.01); *A61K 31/496* (2013.01); *A61K 31/546* (2013.01); *A61K 31/675* (2013.01); *C07D 471/08* (2013.01)

(58) Field of Classification Search
CPC .................................................. A61K 31/407
USPC ........................................................ 514/300
See application file for complete search history.

(56) References Cited

U.S. PATENT DOCUMENTS

| | | | |
|---|---|---|---|
| 7,112,592 B2 | 9/2006 | Lampilas et al. | |
| 7,612,087 B2 | 11/2009 | Aszodi et al. | |
| 9,309,245 B2 | 4/2016 | McGuire et al. | |
| 2004/0157826 A1 | 8/2004 | Lampilas et al. | |
| 2006/0046995 A1 | 3/2006 | Lampilas et al. | |
| 2010/0087648 A1 | 4/2010 | Lampilas et al. | |
| 2010/0092443 A1 | 4/2010 | Levasseur et al. | |
| 2010/0093784 A1 | 4/2010 | Ledoussal et al. | |
| 2010/0137355 A1 | 6/2010 | Lampilas et al. | |
| 2013/0225554 A1 | 8/2013 | Maiti et al. | |
| 2013/0289012 A1 | 10/2013 | Gu et al. | |
| 2013/0296555 A1 | 11/2013 | Gu et al. | |

FOREIGN PATENT DOCUMENTS

| | | |
|---|---|---|
| EP | 2135959 A1 | 12/2009 |
| WO | WO-2009/091856 A2 | 7/2009 |
| WO | WO-2009/133442 A1 | 11/2009 |
| WO | WO-2011/042560 A1 | 4/2011 |
| WO | WO-2013/030733 A1 | 3/2013 |
| WO | WO-2013/030735 A1 | 3/2013 |

(Continued)

OTHER PUBLICATIONS

Bonnefoy, Alain et al., "In vitro activity of AVE1330A, an innovative broad-spectrum non-beta-lactam beta-lactamase inhibitor," J Antimicrobial Chemotherapy 54(2): 410-417 (2004).
International Preliminary Report for PCT/GB2013/050869 issued Oct. 7, 2014.
International Search Report for PCT/GB2013/050869; mailed May 15, 2013.

(Continued)

*Primary Examiner* — Niloofar Rahmani
(74) *Attorney, Agent, or Firm* — McCarter & English, LLP; Steven G. Davis; Michael J. DeGrazia

(57) ABSTRACT

The present invention is directed to compounds which are beta-lacatamase inhibitors. The compounds and their pharmaceutically acceptable salts, are useful in combination with beta-lactam antibiotics, or alone, for the treatment of bacterial infections, including infections caused by drug resistant organisms, including multi-drug resistant organisms. The present invention includes compounds according to formula (Ia):

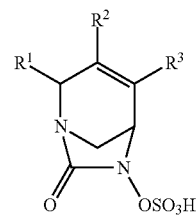

or a pharmaceutically acceptable salt thereof, wherein the values of $R^1$, $R^2$, $R^3$ and $R^4$ are described herein.

22 Claims, No Drawings

(56) References Cited

FOREIGN PATENT DOCUMENTS

| WO | WO-2013/038330 A1 | 3/2013 |
| WO | WO-2013/149121 A1 | 10/2013 |
| WO | WO-2013/149136 A1 | 10/2013 |
| WO | WO-2013/180197 A1 | 12/2013 |
| WO | WO-2014/033560 A1 | 3/2014 |
| WO | WO-2014/141132 A1 | 9/2014 |

OTHER PUBLICATIONS

Shlaes, David "New Beta-lactam-beta-lactamase inhibitor combinations in clinical development," Annals of the New York Academy of Sciences 1277:105-114 (2013).

Aszodi et al. "Design and synthesis of bridged gamma-lactams as analogues of beta-lactam antibiotics," Bioorganic & Medicinal Chemistry Letters. 14(10):2489-92 (2004).

β-LACTAMASE INHIBITOR COMPOUNDS

RELATED APPLICATIONS

This application is a continuation of U.S. application Ser. No. 14/389,854, filed Oct. 1, 2014; which is a 35 U.S.C. §371 national stage filing of International Application No. PCT/GB/2013/050869, filed Apr. 2, 2013; which claims the benefit of U.S. Provisional Application No. 61/618,993, filed on Apr. 2, 2012. The entire contents of each of the aforementioned applications are incorporated herein by reference in their entirety.

FIELD OF THE INVENTION

The present invention relates to novel beta-lactamase inhibitors, their pharmaceutical compositions and methods of use. In addition, the present invention relates to therapeutic methods for the treatment of bacterial infections, including overcoming bacterial antibiotic resistance.

BACKGROUND OF THE INVENTION

The international microbiological and infectious disease community continues to express serious concern that the continuing evolution of antibacterial resistance could result in bacterial strains against which currently available antibacterial agents will be ineffective. The outcome of such an occurrence could have considerable morbidity and mortality. In general, bacterial pathogens may be classified as either Gram-positive or Gram-negative pathogens. Antibiotic compounds with effective activity against both Gram-positive and Gram-negative pathogens are typically regarded as having a broad spectrum of activity.

In the fight against bacterial infection, beta-lactam antibiotics are essential. Beta-lactams are a broad class of drugs which all have a beta-lactam in their core molecular structure, and typically show effectiveness against a broad spectrum of Gram-positive and Gram-negative bacteria by inhibiting the cell wall synthesis of the bacterium. Because the drug target has no eukaryotic analog, their toxicity is low and they are generally well-tolerated. They remain among the most widely prescribed, safe and effective drugs available to combat bacterial infection. However, their effectiveness is limited by highly resistant infectious strains such as methicillin-resistant *Staphylococcus aureus* (MRSA) and multi-drug resistant (MDR) strains of *Pseudomonas aeruginosa, Acinetobacter baumannii, Escherichia coli, Klebsiella pneumonia*, and other Enterobacteriaceae. Such resistant bacteria are major causes of patient morbidity and mortality. Helfand, β-*lactams Against Emerging 'Superbugs': Progress and Pitfalls*, Expert Rev. Clin. Pharmacol. 1(4):559-571 (2008).

Beta-lactam antibiotics, alone and in combination with beta-lactamase inhibitors, continue to represent an essential portion of the antibacterial agents used to combat disease. β-lactam resistance for Gram-negative infections is primarily driven by β-lactamase activity; and the significant dependence on β-lacatam antibiotics has lead to the diversification and increased prevalence of β-lactamases. These β-lactamases are driving resistance to even the newest β-lactam antibiotics. Llarrull, et al., *The Future of Beta-Lactams*, Current Opinion in Microbiology, 13:551-557 (2010).

A major threat to the efficacy of these drugs is the increasing prevalence of extended-spectrum beta-lactamases (ESBLs). Beta-lactamases are enzymes that are secreted by some bacteria that ring open the beta-lactam portion of a beta-lactam antibiotic and thereby deactivate it. There are currently, four classes of beta-lactamases, denoted Class A, Class B, ClassCand Class D. Class A, ClassCand Class D beta-lactamases are serine beta-lactamase inhibitors, while Class B beta-lactamases are metallo-beta-lactamases (MBLs). Bush & Jacoby, *Updated Functional Classification of β-Lactamases*, Antimicrobial Agents and Chemotherapy, 54(3):969-976 (March 2010).

To help improve the effectiveness of beta-lactam antibiotics, some beta-lactamase inhibitors have been developed. However, the currently available β-lactamase inhibitors in many instances are insufficient to counter the constantly increasing diversity of β-lactamases. The three most common serine beta-lactamase agents currently used—clavulanic acid, tazobactam and sulbactam—have activity only against certain Class A enzymes, which severely limits their utility. Additionally, beta-lactamase inhibitors currently in clinical trials, such as Avibactam and MK7655 work primarily on Class A and C enzymes, with minimal effectiveness against Class D beta-lactamases. Bebrone, et al., *Current Challenges in Antimicrobial Chemotherapy: Focus on β-Lactamase Inhibition*, Drugs, 70(6):651-679 (2010). While these agents represent a considerable improvement over the currently available beta-lactamase inhibitors, agents which effectively hit all three serine beta-lactamases are desirable for combating the significant beta-lactam resistance seen today. Currently, there are no approved β-lactamase inhibitors which are effective against Class D β-lactamases, and resistance rates to conventional antibiotics are continuing to rise.

Therefore, there is a need for new β-lactamase inhibitors which are effective against at least D β-lactamases. There is a clear need for new β-lactamase inhibitors which are effective against more than one of Class A, C and/or D β-lactamases.

SUMMARY OF THE INVENTION

The present invention is directed to compounds which are beta-lacatamase inhibitors. The compounds, and their pharmaceutically acceptable salts, are useful in combination with beta-lactam antibiotics, or alone, for the treatment of bacterial infections, including infections caused by drug resistant organisms, including multi-drug resistant organisms. More particularly, the invention relates to compounds of formula (Ia):

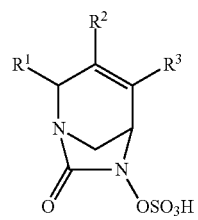

or a pharmaceutically acceptable salt thereof, wherein $R^1$ is —CONR'R", —CN, or $C_1$-$C_3$ alkyl, wherein each alkyl is optionally substituted with $C_1$-$C_3$ alkoxy, —OH, —CN, —NR'R", or —CONR'R"; $R^2$ and $R^3$ are independently selected from H, halo, —CN, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, —CONR'R", or $C(O)_2R'$; wherein the alkyl, alkenyl, cycloalkyl, and alkoxy represented by $R^2$ or $R^3$ are independently and optionally substituted by one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —NR'R", 5-7 membered heterocycle, —C(O)NR'R" or —NR'C(O)R"; and each R' and R" are independently selected from hydrogen, $C_1$-$C_6$ alkyl, $C_3$-$C_6$ cycloalkyl, phenyl, 5 to 6 membered heterocyclyl or a 5 to 6 membered heteroaryl; wherein each alkyl, cycloalkyl, phenyl, heterocyclyl and heteroaryl is optionally and independently substituted with one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —C(O)($C_1$-$C_6$ alkyl), —C(O)($C_1$-$C_6$ alkoxy), —NH$_2$, —NH($C_1$-$C_3$ alkyl), —N($C_1$-$C_3$ alkyl)$_2$, a 5-7 membered heterocyclyl or a 5-7 membered heteroaryl; provided that $R^2$ and $R^3$ are not both hydrogen; and when $R^1$ is —C(O)NR'R", then neither of $R^2$ or $R^3$ is —C(O)NR'R".

DETAILED DESCRIPTION OF THE INVENTION

In one aspect of the invention is a beta-lactamase inhibitor compound according to formula (I):

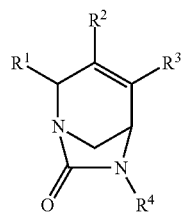

or a pharmaceutically acceptable salt thereof, wherein $R^1$ is —CONR'R", —CN, $C_1$-$C_3$ alkyl or $C_1$-$C_2$ alkoxy, wherein each alkyl and alkoxy is independently and optionally substituted with $C_1$-$C_3$ alkoxy, —OH, —CN, —NR'R", —CONR'R" or a 5-7 membered heterocycle; $R^2$ and $R^3$ are independently selected from H, halo, —CN, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, —CONR'R", C(O)$_2$R', phenyl, 5-6 membered heterocyclyl or 5-6 membered heteroaryl; wherein the alkyl, alkenyl, cycloalkyl, alkoxy, phenyl, heterocyclyl and heteroaryl represented by $R^2$ or $R^3$ are independently and optionally substituted by one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —NR'R", 5-7 membered heterocyclyl, —C(O)NR'R" or —NR'C(O)R"; $R^4$ is —OS(O)$_2$OH, —S(O)$_2$OH, —OP(O)$_2$OH, —P(O)$_2$OH, —C(O)NHS(O)$_2$R$^5$, —OCHFCO$_2$H, —OCF$_2$CO$_2$H, or —OCH$_2$CO$_2$H; $R^5$ is NR'R", phenyl, a 5-6 membered heterocyclyl or a 5 to 6 membered heteroaryl; and each R' and R" is independently selected from hydrogen, $C_1$-$C_6$ alkyl, $C_3$-$C_6$ cycloalkyl, phenyl, 5-7 membered heterocyclyl or a 5-6 membered heteroaryl; wherein each alkyl, cycloalkyl, phenyl, heterocyclyl and heteroaryl is optionally and independently substituted with one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —C(O)($C_1$-$C_6$ alkyl), —C(O)($C_1$-$C_6$ alkoxy), —NH$_2$, —NH($C_1$-$C_3$ alkyl), —N($C_1$-$C_3$ alkyl)$_2$, a 5-6 membered heterocyclyl or a 5-6 membered heteroaryl; or R' and R" are taken together to form a 5-6 membered heterocyclyl or heteroaryl, wherein each heterocyclyl and heteroaryl is optionally and independently substituted with one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —NH$_2$, —NH ($C_1$-$C_3$ alkyl), or —N($C_1$-$C_3$ alkyl)$_2$; provided that $R^2$ and $R^3$ are not both hydrogen; and when $R^1$ is —C(O)NR'R", then neither $R^2$ nor $R^3$ is —C(O)NR'R".

In another aspect of the invention is a compound according to formula (II):

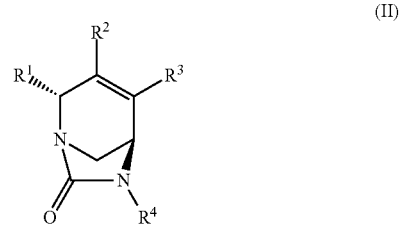

or a pharmaceutically acceptable salt thereof wherein the variables $R^1$, $R^2$, $R^3$ and $R^4$ are as defined for formula (I) above.

In one aspect of the invention is a compound according to formula (III):

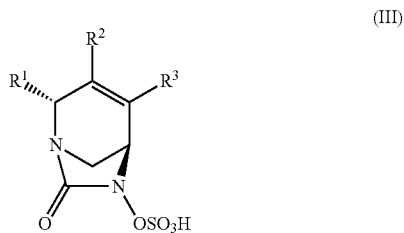

or a pharmaceutically acceptable salt thereof, wherein the variables $R^1$, $R^2$ and $R^3$ are as defined for formula (Ia) above.

In one aspect of the invention, is a compound according to formula (IV):

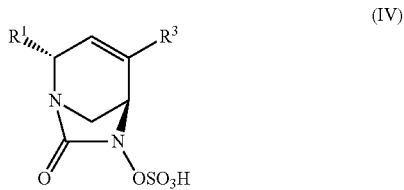

or a pharmaceutically acceptable salt thereof, wherein the variables $R^1$ and $R^3$ are as defined for formula (Ia).

One aspect of the invention is a compound according to formula (V):

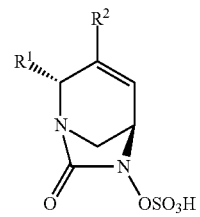

or a pharmaceutically acceptable salt thereof, wherein the variables $R^1$ and $R^2$ are as defined for formula (Ia).

In one aspect of the invention, for any one of formulae (I), (Ia), (II), (III), (IV) or (V), $R^1$ is —CONR'R", —CN, or $C_1$-$C_3$ alkyl, wherein each alkyl is optionally substituted with $C_1$-$C_3$ alkoxy or —OH; and the R' and R" of $R^1$ are independently selected from the group consisting of H, $C_1$-$C_3$ alkyl, or a 5-7 membered heterocyclyl, wherein each alkyl and heterocyclyl of R' and R" is optionally and independently substituted with one or more —OH, $C_1$-$C_3$ alkyl, $C_1$-$C_3$ alkoxy, —$NH_2$, —NH($C_1$-$C_3$ alkyl), —N($C_1$-$C_3$ alkyl)$_2$, or a 5-7 membered heterocyclyl. In one aspect of the invention, for any one of formulae (I), (Ia), (II), (III), (IV) or (V), $R^1$ is —$CH_2OCH_3$, —$CONH(CH_2)$-siderophore, —$CONH_2$,

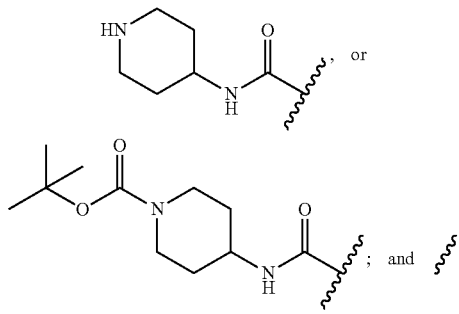

represents the point of attachment to the bridged bicyclic core. In one aspect of the invention, for any one of formulae (I), (Ia), (II), (III), (IV) or (V), $R^1$ is —$CH_2OCH_3$ or —$CONH_2$.

In one aspect of the invention, for any of formulae (I), (II), (III), or (IV), $R^1$ is —$C(O)NH_2$, —CN or $C_1$-$C_3$ alkyl optionally substituted with one or more —OH, $C_1$-$C_3$ alkoxy, halo, —OC(O)NR'R", a siderophore, or —C(O)NH (siderophore), wherein R' and R" are as defined for any one of formulae (I), (Ia), (II), (III), (IV) or (V). In one aspect of the invention, for any one of formulae (I), (II), (III) or (IV), $R^1$ is —$C(O)NH_2$, —CN or $C_1$-$C_2$ alkyl optionally substituted with methoxy, —OH or —CN. In one aspect of the invention, for any one of formulae (I), (Ia), (II), (III), (IV) or (V), $R^1$ is —CONR'R", —$CH_2OCH_3$ or —CN; and the R' and R" of $R^1$ are independently —H, $C_1$-$C_3$ alkyl, or a 5-7 membered heterocyclyl, wherein each alkyl and heterocyclyl of R' and R" is optionally and independently substituted with one or more halo, —CN, —OH, $C_1$-$C_3$ alkyl, $C_1$-$C_3$ haloalkyl, $C_1$-$C_3$ alkoxy, $C_1$-$C_3$ haloalkoxy, —$C(O)(C_1$-$C_6$ alkyl), —$C(O)(C_1$-$C_6$ alkoxy), —$NH_2$, —NH($C_1$-$C_3$ alkyl), —N($C_1$-$C_3$ alkyl)$_2$, or a 5-7 membered heterocyclyl. In one aspect of the invention, for any one of formulae (I), (Ia), (II), (III), (IV) or (V), $R^1$ is —$CONH_2$, —$CONH(CH_2)_nNH_2$

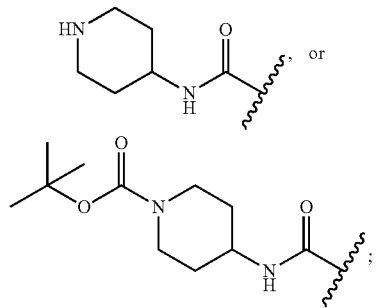

n is an integer from 1 to 3; and

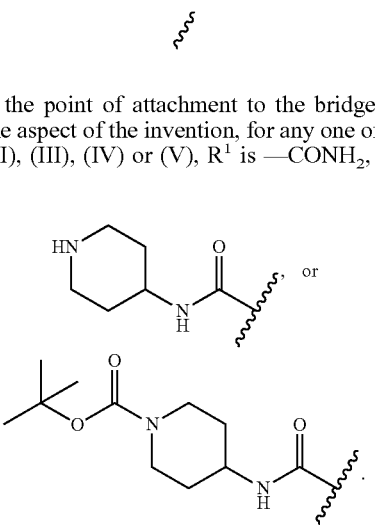

represents the point of attachment to the bridged bicyclic core. In one aspect of the invention, for any one of formulae (I), (Ia), (II), (III), (IV) or (V), $R^1$ is —$CONH_2$, In one aspect of the invention, for any one of formulae (I), (Ia), (II), (III), (IV) or (V), $R^1$ is —$CONH_2$. In one aspect of the invention, for any one of formulae (I), (Ia), (II), (III), (IV) or (V), $R^1$ is —$CH_2OCH_3$. In one aspect of the invention, for any one of formulae (I), (Ia), (II), (III), (IV) or (V), $R^1$ is —CN. In one aspect of the invention, for any one of formulae (I), (Ia), (II), (III), (IV) or (V), $R^1$ is —$CH_2OH$.

In one aspect of the invention, for any one of formulae (I), (Ia), (II), (III) or (V), $R^2$ is selected from the group consisting of H, $C_1$-$C_3$ alkyl, $C_3$-$C_6$ cycloalkyl, and —CONR'R", wherein the alkyl and cycloalkyl represented by $R^2$ and/or $R^3$ are independently and optionally substituted by one or more group selected from halo, —CN, —OH, $C_1$-$C_3$ alkyl, $C_1$-$C_3$ haloalkyl, $C_1$-$C_3$ alkoxy, $C_1$-$C_3$ haloalkoxy, —NR'R", a siderophore, —C(O)NR'R" and —NR'C(O)R". In one aspect of the invention, for any one of formulae (I), (Ia), (II), (III) or (V), $R^2$ is methyl, ethyl, isopropyl, or cyclopropyl, wherein each $R^2$ is optionally and independently substituted with one or more group selected from —OH and $C_1$-$C_3$ alkoxy. In one aspect of the invention, for any one of formulae (I), (Ia), (II), (III) or (V), $R^2$ is methyl.

In one aspect of the invention, for any one of formulae (I), (Ia), (II), (III) or (V), $R^2$ is —H, —CN, $C_1$-$C_3$ alkyl, $C_3$-$C_6$ cycloalkyl, —$CO_2R'$, —CONR'R", or a 5-6 membered heterocyclyl, wherein each alkyl, cycloalkyl, heterocyclyl, R' and R" of $R^2$ is optionally and independently substituted with one or more group selected from halo, —CN, —OH, $C_1$-$C_3$ alkyl, $C_1$-$C_3$ haloalkyl, $C_1$-$C_3$ alkoxy, $C_1$-$C_3$ haloalkoxy, —NR'R", morpholinyl, pyrrolidinyl, piperidinyl, piperazinyl, a siderophore, —C(O)NR'R" and —NR'C(O)R". In one aspect of the invention, for any one of formulae (I), (Ia), (II), (III) or (V), $R^2$ is H, —CN, methyl, ethyl, isopropyl, cyclopropyl, —$CO_2(C_1$-$C_3$ alkyl), —$CONH_2$, —CONH($C_1$-$C_3$ alkyl), —CON($C_1$-$C_3$ alkyl)$_2$, morpholinyl or thiazolyl, wherein when $R^2$ is not hydrogen or cyano, each $R^2$ is optionally and independently substituted with one or more group selected from halo, —CN, —OH, $C_1$-$C_3$ alkyl, $C_1$-$C_3$ haloalkyl, $C_1$-$C_3$ alkoxy, $C_1$-$C_3$ haloalkoxy, —NR'R", morpholinyl, pyrrolidinyl, piperidinyl, piperazinyl, a siderophore, —C(O)NR'R" and —NR'C(O)R". In one aspect of the invention, for any one of formulae (I), (Ia), (II), (III) or (V), $R^2$ is H, —CN, methyl, ethyl, propyl, isopropyl, thiazolyl, —CONR'R", or —$CO_2CH_3$, wherein when $R^2$ is not hydrogen or cyano, each $R^2$ is optionally and independently substituted by one or more fluoro, chloro, bromo, $C_1$-$C_3$ alkyl, $C_1$-$C_3$ haloalkyl, $C_1$-$C_3$ alkoxy or —NR'R"; and R' and R", when present in $R^2$, are independently selected from H and methyl. In one aspect of the invention, for any one of formulae (I), (Ia), (II), (III) or (V), $R^2$ is H, —CN, methyl, isopropyl, —CONHCH$_3$, —CONH(CH$_2$)$_2$NH$_2$, —CO$_2$CH$_3$, —(CH$_2$)NH$_2$, —(CH$_2$)$_2$NH$_2$ or thiazolyl. In one aspect of the invention, for any one of formulae (I), (Ia), (II), or (III), $R^2$ is hydrogen.

In one aspect of the invention, for any one of formulae (I), (Ia), (II), (III) or (IV), $R^3$ is selected from the group consisting of H, $C_1$-$C_3$ alkyl, $C_3$-$C_6$ cycloalkyl, and —CONR'R", wherein the alkyl and cycloalkyl represented by $R^2$ and/or $R^3$ are independently and optionally substituted by one or more group selected from halo, —CN, —OH, $C_1$-$C_3$ alkyl, $C_1$-$C_3$ haloalkyl, $C_1$-$C_3$ alkoxy, $C_1$-$C_3$ haloalkoxy, —NR'R", a siderophore, —C(O)NR'R" and —NR'C(O)R". In one aspect of the invention, for any one of formulae (I), (Ia), (II), (III) or (IV), $R^3$ is $C_1$-$C_3$ alkyl, $C_2$-$C_6$ alkenyl, $C_3$-$C_6$ cycloalkyl, or —CONR'R", each of which is optionally and independently substituted with one or more substituent selected from the group consisting of halo, —CN, —OH, $C_1$-$C_3$ alkyl, cyclopropyl, $C_1$-$C_3$ haloalkyl, $C_1$-$C_3$ alkoxy, $C_1$-$C_3$ haloalkoxy, —NR'R", a siderophore, —C(O)NR'R" and —NR'C(O)R"; and each R' and R" is independently selected from H and $C_1$-$C_3$ alkyl. In one aspect of the invention, for any one of formulae (I), (Ia), (II), (III) or (IV), $R^3$ is methyl, ethyl, isopropyl, cyclopropyl, —CONH$_2$, —CONH($C_1$-$C_3$ alkyl), or —CON($C_1$-$C_3$ alkyl)$_2$, each of which is optionally and independently substituted with one or more group selected from —OH, $C_1$-$C_3$ alkyl, $C_1$-$C_3$ alkoxy, —NR'R", C(O)NR'R" and —NR'C(O)R"; and each R' and R" is independently selected from H and $C_1$-$C_3$ alkyl. In one aspect of the invention, for any one of formulae (I), (Ia), (II), (III) or (IV), $R^3$ is $C_1$-$C_3$ alkyl, cyclopropyl, —CONR'R", wherein each alkyl, and cyclopropyl is optionally and independently substituted with one or more —OH, $C_1$-$C_3$ alkoxy, —NH$_2$, or —NHC(O)($C_1$-$C_3$ alkyl); and each R' and R" are independently selected from H, $C_1$-$C_3$ alkyl, and 5-6 membered heterocyclyl, wherein each alkyl and heterocyclyl represented by R' or R∝ is optionally and independently substituted with one or more —OH, $C_1$-$C_3$ alkyl, or $C_1$-$C_3$ alkoxy. In one aspect of the invention, for any one of formulae (I), (Ia), (II), (III) or (IV), $R^3$ is methyl, —CH$_2$OCH$_3$, or —CONH$_2$.

In one aspect of the invention, for any one of formulae (I), (Ia), (II), (III) or (IV), $R^3$ is H, $C_1$-$C_3$ alkyl, $C_3$-$C_6$ cycloalkyl, —CO$_2$R', —CONR'R", or a 5-6 membered heterocyclyl, each of which is optionally and independently substituted with one or more group selected from halo, —CN, —OH, $C_1$-$C_3$ alkyl, cyclopropyl, $C_1$-$C_3$ haloalkyl, $C_1$-$C_3$ alkoxy, $C_1$-$C_3$ haloalkoxy, —NR'R", morpholinyl, pyrrolidinyl, piperidinyl, piperazinyl, —C(O)NR'R" and —NR'C(O)R"; and wherein each R' and R", when present in $R^3$, is independently selected from H and $C_1$-$C_3$ alkyl. In one aspect of the invention, for any one of formulae (I), (Ia), (II), (III) or (IV), $R^3$ is H, methyl, ethyl, isopropyl, cyclopropyl, —CO$_2$($C_1$-$C_3$ alkyl), —CONH$_2$, —CONH($C_1$-$C_3$ alkyl), —CON($C_1$-$C_3$ alkyl)$_2$, morpholinyl or thiazolyl, each of which is optionally and independently substituted with one or more group selected from halo, —CN, —OH, $C_1$-$C_3$ alkyl, $C_1$-$C_3$ haloalkyl, cyclopropyl, $C_1$-$C_3$ alkoxy, $C_1$-$C_3$ haloalkoxy, —NR'R", morpholinyl, pyrrolidinyl, piperidinyl, piperazinyl, —C(O)NR'R" and —NR'C(O)R"; and wherein, when present in $R^3$, each R' and R" is independently selected from H and $C_1$-$C_3$ alkyl. In one aspect of the invention, for any one of formulae (I), (Ia), (II), (III) or (IV), $R^3$ is H, $C_1$-$C_3$ alkyl, $C_2$-$C_4$ alkenyl, $C_3$-$C_6$ cycloalkyl, —CONR'R", or a heterocyclyl, wherein each alkyl, alkenyl, and heterocyclyl is optionally and independently substituted with one or more halo, —CN, —OH, $C_1$-$C_3$ alkyl, $C_1$-$C_3$ haloalkyl, $C_1$-$C_3$ alkoxy, $C_1$-$C_3$ haloalkoxy, —C(O)($C_1$-$C_6$ alkyl), —C(O)($C_1$-$C_6$ alkoxy), —NH$_2$, —NH($C_1$-$C_3$ alkyl), or —N($C_1$-$C_3$ alkyl)$_2$; and when present in $R^3$, each R' and R" are optionally and independently substituted with one or more halo, —CN, —OH, $C_1$-$C_3$ alkyl, $C_1$-$C_3$ haloalkyl, cyclopropyl, $C_1$-$C_3$ alkoxy, $C_1$-$C_3$ haloalkoxy, —C(O)($C_1$-$C_6$ alkyl), —C(O)($C_1$-$C_6$ alkoxy), —NH$_2$, —NH($C_1$-$C_3$ alkyl), or —N($C_1$-$C_3$ alkyl)$_2$. In one aspect of the invention, for any one of formulae (I), (Ia), (II), (III) or (IV), $R^3$ is —CONR'R"; and one of R' and R" is H and the other is $C_1$-$C_3$ alkyl optionally substituted with one or more halo, —CN, —OH, —CF$_3$, $C_1$-$C_3$ alkoxy, $C_1$-$C_3$ haloalkoxy, cyclopropyl, —C(O)($C_1$-$C_6$ alkyl), —C(O)($C_1$-$C_6$ alkoxy), —NH$_2$, —NH($C_1$-$C_3$ alkyl), or —N($C_1$-$C_3$ alkyl)$_2$. In one aspect of the invention, for any one of formulae (I), (Ia), (II), (III) or (IV), $R^3$ is —CONH(CH$_2$)$_n$NHR'; R' is H, methyl, ethyl, propyl, isopropyl or cyclopropyl; and n is an integer from 1-3. In one aspect of the invention, for any one of formulae (I), (Ia), (II), (III) or (IV), $R^3$ is —CONH(CH$_2$)$_2$NH$_2$. In one aspect of the invention, for any one of formulae (I), (Ia), (II), (III) or (IV), $R^3$ is methyl, isopropyl, isopropenyl, —CONH$_2$ or —CON(CH$_3$)$_2$. In one aspect of the invention, for any one of formulae (I), (Ia), (II), (III) or (IV), $R^3$ is —CH$_2$OCH$_3$. In one aspect of the invention, for any one of formulae (I), (Ia), (II), or (III), $R^3$ is hydrogen.

In one aspect of the invention, for any one of formulae (I), (Ia), (II), (III), (IV) or (V), each R' and R" are independently selected from hydrogen, $C_1$-$C_6$ alkyl, $C_3$-$C_6$ cycloalkyl, phenyl, 5 to 6 membered heterocyclyl or a 5 to 6 membered heteroaryl; wherein each alkyl, cycloalkyl, phenyl, heterocyclyl and heteroaryl is optionally and independently substituted with one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —C(O)($C_1$-$C_6$ alkyl), —C(O)($C_1$-$C_6$ alkoxy), —NH$_2$, —NH($C_1$-$C_3$ alkyl), —N($C_1$-$C_3$ alkyl)$_2$, a 5-7 membered heterocyclyl or a 5-7 membered heteroaryl. In one aspect of the invention, for any one of formulae (I), (Ia), (II), (III), (IV) or (V), each R' and R" are independently selected from H, $C_1$-$C_3$ alkyl, and 5-6 membered heterocyclyl, wherein each alkyl and heterocyclyl represented by R' or R∝ is optionally and independently substituted with one or more —OH, $C_1$-$C_3$ alkyl, or $C_1$-$C_3$ alkoxy. In one aspect of the invention, for any one of formulae (I), (Ia), (II), (III), (IV) or (V), each R' and R" is independently selected from H and $C_1$-$C_3$ alkyl.

In one aspect of the invention, for any one of formulae (I), (Ia), (II), (III), (IV) or (V), each R' and R" is independently selected from hydrogen, $C_1$-$C_6$ alkyl, $C_3$-$C_6$ cycloalkyl, phenyl, 5-7 membered heterocyclyl or a 5-6 membered heteroaryl; wherein each alkyl, cycloalkyl, phenyl, heterocyclyl and heteroaryl is optionally and independently substituted with one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —C(O)($C_1$-$C_6$ alkyl), —C(O)($C_1$-$C_6$ alkoxy), —NH$_2$, —NH($C_1$-$C_3$ alkyl), —N($C_1$-$C_3$ alkyl)$_2$, a 5-6 membered heterocyclyl or a 5-6 membered heteroaryl; or R' and R" are taken together to form a 5-6 membered heterocyclyl or heteroaryl, wherein each heterocyclyl and heteroaryl is optionally and independently substituted with one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —NH$_2$, —NH($C_1$-$C_3$ alkyl), or —N($C_1$-$C_3$ alkyl)$_2$.

In one aspect of the invention, for any one of formulae (I), (Ia), (II), (III), (IV) or (V), each R' and R" is independently selected from hydrogen, and $C_1$-$C_6$ alkyl. In one aspect of the invention, for any one of formulae (I), (Ia), (II), (III), (IV) or (V), each R' and R" is independently selected from hydrogen, methyl, ethyl, propyl and isopropyl. In one aspect of the invention, for any one of formulae (I), (Ia), (II), (III), (IV) or (V), each R' and R" is independently selected from hydrogen and methyl. In one aspect of the invention, for any one of formulae (I), (Ia), (II), (III), (IV) or (V), each R' and R" is independently selected from an $C_1$-$C_3$ alkyl optionally substituted with one or more of methoxy, ethoxy, —OH, —$NH_2$, $NH(CH_3)$, —$N(CH_3)_2$, or a siderophore. In one aspect of the invention, for any one of formulae (I), (Ia), (II), (III), (IV) or (V), one of R' and R" is hydrogen, while the other is selected from any of the possible values listed above.

In one aspect of the invention, for any one of formulae (I), (Ia), (II), (III), (IV) or (V), $R^1$ is —$CH_2OCH_3$; —$CONH_2$, or

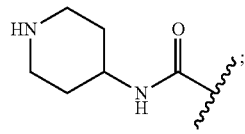

$R^2$ is —H or —$CH_3$; and $R^3$ is —H, —$CH_3$, or —$CONH_2$; provided that $R^2$ and $R^3$ are not both H; and when $R^1$ is —$CONH_2$, or

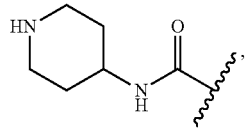 [SMILES: *C(=O)NC1CCNCC1]

then $R^3$ is not —$CONH_2$.

In one aspect of the invention, for any one of formulae (I), (Ia), (II), (I) (IV) or (V), $R^1$ is —$CH_2OCH_3$; —$CONH_2$,

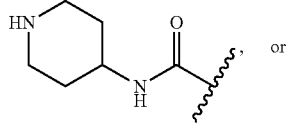

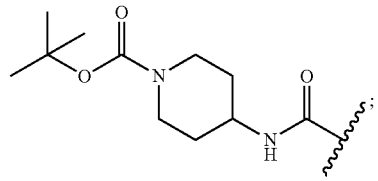

$R^2$ is —H or methyl; $R^3$ is —H, —$CH_3$, —$CONH_2$; and $R_4$ is —$OSO_2OH$.

In one aspect of the invention, for any one of formulae (I), (Ia), (II), (III), (IV) or (V), $R^1$ is —$CH_2OCH_3$; —CONR'R",

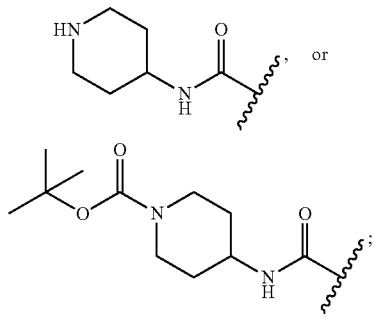

$R^2$ is —H, $C_1$-$C_3$ alkyl or $C_3$-$C_6$ cycloalkyl; $R^3$ is —H, $C_1$-$C_3$ alkyl, $C_3$-$C_6$ cycloalkyl or —CONR'R"; $R^4$ is —$OSO_2OH$; and each R' and R" are independently —H or $C_1$-$C_3$ alkyl.

In either of the two above aspects of the invention, the compound is as defined, provided that $R^2$ and $R^3$ are not both H; and when $R^1$ is —$CONH_2$,

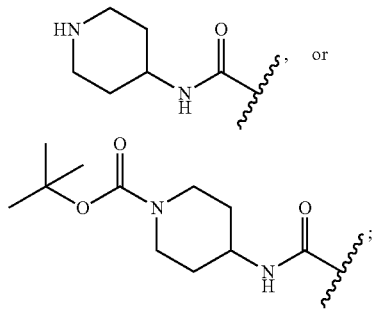

then $R^3$ is not —$CONH_2$.

One aspect of the invention is the compound:

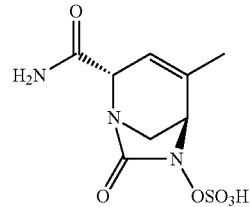

or a pharmaceutically acceptable salt thereof.

One aspect of the invention is the compound:

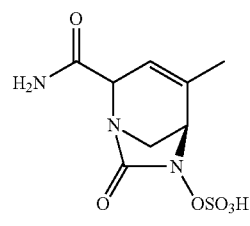

or a pharmaceutically acceptable salt thereof.

One aspect of the invention is the compound:

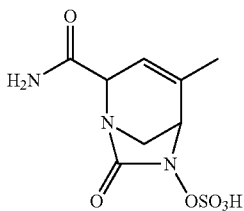

or a pharmaceutically acceptable salt thereof.

Another aspect of the present invention is the compound:

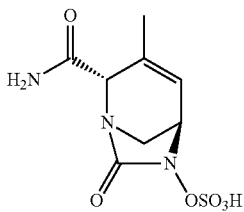

or a pharmaceutically acceptable salt thereof.

One aspect of the invention is the compound:

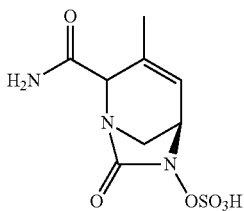

or a pharmaceutically acceptable salt thereof.

One aspect of the invention is the compound:

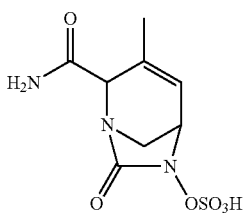

or a pharmaceutically acceptable salt thereof.

Any embodiment described herein can be combined with any other suitable embodiment described herein to provide additional embodiments. For example, where one embodiment individually or collectively describes possible groups for $R^1$ and a separate embodiment describes possible groups for $R^2$, it is understood that these embodiments can be combined to provide an additional embodiment utilizing the possible groups for $R^1$ with the possible groups for $R^2$. Analogously, the invention encompasses any embodiments called out individually for $R^1$, $R^2$, $R^3$, $R^4$, $R^5$, R' and R" in combination with any specific embodiments called out for each of the remaining variables.

Compounds of Formulae (I), (Ia), (II), (III), (IV) and (V) possess beneficial efficacious, metabolic, toxicological and/or pharmacodynamic properties.

In one aspect of the invention, the compound of formula (Ia) is selected from the group consisting of:
(2S,5R)-2-carbamoyl-4-methyl-7-oxo-1,6-diazabicyclo[3.2.1]oct-3-en-6-yl hydrogen sulfate sodium salt;
(2S,5R)-2-cyano-4-methyl-7-oxo-1,6-diazabicyclo[3.2.1]oct-3-en-6-yl hydrogen sulfate sodium salt;
(2S,5R)-4-methyl-7-oxo-2-(piperidinium-4-ylcarbamoyl)-1,6-diazabicyclo[3.2.1]oct-3-en-6-yl sulfate;
(2S,5R)-2-carbamoyl-4-isopropyl-7-oxo-1,6-diazabicyclo[3.2.1]oct-3-en-6-yl hydrogen sulfate sodium salt;
(2S,5R)-2-cyano-4-isopropyl-7-oxo-1,6-diazabicyclo[3.2.1]oct-3-en-6-yl hydrogen sulfate sodium salt;
(2S,5R)-2-(2-aminoethylcarbamoyl)-4-methyl-7-oxo-1,6-diazabicyclo[3.2.1]oct-3-en-6-yl hydrogen sulfate;
(2S,5R)-2-(methoxymethyl)-7-oxo-4-(prop-1-en-2-yl)-1,6-diazabicyclo[3.2.1]oct-3-en-6-yl hydrogen sulfate sodium salt;
(2S,5R)-2-((5-hydroxy-4-oxo-1,4-dihydropyridin-2-yl)methylcarbamoyl)-4-methyl-7-oxo-1,6-diazabicyclo[3.2.1]oct-3-en-6-yl hydrogen sulfate sodium salt;
(2S,5R)-2-carbamoyl-4-(methoxymethyl)-7-oxo-1,6-diazabicyclo[3.2.1]oct-3-en-6-yl hydrogen sulfate sodium salt;
(2S,5R)-2-carbamoyl-3-methyl-7-oxo-1,6-diazabicyclo[3.2.1]oct-3-en-6-yl sodium sulfate;
(2S,5R)-2-carbamoyl-3-isopropyl-7-oxo-1,6-diazabicyclo[3.2.1]oct-3-en-6-yl sodium sulfate;
(2S,5R)-4-carbamoyl-2-(methoxymethyl)-7-oxo-1,6-diazabicyclo[3.2.1]oct-3-en-6-yl hydrogen sulfate, monosodium salt;
(2S,5R)-2,4-bis(methoxymethyl)-7-oxo-1,6-diazabicyclo[3.2.1]oct-3-en-6-yl sulfate Sodium salt;
(2S,5R)-2-(1-(tert-butoxycarbonyl)piperidin-4-ylcarbamoyl)-7-oxo-1,6-diazabicyclo[3.2.1]oct-3-en-6-yl sulfate sodium salt;
(2S,5R)-4-(dimethylcarbamoyl)-2-(methoxymethyl)-7-oxo-1,6-diazabicyclo[3.2.1]oct-3-en-6-yl sulfate sodium salt;
(2S,5R)-2-(hydroxymethyl)-4-methyl-7-oxo-1,6-diazabicyclo[3.2.1]oct-3-en-6-yl hydrogen sulfate Sodium Salt;
(2S,5R)-3-methyl-7-oxo-2-(piperidin-1-ium-4-ylcarbamoyl)-1,6-diazabicyclo[3.2.1]oct-3-en-6-yl sulfate;
(2S,5R)-2-carbamoyl-3-(hydroxymethyl)-7-oxo-1,6-diazabicyclo[3.2.1]oct-3-en-6-yl hydrogen sulfate sodium salt;
(2S,5R)-4-(2-amino-2-oxoethyl)-2-carbamoyl-7-oxo-1,6-diazabicyclo[3.2.1]oct-3-en-6-yl hydrogen sulfate sodium salt;
(2S,5R)-4-carbamoyl-2-(hydroxymethyl)-7-oxo-1,6-diazabicyclo[3.2.1]oct-3-en-6-yl hydrogen sulfate sodium Salt;
(2S,5R)-2-carbamoyl-3,4-dimethyl-7-oxo-1,6-diazabicyclo[3.2.1]oct-3-en-6-yl hydrogen sulfate sodium salt;
(2S,5R)-2-carbamoyl-3-ethyl-7-oxo-1,6-diazabicyclo[3.2.1]oct-3-en-6-yl hydrogen sulfate sodium salt;
(2S,5R)-4-(2-aminoethyl)-2-carbamoyl-7-oxo-1,6-diazabicyclo[3.2.1]oct-3-en-6-yl hydrogen sulfate;
(2S,5R)-2-carbamoyl-3-cyclopropyl-7-oxo-1,6-diazabicyclo[3.2.1]oct-3-en-6-yl hydrogen sulfate sodium salt;
(2S,5R)-4-(2-acetamidoethyl)-2-carbamoyl-7-oxo-1,6-diazabicyclo[3.2.1]oct-3-en-6-yl sulfate sodium salt;
(2S,5R)-2-(methoxymethyl)-4-(methylcarbamoyl)-7-oxo-1,6-diazabicyclo[3.2.1]oct-3-en-6-yl hydrogen sulfate sodium salt;

(2S,5R)-2-carbamoyl-4-cyclopropyl-7-oxo-1,6-diazabicyclo[3.2.1]oct-3-en-6-yl hydrogen sulfate sodium salt;

(2S,5R)-3-(2-methoxyethyl)-2-(methoxymethyl)-7-oxo-1,6-diazabicyclo[3.2.1]oct-3-en-6-yl hydrogen sulfate sodium salt; and (2S,5R)-2-(((1,5-dihydroxy-4-oxo-1,4-dihydropyridin-2-yl)methyl)carbamoyl)-4-methyl-7-oxo-1,6-diazabicyclo[3.2.1]oct-3-en-6-yl hydrogen sulfate sodium salt;

or a pharmaceutically acceptable salt thereof.

Alkyl—As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as 'isopropyl' are specific for the branched chain version only. In one aspect, "alkyl" is methyl.

Alkenyl—As used herein, the term "alkenyl" refers to both straight and branched chain hydrocarbon radicals having the specified number of carbon atoms and containing at least one carbon-carbon double bond. For example, "$C_{2-6}$alkenyl" includes groups such as $C_{2-5}$alkenyl, $C_{2-4}$alkenyl, ethenyl, 2-propenyl, 2-methyl-2-propenyl, 3-butenyl, 4-pentenyl, 5-hexenyl, 2-heptenyl, and 2-methyl-1-heptenyl.

Alkynyl—As used herein, the term "alkynyl" refers to both straight and branched chain hydrocarbon radicals having the specified number of carbon atoms and containing at least one carbon-carbon triple bond. For example, "$C_{2-8}$alkynyl" includes groups such as $C_{2-6}$alkynyl, $C_{2-4}$alkynyl, ethynyl, 2-propynyl, 2-methyl-2-propynyl, 3-butynyl, 4-pentynyl, 5-hexynyl, 2-heptynyl, and 4-methyl-5-heptynyl.

Halo—As used herein, the term "halo" is intended to include fluoro, chloro, bromo and iodo. In one aspect, the "halo" may refer fluoro, chloro, and bromo. In another aspect, "halo" may refer to fluoro and chloro. In still another aspect, "halo" may refer to fluoro. In yet another aspect, "halo" may refer to chloro.

Cycloalkyl—In one aspect, "cycloalkyl" refers to a saturated or partially saturated monocyclic carbon ring, of which one or more —$CH_2$— groups may be optionally replaced with a corresponding number of —C(O)— groups. Illustrative examples of "cycloalkyl" include cyclopropyl, cyclobutyl, cyclopentyl, and cyclopentenyl. In one aspect, "3- to 5-membered carbocyclyl" may be cyclopropyl.

5-7 Membered heterocyclyl—The term "5-7 membered heterocyclyl" refers to a saturated or partially saturated, non-aromatic monocyclic ring containing 5 to 7 ring atoms, of which at least one ring atom is selected from nitrogen, sulfur, and oxygen, and of which a —$CH_2$— group may be optionally replaced by a —C(O)— group. Analogously, "5-6 membered heterocyclyl" refers to a saturated or partially saturated, non-aromatic monocyclic ring containing 5 to 6 ring atoms, of which at least one ring atom is selected from nitrogen, sulfur, and oxygen, and of which a —$CH_2$— group may be optionally replaced by a —C(O)— group. Unless otherwise specified, "5-7 membered heterocyclyl" and "5-6 membered heterocyclyl" groups may be carbon or nitrogen linked. Ring nitrogen atoms may be optionally oxidized to form an N-oxide. Ring sulfur atoms may be optionally oxidized to form S-oxides or sulphones. Illustrative examples of "5-7 membered heterocyclyl" and "5-6 membered heterocyclyl" include, but are not limited to, azetidinyl, dioxidotetrahydrothiophenyl, 2,4-dioxoimidazolidinyl, 3,5-dioxopiperidinyl, furanyl, imidazolyl, isothiazolyl, isoxazolyl, morpholinyl, oxazolyl, oxetanyl, oxoimidazolidinyl, 3-oxo-1-piperazinyl, 2-oxopyrrolidinyl, 2-oxotetrahydrofuranyl, oxo-1,3-thiazolidinyl, piperazinyl, piperidyl, 2H-pyranyl, pyrazolyl, pyridinyl, pyrrolyl, pyrrolidinyl, pyrimidinyl, pyrazinyl, pyrazolyl, pyridazinyl, 4-pyridonyl, tetrahydrofuranyl, tetrahydropyranyl, thiazolyl, 1,3,4-thiadiazolyl, thiazolidinyl, thiomorpholinyl, thiophenyl, 4H-1,2,4-triazolyl, pyridine-N-oxidyl, tetrazolyl, oxadiazolyl, triazolyl, pyrazinyl, triazinyl, and homopiperidinyl. In one embodiment, the terms "5-7membered heterocyclyl" and "5-6 membered heterocyclyl" includes siderophores of 5-7 or 5-6 members which contain at least one heteroatom.

5- or 6-Membered Heteroaryl—The term "5-6 membered heteroaryl" is refers to a monocyclic, aromatic heterocyclyl ring containing 5 or 6 ring atoms, of which at least one ring atom is selected from nitrogen, sulfur, and oxygen. Unless otherwise specified, "5-6 membered heteroaryl" groups may be carbon or nitrogen linked. Ring nitrogen atoms may be optionally oxidized to form an N-oxide. Ring sulfur atoms may be optionally oxidized to form S-oxides. Illustrative examples of "5-6 membered heteroaryl" include furanyl, imidazolyl, isothiazolyl, isoxazole, oxazolyl, pyrazinyl, pyrazolyl, pyridazinyl, pyrimidinyl, pyridinyl, pyrrolyl, tetrazolyl, thiadiazolyl, thiazolyl, thiophenyl, and triazolyl.

6-Membered Heteroaryl—In one aspect, "heterocyclyl," 5- or 6-membered heterocyclyl," "6-membered heterocyclyl," and "5- or 6-membered heteroaryl" may be "6-membered heteroaryl." The term "6-membered heteroaryl" is intended to refer to a monocyclic, aromatic heterocyclyl ring containing 6 ring atoms. Ring nitrogen atoms may be optionally oxidized to form an N-oxide. Illustrative examples of "6-membered heteroaryl" include pyrazinyl, pyridazinyl, pyrimidinyl, and pyridinyl.

Siderophore—In one aspect, a "siderophore" is a low molecular weight moiety that can bind ferric iron. Once bound, these "iron carriers" can facilitate transport of the molecule into a bacterial cell. The term "siderophore" includes, but is not limited to the following heterocyclyls:

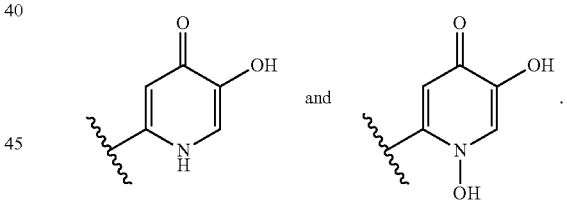

Optionally substituted—As used herein, the phrase "optionally substituted" indicates that substitution is optional and therefore it is possible for the designated group to be either substituted or unsubstituted. In the event a substitution is desired, the appropriate number of hydrogens on the designated group may be replaced with a selection from the indicated substituents, provided that the normal valency of the atoms on a particular substituent is not exceeded, and that the substitution results in a stable compound.

In one aspect, when a particular group is designated as being optionally substituted with one or more substituents, the particular group may be unsubstituted. In another aspect, the particular group may bear one substituent. In another aspect, the particular substituent may bear two substituents. In still another aspect, the particular group may bear three substituents. In yet another aspect, the particular group may bear four substituents. In a further aspect, the particular group may bear one or two substituents. In still a further aspect, the particular group may be unsubstituted, or may bear one or two substituents.

Pharmaceutically Acceptable—As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Effective Amount—As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

Leaving Group—As used herein, the phrase "leaving group" is intended to refer to groups readily displaceable by a nucleophile such as an amine nucleophile, and alcohol nucleophile, or a thiol nucleophile. Examples of suitable leaving groups include halo, such as fluoro, chloro, bromo, and sulfonyloxy group, such as methanesulfonyloxy and toluene-4-sulfonyloxy.

Protecting Group—As used herein, the term "protecting group" is intended to refer to those groups used to prevent selected reactive groups (such as carboxy, amino, hydroxy, and mercapto groups) from undergoing undesired reactions. Illustrative examples of suitable protecting groups for a hydroxy group include acyl groups; alkanoyl groups such as acetyl; aroyl groups, such as benzoyl; silyl groups, such as trimethylsilyl; and arylmethyl groups, such as benzyl. The deprotection conditions for the above hydroxy protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon. Illustrative examples of suitable protecting groups for an amino group include acyl groups; alkanoyl groups such as acetyl; alkoxycarbonyl groups, such as methoxycarbonyl, ethoxycarbonyl, and t-butoxycarbonyl; arylmethoxycarbonyl groups, such as benzyloxycarbonyl; and aroyl groups, such benzoyl. The deprotection conditions for the above amino protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric, phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid, for example boron trichloride). A suitable alternative protecting group for a primary amino group is, for example, a phthaloyl group, which may be removed by treatment with an alkylamine, for example dimethylamino-propylamine or 2-hydroxyethylamine, or with hydrazine. Another suitable protecting group for an amine is, for example, a cyclic ether such as tetrahydrofuran, which may be removed by treatment with a suitable acid such as trifluoroacetic acid. The protecting groups may be removed at any convenient stage in the synthesis using conventional techniques well known in the chemical art, or they may be removed during a later reaction step or during work-up.

Compounds of Formulae (I), (Ia), (II), (III), (IV) or (V) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Compounds of Formulae (I), (Ia), (II), (III), (IV) or (V) have one or more chiral centers, and it is to be understood that the invention encompasses all such stereoisomers, including enantiomers and diastereoisomers. Thus, it is to be understood that, insofar as certain of the compounds of Formulae (I), (Ia), (II), (III), (IV) or (V) may exist in optically active or racemic forms by virtue of one or more asymmetric carbon atoms, the invention includes in its definition any such optically active or racemic form which possesses the above-mentioned activity. The present invention encompasses all such stereoisomers having activity as herein defined.

The synthesis of optically active forms may be carried out by standard techniques of organic chemistry well known in the art, for example by synthesis from optically active starting materials or by resolution of a racemic form. Racemates may be separated into individual enantiomers using known procedures (see, for example, Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using the standard laboratory techniques referred to hereinafter.

Thus, throughout the specification, where reference is made to the compound of Formulae (I), (Ia), (II), (III), (IV) or (V), it is to be understood that the term compound includes isomers, mixtures of isomers, and stereoisomers that are β-lactamase inhibitors.

Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent.

When a specific stereoisomer is provided (whether provided by separation, by chiral synthesis, or by other methods) it is favorably provided substantially isolated from other stereoisomers of the same compound. In one aspect, a mixture containing a particular stereoisomer of a compound of Formulae (I), (Ia), (II), (III), (IV) or (V) may contain less than 30%, particularly less than 20%, and more particularly less than 10% by weight of other stereoisomers of the same compound. In another aspect, a mixture containing a particular stereoisomer of a compound of Formulae (I), (Ia), (II), (III), (IV) or (V) may contain less than 6%, particularly less than 3%, and more particularly less than 2% by weight of other stereoisomers of the compound. In another aspect, a mixture containing a particular stereoisomer of a compound of Formulae (I), (Ia), (II), (III), (IV) or (V) may contain less than 1%, particularly less than 0.5%, and more particularly less than 0.3%, and still more particularly less 0.1% by weight of other stereoisomers of the compound.

It is to be understood that, insofar as certain of the compounds of Formulae (I), (Ia), (II), (III), (IV) or (V) defined above may exist in tautomeric forms, the invention includes in its definition any such tautomeric form which possesses the above-mentioned activity. Thus, the invention relates to all tautomeric forms of the compounds of Formulae (I), (Ia), (II), (III), (IV) or (V) whether explicitly detailed in the specification or not.

It is also to be understood that certain compounds of Formulae (I), (Ia), (II), (III), (IV) or (V) and pharmaceutically salts thereof, can exist in solvated as well as unsolvated forms such as, for example, hydrated forms. It is to be understood that the invention encompasses all such solvated forms. For the sake of clarity, this includes both solvated (e.g., hydrated) forms of the free form of the compound, as well as solvated (e.g., hydrated) forms of the salt of the compound.

For the sake of clarity, it should be understood that the atoms of the compounds of Formulae (I), (Ia), (II), (III), (IV) or (V) and of any of the examples or embodiments disclosed herein, are intended to encompass all isotopes of the atoms. For example, H (or hydrogen) includes any isotopic form of hydrogen including $^{1}H$, $^{2}H$ (D), and $^{3}H$ (T); C includes any isotopic form of carbon including $^{12}C$, $^{13}C$, and $^{14}C$; O includes any isotopic form of oxygen including $^{16}O$, $^{17}O$ and $^{18}O$; N includes any isotopic form of nitrogen including $^{13}N$, $^{14}N$ and $^{15}N$; P includes any isotopic form of phosphorous including $^{31}P$ and $^{32}P$; S includes any isotopic form of sulfur including $^{32}S$ and $^{35}S$; F includes any isotopic form of fluorine including $^{19}F$ and $^{18}F$; Cl includes any isotopic form of chlorine including $^{35}Cl$, $^{37}Cl$ and $^{36}Cl$; and the like. In one aspect, the compounds of Formulae (I), (Ia), (II), (III), (IV) or (V) include isotopes of the atoms covered therein in amounts corresponding to their naturally occurring abundance. However, in certain instances, it may be desirable to enrich one or more atom in a particular isotope which would normally be present in a lower abundance. For example, $^{1}H$ would normally be present in greater than 99.98% abundance; however, in one aspect, a compound of the invention may be enriched in $^{2}H$ or $^{3}H$ at one or more positions where H is present. In another aspect, when a compound of the invention is enriched in a radioactive isotope, for example $^{3}H$ and $^{14}C$, the compound may be useful in drug and/or substrate tissue distribution assays. It is to be understood that the invention encompasses all such isotopic forms which are useful for treating bacterial infections.

In one aspect, the terms "infection" and "bacterial infection" may refer to a gynecological infection. In another aspect the terms "infection" and "bacterial infection" may refer to a respiratory tract infection (RTI). In still another, the terms "infection" and "bacterial infection" may refer to a sexually transmitted disease. In yet another aspect, the terms "infection" and "bacterial infection" may refer to a urinary tract infection (UTI). In a further aspect, the terms "infection" and "bacterial infection" may refer to acute exacerbation of chronic bronchitis (ACEB). In yet a further aspect, the terms "infection" and "bacterial infection" may refer to acute otitis media. In one aspect, the terms "infection" and "bacterial infection" may refer to acute sinusitis. In another aspect, the terms "infection" and "bacterial infection" may refer to an infection caused by drug resistant bacteria. In still another aspect, the terms "infection" and "bacterial infection" may refer to catheter-related sepsis. In yet another aspect, the terms "infection" and "bacterial infection" may refer to chancroid. In a further aspect, the terms "infection" and "bacterial infection" may refer to chlamydia. In still a further aspect, the terms "infection" and "bacterial infection" may refer to community-acquired pneumonia (CAP). In yet a further aspect, the terms "infection" and "bacterial infection" may refer to complicated skin and skin structure infection. In one aspect, the terms "infection" and "bacterial infection" may refer to uncomplicated skin and skin structure infection. In another aspect, the terms "infection" and "bacterial infection" may refer to endocarditis. In still another aspect, the terms "infection" and "bacterial infection" may refer to febrile neutropenia. In yet another aspect, the terms "infection" and "bacterial infection" may refer to gonococcal cervicitis. In a further aspect, the terms "infection" and "bacterial infection" may refer to gonococcal urethritis. In still a further aspect, the terms "infection" and "bacterial infection" may refer to hospital-acquired pneumonia (HAP). In yet another aspect, the terms "infection" and "bacterial infection" may refer to osteomyelitis. In a further aspect, the terms "infection" and "bacterial infection" may refer to sepsis. In still a further aspect, the terms "infection" and "bacterial infection" may refer to syphilis. In a further aspect, the terms "infection" and "bacterial infection" may refer to an intra-abdominal infection (IAI).

In one embodiment of the invention, the terms "infection" and "bacterial infection" refer to a infection caused by Gram-negative bacteria, also referred to as a "Gram-negative infection". In one aspect of this embodiment, the Gram-negative infection is a an infection resistant to one or more antibiotics. In one aspect of this embodiment, the Gram-negative infection is a multi-drug resistant infection.

All the above mentioned infections can be caused by a variety of bacteria that potentially could be treatable with the claimed agents in combination with penicillin-binding protein inhibitors, or by itself. In one embodiment of the invention is a method of treating one or more of the infections listed above comprising administering to a subject suffering from a bacterial infection an effective amount of a compound of Formulae (I), (Ia), (II), (III), (IV) or (V) or a pharmaceutically acceptable salt thereof, in combination with an additional antibiotic agent. In one aspect of this embodiment, the additional antibiotic agent is a β-lactam antibiotic. In one aspect of this embodiment, the additional antibiotic agent is a penicillin-binding protein inhibitor.

In one aspect, there is provided the use of a compound of Formulae (I), (Ia), (II), (III), (IV) or (V), or a pharmaceutically acceptable salt thereof, in the manufacture of a medicament for the production of a bacterial peptidoglycan inhibitory effect, either alone or in combination with a penicillin-binding protein inhibitor, in a warm-blooded animal such as man.

In another aspect, there is provided the use a compound of Formulae (I), (Ia), (II), (III), (IV) or (V), or a pharmaceutically acceptable salt thereof, in the manufacture of a medicament for the treatment of a bacterial infection in a warm-blooded animal such as man. In one aspect, the compound of Formulae (I), (Ia), (II), (III), (IV) or (V), or a pharmaceutically acceptable salt thereof, is administered in combination with an additional antibiotic agent, such as a β-lactam antibiotic. In one aspect of this embodiment, the additional antibiotic agent is a penicillin-binding protein inhibitor.

In still another aspect, there is provided the use of a compound of Formulae (I), (Ia), (II), (III), (IV) or (V), or a pharmaceutically acceptable salt thereof, in the manufacture of a medicament for the treatment of urinary tract infections, pneumonia, prostatitis, skin and soft tissue infections, sepsis, and intra-abdominal infections, in a warm-blooded animal such as man. In one aspect of this embodiment, the compound of Formulae (I), (Ia), (II), (III), (IV) or (V) is administered in combination with an additional antibiotic agent. In one aspect of this embodiment, the additional antibiotic agent is a penicillin-binding protein inhibitor.

In another aspect, there is provided a method for producing a bacterial peptidoglycan inhibitory effect, either alone or in combination with a penicillin-binding protein inhibitor, in a warm-blooded animal such as man, said method comprising administering to said animal an effective amount of a compound of Formulae (I), (Ia), (II), (III), (IV) or (V), or a pharmaceutically acceptable salt thereof.

In a further aspect, there is provided a method for treating a bacterial infection in a warm-blooded animal such as man, said method comprising administering to said animal an effective amount of a compound of Formulae (I), (Ia), (II), (III), (IV) or (V), or a pharmaceutically acceptable salt thereof. In one aspect of this embodiment, the compound of Formulae (I), (Ia), (II), (III), (IV) or (V), or a pharmaceutically acceptable salt thereof, is administered in combination with an additional antibiotic agent. In one aspect of this embodiment, the additional antibiotic agent is a penicillin-binding protein inhibitor. In one aspect, the additional antibiotic agent is a β-lactam antibiotic.

In still a further aspect, there is provided a method for treating urinary tract infections, pneumonia, prostatitis, skin and soft tissue infections, sepsis, and intra-abdominal infections, in a warm-blooded animal such as man, said method comprising administering to said animal an effective amount of a compound of Formulae (I), (Ia), (II), (III), (IV) or (V), or a pharmaceutically acceptable salt thereof. In one aspect of this embodiment, the compound of Formulae (I), (Ia), (II), (III), (IV) or (V), or a pharmaceutically acceptable salt thereof, is administered in combination with an additional antibiotic agent. In one aspect of this embodiment, the additional antibiotic agent is a penicillin-binding protein inhibitor. In one aspect, the additional antibiotic agent is a β-lactam antibiotic.

In yet a further aspect, there is provided a compound of Formulae (I), (Ia), (II), (III), (IV) or (V), or a pharmaceutically acceptable salt thereof, for use in producing a bacterial peptidoglycan inhibitory effect, either alone or in combination with a penicillin-binding protein inhibitor, in a warm-blooded animal such as man. In one aspect, there is provided a compound of Formulae (I), (Ia), (II), (III), (IV) or (V), or a pharmaceutically acceptable salt thereof, for use in treating Gram-negative bacterial infections, either alone or in combination with a beta-lactam antibiotic.

In one aspect of the invention, there is provided a method of inhibiting one or more beta-lactamase enzyme comprising administering a compound of Formulae (I), (Ia), (II), (III), (IV) or (V), or a pharmaceutically acceptable salt thereof, to an animal in need thereof. In a further aspect, the one or more beta-lactamase enzyme is a serine beta-lactamase enzyme. In a further aspect, the one or more beta-lactamase enzyme is selected from the group consisting of Class A, Class C and Class D. In a further aspect, the one or more beta-lactamase enzyme is a Class A enzyme. In a further aspect, the one or more beta-lactamase enzyme is a Class C enzyme. In a further aspect, the one or more beta-lactamase enzyme is a Class D enzyme. In a further aspect, the one or more beta-lactamase enzyme is a Class D enzyme and one or more of Class A and C enzymes.

The beta-lactamase inhibitors of Formulae (I), (Ia), (II), (III), (IV) or (V) can be administered in combination with any β-lactam antibiotic belonging, but not limited to, the classes of clavams, carbapenems, monobactams, penicllins, and or cephalosporins, or with any other compound susceptible to serine β-lactamases. In one aspect of the invention, a compound of formula (I), (Ia), (II), (III), (IV) or (V) is combined with one or more of: penicillin, methicillin, oxacillin, nafcillin, cloxacillin, dicloxacillin, flucloxacillin, temocillin, amoxicillin, ampicillin, co-amoxiclav, azlocillin, carbenicillin, ticarcillin, mezlocillin, piperacillin, cephalexin, cephalothin, CXA-101, cefazolin, cefaclor, cefuroxime, cefamandole, cefotetan, cefoxitin, ceftriaxone, cefotaxime, cefpodoxime, cefixime, ceftazidime, ceftobiprole medocaril, cefepime, cefpirome, ceftaroline, imipenem, meropenem, ertapenem, faropenem, sulopenem, doripenem, PZ-601 (Protez Pharmaceuticals), ME1036 (Forest Labs), BAL30072, MC-1, tomopenem, tebipenemn, aztreonam, tigemonam, nocardicin A, or tabtoxinine-β-lactam. In one aspect of the invention, a compound of Formulae (I), (Ia), (II), (III), (IV) or (V) is combined with meropenem, aztreonam, or ceftazidime. In one aspect of the invention, a compound of Formulae (I), (Ia), (II), (III), (IV) or (V) is combined with meropenem. In one aspect of the invention, a compound of Formulae (I), (Ia), (II), (III), (IV) or (V) is combined with aztreonam. In one aspect of the invention, a compound of Formulae (I), (Ia), (II), (III), (IV) or (V) is combined with ceftazidime. In one aspect of the invention, a compound of Formulae (I), (Ia), (II), (III), (IV) or (V) is combined with ceftaroline fosamil.

In another aspect of the invention, the compound of Formulae (I), (Ia), (II), (III), (IV) or (V) is administered in combination with a β-lactam antibiotic and an additional antibiotic and/or an additional β-lactamase inhibitor. In one aspect of the invention, the additional antibiotic agent is selected from one of the classes of aminoglycosides, spectinomycins, macrolides, ketolides, streptogramins, oxazolidinones, tetracyclines, fluoroquinolones, coumarin antibiotics, glycopeptides, lipoglycopeptides, nitroimidazoles, ansamycins, phenicols, mupirocyn, fosfomycin, tobramycin, linezolid, daptomycin, vancomycin, and the clasess mentioned in ANTIMICROBIAL AGENTS (ASM Press, Ed: A. Bryskier (2005)).

In one aspect of the invention, the compound of Formulae (I), (Ia), (II), (III), (IV) or (V) is administered in combination with a β-lactam antibiotic and a second agent which is designed to address β-lactam resistance. In one aspect of the invention, the compound of Formulae (I), (Ia), (II), (III), (IV) or (V) is administered in combination with a β-lactam antibiotic and a second serine beta-lactamase inhibitor. In one aspect of the invention, the second beta-lactamase inhibitor is selected from sulbactam, tazobactam, avibactam, clavulanic acid, LK-157, LK-176, SA-1-204, SA-2-13, BLI-489 (Pfizer/Wyeth), BAL0029880 and MK7655. In another aspect of the invention, the second agent designed to address β-lactam resistance may be a metallo-beta-lactamase (MBL) inhibitor, also known as a Class B inhibitor.

In one aspect, there is provided a compound of Formulae (I), (Ia), (II), (III), (IV) or (V), or a pharmaceutically acceptable salt thereof, for use in treating a bacterial infection in a warm-blooded animal, such as man.

In another aspect, there is provided a compound of Formulae (I), (Ia), (II), (III), (IV) or (V), or a pharmaceutically acceptable salt thereof, for use in treating urinary tract infections, pneumonia, prostatitis, skin and soft tissue infections, sepsis and intra-abdominal infections, in a warm-blooded animal such as man.

In still another aspect, there is provided a pharmaceutical composition comprising a compound of Formulae (I), (Ia), (II), (III), (IV) or (V), or a pharmaceutically acceptable salt thereof, and at least one pharmaceutically acceptable carrier, diluent, or excipient.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). In one aspect of the invention, the compound of Formulae (I), (Ia), (II), (III), (IV) or (V), or a pharmaceutically acceptable salt thereof, is administered intravenously. In another aspect of the invention, the compound of Formulae (I), (Ia), (II), (III), (IV) or (V), or a pharmaceutically acceptable salt thereof, is administered intravenously in combination with one or more other antibacterial agent. In one aspect of this embodiment, the compound of Formulae (I), (Ia), (II), (III), (IV) or (V), or a pharmaceutically acceptable salt thereof, is administered simultaneously with one or more other antibacterial agents.

The compositions of the invention may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 1000 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

In addition to the compounds of the present invention, the pharmaceutical composition of this invention may also contain or be co-administered (simultaneously, sequentially or separately) with one or more known drugs selected from other clinically useful classes of antibacterial agents (for example, macrolides, quinolones, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. Accordingly, the optimum dosage may be determined by the practitioner who is treating any particular patient.

In addition to its use in therapeutic medicine, the compound of Formulae (I), (II), (III) or (IV) and its pharmaceutically acceptable salts are also useful as pharmacological tools in the development and standardization of in vitro and in vivo test systems for the evaluation of the effects of inhibitors of DNA gyrase in laboratory animals such as cats, dogs, rabbits, monkeys, rats and mice, as part of the search for new therapeutic agents.

Compounds of Formula (I), (Ia), (II), (III), (IV) or (V) may be prepared in a variety of ways. The processes shown below illustrates a method for synthesizing compounds of Formula (Ia) (wherein $R^1$, $R^2$, and $R^3$ unless otherwise defined, are as defined hereinabove). The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used. The Schemes and Processes are not intended to present an exhaustive list of methods for preparing the compounds of Formulae (I), (Ia), (II), (III), (IV) or (V); rather, additional techniques of which the skilled chemist is aware may be also be used for the compounds' synthesis. The claims are not intended to be limited to the structures shown in the Schemes and Processes.

It will also be appreciated that in some of the reactions shown in the Schemes and Processes mentioned herein, it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, *Protective Groups in Organic Synthesis*, published by John Wiley and Sons, (1991)) and as described hereinabove.

The skilled chemist will be able to use and adapt the information contained and referenced within the above references, and accompanying Examples therein and also the Examples and Scheme herein, to obtain necessary starting materials and products.

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature, or could be made from commercially available compounds using adaptations of processes reported in the scientific literature. The reader is further referred to *Advanced Organic Chemistry, 5th Edition*, by Jerry March and Michael Smith, published by John Wiley & Sons (2001), for general guidance on reaction conditions and reagents.

In one aspect, compounds of Formulae (I), (Ia), (II), (III), (IV) or (V), or pharmaceutically acceptable salts thereof, may be prepared by the process outlined in Scheme 1. From the Weinreb amide, compound 1, introduction of substituents at the $R^3$ position of Formula (I), (Ia), (II), (III), (IV) or (V) may be done via a Grignard reaction, followed by the rest of the synthetic steps shown above to yield final compounds. Compounds with different substituents at the $R^4$ position can be synthesized from compound 11 by N—O

SCHEME 1:

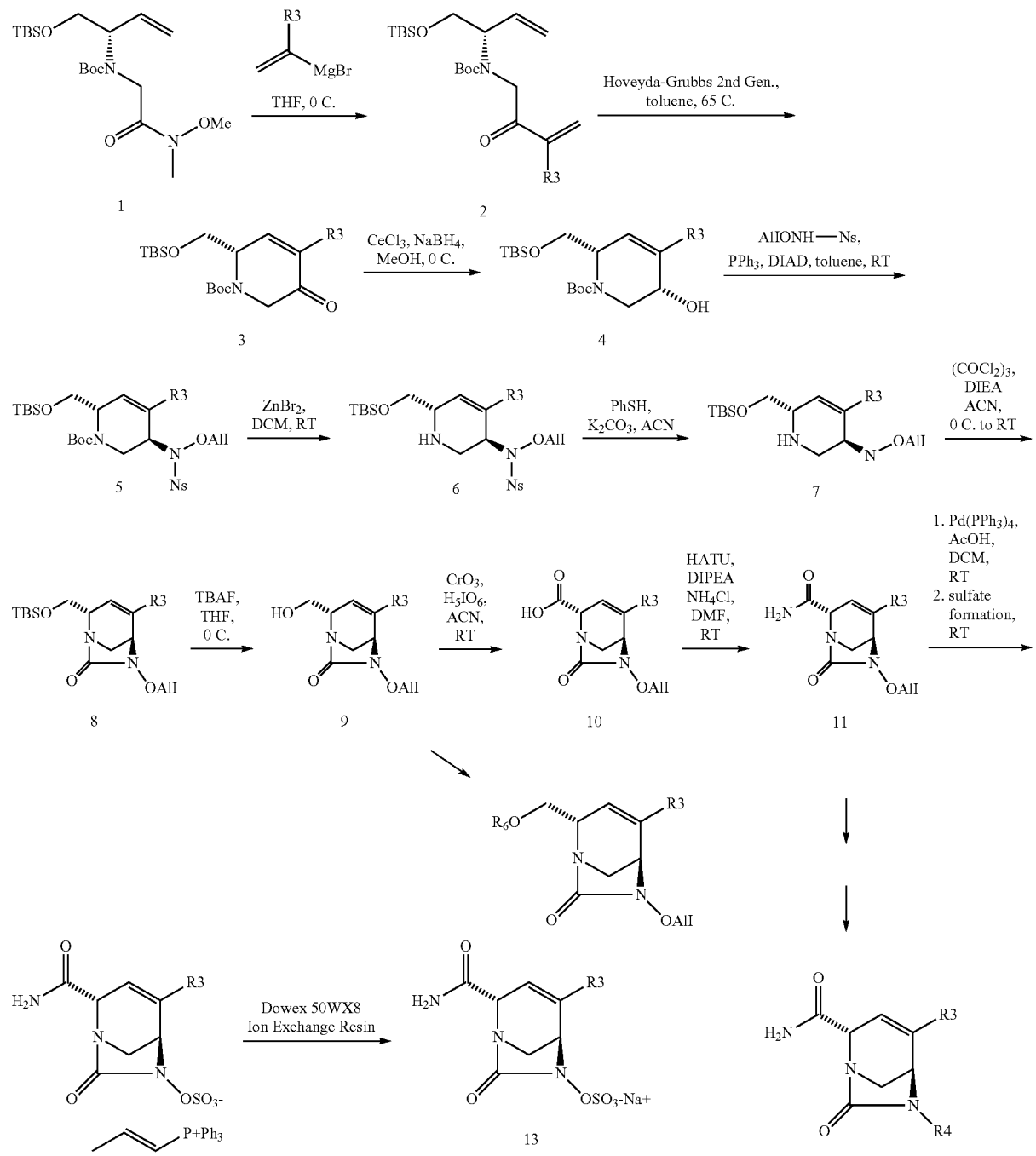

reduction and deallylation followed by subsequent reaction with the amine, such as alkylation or reaction with a substituted sulphone or a substituted isocyanate. Similarly, compounds with R¹=CH₂OR, can be made from intermediate 9, using standard alkylation techniques.

An alternative means of synthesizing compounds with substitutents at R³ utilizes the Baylis-Hillman product of enone followed by standard functional group transformations showing below, wherein the hydroxide group can be transformed into a leaving group, Q, which can subsequently be displaced by an appropriate nucleophile.

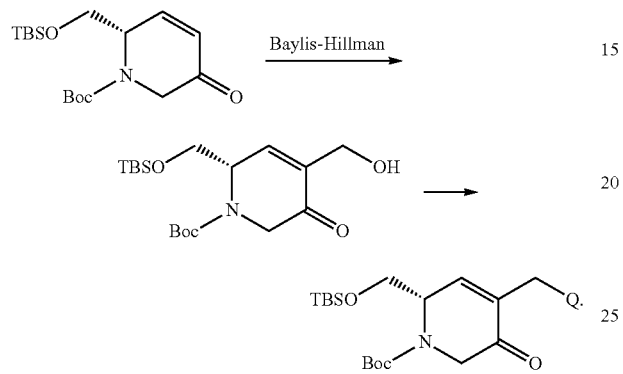

Others R³ analogs can be made through cross-coupling of corresponding halide enone, as shown below.

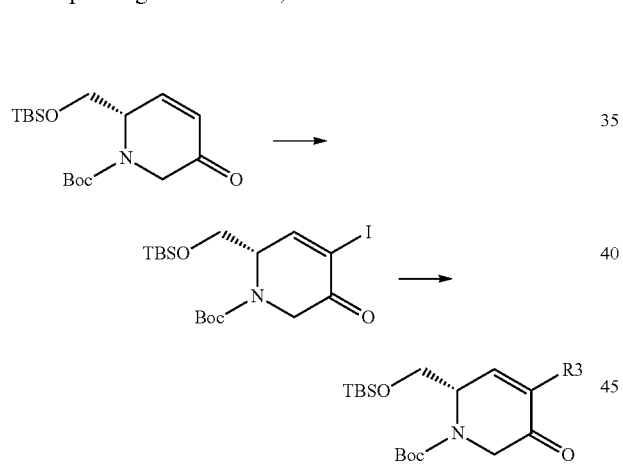

The Weinreb amide, compound 1, can be made easily prepared from corresponding amine by through alkylation, as shown below.

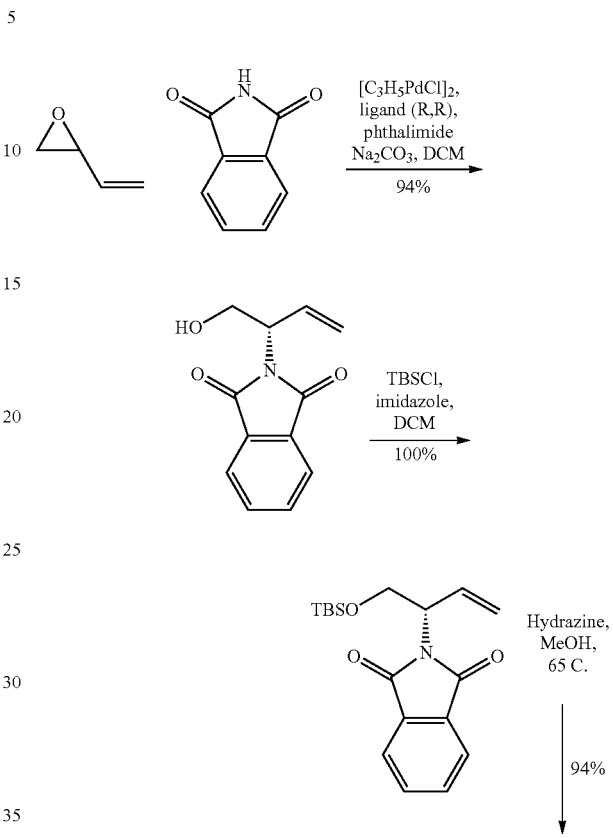

Compounds with substitution at R² can be installed via Michael Addition, according to Scheme 2 below:

SCHEME 2

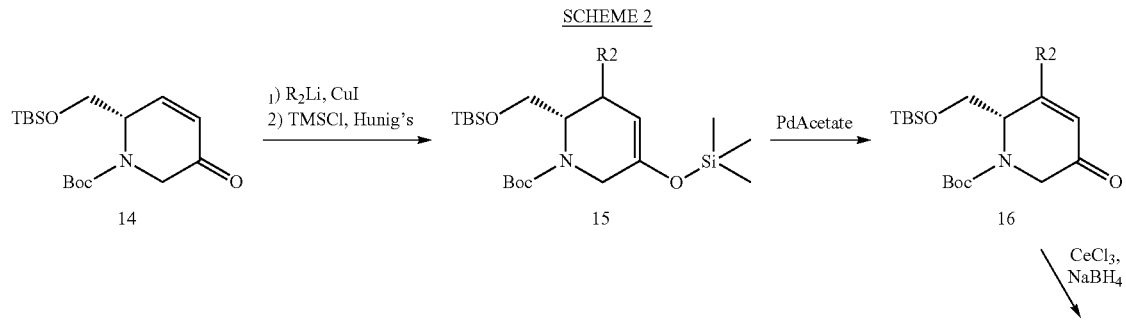

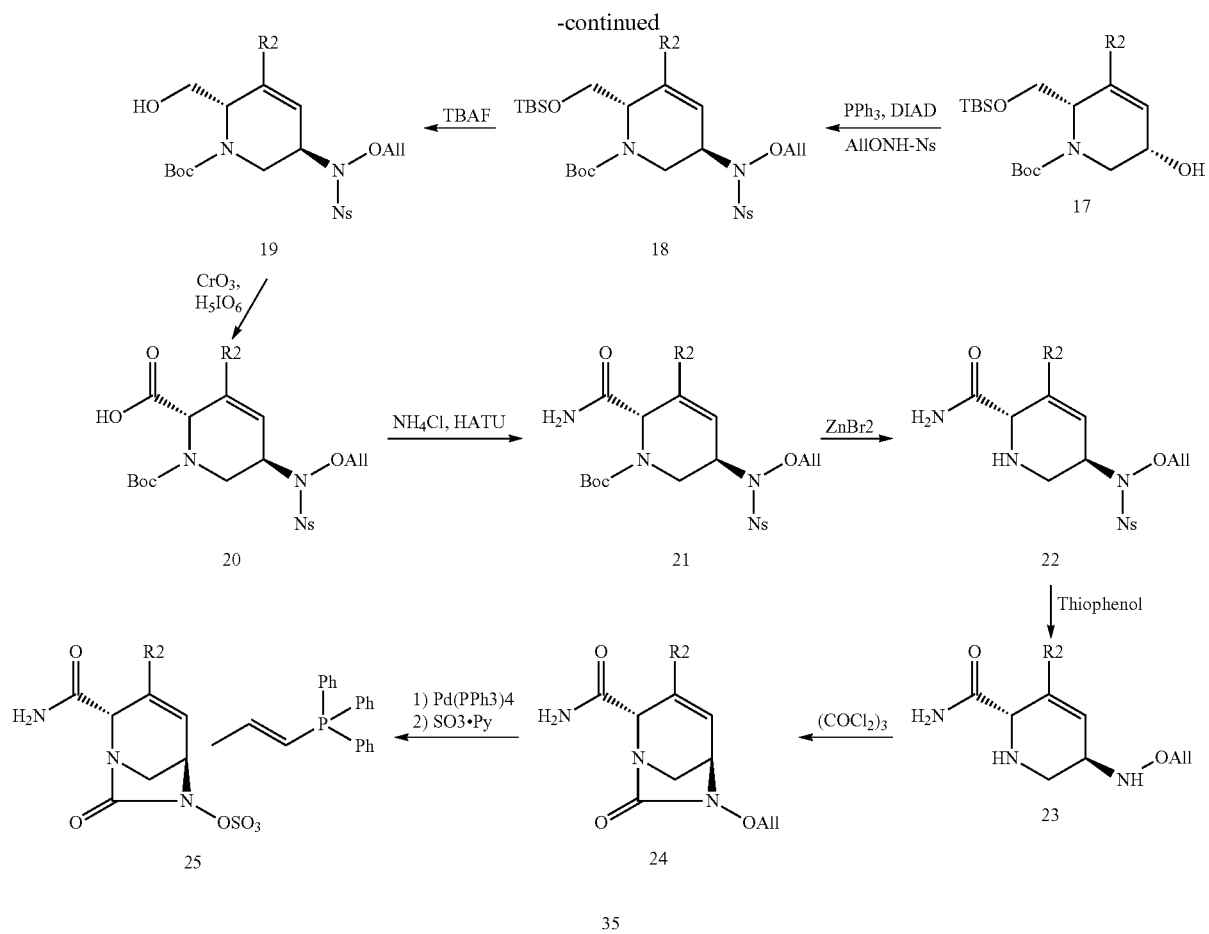

In any of the above-mentioned pharmaceutical compositions, processes, methods, uses, medicaments, and manufacturing features of the instant invention, any of the alternate embodiments of the compounds of the invention described herein also apply.

EXAMPLES

The invention will now be further described with reference to the following illustrative examples in which, unless stated otherwise:

(i) temperatures are given in degrees Celsius (° C.); operations are carried out at room temperature or ambient temperature, that is, in a range of 18-25° C.;
(ii) organic solutions were dried over anhydrous magnesium sulfate; evaporation of organic solvent was carried out using a rotary evaporator under reduced pressure (4.5-30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC or liquid chromatography/mass spectroscopy (LC/MS) and reaction times are given for illustration only;
(v) final products have satisfactory proton nuclear magnetic resonance (NMR) spectra and/or mass spectra data;
(vi) yields are given for illustration only and are not necessarily those which can be obtained by diligent process development; preparations were repeated if more material was required;
(vii) when given, NMR data is in the form of delta values for major diagnostic protons, given in part per million (ppm) relative to tetramethylsilane (TMS) as an internal standard, determined at 300 MHz in DMSO-$d_6$ unless otherwise stated;
(viii) chemical symbols have their usual meanings;
(ix) solvent ratio was given in volume:volume (v/v) terms;
(x) an ISCO Combiflash refers to flash chromatography on silica gel using Isco Combiflash® separation system: RediSep normal phase flash column, flow rate, 30-40 ml/min;
(xi) the following abbreviations may have been used:
ACN Acetonitrile
BINAP 2,2'-bis(diphenylphosphino)-1,1'-binapthyl
Boc$_2$O tert-butyloxycarbonyl anhydride
DAST Diethylaminosulfur trifluoride
DCM dichloromethane
DIPEA/DIEA N, N-diisopropylethylamine
DMAc N,N-dimethylacetamide
DMF N,N-dimethylformamide
DMAP 4-dimethylaminopyridine
DMSO dimethylsulfoxide
ee enantiomeric excess
EtOAc/EA ethyl acetate
Et$_2$O diethyl ether
GC gas chromatography
HATU O-(7-Azabenzotriazol-1-yl)-N,N,N',N'-tetramethyluronium hexafluorophosphate
Hex hexanes
HPLC high-performance liquid chromatography hr/h hours
LDA Lithium diisopropylamide
MeCN acetonitrile
MeOH methanol
mins/min minutes
o/n overnight
Pd$_2$(dba)$_3$ Tris(dibenzylideneacetone)dipalladium(0)
iPrOH i-propanol
rac. racemic
TBAF tetra-n-butylammonium fluoride
TEA triethylamine
TFA trifluoroacetic acid
THF tetrahydrofuran
TMS trimethyl silyl
Tosyl, Ts para-toluenesulfonyl Example 1

(2S,5R)-2-carbamoyl-4-methyl-7-oxo-1,6-diazabicyclo[3.2.1]oct-3-en-6-yl hydrogen sulfate sodium salt

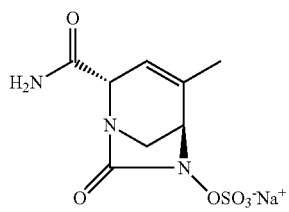

Dowex® 50WX8-100, ion-exchange resin (39 g) was conditioned by stirring for 3 hours in 2N sodium hydroxide (95 mL). The resin was then loaded into a cartridge and washed with water until pH 7. It was then washed with (1/1) acetone/water, followed by water again. (E)-triphenyl(prop-1-enyl)phosphonium (2S,5R)-2-carbamoyl-4-methyl-7-oxo-1,6-diazabicyclo[3.2.1]oct-3-en-6-yl sulfate (Intermediate 17, 0.2997 g, 0.52 mmol) was taken up in acetone and diluted with water. The solution was loaded on the resin and eluted with water. The fractions containing desired product were combined and lyophilized. The desired product was obtained as a light yellow solid (140 mg, 90%).

Optical rotation: (0.1 g/dL, MeOH)=−219
MS: 278 ES+ (C$_8$H$_{11}$N$_3$O$_6$S)
$^1$H NMR (300 MHz, DMSO-d$_6$) δ: 1.78 (m, 3H); 3.20 (m, 2H); 3.96 (m, 1H); 4.11 (m, 1H); 5.42 (m, 1H); 7.25 (bs, 1H); 7.51 (bs, 1H).

Route 1

Intermediate 1: (S)-2-(1-hydroxybut-3-en-2-yl)isoindoline-1,3-dione

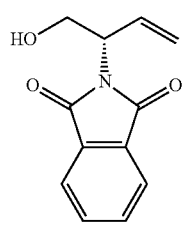 [SMILES: C=C[C@@H](CO)N1C(=O)c2ccccc2C1=O]

A 2-L reaction flask containing a stir bar and sodium carbonate (1.981 g, 18.69 mmol) was placed under high vacuum and dried with a heating gun for ten minutes. Upon cooling, the flask was backfilled with nitrogen. To it was added allylpalladium chloride dimer (0.553 g, 1.53 mmol), (1R,2R)-(+)-1,2-diaminocyclohexane-N,N'-bis(2-diphenylphosphino-1-naphthoyl) (CAS 174810-09-4)(3.36 g, 4.25 mmol), and phthalimide (50 g, 339.83 mmol). The flask was then purged with nitrogen for ten minutes. 1.4 L methylene chloride, previously degassed with a nitrogen line for ten minutes, was then added. This suspension was placed under an atmosphere of nitrogen; it was alternately stirred and sonicated over a ten-minute period to facilitate solvation. At that time it was a yellow or light orange solution containing white solid. To this mixture was added 2-vinyloxirane (24.06 g, 343.23 mmol). The resulting mixture was stirred under a nitrogen atmosphere at ambient temperature for approximately 48 hours. Analysis during that time by LCMS and TLC (1:1 hexanes:ethyl acetate) suggested progression of the reaction, and final analyses by those methods suggested complete conversion of starting material to one major product. The reaction mixture was filtered, and the filtrate was concentrated under reduced pressure. The yellow, viscous fluid was injected onto a 330-g silica column: a minimal volume of methylene chloride was used to thin the crude material. Silica gel chromatography (15-75% ethyl acetate in hexanes, 40 minutes, 330-g column) was used to isolate the desired product as a viscous yellow fluid that became a pale yellowish white solid (69.6 g, 94%) over a period of hours under reduced pressure.

Optical Rotation: (2.02 g/100 mL, methylene chloride) literature value=−72.2, obtained value=−71.
$^1$H NMR (300 MHz, DMSO-d$_6$) δ: 3.66 (ddd, J=11.00, 6.47, 5.76 Hz, 1H) 3.97 (ddd, J=10.95, 9.63, 5.67 Hz, 1H) 4.69-4.79 (m, 1H) 5.01 (dd, J=6.52, 5.76 Hz, 1H) 5.18 (dt, J=2.79, 1.35 Hz, 1H) 5.23 (dt, J=9.44, 1.42 Hz, 1H) 6.07 (ddd, J=17.28, 10.67, 6.42 Hz, 1H) 7.86 (q, J=1.83 Hz, 4H)

Intermediate 2: (S)-2-(1-(tert-butyldimethylsilyloxy)but-3-en-2-yl)isoindoline-1,3-dione

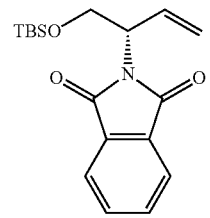 [SMILES: C=C[C@@H](CO[Si](C)(C)C(C)(C)C)N1C(=O)c2ccccc2C1=O]

To a stirred solution of (S)-2-(1-hydroxybut-3-en-2-yl)isoindoline-1,3-dione (Intermediate 1, 69.4 g, 319.49 mmol) and imidazole (26.1 g, 383.39 mmol) in methylene chloride (160 mL), at ambient temperature under an atmosphere of nitrogen, was added tert-butyldimethylchlorosilane (55.4 g, 367.41 mmol) as a solid. This addition was performed over approximately ten minutes. Warming of the mixture was observed during this addition. After two hours stirring, the solution was poured into a saturated solution of aqueous sodium bicarbonate (approximately 150 mL); this biphasic mixture was shaken, and the organic layer was separated. The aqueous layer was back-extracted three times with 200 mL methylene chloride each time. The organic layers were combined, dried over magnesium sulfate, filtered, and concentrated in vacuo. The desired product was obtained as a pale yellow solid after drying overnight under high vacuum (107 g, 101%).

¹H NMR (300 MHz, DMSO-d₆) δ: −0.13 (s, 3H) −0.04 (s, 3H) 0.67 (s, 9H) 3.85 (dd, J=10.20, 5.85 Hz, 1H) 4.08 (t, J=10.01 Hz, 1H) 4.76-4.86 (m, 1H) 5.20-5.33 (m, 1H) 5.25 (dt, J=2.79, 1.35 Hz, 1H) 6.08 (ddd, J=17.23, 10.53, 6.42 Hz, 1H) 7.86 (dq, J=4.51, 2.21 Hz, 4H).

Intermediate 3: (S)-1-(tert-butyldimethylsilyloxy)but-3-en-2-amine

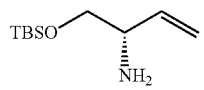

To a stirred solution of (S)-2-(1-(tert-butyldimethylsilyloxy)but-3-en-2-yl)isoindoline-1,3-dione (Intermediate 2, 108.28 g, 326.65 mmol) in methanol (1000 ml), at ambient temperature under a nitrogen atmosphere, was added hydrazine (35.9 ml, 1143.29 mmol). The yellow solution was heated to 65° C. Within 30 minutes of reaching reaction temperature, a white precipitate was observed in the reaction mixture; this solid quickly became the bulk of the mixture, and at that time water (about 150 mL) was added to the reaction mixture. The reaction continued stirring without interruption and within a few minutes the solid dissolved. Upon complete conversion as indicated by LCMS analysis (both starting material and product give strong UV signals and are easily identified by LCMS), the heat was removed and more water was added (a total water content of 600 mL). The mixture was allowed to come to ambient temperature. The methanol was removed in vacuo at 35° C. (moderately reduced pressure); vacuum was removed and the aqueous was warmed to about 50° C. and then extracted with 4×200-mL methylene chloride. This approach can lead to difficulty in separation of water from organic, so plenty of brine should be used as the last step of the workup. The organic extracts were combined, washed with saturated sodium bicarbonate (aq), washed with brine, dried over sodium sulfate, filtered, and concentrated in vacuo at not more than 30° C. The desired product was obtained as a yellow liquid (58.5 g, 94%).

¹H NMR (300 MHz, DMSO-d₆) δ: 0.03 (s, 6H) 0.86 (s, 9H) 1.51 (br. s., 2H) 3.22-3.30 (m, 1H) 3.33-3.48 (m, 2H) 4.98-5.05 (m, 1H) 5.17 (dt, J=17.28, 1.84 Hz, 1H) 5.79 (ddd, J=17.37, 10.39, 5.67 Hz, 1H).

Intermediate 4: 2-bromo-N-methoxy-N-methylacetamide

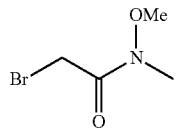

A stirred solution of potassium carbonate (343 g, 2.48 mol) in water (about 800 mL) was prepared and cooled in an ice bath for 15 minutes under nitrogen. To it was added O,N-dimethylhydroxylamine hydrochloride (110 g, 1.13 mol) and diethyl ether (about 800 mL). To this mixture was then added bromoacetyl bromide (273 g, 1.35 mol) by addition funnel over twenty minutes. The ice bath was removed and the mixture was stirred under nitrogen for two hours. The layers were separated and the aqueous layer was extracted with ether (about 350 mL).

The organic layers were combined, dried over magnesium sulfate, filtered, and concentrated in vacuo. The desired product was obtained as a yellow liquid (143 g, 70%).

¹H NMR (300 MHz, CDCl₃) δ: 3.24 (s, 3H); 3.80 (s, 3H); 4.01 (s, 2H).

Intermediate 5: (S)-tert-butyl 1-(tert-butyldimethylsilyloxy)but-3-en-2-yl(2-(methoxy(methyl)amino)-2-oxoethyl)carbamate

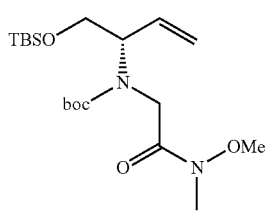

A suspension of (S)-1-(tert-butyldimethylsilyloxy)but-3-en-2-amine (Intermediate 3, 60.4 g, 300 mmol) and cesium carbonate (103 g, 315 mmol) in acetonitrile (about 700 mL) and water (about 120 mL) was prepared and stirred in an ice bath under nitrogen for 5 minutes. The mixture was biphasic and remained so for the duration of the reaction. To this mixture was then added 2-bromo-N-methoxy-N-methylacetamide (Intermediate 4, 57.0 g, 285 mmol) by addition funnel over 10 minutes. The mixture was stirred for two days, with the temperature maintained near 0° C. The mixture was kept in the freezer overnight. Analysis by TLC (ethyl acetate, potassium permanganate stain, starting amine R$_f$~0.25) indicated high but incomplete conversion of starting amine. Another 0.05 eq of the electrophile was added. The starting amine never disappeared completely by TLC.

To the mixture was added di-tert-butyl dicarbonate (165 mL, 2M solution in THF); the mixture was stirred until analysis by TLC (ethyl acetate, potassium permanganate stain) indicated consumption of intermediate. The organic layer was separated from the aqueous (TLC indicated that no product remained in the aqueous), and the organic layer was concentrated in vacuo. Silica gel chromatography (5-55% ethyl acetate in hexanes), split into 3 batches, afforded the desired product as a pale yellow oil (80 g, 66%).

¹H NMR (300 MHz, DMSO-d₆) δ: 0.02 (d, J=5.10 Hz, 6H) 0.84 (s, 9H) 1.33 (s, 6H) 1.38 (s, 3H) 3.02-3.15 (m, 3H) 3.61-3.68 (m, 3H) 3.70-3.86 (m, 2H) 3.95-4.12 (m, 2H) 4.23-4.68 (m, 1H) 5.08-5.31 (m, 2H) 5.75-5.96 (m, 1H).

Intermediate 6: (S)-tert-butyl 1-(tert-butyldimethylsilyloxy)but-3-en-2-yl(3-methyl-2-oxobut-3-enyl)carbamate

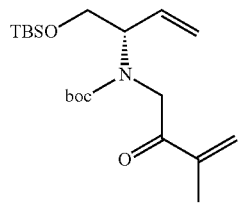

To a solution of (S)-tert-butyl 1-(tert-butyldimethylsilyloxy)but-3-en-2-yl(2-(methoxy(methyl)amino)-2-oxoethyl)carbamate (Intermediate 5, 30.79 g, 76.48 mmol) in THF (200 mL) at 0° C. was added prop-1-en-2-ylmagnesium bromide (0.5M in THF) (300 mL, 149.90 mmol). The reaction mixture was stirred at 0° C. for 1 hour. The reaction mixture was quenched with 200 mL 10% citric acid, diluted further with 100 mL water and extracted with ether. The organics were concentrated and the resulting oil was dissolved in ether and washed with water and brine. The organics were dried over magnesium sulfate, filtered and concentrated. Silica gel chromatography (0%-20% ethyl acetate/hexanes) afforded the desired product (26.2 g, 89%) as a colorless oil.

MS: 384 ES+ ($C_2OH_{37}NO_4Si$)

$^1$H NMR (300 MHz, DMSO-$d_6$) δ: 0.02 (d, 6H); 0.83 (s, 9H); 1.27-1.38 (m, 9H); 1.80 (m, 3H); 3.71 (m, 2H); 4.34 (m, 2H); 4.61 (m, 1H); 5.17 (m, 2H); 5.77 (m, 1H); 5.85 (m, 1H); 6.03 (m, 1H).

Intermediate 7: (S)-tert-butyl 2-((tert-butyldimethylsilyloxy)methyl)-4-methyl-5-oxo-5,6-dihydropyridine-1 (2H)-carboxylate

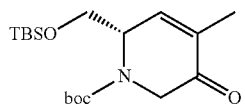

A solution of (S)-tert-butyl 1-(tert-butyldimethylsilyloxy)but-3-en-2-yl(3-methyl-2-oxobut-3-enyl)carbamate (Intermediate 6, 26.18 g, 68.25 mmol) in toluene (600 mL) was purged with nitrogen for 15 minutes. (1,3-Bis-(2,4,6-trimethylphenyl)-2-imidazolidinylidene)dichloro(o-isopropoxyphenylmethylene)ruthenium (0.987 g, 1.57 mmol) was then added. The reaction mixture was heated at 65° C. for 1.5 hours. The reaction mixture was concentrated onto silica gel. Silica gel chromatography (0%-15% ethyl acetate/hexanes) afforded the desired product (21.18 g, 87%) as a colorless oil.

MS: 356 ES+ ($C_{18}H_{33}NO_4Si$)

$^1$H NMR (300 MHz, DMSO-$d_6$) δ: 0.01 (d, 6H); 0.81 (s, 9H); 1.42 (s, 9H); 1.75 (m, 3H); 3.74-3.89 (m, 3H); 4.04-4.32 (m, 1H); 4.67 (m, 1H); 6.88 (m, 1H).

Intermediate 8: (2S,5S)-tert-butyl 2-((tert-butyldimethylsilyloxy)methyl)-5-hydroxy-4-methyl-5,6-dihydropyridine-1(2H)-carboxylate

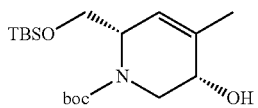

To a solution of cerium(III) chloride (14.68 g, 59.57 mmol) and (S)-tert-butyl 2-((tert-butyldimethylsilyloxy)methyl)-4-methyl-5-oxo-5,6-dihydropyridine-1(2H)-carboxylate (Intermediate 7, 21.18 g, 59.57 mmol) in methanol (300 mL) at 0° C. was added sodium borohydride (2.254 g, 59.57 mmol) portionwise. After 15 minutes, the reaction mixture was diluted with saturated ammonium chloride (100 mL) and water (100 mL), then extracted twice with diethyl ether. The organic extracts were washed with brine, dried over magnesium sulfate, filtered and concentrated. Silica gel chromatography (0%-20% ethyl acetate/hexanes) afforded the desired product (19.45 g, 91%) as a colorless oil.

MS: 358 ES+ ($C_{18}H_{35}NO_4Si$)

$^1$H NMR (300 MHz, DMSO-$d_6$) δ: 0.02 (s, 6H); 0.86 (s, 9H); 1.39 (s, 9H); 1.69 (m, 3H); 2.63-2.72 (m, 1H); 3.59 (m, 2H); 3.82 (m, 1H); 4.03 (m, 1H); 4.21 (m, 1H); 5.04 (d, 1H); 5.38 (m, 1H).

Intermediate 9: N-(allyloxy)-2-nitrobenzenesulfonamide

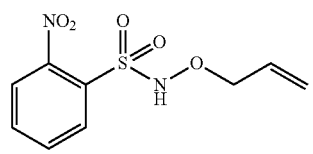 [SMILES: C=CCONS(=O)(=O)c1ccccc1[N+](=O)[O-]]

To a stirred solution of O-allylhydroxylamine hydrochloride (147.05 g, 1341.59 mmol) in DCM (2.5 L) at 0° C., pyridine (318 mL, 3948 mmol) was added followed by the addition of 2-nitrobenzene-1-sulfonyl chloride (250 g, 1128.05 mmol) portionwise as a solid. The reaction mixture was then stirred at the same temperature for 1 h. Completion of the reaction was monitored by TLC. The reaction mixture was quenched with 1.5 N HCl (1 L). The organic layer was separated, washed with water (250 mL), brine (250 mL), dried over anhydrous $Na_2SO_4$, filtered and concentrated under vacuum to yield the residue. The crude was purified by crystallization using EtOAc:petroleum ether (1:3) (800 mL) and afforded 202 g of the title compound as a light brown solid. The mother liquor was concentrated and purified by silica gel column chromatography (mesh 60-120) using petroleum ether:EtOAc (7:3) to yield another 19.1 g of the title compound as a yellow solid. The total yield is 76%.

UPLC: 257 (M-1) for $C_9H_{10}N_2O_5S$ $^1$HNMR (400 MHz, DMSO-$d_6$): δ 4.36-4.38 (m, 2H), 5.22-5.32 (m, 2H), 5.84-5.91 (m, 1H), 7.92-7.96 (m, 2H), 8.02-8.05 (m, 2H), 11.07 (s, 1H).

Intermediate 10: (2S,5R)-tert-butyl 5-(N-(allyloxy)-2-nitrophenylsulfonamido)-2-((tert-butyldimethylsilyloxy)methyl)-4-methyl-5,6-dihydropyridine-1 (2H)-carboxylate

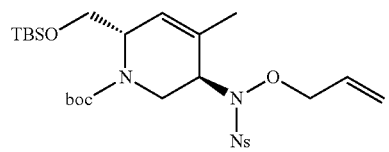

To a solution of (2S,5S)-tert-butyl 2-((tert-butyldimethylsilyloxy)methyl)-5-hydroxy-4-methyl-5,6-dihydropyridine-1(2H)-carboxylate (Intermediate 8, 19.45 g, 54.40 mmol) in toluene (300 mL) at room temperature was added triphenylphosphine (17.06 g, 65.28 mmol), N-(allyloxy)-2-nitrobenzenesulfonamide (Intermediate 9, 14.05 g, 54.40 mmol) and diisopropyl azodicarboxylate (12.85 mL, 65.28 mmol). After 2 hours the reaction mixture was concentrated onto silica gel and purified. Silica gel chromatography (0%-50% ethyl acetate/hexanes) afforded the desired product (25.2 g, 78%) as a yellow oil.

MS: 598 ES+ ($C_{27}H_{43}N_3O_8SSi$)

$^1$H NMR (300 MHz, DMSO-$d_6$) δ: 0.00 (s, 6H); 0.83 (s, 9H); 1.31 (m, 9H); 1.34 (m, 3H); 3.10-3.25 (m, 1H); 3.59 (m, 2H); 3.99-4.41 (m, 5H); 5.17 (m, 2H); 5.72 (m, 2H); 7.93-8.16 (m, 4H).

Intermediate 11: N-(allyloxy)-N-((3R,6S)-6-((tert-butyldimethylsilyloxy)methyl)-4-methyl-1,2,3,6-tetrahydropyridin-3-yl)-2-nitrobenzenesulfonamide

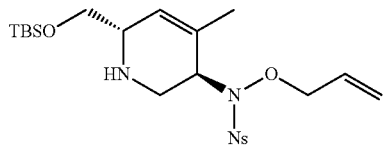

To a solution of (2S,5R)-tert-butyl 5-(N-(allyloxy)-2-nitrophenylsulfonamido)-2-((tert-butyldimethylsilyloxy)methyl)-4-methyl-5,6-dihydropyridine-1(2H)-carboxylate (Intermediate 10, 13.38 g, 22.38 mmol) in DCM (200 mL) at room temperature was added zinc bromide (3.36 mL, 67.15 mmol). The reaction mixture was stirred at room temperature overnight then diluted with DCM and washed with saturated sodium bicarbonate and brine. The organic layer was dried over magnesium sulfate, filtered and concentrated to afford the desired product as an orange oil (11.14 g, 100%).

MS: 498 ES+ ($C_{22}H_{35}N_3O_6SSi$)

$^1$H NMR (300 MHz, DMSO-$d_6$) δ: 0.01 (s, 6H); 0.85 (s, 9H); 1.61 (m, 3H); 2.67 (m, 1H); 2.81 (m, 1H); 3.20 (m, 1H); 3.44 (m, 2H); 4.05 (m, 1H); 4.30 (m, 1H); 4.40 (m, 1H); 5.22 (m, 2H); 5.82 (m, 2H); 7.90-8.15 (m, 4H).

Intermediate 12: O-allyl-N-((3R,6S)-6-((tert-butyldimethylsilyloxy)methyl)-4-methyl-1,2,3,6-tetrahydropyridin-3-yl)hydroxylamine

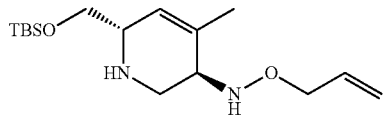 [SMILES: C=CCON[C@H]1CN[C@H](CO[Si](C)(C)C(C)(C)C)C=C1C]

To a solution of N-(allyloxy)-N-((3R,6S)-6-((tert-butyldimethylsilyloxy)methyl)-4-methyl-1,2,3,6-tetrahydropyridin-3-yl)-2-nitrobenzenesulfonamide (Intermediate 11, 11.58 g, 23.27 mmol) and potassium carbonate (16.08 g, 116.34 mmol) in acetonitrile (200 mL) at room temperature was added benzenethiol (11.95 mL, 116.34 mmol). After 3 hours, the reaction mixture was concentrated to dryness and DCM was added. The resulting solids were removed by filtration. The filtrate was concentrated onto silica gel. Silica gel chromatography (0%-100% ethyl acetate/hexanes) afforded the desired product (5.06 g, 69.6%) as an orange oil.

MS: 313 ES+ ($C_{16}H_{32}N_2O_2Si$)

$^1$H NMR (300 MHz, DMSO-$d_6$) δ: 0.03 (s, 6H); 0.86 (s, 9H); 1.71 (m, 3H); 2.17 (m, 1H); 2.81 (m, 2H); 3.11 (m, 2H); 3.43 (m, 2H); 4.09 (m, 2H); 5.10-5.25 (m, 2H); 5.48 (m, 1H); 5.87-5.96 (m, 1H); 6.35 (d, 1H).

Intermediate 13: (2S,5R)-6-(allyloxy)-2-((tert-butyldimethylsilyloxy)methyl)-4-methyl-1,6-diazabicyclo[3.2.1]oct-3-en-7-one

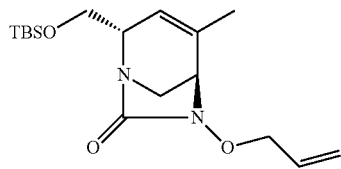 [SMILES: C=CCON1C(=O)N2C[C@H]1C(C)=C[C@H]2CO[Si](C)(C)C(C)(C)C]

To a solution of O-allyl-N-((3R,6S)-6-((tert-butyldimethylsilyloxy)methyl)-4-methyl-1,2,3,6-tetrahydropyridin-3-yl)hydroxylamine (Intermediate 12, 2 g, 6.40 mmol) and N,N-diisopropylethylamine (4.46 mL, 25.60 mmol) in acetonitrile (555 mL) at 0° C. was added triphosgene (0.760 g, 2.56 mmol) as a solution in acetonitrile (45 mL). The triphosgene solution was added via syringe pump at a rate of 0.1 mL/min. Once addition was complete the reaction was stirred at room temperature overnight. The reaction mixture was concentrated to dryness, diluted with ethyl acetate, washed with water and brine, dried over magnesium sulfate, filtered and concentrated. The aqueous washes were found to contain some product and were extracted twice with ethyl acetate. The combined organics were dried over magnesium sulfate, filtered and combined with previous extracts. Silica gel chromatography (0%-20% ethyl acetate/hexanes) afforded the desired product (1.980 g, 91%) as a light orange oil.

MS: 339 ES+ ($C_{17}H_{30}N_2O_3Si$)

$^1$H NMR (300 MHz, CDCl$_3$) δ: 0.07 (s, 6H); 0.89 (s, 9H); 1.87 (m, 3H); 3.24 (m, 1H); 3.41 (m, 1H); 3.61 (m, 1H); 3.86 (m, 3H); 4.43 (m, 2H); 5.33 (m, 3H); 6.01 (m, 1H).

Intermediate 14: (2S,5R)-6-(allyloxy)-2-(hydroxymethyl)-4-methyl-1,6-diazabicyclo[3.2.1]oct-3-en-7-one

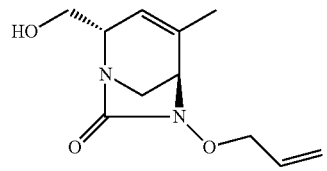 [SMILES: C=CCON1C(=O)N2C[C@H]1C(C)=C[C@H]2CO]

To a solution of (2S,5R)-6-(allyloxy)-2-((tert-butyldimethylsilyloxy)methyl)-4-methyl-1,6-diazabicyclo[3.2.1]oct-3-en-7-one (Intermediate 13, 1.76 g, 5.20 mmol) in THF (20 mL) at 0° C. was added tetrabutylammonium fluoride (1M in THF) (6.76 mL, 6.76 mmol). Stirred at 0° C. for 1 hour. The reaction mixture was concentrated onto silica gel. Silica gel chromatography (50%-100% ethyl acetate/hexanes) afforded the desired product (1.070 g, 92%) as a colorless oil.

MS: 225 ES+ ($C_{11}H_{16}N_2O_3$)

$^1$H NMR (300 MHz, DMSO-$d_6$) δ: 1.77 (m, 3H); 3.03 (m, 1H); 3.23 (m, 1H); 3.49-3.60 (m, 3H); 3.78 (m, 1H); 4.36 (m, 2H); 4.84 (m, 1H); 5.24-5.39 (m, 3H); 5.90-6.01 (m, 1H).

Intermediate 15: (2S,5R)-6-(allyloxy)-4-methyl-7-oxo-1,6-diazabicyclo[3.2.1]oct-3-ene-2-carboxylic acid

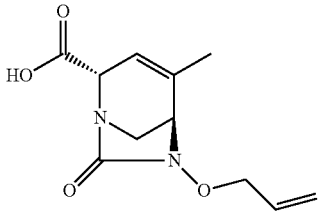 [SMILES: C=CCON1C(=O)N2C[C@H]1C(C)=C[C@H]2C(=O)O]

To a solution of periodic acid (2 g, 10.42 mmol) in wet acetonitrile (20 mL) (0.75% water by volume) at room temperature was added chromium(VI) oxide (4 mg, 0.04 mmol). The mixture was stirred until complete dissolution was achieved. This solution (5.47 mL, 3 eq) was added dropwise at 0° C. to a solution of (2S,5R)-6-(allyloxy)-2-(hydroxymethyl)-4-methyl-1,6-diazabicyclo[3.2.1]oct-3-en-7-one (Intermediate 14, 0.212 g, 0.95 mmol) in wet acetonitrile (10 mL) (0.75% by volume). The reaction mixture went from clear orange to cloudy brownish color to cloudy green suspension. After 30 minutes, LC/MS showed desired product mass and some remaining starting material. Another equivalent of the oxidizing agent solution (1.82 mL) was added. After 30 minutes, the reaction mixture was diluted with ethyl acetate and washed with 1 to 1 brine/water. The organics were dried over magnesium sulfate, filtered and concentrated to afford a green foam (0.193 g, 86%).

MS: 239 ES+ ($C_{11}H_{14}N_2O_4$)

$^1$H NMR (300 MHz, DMSO-$d_6$) δ: 1.80 (m, 3H); 3.19 (m, 2H); 3.85 (m, 1H); 4.27 (m, 1H); 3.37 (m, 2H); 5.28-5.43 (m, 3H); 5.89-6.00 (m, 1H).

Intermediate 16: (2S,5R)-6-(allyloxy)-4-methyl-7-oxo-1,6-diazabicyclo[3.2.1]oct-3-ene-2-carboxamide

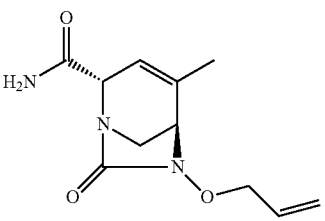 [SMILES: C=CCON1C(=O)N2C[C@H]1C(C)=C[C@H]2C(N)=O]

To a solution of (2S,5R)-6-(allyloxy)-4-methyl-7-oxo-1,6-diazabicyclo[3.2.1]oct-3-ene-2-carboxylic acid (Intermediate 15, 0.193 g, 0.81 mmol) in DMF (4 mL) at room temperature was added ammonium chloride (0.130 g, 2.43 mmol), O-(7-azabenzotriazol-1-yl)-N,N,N',N'-tetramethyluronium hexafluorophosphate (0.462 g, 1.22 mmol) and N,N-diisopropylethylamine (0.564 mL, 3.24 mmol). After 10 minutes the reaction mixture was diluted with ethyl acetate and washed with saturated sodium bicarbonate and brine. The combined aqueous washes were extracted once with ethyl acetate. The combined organic extracts were dried over magnesium sulfate, filtered and concentrated. Silica gel chromatography (0%-100% ethyl acetate/hexanes) afforded a brown oil. The oil was taken up in ethyl acetate and washed twice with a 1 to 1 brine/water mixture to remove DMF. The organic layer was dried over magnesium sulfate, filtered and concentrated to afford a light tan foam (0.048 g, 25%).

MS: 238 ES+ ($C_{11}H_{15}N_3O_3$)

$^1$H NMR (300 MHz, DMSO-$d_6$) δ: 1.79 (m, 3H); 3.19 (m, 2H); 3.81 (m, 1H); 4.12 (m, 1H); 4.36 (m, 2H); 5.24-5.45 (m, 3H); 5.89-6.00 (m, 1H); 7.28 (bs, 1H); 7.49 (bs, 1H).

Intermediate 17: (E)-triphenyl(prop-1-enyl)phosphonium (2S,5R)-2-carbamoyl-4-methyl-7-oxo-1,6-diazabicyclo[3.2.1]oct-3-en-6-yl sulfate

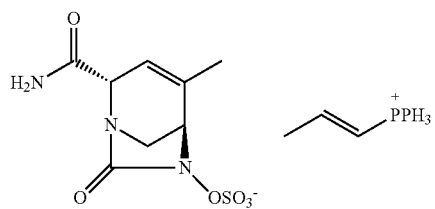

To a solution of (2S,5R)-6-(allyloxy)-4-methyl-7-oxo-1,6-diazabicyclo[3.2.1]oct-3-ene-2-carboxamide (Intermediate 16, 196.9 mg, 0.83 mmol) and acetic acid (0.095 mL, 1.66 mmol) (dried over sodium sulfate) in DCM (9 mL) at room temperature was added tetrakis(triphenylphosphine)palladium(0) (959 mg, 0.83 mmol). The solution was stirred at room temperature for ~45 minutes and turned dark orange. To the reaction mixture was added pyridine (9.00 mL) and sulfur trioxide-pyridine complex (793 mg, 4.98 mmol). The suspension was stirred overnight at room temperature. The suspension was evaporated to dryness and then resuspended in DCM. The solids were filtered off through a 0.45 t nalgene filter. The filtrate was concentrated to afford an orange oil. Silica gel chromatography (0%-100% acetone/DCM) afforded the desired product (300 mg, 62.3%) as a yellow foam.

MS: 278 ES+, 303 ES+ ($C_8H_{10}N_3O_6S$, $C_{21}H_{20}P$)

$^1$H NMR (300 MHz, DMSO-$d_6$) δ: 1.78 (m, 3H); 2.17 (m, 3H); 3.20 (m, 2H); 3.96 (m, 1H); 4.11 (m, 1H); 5.42 (m, 1H); 6.57-6.74 (m, 1H); 7.22-7.30 (m, 2H); 7.50 (m, 1H); 7.68-7.92 (m, 15H).

Route 2

Intermediate 18: (2S,5R)-tert-butyl 5-(N-(allyloxy)-2-nitrophenylsulfonamido)-2-(hydroxymethyl)-4-methyl-5,6-dihydropyridine-1(2H)-carboxylate

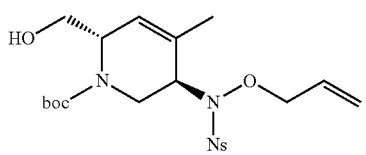

To a solution of (2S,5R)-tert-butyl 5-(N-(allyloxy)-2-nitrophenylsulfonamido)-2-((tert-butyldimethylsilyloxy)methyl)-4-methyl-5,6-dihydropyridine-1(2H)-carboxylate (Intermediate 10, 1 g, 1.67 mmol) in THF (11 mL) at 0° C. was added tetrabutylammonium fluoride (1M in THF) (2.175 mL, 2.17 mmol). After 90 minutes the reaction mixture was concentrated onto silica gel. Silica gel chromatography (0%-70% ethyl acetate/hexanes) afforded the desired product (0.732 g, 90%) as a tan foam.

MS: 484 ES+ ($C_{21}H_{29}N_3O_8S$)

$^1$H NMR (300 MHz, DMSO-$d_6$) δ: 1.31 (m, 9H); 1.35 (m, 3H); 3.20 (m, 1H); 3.41 (m, 2H); 3.96-4.37 (m, 5H); 4.76 (m, 1H); 5.19 (m, 2H); 5.66-5.84 (m, 2H); 7.94-8.18 (m, 4H).

Intermediate 19: (2S,5R)-5-(N-(allyloxy)-2-nitrophenylsulfonamido)-1-(tert-butoxycarbonyl)-4-methyl-1,2,5,6-tetrahydropyridine-2-carboxylic acid

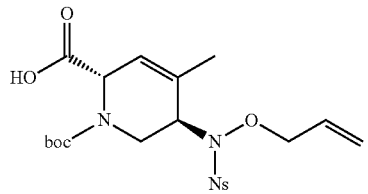

To a solution of periodic acid (6 g, 31.26 mmol) in wet acetonitrile (60 mL) (0.75% water by volume) at room temperature was added chromium(VI) oxide (10 mg, 0.10 mmol). The mixture was stirred until complete dissolution was achieved.

To a solution of (2S,5R)-tert-butyl 5-(N-(allyloxy)-2-nitrophenylsulfonamido)-2-(hydroxymethyl)-4-methyl-5,6-dihydropyridine-1(2H)-carboxylate (Intermediate 18, 5 g, 10.34 mmol) in wet acetonitrile (60 mL) (0.75% by volume) at 0° C. was added dropwise the previously formed periodic acid/chromium oxide solution (60 mL, 3 eq). After 30 minutes the reaction was complete by LC/MS. The reaction mixture was diluted with ether and washed with 10% citric acid, saturated sodium bicarbonate and brine. The organics were dried over magnesium sulfate, filtered and concentrated to afford an orange foam (4.16 g, 81%).

MS: 498 ES+ ($C_{21}H_{27}N_3O_9S$)

$^1$H NMR (300 MHz, DMSO-$d_6$) δ: 1.26 (m, 9H); 1.31 (m, 3H); 3.02-3.25 (m, 1H); 3.90 (m, 1H); 4.17 (m, 3H); 4.65-4.77 (m, 1H); 5.12-5.21 (m, 2H); 5.68 (m, 1H); 5.88 (m, 1H); 7.92-8.17 (m, 4H).

Intermediate 20: (2S,5R)-tert-butyl 5-(N-(allyloxy)-2-nitrophenylsulfonamido)-2-carbamoyl-4-methyl-5,6-dihydropyridine-1(2H)-carboxylate

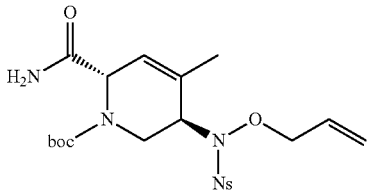

To a solution of (2S,5R)-5-(N-(allyloxy)-2-nitrophenylsulfonamido)-1-(tert-butoxycarbonyl)-4-methyl-1,2,5,6-tetrahydropyridine-2-carboxylic acid (Intermediate 19, 4.16 g, 8.36 mmol) in DMF (35 mL) at room temperature was added ammonium chloride (0.895 g, 16.72 mmol), HATU (4.77 g, 12.54 mmol) and DIEA (5.84 mL, 33.45 mmol). After 15 minutes the reaction mixture was diluted with ethyl acetate, washed with saturated sodium bicarbonate and twice with 1:1 brine:water. The organics were dried over magnesium sulfate, filtered and concentrated. Silica gel chromatography (0%-80% ethyl acetate/hexanes) was run twice to afforded the desired product (2.16 g, 52%) as a yellow foam.

MS: 497 ES+ ($C_{21}H_{28}N_4O_8S$)

$^1$H NMR (300 MHz, DMSO-$d_6$) δ: 1.26 (m, 9H); 1.37 (m, 3H); 3.12-3.35 (m, 1H); 3.80 (m, 1H); 4.18 (m, 3H); 4.64-4.79 (m, 1H); 5.13-5.22 (m, 2H); 5.68 (m, 1H); 5.88 (m, 1H); 7.04 (m, 1H); 7.45 (bs, 1H); 7.90-8.18 (m, 4H).

Intermediate 21: (2S,5R)-5-(N-(allyloxy)-2-nitrophenylsulfonamido)-4-methyl-1,2,5,6-tetrahydropyridine-2-carboxamide

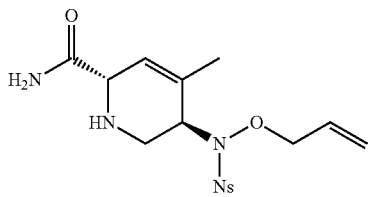

To a solution of (2S,5R)-tert-butyl 5-(N-(allyloxy)-2-nitrophenylsulfonamido)-2-carbamoyl-4-methyl-5,6-dihydropyridine-1(2H)-carboxylate (Intermediate 20, 2.16 g, 4.35 mmol) in DCM (20 mL) at room temperature was added zinc bromide (0.700 mL, 13.05 mmol). After stirring overnight at room temperature, the reaction mixture was diluted with dichloromethane and washed with saturated sodium bicarbonate and brine. The organics were dried over magnesium sulfate, filtered and concentrated to afford the desired product (1.450 g, 84%) as a yellow foam.

MS: 397 ES+ ($C_{16}H_{20}N_4O_6S$)

$^1$H NMR (300 MHz, DMSO-$d_6$) δ: 1.65 (m, 3H); 2.71 (m, 3H); 3.76 (m, 1H); 3.95 (m, 1H); 4.18-4.42 (m, 2H); 5.23 (m, 2H); 5.82 (m, 1H); 6.02 (m, 1H); 7.05 (bs, 1H); 7.30 (bs, 1H); 7.93-8.18 (m, 4H).

Intermediate 22: (2S,5R)-5-(allyloxyamino)-4-methyl-1,2,5,6-tetrahydropyridine-2-carboxamide and (2R,5R)-5-(allyloxyamino)-4-methyl-1,2,5,6-tetrahydropyridine-2-carboxamide

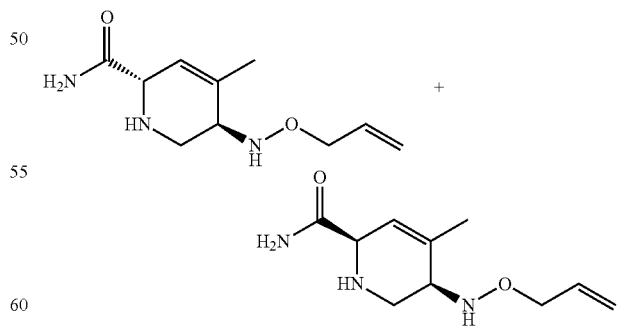

To a solution of (2S,5R)-5-(N-(allyloxy)-2-nitrophenylsulfonamido)-4-methyl-1,2,5,6-tetrahydropyridine-2-carboxamide (Intermediate 21, 1.4 g, 3.53 mmol) and cesium carbonate (9.21 g, 28.25 mmol) in THF (100 mL) at room temperature was added PS-thiophenol (3-(3-mercaptophenyl)propanamidomethylpolystyrene) (1.55 mmol/g) (9.12 g, 14.13 mmol). After stirring overnight at room temperature, the reaction mixture was filtered through a fritted funnel and the resin was washed twice with DCM. The filtrate was concentrated to afford a yellow oil. Silica gel chromatography (0%-5% methanol/dichloromethane) afforded a 3 to 1 mixture of trans and cis isomers (0.473 g, 63.4%) as a light yellow oil. The mixture was taken forward without separation.

MS: 212 ES+ ($C_{10}H_{17}N_3O_2$)

$^1$H NMR (300 MHz, DMSO-$d_6$) δ: 1.73 (m, 3H); 2.63 (m, 1H); 2.97 (m, 1H); 3.01 (m, 1H); 3.60 (m, 1H); 4.12 (m, 2H); 5.11-5.26 (m, 2H); 5.92 (m, 1H); 6.45 (m, 1H); 7.00 (m, 1H); 7.33 (bs, 1H).

Intermediate 16: (2S,5R)-6-(allyloxy)-4-methyl-7-oxo-1,6-diazabicyclo[3.2.1]oct-3-ene-2-carboxamide

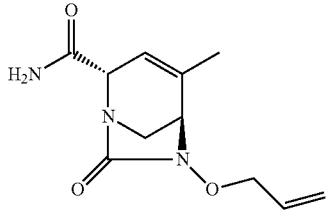

To a solution of (2R,5R)-5-(allyloxyamino)-4-methyl-1,2,5,6-tetrahydropyridine-2-carboxamide and (2R,5R)-5-(allyloxyamino)-4-methyl-1,2,5,6-tetrahydropyridine-2-carboxamide (Intermediate 22, 0.429 g, 2.03 mmol) and N,N-diisopropylethylamine (1.415 mL, 8.12 mmol) in acetonitrile (170 mL) at 0° C. was added triphosgene (0.241 g, 0.81 mmol) as a solution in acetonitrile (1.5 mL). The triphosgene solution was added at a rate of 0.1 mL/min. Once addition was complete the reaction was warmed to room temperature and stirred over weekend. The reaction mixture was diluted with ethyl acetate, washed with saturated sodium bicarbonate and brine, dried over magnesium sulfate, filtered and concentrated. Silica gel chromatography (0%-20% ethyl acetate/hexanes) afforded (2S,5R)-6-(allyloxy)-4-methyl-7-oxo-1,6-diazabicyclo[3.2.1]oct-3-ene-2-carboxamide (0.312 g, 64.8%) as a light yellow oil.

MS: 238 ES+ ($C_{11}H_{15}N_3O_3$)

$^1$H NMR (300 MHz, DMSO-$d_6$) δ: 1.79 (m, 3H); 3.19 (m, 2H); 3.81 (m, 1H); 4.12 (m, 1H); 4.36 (m, 2H); 5.24-5.45 (m, 3H); 5.89-6.00 (m, 1H); 7.28 (bs, 1H); 7.49 (bs, 1H).

The final two steps of Route 2 to yield Example 1 are equivalent for those shown for above for Route 1.

Example 2

(2S,5R)-2-cyano-4-methyl-7-oxo-1,6-diazabicyclo[3.2.1]oct-3-en-6-yl hydrogen sulfate sodium salt

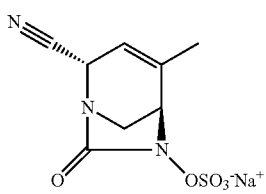

The title compound was prepared from (E)-triphenyl(prop-1-enyl)phosphonium (2S,5R)-2-cyano-4-methyl-7-oxo-1,6-diazabicyclo[3.2.1]oct-3-en-6-yl sulfate (Intermediate 24, 0.1167 g, 0.21 mmol) following the procedure described for Example 1 above. The desired product was obtained as a white solid (53.6 mg, 91%).

Optical rotation: (0.1 g/dL, DMSO)=−262

MS: 258 ES− ($C_8H_9N_3O_5S$)

$^1$H NMR (600 MHz, DMSO-$d_6$) δ: 1.82 (s, 3H); 3.26 (m, 1H); 3.44 (m, 1H); 4.08 (m, 1H); 4.95 (m, 1H); 5.33 (m, 1H).

Intermediate 23: (2S,5R)-6-(allyloxy)-4-methyl-7-oxo-1,6-diazabicyclo[3.2.1]oct-3-ene-2-carbonitrile

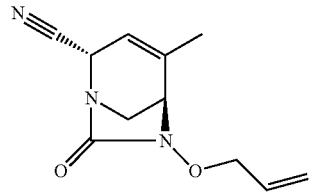 [SMILES: C=CCON1C(=O)N2C[C@H]1C(C)=C[C@H]2C#N]

To a solution of (2S,5R)-6-(allyloxy)-4-methyl-7-oxo-1,6-diazabicyclo[3.2.1]oct-3-ene-2-carboxamide (Intermediate 16, 146 mg, 0.62 mmol) in DCM (6 mL), under nitrogen, at room temperature was added methoxycarbonylsulfamoyl) triethyl-ammonium hydroxide inner salt (Burgess Reagent) (660 mg, 2.77 mmol) portionwise over 2 hours. The reaction was stirred at room temperature for an additional 30 minutes. The reaction mixture was washed with 1:1 brine:water. The organic layer was dried over magnesium sulfate, filtered and concentrated. Silica gel chromatography (0%-25% ethyl acetate/hexanes) afforded (2S,5R)-6-(allyloxy)-4-methyl-7-oxo-1,6-diazabicyclo[3.2.1]oct-3-ene-2-carbonitrile (112 mg, 83%) as a colorless oil.

MS: 220 ES+ ($C_{11}H_{13}N_3O_2$)

$^1$H NMR (300 MHz, DMSO-$d_6$) δ: 1.83 (m, 3H); 3.27 (m, 1H); 3.40 (m, 1H); 3.97 (m, 1H); 4.38 (m, 2H); 4.97 (m, 1H); 5.26-5.39 (m, 3H); 5.88-5.99 (m, 1H).

Intermediate 24: (2S,5R)-6-(allyloxy)-4-methyl-7-oxo-1,6-diazabicyclo[3.2.1]oct-3-ene-2-carbonitrile

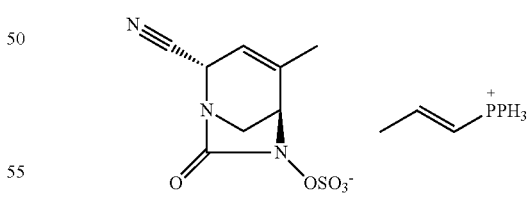

The title compound was prepared from (2S,5R)-6-(allyloxy)-4-methyl-7-oxo-1,6-diazabicyclo[3.2.1]oct-3-ene-2-carbonitrile (Intermediate 23, 111.8 mg, 0.51 mmol) following the procedure described for Intermediate 17. The desired product was obtained as an off-white foam (117 mg, 40.8%).

MS: 258 ES−, 303 ES+ ($C_8H_8N_3O_5S$, $C_{21}H_{20}P$)

$^1$H NMR (300 MHz, DMSO-$d_6$) δ: 1.83 (m, 3H); 2.17 (m, 3H); 3.26 (m, 1H); 3.45 (m, 1H); 4.08 (m, 1H); 4.94 (m, 1H); 5.33 (m, 1H); 6.59-6.72 (m, 1H); 7.22-7.39 (m, 1H); 7.68-7.92 (m, 15H).

Example 3

(2S,5R)-4-methyl-7-oxo-2-(piperidinium-4-ylcarbamoyl)-1,6-diazabicyclo[3.2.1]oct-3-en-6-yl sulfate

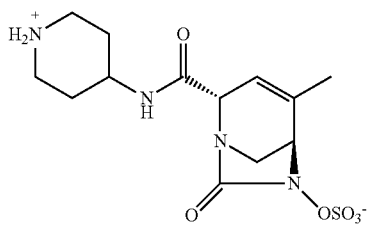

To a solution of (E)-triphenyl(prop-1-enyl)phosphonium (2S,5R)-2-(1-(tert-butoxycarbonyl)piperidin-4-ylcarbamoyl)-4-methyl-7-oxo-1,6-diazabicyclo[3.2.1]oct-3-en-6-yl sulfate (Intermediate 26, 0.1521 g, 0.20 mmol) in DCM (3 mL) at 0° C. was added trifluoroacetic acid (0.031 mL, 0.40 mmol). After 30 minutes more trifluoroacetic acid (0.031 mL, 0.40 mmol) was added. After another 30 minutes, another 6 equivalents of TFA was added at 0° C. Reaction mixture was allowed to warm to room temperature. After 1 hour, the reaction was not complete. The reaction mixture was stored in the freezer overnight. In the morning, another 5 eq TFA were added at 0° C. Reaction allowed to warm to room temperature. After 4 hours, the reaction mixture was concentrated and coevaported with DCM three times. The sticky oil was then triturated with ether and concentrated to afford a yellow solid. The solid was dissolved in water and washed twice with DCM. The aqueous phase was lyophilized. Purification was done on reverse phase HPLC (0-10% methanol in water, YMC Carotenoid C30, 19 mm×150 mm, 5 μm) to afford the title compound as a white solid (3 mg, 4.3%).

MS: 361 ES+ ($C_{13}H_{20}N_4O_6S$)

$^1$H NMR (300 MHz, DMSO-$d_6$) δ: 1.53 (m, 3H); 1.73 (m, 3H); 1.78 (m, 3H); 2.82 (m, 3H); 3.16 (m, 2H); 3.77 (m, 1H); 3.97 (m, 1H); 4.14 (m, 1H); 5.37 (m, 1H); 6.49 (m, 1H); 8.13 (m, 1H).

Route 1

Intermediate 25: tert-butyl 4-((2S,5R)-6-(allyloxy)-4-methyl-7-oxo-1,6-diazabicyclo[3.2.1]oct-3-enecarboxamido)piperidine-1-carboxylate

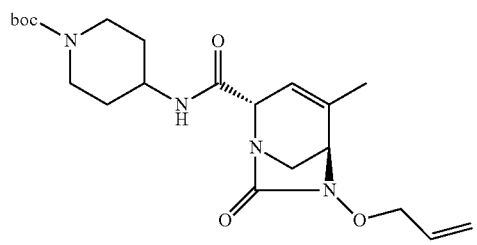

To a solution of (2S,5R)-6-(allyloxy)-4-methyl-7-oxo-1,6-diazabicyclo[3.2.1]oct-3-ene-2-carboxylic acid (Intermediate 15, 0.407 g, 1.71 mmol) in DMF (7 mL) at room temperature was added 1-Boc-4-amino-piperidine hydrochloride (0.809 g, 3.42 mmol), O-(7-azabenzotriazol-1-yl)-N,N,N',N'-tetramethyluronium hexafluorophosphate (1.299 g, 3.42 mmol) and N,N-diisopropylethylamine (1.190 mL, 6.83 mmol). After 30 minutes, the reaction mixture was diluted with ethyl acetate and washed with saturated sodium bicarbonate, brine and 1/1 brine/water. The organics were dried over magnesium sulfate, filtered and concentrated. Silica gel chromatography (0%-60% ethyl acetate/hexanes) afforded the desired product (0.502 g, 69.9%) as an off-white foam.

MS: 421 ES+ ($C_{21}H_{32}N_4O_5$)

$^1$H NMR (300 MHz, DMSO-$d_6$) δ: 1.32 (m, 2H); 1.39 (s, 9H); 1.66 (m, 2H); 1.79 (m, 3H); 2.81 (m, 2H); 3.14 (m, 1H); 3.32 (m, 1H); 3.73 (m, 1H); 3.84 (m, 3H); 4.14 (m, 1H); 4.36 (m, 2H); 5.24-5.42 (m, 3H); 5.88-6.02 (m, 1H); 8.00 (m, 1H).

Intermediate 26: (E)-triphenyl(prop-1-enyl)phosphonium (2S,5R)-2-(1-(tert-butoxycarbonyl)piperidin-4-ylcarbamoyl)-4-methyl-7-oxo-1,6-diazabicyclo[3.2.1]oct-3-en-6-yl sulfate

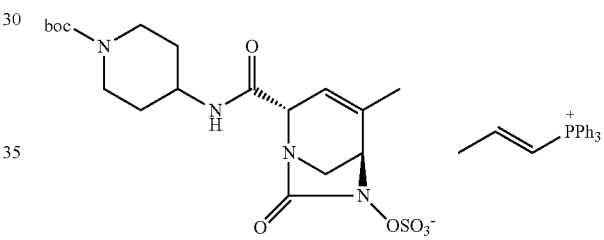

To a solution of tert-butyl 4-((2S,5R)-6-(allyloxy)-4-methyl-7-oxo-1,6-diazabicyclo[3.2.1]oct-3-enecarboxamido)piperidine-1-carboxylate (Intermediate 25, 0.502 g, 1.19 mmol) and acetic acid (0.137 mL, 2.39 mmol) (dried over sodium sulfate) in DCM (15 mL) at room temperature was added tetrakis(triphenylphosphine)palladium(0) (0.690 g, 0.60 mmol). The solution was stirred at room temperature for 30 minutes and turned from yellow to orange. To the reaction mixture was added pyridine (15 mL) and sulfur trioxide-pyridine complex (1.520 g, 9.55 mmol). The suspension was stirred overnight at room temperature. The suspension was evaporated to dryness and then resuspended in DCM. The solids were filtered off through a 0.45 nalgene filter. The filtrate was concentrated to afford an orange oil. Silica gel chromatography (0%-50% acetone/DCM) afforded the desired product (0.152 g, 16.7%) as a white foam.

MS: 459 ES-, 303 ES+ ($C_{18}H_{27}N_4O_8S$, $C_{21}H_{20}P$)

$^1$H NMR (300 MHz, DMSO-$d_6$) δ: 1.36 (m, 2H); 1.41 (s, 9H); 1.68 (m, 2H); 1.78 (m, 3H); 2.11 (m, 2H); 2.18 (m, 2H); 2.83 (m, 2H); 3.20 (m, 1H); 3.31 (m, 1H); 3.76 (m, 1H); 3.87 (m, 2H); 3.98 (m, 1H); 4.14 (m, 1H); 5.40 (m, 1H); 6.59-6.74 (m, 1H); 7.24-7.33 (m, 1H); 7.69-8.01 (m, 15H).

Route 2

Intermediate 27: (2S,5R)-1-tert-butyl 2-methyl 5-(N-(allyloxy)-2-nitrophenylsulfonamido)-4-methyl-5,6-dihydropyridine-1,2(2H)-dicarboxylate

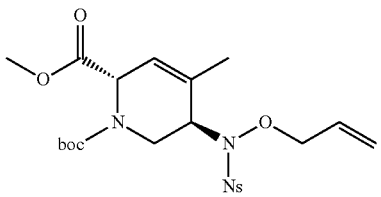

To a solution of (2S,5R)-5-(N-(allyloxy)-2-nitrophenylsulfonamido)-1-(tert-butoxycarbonyl)-4-methyl-1,2,5,6-tetrahydropyridine-2-carboxylic acid (Intermediate 19, 3 g, 6.03 mmol) and potassium carbonate (3.33 g, 24.12 mmol) in DMF (30 mL) at room temperature was added methyl iodide (0.454 mL, 7.24 mmol). After 1 hour the reaction mixture was diluted with ethyl acetate and washed three times with water. The organics were dried over magnesium sulfate, filtered and concentrated. Silica gel chromatography (0%-30% ethyl acetate/hexanes) afforded the desired product (2.060 g, 66.8%) as an off-white foam.

MS: 512 ES+ ($C_{22}H_{29}N_3O_9S$)

$^1$H NMR (300 MHz, DMSO-$d_6$) δ: 1.27 (m, 9H); 1.71 (m, 3H); 2.98-3.19 (m, 1H); 3.65 (m, 3H); 3.91 (m, 1H); 4.17 (m, 3H); 4.81-4.96 (m, 1H); 5.12-5.21 (m, 2H); 5.67 (m, 1H); 5.86 (m, 1H); 7.94-8.17 (m, 4H).

Intermediate 28: (2S,5R)-methyl 5-(N-(allyloxy)-2-nitrophenylsulfonamido)-4-methyl-1,2,5,6-tetrahydropyridine-2-carboxylate

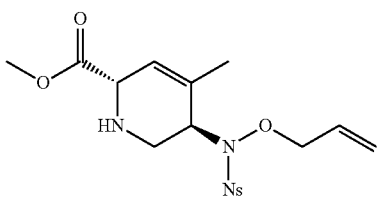

To a solution of (2S,5R)-1-tert-butyl 2-methyl 5-(N-(allyloxy)-2-nitrophenylsulfonamido)-4-methyl-5,6-dihydropyridine-1,2(2H)-dicarboxylate (Intermediate 27, 2.06 g, 4.03 mmol) in DCM (20 mL) at room temperature was added zinc bromide (0.648 mL, 12.08 mmol). After stirring overnight, the reaction mixture was diluted with dichloromethane and washed with saturated sodium bicarbonate and brine. The organics were dried over magnesium sulfate, filtered and concentrated to afford the desired product (1.650 g, 100%) as a light yellow foam.

MS: 412 ES+ ($C_{17}H_{21}N_3O_7S$)

$^1$H NMR (300 MHz, DMSO-$d_6$) δ: 1.56 (m, 3H); 2.68 (m, 1H); 2.91 (m, 1H); 3.61 (s, 3H); 4.01 (m, 2H); 4.28 (m, 1H); 4.48 (m, 1H); 5.18-5.28 (m, 2H); 5.85 (m, 2H); 7.91-8.17 (m, 4H).

Intermediate 29: (2S,5R)-methyl 5-(allyloxyamino)-4-methyl-1,2,5,6-tetrahydropyridine-2-carboxylate and (2R,5R)-methyl 5-(allyloxyamino)-4-methyl-1,2,5,6-tetrahydropyridine-2-carboxylate

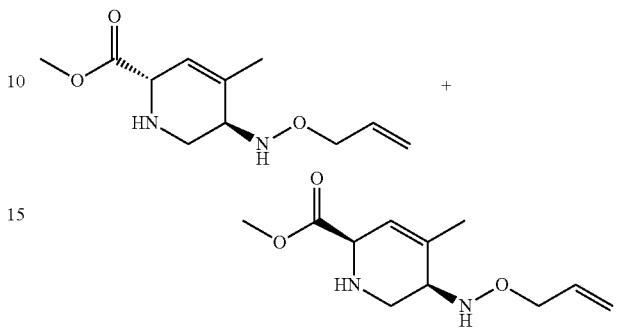

To a solution of (2S,5R)-methyl 5-(N-(allyloxy)-2-nitrophenylsulfonamido)-4-methyl-1,2,5,6-tetrahydropyridine-2-carboxylate (Intermediate 28, 1.65 g, 4.01 mmol) and cesium carbonate (7.84 g, 24.06 mmol) in THF (100 mL) at room temperature was added PS-thiophenol (3-(3-mercaptophenyl)propanamidomethylpolystyrene) (1.55 mmol/g) (7.76 g, 12.03 mmol). After 3 hours the reaction mixture was filtered and the resin was washed with DCM. The filtrate was concentrated to afford a yellow oil. Silica gel chromatography (0%-50% methanol/DCM) afforded a 1 to 1 mixture of (2S,5R)-methyl 5-(allyloxyamino)-4-methyl-1,2,5,6-tetrahydropyridine-2-carboxylate and (2R,5R)-methyl 5-(allyloxyamino)-4-methyl-1,2,5,6-tetrahydropyridine-2-carboxylate (0.680 g, 74.9%) as an orange oil. The mixture was taken forward without separation.

MS: 227 ES+ ($C_{11}H_{18}N_2O_3$)

$^1$H NMR (300 MHz, DMSO-$d_6$) δ: 1.74 (m, 6H); 2.70 (m, 3H); 3.03 (m, 4H); 3.61 (s, 3H); 3.64 (s, 3H); 3.90 (m, 2H); 4.10 (m, 4H); 5.11-5.25 (m, 5H); 5.60 (m, 2H); 5.91 (m, 2H); 6.25 (m, 1H); 6.41 (m, 1H).

Intermediate 30 and Intermediate 31: (2S,5R)-methyl 6-(allyloxy)-4-methyl-7-oxo-1,6-diazabicyclo[3.2.1]oct-3-ene-2-carboxylate and (2R,5R)-methyl 6-(allyloxy)-4-methyl-7-oxo-1,6-diazabicyclo[3.2.1]oct-3-ene-2-carboxylate

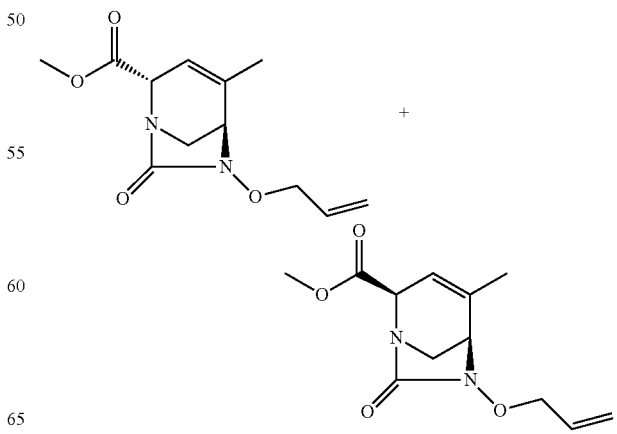

To a solution of (2S,5R)-methyl-(allyloxyamino)-4-methyl-1,2,5,6-tetrahydropyridine-2-carboxylate and (2R,5R)-methyl 5-(allyloxyamino)-4-methyl-1,2,5,6-tetrahydropyridine-2-carboxylate (1 to 1 mixture) (Intermediate 29, 0.68 g, 3.01 mmol) and N,N-diisopropylethylamine (2.094 mL, 12.02 mmol) in acetonitrile (250 mL) at 0° C. was added triphosgene (0.357 g, 1.20 mmol) as a solution in acetonitrile (3 mL). The triphosgene solution was added via syringe pump at a rate of 1 mL/hr. Once addition was complete, the reaction was warmed to room temperature and stirred overnight. The reaction mixture was diluted with ethyl acetate, washed with saturated sodium bicarbonate and brine, dried over magnesium sulfate, filtered and concentrated. Silica gel chromatography (0%-60% ethyl acetate/hexanes) afforded the desired trans product (Intermediate 30, 0.292 g, 38%) and the undesired cis product (Intermediate 31, 0.191 g, 25%). The cis isomer can be converted to the trans isomer by stirring in acetonitrile with 3 equivalents of triethylamine for 1 hour, followed by similar work as for the reaction mixture.

MS: 253 ES+ ($C_{12}H_{16}N_2O_4$) for both cis and trans $^1$H NMR (300 MHz, DMSO-$d_6$) trans Intermediate 30 δ: 1.80 (m, 3H); 3.12 (m, 1H); 3.22 (m, 1H); 3.69 (s, 3H); 3.87 (m, 1H); 4.38 (m, 3H); 5.24-5.42 (m, 3H); 5.94 (m, 1H).

$^1$H NMR (300 MHz, DMSO-$d_6$) cis Intermediate 31 δ: 1.82 (m, 3H); 3.19 (m, 1H); 3.34 (m, 1H); 3.64 (s, 3H); 3.89 (m, 1H); 4.34 (m, 2H); 4.61 (m, 1H), 5.23-5.37 (m, 2H); 5.50 (m, 1H); 5.92 (m, 1H).

Intermediate 32: (2R,5R)-6-(allyloxy)-4-methyl-7-oxo-1,6-diazabicyclo[3.2.1]oct-3-ene-2-carboxylic acid

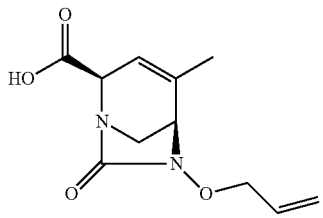 [SMILES: C=CCON1C(=O)N2C[C@H]1C(C)=C[C@@H]2C(=O)O]

To a solution of (2S,5R)-methyl 6-(allyloxy)-4-methyl-7-oxo-1,6-diazabicyclo[3.2.1]oct-3-ene-2-carboxylate (Intermediate 30, 0.479 g, 1.90 mmol) in THF (10 mL) and water (5 mL) at 0° C. was added lithium hydroxide (0.045 g, 1.90 mmol). The reaction was stirred at 0° C. for 2 hours. Another 0.5 eq lithium hydroxide was added. After 2 hours the reaction mixture was neutralized carefully with 1N HCl at 0° C. and the THF was evaporated. The aqueous was frozen and lyophilized to afford a light orange solid (0.464 g, 103% crude).

MS: 239 ES+ ($C_{11}H_{14}N_2O_4$)

$^1$H NMR (300 MHz, DMSO-$d_6$) δ: 1.72 (m, 3H); 2.38 (m, 1H); 3.00 (m, 1H); 3.47 (m, 1H); 3.68 (m, 1H); 3.83 (m, 1H); 4.33 (m, 1H); 5.15-55 (m, 4H); 5.94 (m, 1H).

Intermediate 25: tert-butyl 4-((2S,5R)-6-(allyloxy)-4-methyl-7-oxo-1,6-diazabicyclo[3.2.1]oct-3-enecarboxamido)piperidine-1-carboxylate

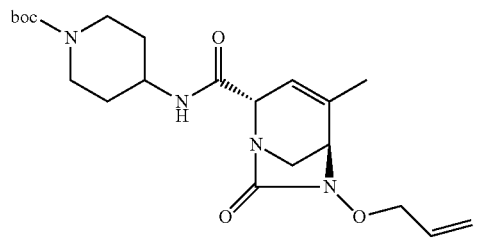

The title compound was prepared from (2R,5R)-6-(allyloxy)-4-methyl-7-oxo-1,6-diazabicyclo[3.2.1]oct-3-ene-2-carboxylic acid (Intermediate 32) following the procedure described in Route 1 for Intermediate 25. See Route 1 for final 2 steps.

Example 4

(2S,5R)-2-carbamoyl-4-isopropyl-7-oxo-1,6-diazabicyclo[3.2.1]oct-3-en-6-yl hydrogen sulfate sodium salt

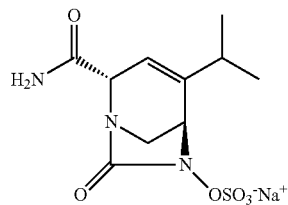

The title compound was prepared from (E)-triphenyl (prop-1-enyl)phosphonium (2S,5R)-2-carbamoyl-4-isopropyl-7-oxo-1,6-diazabicyclo[3.2.1]oct-3-en-6-yl sulfate (Intermediate 44, 71.1 mg, 0.12 mmol) following the procedure described for Example 1. The desired product was obtained as a light yellow solid (31.9 mg, 83%).

Optical rotation: (0.1 g/dL, MeOH)=−212

MS: 306 ES+ ($C_{10}H_{15}N_3O_6S$)

$^1$H NMR (300 MHz, DMSO-$d_6$) δ: 0.99 (m, 6H); 2.27 (m, 1H); 3.15 (m, 1H); 3.26 (m, 1H); 4.12 (m, 2H); 5.38 (m, 1H); 7.26 (bs, 1H); 7.52 (bs, 1H).

Intermediate 33: (E)-2,4,6-triisopropyl-N'-(3-methylbutan-2-ylidene)benzenesulfonohydrazide

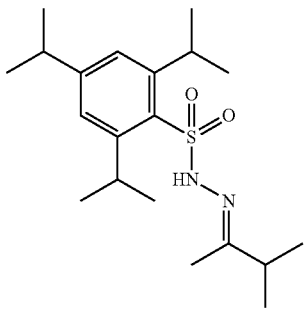 [SMILES: C/C(=N\NS(=O)(=O)c1c(C(C)C)cc(C(C)C)cc1C(C)C)C(C)C]

To a suspension of 2,4,6-triisopropylbenzenesulfonyl hydrazide (5.06 g, 16.95 mmol) and 3-methylbutan-2-one (1.814 mL, 16.95 mmol) in ethanol (20 mL) was added 2 drops of concentrated hydrochloric acid. The suspension became a solution and within a minute or two a white solid began to precipitate. The reaction mixture was placed in the fridge for 2 hours. The white precipitate was collected by filtration to afford the desired product (4.44 g, 71%).

MS: 367 ES+ ($C_{20}H_{34}N_2O_2S$)

$^1$H NMR (300 MHz, DMSO-$d_6$) δ: 0.87 (d, 6H); 1.17 (m, 18H); 1.75 (s, 3H); 2.31 (m, 1H); 2.90 (m, 1H); 4.24 (m, 2H); 7.19 (s, 2H); 9.96 (s, 1H).

Intermediate 34: (S)-tert-butyl 1-(tert-butyldimethylsilyloxy)but-3-en-2-yl(4-methyl-3-methylene-2-oxopentyl)carbamate

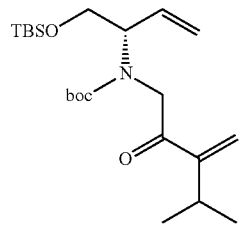

To a suspension of (E)-2,4,6-triisopropyl-N'-(3-methylbutan-2-ylidene)benzenesulfonohydrazide (Intermediate 33, 8 g, 21.82 mmol) in hexane (65 mL) and TMEDA (6.50 mL) at –78° C. was added dropwise n-butyllithium (1.6M in hexanes) (34.1 mL, 54.56 mmol). The reaction mixture turned orange and was stirred for 30 minutes at –78° C., then was warmed to 0° C. and bubbling started immediately. The suspension became a yellow solution. After ~15 minutes the bubbling stopped and (S)-tert-butyl 1-(tert-butyldimethylsilyloxy)but-3-en-2-yl(2-(methoxy(methyl)-amino)-2-oxoethyl)carbamate (Intermediate 5, 4.39 g, 10.91 mmol) was added as a solution in hexane (2 mL). After ~15 minutes LC/MS shows desired product and no remaining Weinreb amide starting material. The reaction mixture was quenched with saturated sodium bicarbonate and extracted with ether twice. The ether extracts were dried over magnesium sulfate, filtered and concentrated to afford a yellow oil. Silica gel chromatography (0%-10% ethyl acetate/hexanes) afforded the desired product (2.219 g, 49.4%) as a light yellow oil.

MS: 412 ES+ ($C_{22}H_{41}NO_4Si$)

$^1$H NMR (300 MHz, DMSO-$d_6$) δ: 0.01 (m, 6H); 0.82 (m, 9H); 0.98 (m, 6H); 1.28-1.38 (m, 9H); 2.77 (m, 1H); 3.71 (m, 2H); 4.33 (m, 2H); 4.62 (m, 1H); 5.16 (m, 2H); 5.77 (m, 2H); 6.06 (m, 1H).

Intermediate 35: (S)-tert-butyl 2-((tert-butyldimethylsilyloxy)methyl)-4-isopropyl-5-oxo-5,6-dihydropyridine-1(2H)-carboxylate

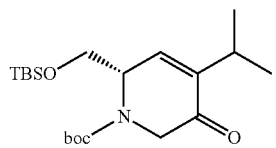

The title compound was prepared from (S)-tert-butyl 1-(tert-butyldimethylsilyloxy)but-3-en-2-yl(4-methyl-3-methylene-2-oxopentyl)carbamate (Intermediate 34, 0.839 g, 2.04 mmol) following the procedure described for Intermediate 7, using 0.32 eq of (1,3-Bis-(2,4,6-trimethylphenyl)-2-imidazolidinylidene)dichloro(o-isopropoxyphenylmethylene)ruthenium. The desired product was obtained as a colorless oil (0.667 g, 85%).

MS: 384 ES+ ($C_{20}H_{37}NO_4Si$)

$^1$H NMR (300 MHz, DMSO-$d_6$) δ: 0.00 (m, 6H); 0.80 (s, 9H); 1.00 (m, 6H); 1.42 (s, 9H); 2.77 (m, 1H); 3.85 (m, 3H); 4.26 (m, 1H); 4.69 (m, 1H); 6.80 (m, 1H).

Intermediate 36: (2S,5S)-tert-butyl 2-((tert-butyldimethylsilyloxy)methyl)-5-hydroxy-4-isopropyl-5,6-dihydropyridine-1(2H)-carboxylate

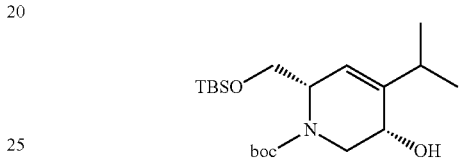

The title compound was prepared from (S)-tert-butyl 2-((tert-butyldimethylsilyloxy)methyl)-4-isopropyl-5-oxo-5,6-dihydropyridine-1(2H)-carboxylate (Intermediate 35, 0.667 g, 1.74 mmol) following the procedure described for Intermediate 8. The desired product was obtained as a colorless oil (0.464 g, 69%).

MS: 386 ES+ ($C_{20}H_{39}NO_4Si$)

$^1$H NMR (300 MHz, DMSO-$d_6$) δ: 0.02 (s, 6H); 0.86 (s, 9H); 0.98 (s, 6H); 1.39 (s, 9H); 2.64 (m, 2H); 3.59 (m, 2H); 3.99 (m, 2H); 4.21 (m, 1H); 5.04 (d, 1H); 5.36 (m, 1H).

Intermediate 37: (2S,5R)-tert-butyl 5-(N-(allyloxy)-2-nitrophenylsulfonamido)-2-((tert-butyldimethylsilyloxy)methyl)-4-isopropyl-5,6-dihydropyridine-1(2H)-carboxylate

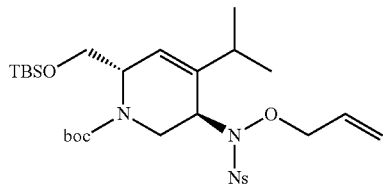

The title compound was prepared from (2S,5S)-tert-butyl 2-((tert-butyldimethylsilyloxy)methyl)-5-hydroxy-4-isopropyl-5,6-dihydropyridine-1(2H)-carboxylate (Intermediate 36, 1.2 g, 3.11 mmol) following the procedure described for Intermediate 10, using 2.4 equivalents each of triphenylphosphine and diisopropylazodicarboxylate. The desired product was obtained as yellow foam (1.22 g, 62%).

MS: 626 ES+ ($C_{29}H_{47}N_3O_8SSi$)

$^1$H NMR (300 MHz, DMSO-$d_6$) δ: 0.00 (s, 6H); 0.83 (s, 9H); 1.00 (m, 6H); 1.34 (m, 9H); 3.18 (m, 1H); 3.59 (m, 2H); 4.22 (m, 4H); 4.46 (m, 1H); 5.18 (m, 2H); 5.73 (m, 2H); 7.91-8.18 (m, 4H).

Intermediate 38: (2S,5R)-tert-butyl 5-(N-(allyloxy)-2-nitrophenylsulfonamido)-2-(hydroxymethyl)-4-isopropyl-5,6-dihydropyridine-1(2H)-carboxylate

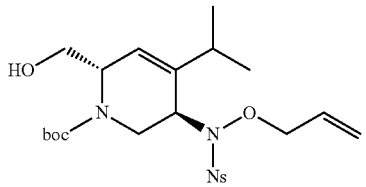

The title compound was prepared from (2S,5R)-tert-butyl 5-(N-(allyloxy)-2-nitrophenylsulfonamido)-2-((tert-butyldimethylsilyloxy)methyl)-4-isopropyl-5,6-dihydropyridine-1(2H)-carboxylate (Intermediate 37, 0.361 g, 0.58 mmol) following the procedure described for Intermediate 18. The desired product was obtained as a tan foam (0.257 g, 87%).

MS: 512 ES+ ($C_{23}H_{33}N_3O_8S$)

$^1$H NMR (300 MHz, DMSO-$d_6$) δ: 0.93 (m, 6H); 1.35 (m, 9H); 3.13 (m, 1H); 3.40 (m, 2H); 4.18 (m, 3H); 4.41 (m, 1H); 4.75 (m, 1H); 5.20 (m, 2H); 5.74 (m, 2H); 7.92-8.19 (m, 4H).

Intermediate 39: (2S,5R)-5-(N-(allyloxy)-2-nitrophenylsulfonamido)-1-(tert-butoxycarbonyl)-4-isopropyl-1,2,5,6-tetrahydropyridine-2-carboxylic acid

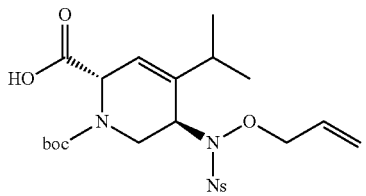

The title compound was prepared from (2S,5R)-tert-butyl 5-(N-(allyloxy)-2-nitrophenylsulfonamido)-2-(hydroxymethyl)-4-isopropyl-5,6-dihydropyridine-1(2H)-carboxylate (Intermediate 38, 0.727 g, 1.42 mmol) following the procedure described for Intermediate 19. The desired product was obtained as an off-white foam (0.65 g, 87%).

MS: 526 ES+ ($C_{23}H_{31}N_3O_9S$)

$^1$H NMR (300 MHz, DMSO-$d_6$) δ: 1.00 (m, 6H); 1.26 (m, 9H); 2.95-3.13 (m, 1H); 3.95 (m, 1H); 4.10-4.34 (m, 3H); 4.77-4.91 (m, 1H); 5.19 (m, 2H); 5.67-5.87 (m, 2H); 7.92-8.20 (m, 4H).

Intermediate 40: (2S,5R)-tert-butyl 5-(N-(allyloxy)-2-nitrophenylsulfonamido)-2-carbamoyl-4-isopropyl-5,6-dihydropyridine-1(2H)-carboxylate

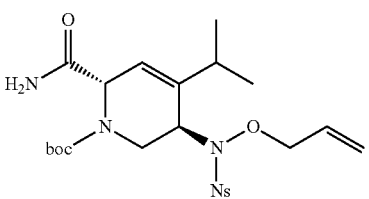

The title compound was prepared from (2S,5R)-5-(N-(allyloxy)-2-nitrophenylsulfonamido)-1-(tert-butoxycarbonyl)-4-isopropyl-1,2,5,6-tetrahydropyridine-2-carboxylic acid (Intermediate 39, 0.65 g, 1.24 mmol) following the procedure described for Intermediate 20. The desired product was obtained as an off-white solid (0.322 g, 51%).

MS: 525 ES+ ($C_{23}H_{32}N_4O_8S$)

$^1$H NMR (300 MHz, CDCl$_3$) δ: 1.00 (m, 6H); 1.31 (m, 9H); 3.20 (m, 1H); 4.20 (m, 3H); 4.70-4.87 (m, 1H); 5.19 (m, 2H); 5.69 (m, 1H); 5.86 (m, 1H); 7.03 (m, 1H); 7.47 (m, 1H); 7.94-8.21 (m, 4H).

Intermediate 41: (2S,5R)-5-(N-(allyloxy)-2-nitrophenylsulfonamido)-4-isopropyl-1,2,5,6-tetrahydropyridine-2-carboxamide

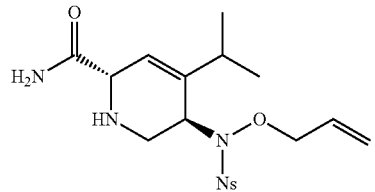

The title compound was prepared from (2S,5R)-tert-butyl 5-(N-(allyloxy)-2-nitrophenylsulfonamido)-2-carbamoyl-4-isopropyl-5,6-dihydropyridine-1(2H)-carboxylate (Intermediate 40, 0.427 g, 0.81 mmol) following the procedure described for Intermediate 21. The desired product was obtained as yellow foam (0.247 g, 71%).

MS: 425 ES+ ($C_{18}H_{24}N_4O_6S$)

$^1$H NMR (300 MHz, DMSO-$d_6$) δ: 0.95 (m, 6H); 2.25 (m, 1H); 2.67 (m, 2H); 3.81 (m, 1H); 4.07 (m, 1H); 4.30 (m, 2H); 5.24 (m, 2H); 5.83 (m, 1H); 6.03 (m, 1H); 7.03 (m, 1H); 7.32 (m, 1H); 7.93-8.18 (m, 4H).

Intermediate 42: (2S,5R)-5-(allyloxyamino)-4-isopropyl-1,2,5,6-tetrahydropyridine-2-carboxamide

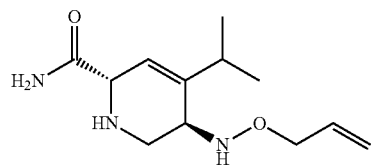 [SMILES: C=CCON[C@H]1CN[C@H](C(N)=O)C=C1C(C)C]

The title compound was prepared from (2S,5R)-5-(N-(allyloxy)-2-nitrophenylsulfonamido)-4-isopropyl-1,2,5,6-tetrahydropyridine-2-carboxamide (Intermediate 41, 0.247 g, 0.58 mmol) following the procedure described for Intermediate 22. The desired product was obtained as a light yellow solid (98 mg, 71%)

MS: 240 ES+ ($C_{12}H_{21}N_3O_2$)

$^1$H NMR (300 MHz, DMSO-$d_6$) δ: 0.99 (m, 6H); 2.37 (m, 1H); 3.04 (m, 1H); 3.17 (m, 1H); 3.60 (m, 1H); 4.11 (m, 2H); 5.11-5.26 (m, 2H); 5.78 (m, 1H); 5.86-6.00 (m, 1H); 6.31 (m, 1H); 7.01 (bs, 1H); 7.36 (bs, 1H).

Intermediate 43: (2S,5R)-6-(allyloxy)-4-isopropyl-7-oxo-1,6-diazabicyclo[3.2.1]oct-3-ene-2-carboxamide

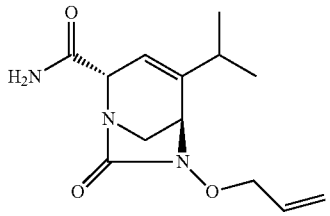 [SMILES: C=CCON1C(=O)N2C[C@H]1C(C(C)C)=C[C@H]2C(N)=O]

The title compound was prepared from (2S,5R)-5-(allyloxyamino)-4-isopropyl-1,2,5,6-tetrahydropyridine-2-carboxamide (0.0981 g, 0.41 mmol) and N,N-diisopropylethylamine (Intermediate 42, 0.286 mL, 1.64 mmol) following the procedure described for Intermediate 16. The desired product was obtained as a light yellow oil (69 mg, 63%).

MS: 266 ES+ ($C_{13}H_{19}N_3O_3$)

$^1$H NMR (300 MHz, DMSO-$d_6$) δ: 1.00 (m, 6H); 2.28 (m, 1H); 3.19 (m, 2H); 4.02 (m, 1H); 4.14 (m, 1H); 4.37 (m, 2H); 5.28-5.42 (m, 3H); 5.90-6.01 (m, 1H); 7.28 (bs, 1H); 7.51 (bs, 1H).

Intermediate 44: (E)-triphenyl(prop-1-enyl)phosphonium (2S,5R)-2-carbamoyl-4-isopropyl-7-oxo-1,6-diazabicyclo[3.2.1]oct-3-en-6-yl sulfate

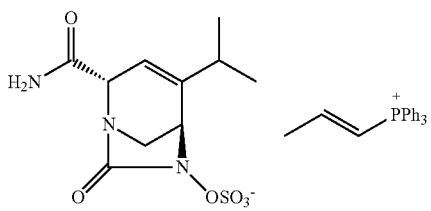

The title compound was prepared from 2S,5R)-6-(allyloxy)-4-isopropyl-7-oxo-1,6-diazabicyclo[3.2.1]oct-3-ene-2-carboxamide (Intermediate 43, 68.7 mg, 0.26 mmol) following the procedure described for Intermediate 17, using 1 equivalent of tetrakis(triphenylphosphine)-palladium. The desired product was obtained as a yellow oil (71 mg, 45%).

MS: 306 ES+, 303 ES+ ($C_{10}H_{15}N_3O_6S$, $C_{21}H_{20}P$)

Example 5

(2S,5R)-2-cyano-4-isopropyl-7-oxo-1,6-diazabicyclo[3.2.1]oct-3-en-6-yl hydrogen sulfate sodium salt

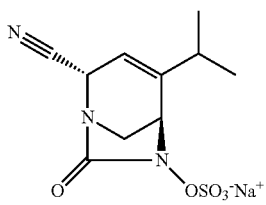

The title compound was prepared from (E)-triphenyl(prop-1-enyl)phosphonium (2S,5R)-2-cyano-4-isopropyl-7-oxo-1,6-diazabicyclo[3.2.1]oct-3-en-6-yl sulfate (Intermediate 46, 47.2 mg, 0.08 mmol) following the procedure described for Example 1. The desired product was obtained as a white solid (18.2 mg, 73%).

Optical rotation: (0.1 g/dL, DMSO)=−168

MS: 286 ES− ($C_{10}H_{13}N_3O_5S$)

$^1$H NMR (600 MHz, DMSO-$d_6$) δ: 1.00 (m, 6H); 2.30 (m, 1H); 3.20 (m, 1H); 3.50 (m, 1H); 4.24 (m, 1H); 4.97 (m, 1H); 5.25 (m, 1H).

Intermediate 45: (2S,5R)-6-(allyloxy)-4-isopropyl-7-oxo-1,6-diazabicyclo[3.2.1]oct-3-ene-2-carbonitrile

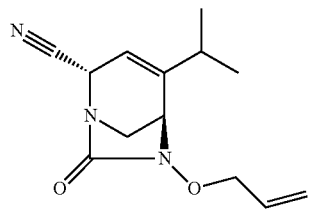 [SMILES: C=CCON1C(=O)N2C[C@H]1C(C(C)C)=C[C@H]2C#N]

The title compound was prepared from 2S,5R)-6-(allyloxy)-4-isopropyl-7-oxo-1,6-diazabicyclo[3.2.1]oct-3-ene-2-carboxamide (Intermediate 43, 143.9 mg, 0.54 mmol) following the procedure described for Intermediate 23. The desired product was obtained as a colorless oil (114 mg, 85%).

MS: 248 ES+ ($C_{13}H_{17}N_3O_2$)

$^1$H NMR (300 MHz, DMSO-$d_6$) δ: 1.00 (m, 6H); 2.32 (m, 1H); 3.21 (m, 1H); 3.45 (m, 1H); 4.18 (m, 1H); 4.38 (m, 2H); 4.98 (m, 1H); 5.25-5.39 (m, 3H); 5.86-6.00 (m, 1H).

Intermediate 46: (E)-triphenyl(prop-1-enyl)phosphonium (2S,5R)-2-cyano-4-isopropyl-7-oxo-1,6-diazabicyclo[3.2.1]oct-3-en-6-yl sulfate

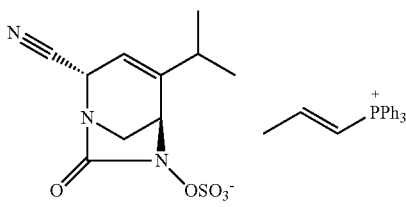

The title compound was prepared from (2S,5R)-6-(allyloxy)-4-isopropyl-7-oxo-1,6-diazabicyclo[3.2.1]oct-3-ene-2-carbonitrile (Intermediate 45, 114.1 mg, 0.46 mmol) following the procedure described for Intermediate 17, using 0.75 equivalents of tetrakis(triphenyl-phosphine)palladium. The desired product was obtained as a light yellow oil (47.2 mg, 17%).

MS: 286 ES−, 303 ES+ ($C_{10}H_{12}N_3O_5S$, $C_{21}H_{20}P$)

$^1$H NMR (300 MHz, DMSO-$d_6$) δ: 1.01 (m, 6H); 2.17 (m, 3H); 3.21 (m, 1H); 3.50 (m, 1H); 4.24 (m, 1H); 4.98 (m, 1H); 5.26 (m, 1H); 6.64-6.73 (m, 1H); 7.23-7.37 (m, 1H); 7.51-7.65 (m, 1H); 7.68-7.95 (m, 15H).

Example 6

(2S,5R)-2-(2-aminoethylcarbamoyl)-4-methyl-7-oxo-1,6-diazabicyclo[3.2.1]oct-3-en-6-yl hydrogen sulfate

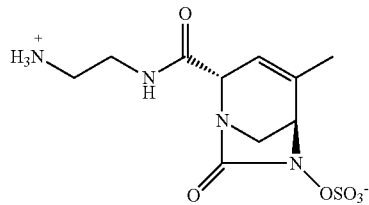

To a solution of (E)-triphenyl(prop-1-enyl)phosphonium (2S,5R)-2-(2-(tert-butoxycarbonylamino)ethylcarbamoyl)-4-methyl-7-oxo-1,6-diazabicyclo[3.2.1]oct-3-en-6-yl sulfate (Intermediate 48, 0.238 g, 0.33 mmol) in DCM (2 mL) at 0° C. was added TFA (2 mL). After 30 minutes the reaction mixture was concentrated to afford an orange oil. The oil was triturated with ether three times and ethyl acetate three times to afford an orange solid. Purification was done on reverse phase HPLC (0-10% acetonitrile in water, YMC Carotenoid C30, 19 mm×150 mm, 5 μm) to afford the title compound as a white solid (25.4 mg, 13%).

Optical rotation: (0.1 g/dL, DMSO)=−120.

MS: 321 ES+ ($C_{10}H_{16}N_4O_6S$)

$^1$H NMR (300 MHz, DMSO-$d_6$) δ: 1.80 (m, 3H); 2.88 (m, 2H); 3.17 (m, 1H); 3.24 (m, 1H); 3.39 (m, 2H); 3.99 (m, 1H); 4.21 (m, 1H); 4.48 (m, 1H); 7.43 (m, 2H); 8.25 (m, 1H).

Intermediate 47: tert-butyl 2-((2S,5R)-6-(allyloxy)-4-methyl-7-oxo-1,6-diazabicyclo[3.2.1]oct-3-enecarboxamido)ethylcarbamate

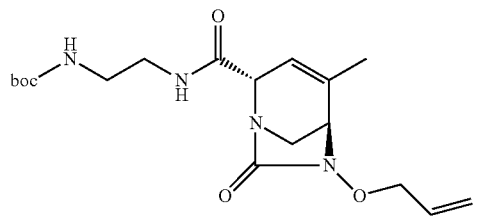

The title compound was prepared from (2R,5R)-6-(allyloxy)-4-methyl-7-oxo-1,6-diazabicyclo[3.2.1]oct-3-ene-2-carboxylic acid (Intermediate 15, 0.348 g, 1.46 mmol) and N-Boc-ethylenediamine hydrochloride (0.287 g, 1.46 mmol) following the procedure described for Intermediate 25. The desired product was obtained as a light pink foam (230 mg, 41%).

MS: 381 ES+ ($C_{18}H_{28}N_4O_5$)

$^1$H NMR (300 MHz, DMSO-$d_6$) δ: 1.37 (s, 9H); 1.79 (m, 3H); 3.00 (m, 2H); 3.16 (m, 4H); 3.82 (m, 1H); 4.14 (m, 1H); 4.37 (m, 2H); 5.24-5.47 (m, 3H); 5.90-6.00 (m, 1H); 6.81 (m, 1H); 8.07 (m, 1H).

Intermediate 48: (E)-triphenyl(prop-1-enyl)phosphonium (2S,5R)-2-(2-(tert-butoxy-carbonylamino)ethylcarbamoyl)-4-methyl-7-oxo-1,6-diazabicyclo[3.2.1]oct-3-en-6-yl sulfate

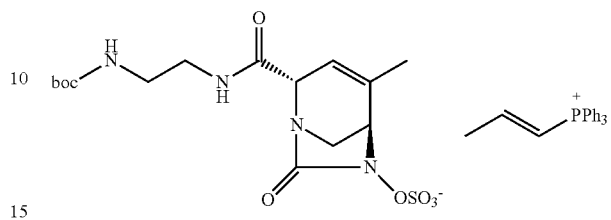

To a solution of tert-butyl 2-((2S,5R)-6-(allyloxy)-4-methyl-7-oxo-1,6-diazabicyclo[3.2.1]oct-3-enecarboxamido)ethylcarbamate (Intermediate 47, 230 mg, 0.60 mmol) and acetic acid (0.069 mL, 1.21 mmol) (dried over sodium sulfate) in DCM (9 mL) at room temperature was added tetrakis(triphenylphosphine)palladium(0) (349 mg, 0.30 mmol). The solution was stirred at room temperature for 1 hour. To the reaction mixture was added pyridine (9.00 mL) and sulfur trioxide-pyridine complex (577 mg, 3.63 mmol). The suspension was stirred overnight at room temperature. The suspension was evaporated to dryness and then resuspended in DCM. The solids were filtered off through a 0.45 t nalgene filter. The filtrate was concentrated to afford an orange oil. This was taken up in DCM again and filtered through a 0.45 t filter. The filtrate was concentrated to afford an orange oil. The crude material was taken to the next step without purification.

MS: 419 ES−, 303 ES+ ($C_{15}H_{23}N_4O_8S$, $C_{21}H_{20}P$)

Example 7

(2S,5R)-2-(methoxymethyl)-7-oxo-4-(prop-1-en-2-yl)-1,6-diazabicyclo[3.2.1]oct-3-en-6-yl hydrogen sulfate sodium salt

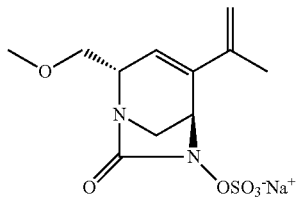

The title compound was prepared from (E)-triphenyl (prop-1-enyl)phosphonium (2S,5R)-2-(methoxymethyl)-7-oxo-4-(prop-1-en-2-yl)-1,6-diazabicyclo[3.2.1]oct-3-en-6-yl sulfate (Intermediate 60, 0.283 g, 0.47 mmol) following the procedure described for Example 1. The desired product was obtained after reverse phase HPLC purification (2-10% acetonitrile in water, Synergi Hydro RP, 19 mm×150 mm, 5 μm) as a white solid (40 mg, 26%).

Optical rotation: (0.1 g/dL, MeOH)=−170.

MS: 305 ES+ ($C_{11}H_{16}N_2O_6S$)

$^1$H NMR (300 MHz, DMSO-$d_6$) δ: 1.80 (s, 3H); 3.24 (m, 5H); 3.57 (m, 2H); 3.82 (m, 1H); 4.48 (m, 1H); 5.02 (m, 1H); 5.43 (m, 1H); 5.57 (m, 1H).

Intermediate 49: (S)-tert-butyl 1-(tert-butyldimethylsilyloxy)but-3-en-2-yl(2-oxopent-3-enyl)carbamate

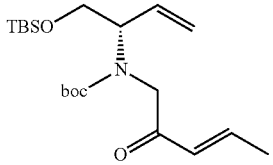

To a solution of (S)-tert-butyl 1-(tert-butyldimethylsilyloxy)but-3-en-2-yl(2-(methoxy(methyl)amino)-2-oxoethyl)carbamate (Intermediate 5, 32.5 g, 80.73 mmol) in THF (400 mL) under nitrogen at 0° C. was added prop-1-enylmagnesium bromide (323 ml, 161.45 mmol) dropwise. The reaction mixture was stirred at 0° C. for 1 hour, then quenched with 400 mL 10% citric acid, diluted further with 100 mL water and extracted with ether. The organics were concentrated and the resulting oil was dissolved in ether and washed with water and brine. The organics were dried over magnesium sulfate, filtered and concentrated. Silica gel chromatography (5%-20% ethyl acetate/hexanes) afforded the desired product as a colorless oil (27 g, 87%).

MS: 384 ES+ ($C_{20}H_{37}NO_4Si$)

$^1$H NMR (300 MHz, CDCl$_3$) δ: 0.05 (2, 6H); 0.88 (s, 9H); 1.39-1.47 (m, 9H); 1.90 (m, 3H); 3.80 (m, 2H); 4.05-4.18 (m, 2H); 4.43-4.76 (m, 1H); 5.22 (m, 2H); 5.86 (m, 1H); 6.21 (m, 1H); 6.91 (m, 1H).

Intermediate 50: (S)-tert-butyl 2-((tert-butyldimethylsilyloxy)methyl)-5-oxo-5,6-dihydropyridine-1(2H)-carboxylate

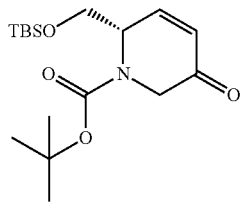 [SMILES: CC(C)(C)OC(=O)N1CC(=O)C=C[C@H]1CO[Si](C)(C)C(C)(C)C]

(S)-tert-butyl 1-(tert-butyldimethylsilyloxy)but-3-en-2-yl (2-oxopent-3-enyl)carbamate (Intermediate 49, 27.0 g, 70.39 mmol) was dissolved in toluene (650 ml). The solution was purged with nitrogen for 15 minutes before the addition of Hoveyda-Grubbs Catalyst 2nd Generation (0.885 g, 1.41 mmol). The reaction mixture was heated under nitrogen at 65° C. After 2 hours LCMS showed complete formation of the product. The reaction mixture was concentrated under reduced pressure. Silica gel chrimatography (10%-35% ethyl acetate/hexanes) afforded the desired product as a solid (17.0 g, 70%).

Optical Rotation: 0.1 g/dL, methylene chloride=−175

MS: 342 ES+ ($C_{17}H_{31}NO_4Si$)

$^1$H NMR (300 MHz, DMSO-d$_6$) δ: 0.01 (s, 6H); 0.82 (s, 9H); 1.43 (s, 9H); 3.78-3.93 (m, 3H); 4.29 (m, 1H); 4.70 (m, 1H); 6.19 (dd, 1H); 7.15 (m, 1H).

Intermediate 51: (S)-tert-butyl 2-((tert-butyldimethylsilyloxy)methyl)-4-iodo-5-oxo-5,6-dihydropyridine-1 (2H)-carboxylate

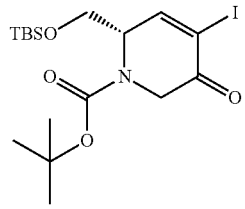 [SMILES: CC(C)(C)OC(=O)N1CC(=O)C(I)=C[C@H]1CO[Si](C)(C)C(C)(C)C]

To a solution of (S)-tert-butyl 2-((tert-butyldimethylsilyloxy)methyl)-5-oxo-5,6-dihydropyridine-1(2H)-carboxylate (Intermediate 50, 10 g, 29.28 mmol) and 4-dimethylaminopyridine (0.894 g, 7.32 mmol) in THF (100 mL)/water (100 mL) at room temperature was added potassium carbonate (3.24 g, 23.42 mmol) and iodine (8.92 g, 35.14 mmol). After stirring for 15 minutes, the reaction mixture was diluted with ether and washed with saturated sodium thiosulfate twice, then 5% citric acid and brine. The organics were dried over magnesium sulfate, filtered and concentrated. Silica gel chromatography (0%-15% ethyl acetate/hexanes) afforded the desired product as a tan oil (11.6 g, 85%).

MS: 468 ES+ ($C_{17}H_{30}INO_4Si$)

$^1$H NMR (300 MHz, CDCl$_3$) δ: 0.04 (s, 6H); 0.86 (s, 9H); 1.49 (s, 9H); 3.81 (m, 1H); 3.95 (m, 1H); 4.17 (m, 1H); 4.79 (m, 2H); 7.67 (m, 1H).

Intermediate 52: (2S,5R)-tert-butyl 2-((tert-butyldimethylsilyloxy)methyl)-5-hydroxy-4-iodo-5,6-dihydropyridine-1(2H)-carboxylate

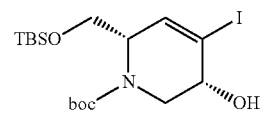

The title compound was prepared from (S)-tert-butyl 2-((tert-butyldimethylsilyloxy)methyl)-4-iodo-5-oxo-5,6-dihydropyridine-1(2H)-carboxylate (Intermediate 51, 10 g, 21.39 mmol) following the procedure described for Intermediate 8. The desired product was obtained as a colorless oil (8.87 g, 88%).

MS: 470 ES+ ($C_{17}H_{32}INO_4Si$)

$^1$H NMR (300 MHz, DMSO-d$_6$) δ: 0.03 (s, 6H); 0.86 (s, 9H); 1.40 (s, 9H); 2.87 (m, 1H); 3.65 (m, 2H); 3.79 (m, 1H); 4.21 (m, 2H); 5.74 (d, 1H); 6.44 (m, 1H).

Intermediate 53: (2S,5S)-tert-butyl 2-((tert-butyldimethylsilyloxy)methyl)-5-hydroxy-4-(prop-1-en-2-yl)-5,6-dihydropyridine-1(2H)-carboxylate

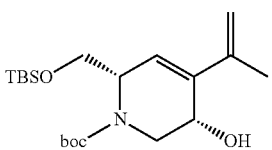

A solution of (2S,5R)-tert-butyl 2-((tert-butyldimethylsilyloxy)methyl)-5-hydroxy-4-iodo-5,6-dihydropyridine-1(2H)-carboxylate (Intermediate 52, 8.57 g, 18.26 mmol), potassium trifluoro(prop-1-en-2-yl)borate (5.40 g, 36.51 mmol), potassium carbonate (3.11 mL, 54.77 mmol) and dichloro[1,1'-bis(di-t-butylphosphino)ferrocene]palladium (II) (1.190 g, 1.83 mmol) in dioxane (200 mL) and water (66.7 mL) at room temperature was purged with argon for 5 minutes then heated at 70° C. The reaction mixture was concentrated onto silica gel. Silica gel chromatography (0%-20% ethyl acetate/hexanes) afforded a 2 to 1 mixture of desired product and starting material as a brown oil (5.36 g, 77%).

MS: 384 ES+ ($C_{20}H_{37}NO_4Si$)2

Intermediate 54: (2S,5R)-tert-butyl 5-(N-(allyloxy)-2-nitrophenylsulfonamido)-2-((tert-butyldimethylsilyloxy)methyl)-4-(prop-1-en-2-yl)-5,6-dihydropyridine-1(2H)-carboxylate

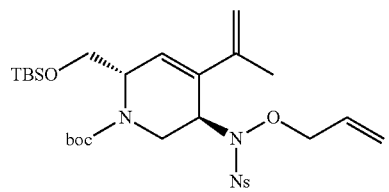

The title compound was prepared from (2S,5S)-tert-butyl 2-((tert-butyldimethylsilyloxy)methyl)-5-hydroxy-4-(prop-1-en-2-yl)-5,6-dihydropyridine-1(2H)-carboxylate (Intermediate 53, 3.86 g, 10.06 mmol) following the procedure described for Intermediate 10. The desired product was obtained as light yellow foam (3.25 g, 52%).

MS: 624 ES+ ($C_{29}H_{45}N_3O_8SSi$)

Intermediate 55: N-(allyloxy)-N-((3R,6S)-6-((tert-butyldimethylsilyloxy)methyl)-4-(prop-1-en-2-yl)-1,2,3,6-tetrahydropyridin-3-yl)-2-nitrobenzenesulfonamide

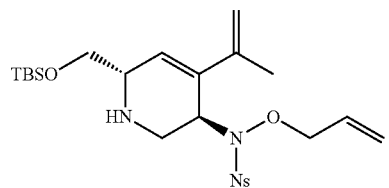

The title compound was prepared from (2S,5R)-tert-butyl 5-(N-(allyloxy)-2-nitrophenylsulfonamido)-2-((tert-butyldimethylsilyloxy)methyl)-4-(prop-1-en-2-yl)-5,6-dihydropyridine-1(2H)-carboxylate (Intermediate 54, 3.04 g, 4.87 mmol) following the procedure described for Intermediate 21. The desired product was obtained as an orange oil (2.53 g, 99%).

MS: 524 ES+ ($C_{24}H_{37}N_3O_6SSi$)

Intermediate 56: O-allyl-N-((3R,6S)-6-((tert-butyldimethylsilyloxy)methyl)-4-(prop-1-en-2-yl)-1,2,3,6-tetrahydropyridin-3-yl)hydroxylamine

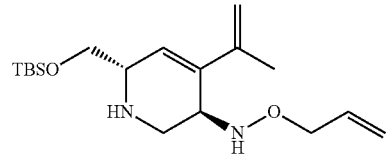 [SMILES: C=CCON[C@H]1CN[C@H](CO[Si](C)(C)C(C)(C)C)C=C1C(=C)C]

The desired product was prepared from N-(allyloxy)-N-((3R,6S)-6-((tert-butyldimethylsilyloxy)methyl)-4-(prop-1-en-2-yl)-1,2,3,6-tetrahydropyridin-3-yl)-2-nitrobenzenesulfonamide (Intermediate 55, 2.45 g, 4.68 mmol) following the procedure described for Intermediate 22. The desired product was obtained as yellow oil (1.19 g, 75%).

MS: 339 ES+ ($C_{18}H_{34}N_2O_2Si$)

Intermediate 57: (2S,5R)-6-(allyloxy)-2-((tert-butyldimethylsilyloxy)methyl)-4-(prop-1-en-2-yl)-1,6-diazabicyclo[3.2.1]oct-3-en-7-one

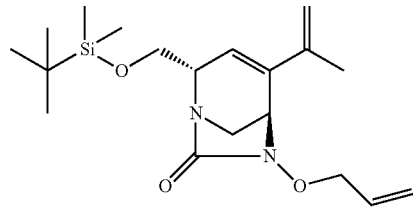 [SMILES: C=CCON1C(=O)N2C[C@H]1C(C(=C)C)=C[C@H]2CO[Si](C)(C)C(C)(C)C]

The title compound was prepared from O-allyl-N-((3R,6S)-6-((tert-butyldimethylsilyloxy)-methyl)-4-(prop-1-en-2-yl)-1,2,3,6-tetrahydropyridin-3-yl)hydroxylamine (Intermediate 56, 1.22 g, 3.60 mmol) following the procedure described for Intermediate 16. The desired product was obtained as a light yellow oil (1.16 g, 88%).

MS: 365 ES+ ($C_{18}H_{32}N_2O_3Si$)

Intermediate 58: (2S,5R)-6-(allyloxy)-2-(hydroxymethyl)-4-(prop-1-en-2-yl)-1,6-diazabicyclo[3.2.1]oct-3-en-7-one

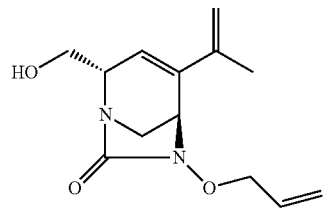 [SMILES: C=CCON1C(=O)N2C[C@H]1C(C(=C)C)=C[C@H]2CO]

The title compound was obtained from (2S,5R)-6-(allyloxy)-2-((tert-butyldimethylsilyloxy)-methyl)-4-(prop-1-en-2-yl)-1,6-diazabicyclo[3.2.1]oct-3-en-7-one (Intermediate 57, 1.16 g, 3.18 mmol) following the procedure described for Intermediate 14. The desired product was obtained as a colorless oil (741 mg, 93%).

MS: 251 ES+ ($C_{13}H_{18}N_2O_3$)

Intermediate 59: (2S,5R)-6-(allyloxy)-2-(methoxymethyl)-4-(prop-1-en-2-yl)-1,6-diazabicyclo[3.2.1]oct-3-en-7-one

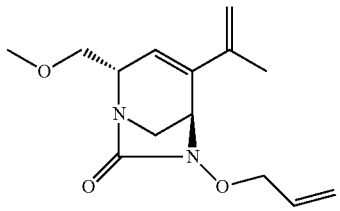 [SMILES: C=CCON1C(=O)N2C[C@H]1C(C(=C)C)=C[C@H]2COC]

To a solution of (2S,5R)-6-(allyloxy)-2-(hydroxymethyl)-4-(prop-1-en-2-yl)-1,6-diazabicyclo[3.2.1]oct-3-en-7-one (Intermediate 58, 0.289 g, 1.15 mmol) in DMF (10 mL) at 0° C. was added methyl iodide (0.435 mL, 6.93 mmol) followed by sodium hydride (60% in mineral oil) (0.051 g, 1.27 mmol). The reaction was stirred for 1.5 hours at 0° C. The reaction mixture was diluted with ethyl acetate and washed twice with water. The organics were dried over magnesium sulfate, filtered and concentrated. Silica gel chromatography (0%-50% ethyl acetate/hexanes) afforded the desired product as a pale yellow oil (233 mg, 76%).

MS: 265 ES+ ($C_{14}H_{20}N_2O_3$)

Intermediate 60: (E)-triphenyl(prop-1-enyl)phosphonium (2S,5R)-2-(methoxymethyl)-7-oxo-4-(prop-1-en-2-yl)-1, 6-diazabicyclo[3.2.1]oct-3-en-6-yl sulfate

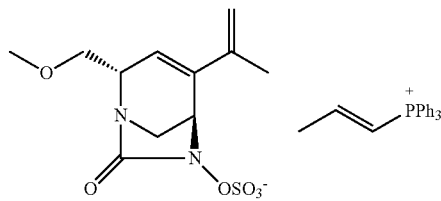

The title compound was prepared from 2S,5R)-6-(allyloxy)-2-(methoxymethyl)-4-(prop-1-en-2-yl)-1,6-diazabicyclo[3.2.1]oct-3-en-7-one (Intermediate 59, 233 mg, 0.88 mmol) following the procedure described for Intermediate 17. The desired product was obtained as an off-white foam (283 mg, 53%).

MS: 305 ES+, 303 ES+ ($C_{11}H_{16}N_2O_6S$, $C_{21}H_{20}P$)

Example 8

(2S,5R)-2-((5-hydroxy-4-oxo-1,4-dihydropyridin-2-yl)methylcarbamoyl)-4-methyl-7-oxo-1,6-diazabicyclo[3.2.1]oct-3-en-6-yl hydrogen sulfate sodium salt

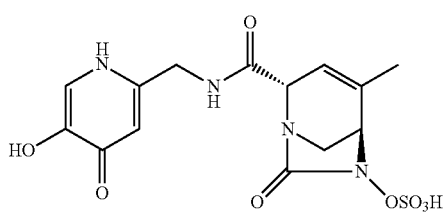

To a solution of (2S,5R)-2-((4,5-bis(4-methoxybenzyloxy)pyridin-2-yl)methylcarbamoyl)-4-methyl-7-oxo-1,6-diazabicyclo[3.2.1]oct-3-en-6-yl hydrogen sulfate (Intermediate 68, 58 mg, 0.09 mmol) in DCM (2 mL) at room temperature was added trifluoroacetic acid (0.505 mL, 6.55 mmol). The reaction mixture was stirred for 10 minutes and then concentrated. The resulting residue was dissolved in DCM and concentrated twice more. The product was purified twice by C18 RediSepRf Gold column (15.5 g) eluting with water manually using a syringe. The desired product was obtained after lyophilization as a white solid (3.4 mg, 9%).

MS: 401 ES+ ($C_{14}H_{16}N_4O_8S$)
$^1$H NMR (300 MHz, $D_2O$) δ: 1.93 (m, 3H); 3.25 (m, 1H); 3.58 (m, 1H); 4.20 (m, 1H); 4.50 (m, 2H); 4.59 (m, 1H); 5.67 (m, 1H); 6.76 (s, 1H); 7.77 (s, 1H).

Intermediate 61: 2-(hydroxymethyl)-5-(4-methoxybenzyloxy)-4H-pyran-4-one

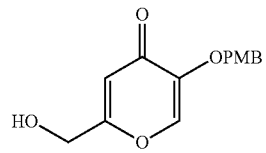

To a solution of 5-hydroxy-2-(hydroxymethyl)-4H-pyran-4-one (Alfa Aesar, 5.11 g, 35.96 mmol) in DMF (70 mL) at room temperature was added potassium carbonate (9.94 g, 71.92 mmol) and 1-(chloromethyl)-4-methoxybenzene (5.86 mL, 43.15 mmol) dropwise. The reaction mixture was heated at 80° C. for 1 hour then concentrated. To the resulting slurry was added ice water. The precipitate was collected by filtration then triturated with ethyl acetate and filtered again. The title compound was obtained as a tan solid (6.44 g, 68%).

MS: 263 ES+ ($C_{14}H_{14}O_5$)
$^1$H NMR (300 MHz, DMSO-$d_6$) δ: 3.76 (s, 3H); 4.28 (s, 2H); 4.86 (s, 2H); 5.75 (m, 1H); 6.31 (s, 1H); 6.94 (m, 2H); 7.33 (m, 2H); 8.13 (s, 1H).

Intermediate 62: 2-(hydroxymethyl)-5-(4-methoxybenzyloxy)pyridin-4(1H)-one

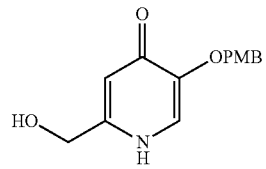

2-(hydroxymethyl)-5-(4-methoxybenzyloxy)-4H-pyran-4-one (Intermediate 63, 6.44 g, 24.56 mmol) and ammonia (7N in MeOH) (59.6 ml, 417.45 mmol) were combined in a pressure reactor vessel and heated at 90° C. for 5 hours. The reaction mixture was cooled overnight then concentrated. The solid was suspended in water then collected by filtration. The title compound was obtained as a brown solid (3.48 g, 54%).

MS: 262 ES+ ($C_{14}H_{15}NO_4$)

$^1$H NMR (300 MHz, DMSO-d$_6$) δ: 3.75 (s, 3H); 4.32 (s, 2H); 4.93 (s, 2H); 5.53 (m, 1H); 6.07 (m, 1H); 6.92 (m, 2H); 7.26 (m, 1H); 7.32 (m, 2H); 11.02 (m, 1H).

Intermediate 63: (4,5-bis(4-methoxybenzyloxy)pyridin-2-yl)methanol

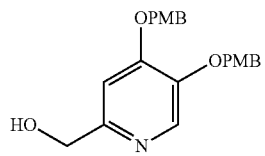

To a solution of 2-(hydroxymethyl)-5-(4-methoxybenzyloxy)pyridin-4(1H)-one (Intermediate 62, 3.48 g, 13.32 mmol) in DMF (100 mL) at room temperature was added 4-methoxybenzyl chloride (1.987 mL, 14.65 mmol) followed by potassium carbonate (2.273 mL, 39.96 mmol). The reaction mixture was stirred for 1 hour at room temperature then heated at 80° C. for 1.5 hours. The reaction mixture was cooled to room temperature, poured into water and extracted twice with ethyl acetate. The combined extracts were washed with water and brine. The ethyl acetate layer was concentrated to afford an oil. To the oil was added 1N HCl and a light brown solid crashed out. This was collected by filtration. The solid was taken up in ethyl acetate and washed with saturated sodium bicarbonate. The organics were dried over magnesium sulfate, filtered and concentrated to afford the title compound as a brown solid (2.62 g, 52%).

MS: 382 ES+ (C$_{22}$H$_{23}$NO$_5$)

$^1$H NMR (300 MHz, DMSO-d$_6$) δ: 3.74 (s, 3H); 3.76 (s, 3H); 4.42 (m, 2H); 5.05 (s, 2H); 5.12 (s, 2H); 5.27 (m, 1H); 6.93 (m, 4H); 7.17 (s, 1H); 7.32 (m, 4H); 8.07 (s, 1H).

Intermediate 64: 2-((4,5-bis(4-methoxybenzyloxy)pyridin-2-yl)methyl)isoindoline-1,3-dione

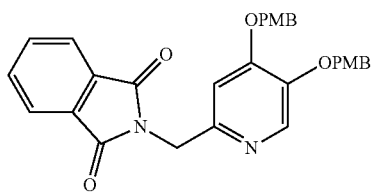

To a solution of (4,5-bis(4-methoxybenzyloxy)pyridin-2-yl)methanol (Intermediate 63, 1.5 g, 3.93 mmol), phthalimide (0.579 g, 3.93 mmol) and triphenylphosphine (1.028 g, 3.93 mmol) in THF (15 mL) at room temperature was added diisopropyl azodicarboxylate (2.091 mL, 10.62 mmol). The reaction was stirred at room temperature overnight then concentrated onto silica gel. Silica gel chromatography (0%-70% ethyl acetate) afforded the title compound as a light brown solid (1.1 g, 55%).

MS: 511 ES+ (C$_{30}$H$_{26}$N$_2$O$_6$)

$^1$H NMR (300 MHz, DMSO-d$_6$) δ: 3.73 (s, 3H); 3.74 (s, 3H); 4.78 (s, 2H); 5.01 (s, 2H); 5.10 (s, 2H); 6.89 (m, 4H); 7.16 (s, 1H); 7.32 (m, 4H); 7.89 (m, 4H); 8.01 (s, 1H).

Intermediate 65: (4,5-bis(4-methoxybenzyloxy)pyridin-2-yl)methanamine

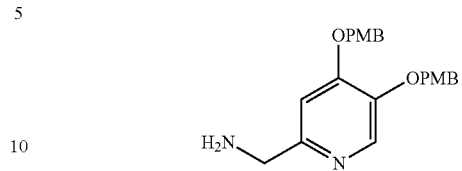

To a solution of 2-((4,5-bis(4-methoxybenzyloxy)pyridin-2-yl)methyl)isoindoline-1,3-dione (Intermediate 64, 1.1 g, 2.15 mmol) in chloroform (20 mL) and methanol (10 mL) at room temperature was added hydrazine hydrate (0.328 mL, 4.31 mmol). The reaction was stirred overnight at room temperature. Another 1 eq of hydrazine hydrate was added. After 4 hours the reaction mixture was filtered to remove the solids. The filtrate was concentrated to afford an orange oil. The oil was dissolved in methanol and ether was added to crash out more solids. This was repeated until no 2,3-dihydrophthalazine-1,4-dione by product remained. The title compound was obtained as an orange foam (0.82 g, 100%).

MS: 381 ES+ (C$_{22}$H$_{24}$N$_2$O$_4$)

$^1$H NMR (300 MHz, DMSO-d$_6$) δ: 3.66 (s, 2H); 3.74 (s, 3H); 3.76 (s, 3H); 5.03 (s, 2H); 5.11 (s, 2H); 6.92 (m, 4H); 7.20 (s, 1H); 7.35 (m, 4H); 8.05 (s, 1H).

Intermediate 66: (2S,5R)-6-(allyloxy)-N-((4,5-bis(4-methoxybenzyloxy)pyridin-2-yl)methyl)-4-methyl-7-oxo-1,6-diazabicyclo[3.2.1]oct-3-ene-2-carboxamide

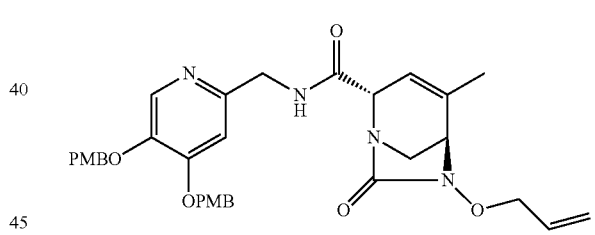

To a solution of (R)-6-(allyloxy)-4-methyl-7-oxo-1,6-diazabicyclo[3.2.1]oct-3-ene-2-carboxylic acid (Intermediate 32, 0.469 g, 1.97 mmol) in DMF (10 mL) at room temperature was added (4,5-bis(4-methoxybenzyloxy)pyridin-2-yl)methanamine (Intermediate 65, 0.824 g, 2.17 mmol), O-(7-azabenzotriazol-1-yl)-N,N,N',N'-tetramethyluronium hexafluorophosphate (1.497 g, 3.94 mmol) and N,N-diisopropylethylamine (1.372 mL, 7.87 mmol). After 30 minutes the reaction mixture was diluted with ethyl acetate and washed with saturated sodium bicarbonate, brine, and 1/1 brine/water twice. The organics were dried over magnesium sulfate, filtered and concentrated. Silica gel chromatography (0%-50% ethyl acetate/hexanes) afforded the title compound as a light pink foam (0.427 g, 36%).

MS: 601 ES+ (C$_{33}$H$_{36}$N$_4$O$_7$)

$^1$H NMR (300 MHz, DMSO-d$_6$) δ: 1.80 (m, 3H); 3.20 (m, 2H); 3.74 (s, 3H); 3.76 (s, 3H); 3.80 (m, 1H); 4.28 (m, 3H); 4.38 (m, 2H); 5.05 (s, 2H); 5.08 (s, 2H); 5.26 (m, 2H); 5.49 (m, 1H); 5.95 (m, 1H); 6.93 (m, 4H); 7.03 (s, 1H); 7.35 (m, 4H); 8.09 (s, 1H); 8.53 (m, 1H).

67

Intermediate 67: (E)-triphenyl(prop-1-enyl)phosphonium (2S,5R)-2-((4,5-bis(4-methoxy-benzyloxy)pyridin-2-yl)methylcarbamoyl)-4-methyl-7-oxo-16-diazabicyclo[3.2.1]oct-3-en-6-yl sulfate

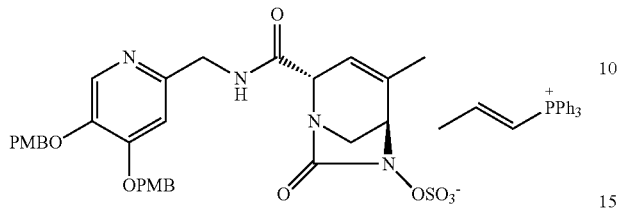

To a solution of (2S,5R)-6-(allyloxy)-N-((4,5-bis(4-methoxybenzyloxy)pyridin-2-yl)methyl)-4-methyl-7-oxo-1,6-diazabicyclo[3.2.1]oct-3-ene-2-carboxamide (Intermediate 66, 0.427 g, 0.71 mmol) and acetic acid (0.081 mL, 1.42 mmol) (dried over sodium sulfate) in DCM (10 mL) at room temperature was added tetrakis(triphenylphosphine)palladium(0) (0.821 g, 0.71 mmol). The solution was stirred at room temperature for 1 hour. To the reaction mixture was added pyridine (10.00 mL) and sulfur trioxide-pyridine complex (0.679 g, 4.27 mmol). The suspension was stirred overnight at room temperature. The suspension was evaporated to dryness and then resuspended in DCM. The solids were filtered off through a 0.45 nalgene filter. The filtrate was concentrated and loaded onto a 24 g RediSep silica column through a 0.45 nalgene filter. Silica gel chromatography (0%-100% acetone/DCM) afforded the title compound as a yellow foam (0.393 g, 59%).

MS: 639 ES−, 303 ES+ ($C_{30}H_{32}N_4O_{10}S$, $C_{21}H_{20}P$)

Intermediate 68: (2S,5R)-2-((4,5-bis(4-methoxybenzyloxy)pyridin-2-yl)methylcarbamoyl)-4-methyl-7-oxo-1,6-diazabicyclo[3.2.1]oct-3-en-6-yl hydrogen sulfate sodium salt

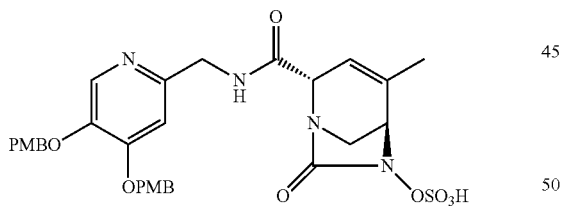

The Dowex® 50WX8-100, ion-exchange resin (35 g) was conditioned by stirring for 3 hours in 2N sodium hydroxide (80 mL). The resin was then loaded into a glass column (2×12 inches) and washed with water until the pH was 7. It was then washed with (1/1) acetone/water (~500 mL), followed by water (~500 mL). (E)-triphenyl(prop-1-enyl)phosphonium (2S,5R)-2-((4,5-bis(4-methoxybenzyloxy)pyridin-2-yl)methylcarbamoyl)-4-methyl-7-oxo-1,6-diazabicyclo[3.2.1]oct-3-en-6-yl sulfate (Intermediate 67, 0.393 g, 0.42 mmol) was taken up in acetone (~2 mL) and diluted with water (~4 mL). The yellow solution was loaded on the resin and eluted with water. The title compound was obtained after lyophilization as an off-white solid (124 mg, 45%).

MS: 641 ES+ ($C_{30}H_{32}N_4O_{10}S$)

68

$^1$H NMR (300 MHz, DMSO-$d_6$) δ: 1.79 (m, 3H); 3.23 (m, 2H); 3.75 (m, 6H); 3.98 (m, 1H); 4.27 (m, 3H); 5.07 (m, 4H); 5.47 (m, 1H); 6.93 (m, 4H); 7.03 (s, 1H); 7.34 (m, 4H); 8.10 (s, 1H).

Example 9

(2S,5R)-2-carbamoyl-4-(methoxymethyl)-7-oxo-1,6-diazabicyclo[3.2.1]oct-3-en-6-yl hydrogen sulfate sodium salt

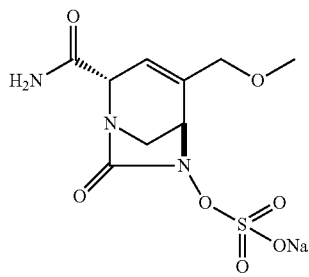

The Dowex® 50WX8-100, ion-exchange resin (10 g) was conditioned by stirring for 3 hours in 2N sodium hydroxide (30 mL). The resin was then loaded into a cartridge and washed with water until the pH was 7. It was then washed with (1/1) acetone/water (~100 mL), followed by water (~100 mL). (E)-triphenyl(prop-1-enyl)phosphonium (2S,5R)-2-carbamoyl-4-(methoxymethyl)-7-oxo-1,6-diazabicyclo[3.2.1]oct-3-en-6-yl sulfate (Intermediate 76, 131 mg, mmol) was taken up in water (~1 mL) and minimum acetonitrile. The yellow solution was loaded on the resin and washed through with water. The title compound was obtained after lyophilization as an off-white solid (38 mg, 50%).

MS: 308 ES+ ($C_9H_{12}N_3NaO_7S$)

$^1$H NMR (300 MHz, $D_2O$) δ: 3.43 (d, 1H); 3.53 (s, 3H); 3.59 (m, 1H); 3.80 (m, 1H); 4.24 (q, 2H); 4.45 (m, 1H); 6.11 (m, 1H).

Intermediate 69: (S)-tert-butyl 2-((tert-butyldimethylsilyloxy)methyl)-4-(methoxymethyl)-5-oxo-5,6-dihydropyridine-1(2H)-carboxylate

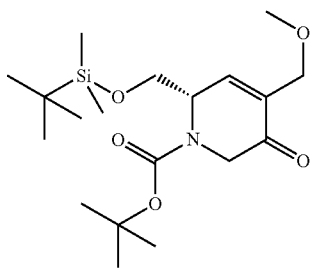 [SMILES: COCC1=C[C@@H](CO[Si](C)(C)C(C)(C)C)N(C(=O)OC(C)(C)C)CC1=O]

To a stirred solution of (S)-tert-butyl 2-((tert-butyldimethylsilyloxy)methyl)-4-(hydroxymethyl)-5-oxo-5,6-dihydropyridine-1(2H)-carboxylate (17.37 g, 46.75 mmol) in DCM (480 mL) was added N1,N1,N8,N8-tetramethylnaphthalene-1,8-diamine (60.1 g, 280.51 mmol). Then it was cooled to 0° C. and trimethyloxonium tetrafluoroborate (20.74 g, 140.25 mmol) was added. It was then stirred at rt for 6 h. Then it was concentrated under reduced pressure. The residue was then taken up in 100 mL Et$_2$O and filtered, washed with 400 mL Et$_2$O. The organic layer was then washed with 10% citric acid, aq. NaHCO$_3$, brine, dried over MgSO$_4$, filtered and concentrated to afford the desired product (16.73 g, 93%) as an oil.

MS: 386 ES+ (C$_{19}$H$_{35}$NO$_5$Si)

$^1$H NMR (300 MHz, CDCl$_3$) δ: 0.01 (s, 6H); 0.81 (s, 9H); 1.42 (s, 9H); 3.28 (s, 3H); 3.91 (m, 5H); 4.33 (d, 1H); 4.78 (m, 1H); 7.01 (s, 1H).

Intermediate 70: (2S)-tert-butyl 2-((tert-butyldimethylsilyloxy)methyl)-5-hydroxy-4-(methoxymethyl)-5,6-dihydropyridine-1(2H)-carboxylate

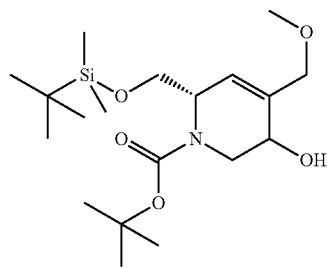 [SMILES: COCC1=C[C@@H](CO[Si](C)(C)C(C)(C)C)N(C(=O)OC(C)(C)C)CC1O]

(S)-tert-butyl 2-((tert-butyldimethylsilyloxy)methyl)-4-(methoxymethyl)-5-oxo-5,6-dihydropyridine-1(2H)-carboxylate) (Intermediate 69, crude, 16.73 g, 43.39 mmol) was dissolved in MeOH (100 mL), cooled to 0° C. and CeCl$_3$ (10.69 g, 43.39 mmol) was added to give a solution. Then NaBH$_4$ (1.642 g, 43.39 mmol) was added slowly as solid, and the mixture was stirred from 0° C. to rt for 30 min. The volatile solvent was removed. The white solid was redissolved in 200 mL EtOAc and washed with sat. NaHCO$_3$, brine, dried over MgSO$_4$, filtered and concentrated. The residue was purified by silica gel column (0-100% EA/Hex) to afford 13.78 g, 82% as an colorless oil.

MS: 410 ES+ (C$_{19}$H$_{37}$NO$_5$Si+Na$^+$)

$^1$H NMR (300 MHz, CDCl$_3$) δ: 0.04 (s, 6H); 0.89 (s, 9H); 1.46 (s, 9H); 3.10 (m, 1H); 3.36 (s, 3H); 3.68 (m, 1H); 3.72 (m, 1H); 4.11 (m, 2H); 4.24 (m, 2H); 4.39 (m, 1H); 5.75 (m, 1H).

Intermediate 71: (2S,5R)-tert-butyl 5-(allyloxy(tert-butoxycarbonyl)amino)-2-((tert-butyldimethylsilyloxy)methyl)-4-(methoxymethyl)-5,6-dihydropyridine-1(2H)-carboxylate

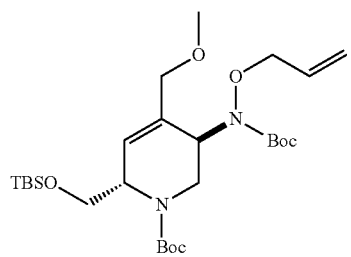 [SMILES: C=CCON(C(=O)OC(C)(C)C)[C@H]1CN(C(=O)OC(C)(C)C)[C@H](CO[Si](C)(C)C(C)(C)C)C=C1COC]

To a stirred solution of (2S,5S)-tert-butyl 2-((tert-butyldimethylsilyloxy)methyl)-5-hydroxy-4-(methoxymethyl)-5,6-dihydropyridine-1(2H)-carboxylate (Intermediate 70, 13.78 g, 35.55 mmol) in DCM (200 mL) at 0° C., pyridine (14.38 mL, 177.77 mmol) and N,N-dimethylpyridin-4-amine (217 mg, 1.78 mmol) was added. Then methanesulfonic anhydride (9.29 g, 53.33 mmol) was added. The mixture was then stirred from 0° C. to rt for 2 hrs. It was diluted with DCM (200 mL) and washed with brine, dried over MgSO$_4$, filtered and concentrated to give (2S,5S)-tert-butyl 2-((tert-butyldimethylsilyloxy)methyl)-4-(methoxymethyl)-5-(methylsulfonyloxy)-5,6-dihydropyridine-1(2H)-carboxylate (crude, 16.9 g) as an pale yellow oil. It was used directly for the next step.

To a stirred solution of tert-butyl allyloxycarbamate (7.39 g, 42.66 mmol) in DMF (150 mL) at rt, potassium 2-methylpropan-2-olate (42.66 mL, 42.66 mmol) was added and gave a purple solution. After 30 min at rt, the mixture was cooled to 0° C. and (2S,5S)-tert-butyl 2-((tert-butyldimethylsilyloxy)methyl)-4-(methoxymethyl)-5-(methylsulfonyloxy)-5,6-dihydropyridine-1(2H)-carboxylate (crude, 16.55 g, 35.55 mmol) in 50.0 mL DMF was added. The mixture was then warmed up to rt for 1 h. It was then diluted with ethyl acetate (200 mL) and washed aqueous sat. NaHCO$_3$ solution, brine, dried over MgSO$_4$, filtered and concentrated to give a residue which contains some starting material. The crude was purified on a silica gel column yielding a colorless oil. (19.3 g). $^1$HNMR shows still a mixture (with hydroxyamine starting material). It was used directly in TBS deprotection.

MS: 565 ES+ (C$_{27}$H$_{50}$N$_2$O$_7$Si+Na$^+$)

$^1$H NMR (300 MHz, CDCl$_3$) δ: 0.04 (s, 6H); 0.89 (s, 9H); 1.47 (s, 9H); 1.52 (s, 9H); 3.14 (m, 1H); 3.31 (s, 3H); 3.72 (m, 3H); 4.15 (m, 3H); 4.44 (m, 3H); 5.28 (m, 2H); 5.97 (m, 2H).

Intermediate 72: (2S,5R)-tert-butyl 5-(allyloxy(tert-butoxycarbonyl)amino)-2-(hydroxymethyl)-4-(methoxymethyl)-5,6-dihydropyridine-1(2H)-carboxylate

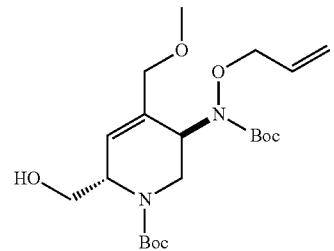 [SMILES: C=CCON(C(=O)OC(C)(C)C)[C@H]1CN(C(=O)OC(C)(C)C)[C@H](CO)C=C1COC]

To a stirred solution of (2S,5R)-tert-butyl 5-(allyloxy(tert-butoxycarbonyl)amino)-2-((tert-butyldimethylsilyloxy)methyl)-4-(methoxymethyl)-5,6-dihydropyridine-1(2H)-carboxylate (Intermediate 71, 35.55 mmol) in THF (100 mL) at 0° C., TBAF (39.11 mL, 39.11 mmol) was added. After 1 hr at 0° C., it was then concentrated to give a residue which was purified by silica gel column (0-100% EA/Hex) to give the desired product (8.82 g, 57.9% over 3 steps) as a colorless oil.

MS: 451 ES+ (C$_{21}$H$_{36}$N$_2$O$_7$+Na$^+$)

$^1$H NMR (300 MHz, CDCl$_3$) δ: 1.47 (s, 9H); 1.52 (s, 9H); 3.14 (dd, 1H); 3.34 (s, 3H); 3.71 (m, 3H); 3.98 (d, 1H), 4.18 (m, 2H); 4.40 (m, 2H); 4.67 (m, 1H); 5.20 (m, 2H); 5.79 (m, 1H); 5.97 (s, 1H).

Intermediate 73: (2S,5R)-tert-butyl 5-(allyloxy(tert-butoxycarbonyl)amino)-2-carbamoyl-4-(methoxymethyl)-5,6-dihydropyridine-1(2H)-carboxylate

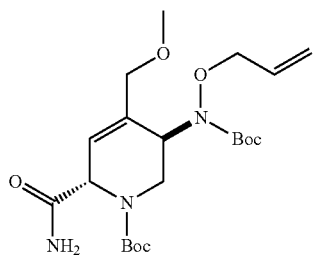 [SMILES: C=CCON(C(=O)OC(C)(C)C)[C@H]1CN(C(=O)OC(C)(C)C)[C@H](C(N)=O)C=C1COC]

Stock oxidation solution: ~480 mg conc. HNO₃ and ~160 mg Na₂Cr₂O₇·2H₂O was dissolved in 32 mL H₂O at rt.

To a stirred solution of (2S,5R)-tert-butyl 5-(allyloxy(tert-butoxycarbonyl)amino)-2-(hydroxymethyl)-4-(methoxymethyl)-5,6-dihydropyridine-1(2H)-carboxylate (Intermediate 72, 8.82 g, 20.58 mmol) in 100 mL MeCN at 0° C., was added sodium periodate (19.37 g, 90.56 mmol). Then 12 mL of the stock oxidation solution was added. The suspension was then stirred at rt for 2 d. An additional 16 mL the above stock solution was added and stirred for 2 more days. The mixture was diluted with 150 mL ethyl acetate, 50 mL 1M pH 7 buffer, and 50 mL 2M NaHSO₃. The aqueous was extracted with 20 mL ethyl acetate. The ethyl acetate layer was then washed with brine. The aqueous layer was checked by LCMS and found containing desired carboxylic acid. The aqueous layer was then extracted with 50 mL ethyl acetate and washed with brine. The combined organic layers was dried over MgSO₄, filtered and concentrated to afford a yellow dry film, (crude 7.11 g, 78%) which was used directly without further purification.

To a stirred solution of (2S,5R)-5-(allyloxy(tert-butoxycarbonyl)amino)-1-(tert-butoxycarbonyl)-4-(methoxymethyl)-1,2,5,6-tetrahydropyridine-2-carboxylic acid (crude, 7.11 g, 16.07 mmol), ammonium chloride (1.719 g, 32.14 mmol), HATU (12.22 g, 32.14 mmol) in DMF (50.0 mL) at rt, was added DIPEA (8.31 g, 64.27 mmol). After stirring at rt for 1 hr, 100 mL EtOAc was added. The organic layer was washed with water, brine. The residue was purified by silica gel column (0-100% Hex/EA) to afford the desired product (3.07 g, 43.3%) as an off-white solid.

MS: 442 ES+ (C₂₁H₃₅N₃O₇)

¹H NMR (300 MHz, CD₃OD) δ: 1.47 (s, 9H); 1.52 (s, 9H); 3.17 (d, 1H); 3.34 (s, 3H); 4.04 (m, 1H); 4.12 (m, 4H); 4.44 (m, 2H); 5.21 (m, 2H); 5.77 (m, 1H); 6.22 (s, 1H).

Intermediate 74: (2S,5R)-5-(allyloxyamino)-4-(methoxymethyl)-1,2,5,6-tetrahydropyridine-2-carboxamide

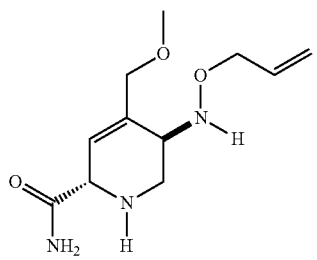 [SMILES: C=CCON[C@H]1CN[C@H](C(N)=O)C=C1COC]

(2S,5R)-tert-butyl 5-(allyloxy(tert-butoxycarbonyl)amino)-2-carbamoyl-4-(methoxymethyl)-5,6-dihydropyridine-1(2H)-carboxylate (Intermediate 73, 3.07 g, 6.95 mmol) was dissolved in 20 mL DCM. Then 5.36 mL TFA was added dropwise at 0° C. The mixture was stirred at rt for 3 h. The solvent was removed in vacuo and co-evaporated twice with 5 mL MeOH. The residue was dissolved in MeOH (10 mL) and ammonium hydroxide (30% in water) was added until it was basic. The mixture was rotovapored at rt and the residue was freeze-dried over night to give a solid. It was dissolved in DCM and purified on silica gel eluting with 0-100% MeOH/DCM to give a off-white solid (1.12 g, 66.8%).

MS: 242 ES+ (C₁H₁₉N₃O₃)

¹H NMR (300 MHz, CD₃OD) δ: 3.31 (s, 3H); 3.55 (m, 3H); 4.05 (m, 4H); 4.58 (m, 1H); 5.20 (m, 2H); 5.96 (m, 2H).

Intermediate 75: (2S,5R)-6-(allyloxy)-4-(methoxymethyl)-7-oxo-1,6-diazabicyclo[3.2.1]oct-3-ene-2-carboxamide

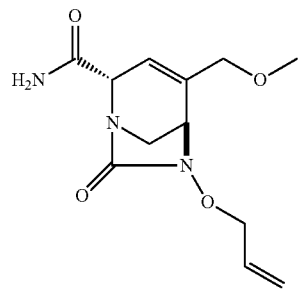 [SMILES: C=CCON1C(=O)N2C[C@H]1C(COC)=C[C@H]2C(N)=O]

To a stirred solution of (2S,5R)-5-(allyloxyamino)-4-(methoxymethyl)-1,2,5,6-tetrahydropyridine-2-carboxamide (Intermediate 74, 1.12 g, 4.64 mmol) in acetonitrile (100 mL), N-ethyl-N-isopropylpropan-2-amine (4.04 mL, 3.00 g, 23.21 mmol) was added, then triphosgene (551 mg, 1.86 mmol) in 20 mL acetonitrile was added slowly via syringe pump over 4 h at 0° C. It was stirred from 0° C. to rt overnight. The solution was concentrated to give a residue, which was then taken up in 50 mL EtOAc and washed with brine, dried over MgSO₄, filtered and concentrated. The residue was purified on a silica gel column eluting with 0-100% ethyl acetate/hexanes gave a yellow oil (420 mg, 34%).

MS: 268 ES+ (C₁₂H₁₇N₃O₄)

¹H NMR (300 MHz, CD₂Cl₂) δ: 3.03 (d, 1H); 3.28 (s, 3H); 3.40 (m, 2H); 3.95 (m, 3H); 4.38 (m, 2H); 5.30 (m, 2H); 5.98 (m, 2H); 6.83 (bs, 2H).

Intermediate 76: (E)-triphenyl(prop-1-enyl)phosphonium (2S,5R)-2-carbamoyl-4-(methoxymethyl)-7-oxo-1,6-diazabicyclo[3.2.1]oct-3-en-6-yl sulfate

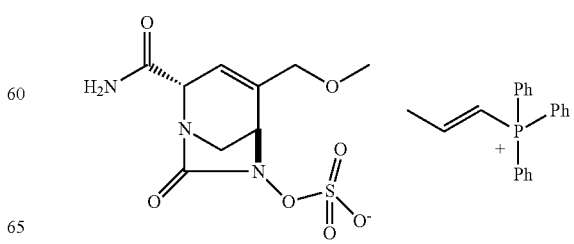

To a solution of (2S,5R)-6-(allyloxy)-4-(methoxymethyl)-7-oxo-1,6-diazabicyclo[3.2.1]oct-3-ene-2-carboxamide (Intermediate 75, 120 mg, 0.45 mmol) and acetic acid (0.051 mL, 0.90 mmol) (dried over sodium sulfate) in DCM (4.0 mL) at room temperature was added tetrakis(triphenylphosphine)palladium(0) (519 mg, 0.45 mmol). The solution was stirred at room temperature for 1 hour. To the reaction mixture was added pyridine (2.0 mL) and sulfur trioxide-pyridine complex (429 mg, 2.69 mmol). The suspension was stirred overnight at room temperature. The suspension was evaporated to dryness and then resuspended in DCM. The solids were filtered off through a 0.45 t nalgene filter. The filtrate was concentrated and loaded onto a 24 g RediSep silica gel column through a 0.45 t nalgene filter. Silica gel chromatography (0%-100% acetone/DCM) afforded the title compound as a yellow foam (0.131 g, 48%).

MS: 304 ES+ ($C_{30}H_{32}N_3O_7PS$, $C_{21}H_{20}P$)

Example 10

(2S,5R)-2-carbamoyl-3-methyl-7-oxo-1,6-diazabicyclo[3.2.1]oct-3-en-6-yl sodium sulfate

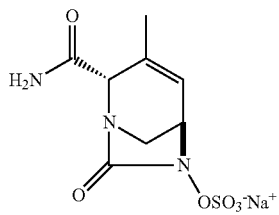

The Dowex® 50WX8-100, ion-exchange resin (25 g, 0.33 mmol) was conditioned by stirring for 3 hours in 2N sodium hydroxide (61 mL, 0.33 mmol). The resin was then loaded into a cartridge and washed with water until the pH was 7. It was then washed with (1/1) acetone/water, followed by water. (E)-triphenyl(prop-1-enyl)phosphonium (2S,5R)-2-carbamoyl-3-methyl-7-oxo-1,6-diazabicyclo[3.2.1]oct-3-en-6-yl sulfate (Intermediate 87, 68 mg, 0.12 mmol) was taken up in water. Acetone was added dropwise until everything was in solution. The yellow solution was loaded on the resin and washed through with water. The fractions containing desired product were combined and lyophilized (25 mg, 79%) yielding a white solid.

Optical rotation: (0.1 g/dL, MeOH)=−287.
MS: 276 ES− ($C_8H_{10}N_3O_6SNa$)
$^1$H NMR (300 MHz, DEUTERIUM OXIDE) δ: 1.76 (dd, J=1.41, 0.85 Hz, 3H) 3.40-3.49 (m, 1H) 3.50-3.58 (m, 1H) 4.27 (dd, J=5.09, 2.45 Hz, 1H) 4.44 (s, 1H) 6.23-6.31 (m, 1H).

Intermediate 77: (6S)-tert-butyl 6-((tert-butyldimethylsilyloxy)methyl)-5-methyl-3-(trimethylsilyloxy)-5,6-dihydropyridine-1(2H)-carboxylate

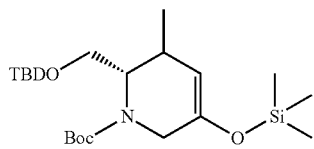

Methyllithium in Et$_2$O (73.2 mL, 117.12 mmol) was added dropwise over 20 min. to a suspension of copper(I) iodide (11.15 g, 58.56 mmol) in Et$_2$O (160 mL) and stirred at 0° C. under nitrogen. After 45 min (S)-tert-butyl 2-((tert-butyldimethylsilyloxy)methyl)-5-oxo-5,6-dihydropyridine-1(2H)-carboxylate (10 g, 29.28 mmol) in Et$_2$O (20 mL) was added dropwise and continued stirring for 45 min. TMs-Cl in THF (58.6 mL, 58.56 mmol) was added, followed by triethylamine (8.16 mL, 58.56 mmol). The resultant mixture was stirred at rt for 2 h, diluted with ethylacetate washed with ice-cold sat. NaHCO$_3$ (3×) and brine, dried over Na$_2$SO$_4$, filtered and concentrated in vacuo to obtain the desired product as a crude yellow oil (~12.58 g, 29.27 mmol).

MS: 330 ES+ ($C_{21}H_{43}NO_4Si_2$)
$^1$H NMR (300 MHz, CHLOROFORM-d) δ: 0.05-0.08 (m, 6H) 0.21 (br. s., 9H) 0.89 (br. s., 9H) 1.04 (d, J=6.40 Hz, 2H) 1.48 (s, 9H) 2.34 (br. s., 1H) 3.42 (br. s., 2H) 3.54 (dd, J=7.44, 3.67 Hz, 1H) 3.91-4.04 (m, 1H) 4.07-4.20 (m, 1H) 4.87 (br. s., 1H)

Intermediate 78: (S)-tert-butyl 2-((tert-butyldimethylsilyloxy)methyl)-3-methyl-5-oxo-5,6-dihydropyridine-1 (2H)-carboxylate

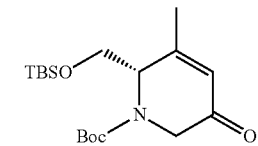 [SMILES: CC1=CC(=O)CN(C(=O)OC(C)(C)C)[C@@H]1CO[Si](C)(C)C(C)(C)C]

The crude (6S)-tert-butyl 6-((tert-butyldimethylsilyloxy)methyl)-5-methyl-3-(trimethylsilyloxy)-5,6-dihydropyridine-1(2H)-carboxylate (Intermediate 77, 12.58 g, 29.27 mmol) in 8 mL ACN was stirred at rt with Pd(OAc)$_2$ (6.57 g, 29.27 mmol) for 2 days. The mixture was diluted with 160 mL EtOAc, filtered through celite, concentrated in vacuo and subjected to flash chromatography (220 g, 0-30% EA/Hex) to obtain the desired product (6.07 g, 58.3%) (over two steps) as a beige solid.

MS: 256 ES+ ($C_{18}H_{33}NO_4Si$)
$^1$H NMR (300 MHz, CHLOROFORM-d) δ: −0.02-0.07 (m, 6H) 0.80-0.91 (m, 9H) 1.49 (s, 9H) 2.04 (d, J=1.13 Hz, 3H) 3.69-4.06 (m, 3H) 4.32-4.73 (m, 2H) 6.08 (s, 1H)

Intermediate 79: (2S,5S)-tert-butyl 2-((tert-butyldimethylsilyloxy)methyl)-5-hydroxy-3-methyl-5,6-dihydropyridine-1(2H)-carboxylate

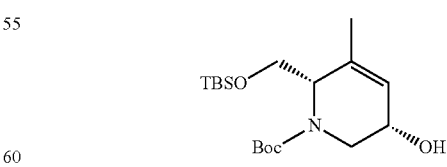

To a stirred solution of cerium(III) chloride heptahydrate (6.36 g, 17.07 mmol) and (S)-tert-butyl 2-((tert-butyldimethylsilyloxy)methyl)-3-methyl-5-oxo-5,6-dihydropyridine-1(2H)-carboxylate (Intermediate 78, 6.07 g, 17.07 mmol) in MeOH (100 mL) at 0° C., sodium tetrahydroborate (0.646 g, 17.07 mmol) was added as a solid. The mixture was stirred at ambient temp for 1 h. The mixture was concentrated and diluted with NH₄Cl(aq), H₂O and extracted with ether. The ether layer was separated and washed with brine, dried over Na₂SO₄, filtered and concentrated to give the desired product (5.48 g, 90%) as a yellow oil.

MS: 258 ES+ ($C_{18}H_{35}NO_4Si$)

¹H NMR (300 MHz, CHLOROFORM-d) δ: 0.06 (s, 6H) 0.78-0.94 (m, 9H) 1.38-1.50 (m, 9H) 1.56 (br. s., 1H) 1.78 (s, 3H) 2.90-3.39 (m, 1H) 3.67-4.28 (m, 5H) 5.80 (br. s., 1H).

Intermediate 80: (2S,5R)-tert-butyl 5-(N-(allyloxy)-2-nitrophenylsulfonamido)-2-((tert-butyldimethylsilyloxy)methyl)-3-methyl-5,6-dihydropyridine-1(2H)-carboxylate

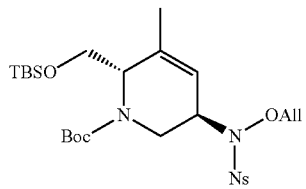

To a stirred suspension of (2S,5S)-tert-butyl 2-((tert-butyldimethylsilyloxy)methyl)-5-hydroxy-3-methyl-5,6-dihydropyridine-1(2H)-carboxylate (Intermediate 79, 5.48 g, 15.33 mmol), N-(allyloxy)-2-nitrobenzenesulfonamide (7.92 g, 30.65 mmol) and triphenylphosphine (12.06 g, 45.98 mmol) in toluene (20 mL) was cooled in an ice-bath and added dropwise (E)-diisopropyl diazene-1,2-dicarboxylate (8.91 ml, 45.98 mmol). Reaction was let warm up to rt and continued to stir at rt for 2 h. The reaction mixture was evaporated and the crude product was loaded onto silica gel, purified via flash chromatography (750 g, 0-50%) to obtain the desired product (7.05 g, 77%) as a yellow oil.

MS: 598 ES+ ($C_{27}H_{43}N_3O_8SSi$)

Intermediate 81: (2S,5R)-tert-butyl 5-(N-(allyloxy)-2-nitrophenylsulfonamido)-2-(hydroxymethyl)-3-methyl-5,6-dihydropyridine-1(2H)-carboxylate

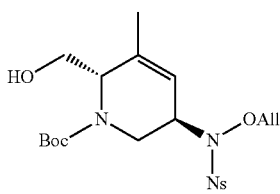

(2S,5R)-tert-butyl 5-(N-(allyloxy)-2-nitrophenylsulfonamido)-2-((tert-butyldimethylsilyloxy)methyl)-3-methyl-5,6-dihydropyridine-1(2H)-carboxylate (Intermediate 80, 7.05 g, 11.79 mmol) in THF (100 mL) was charged with nitrogen and cooled in an ice-bath. Tetrabutylammonium fluoride in THF (14.15 mL, 14.15 mmol) was added to the solution and stirred at rt. The reaction mixture was evaporated and the crude product was loaded onto silica and purified via flash chromatography (30-100% EA/Hexanes, 40 g column), to obtain the desired product (4.52 g, 79%) as a pale yellow foam.

MS: 484 ES+ ($C_{21}H_{29}N_3O_8S$)

¹H NMR (300 MHz, CHLOROFORM-d) δ: 1.43 (br. s., 9H) 1.80 (br. s., 3H) 3.35 (br. s., 1H) 3.73 (d, J=6.22 Hz, 1H) 3.88 (br. s., 1H) 4.35 (br. s., 5H) 5.15-5.29 (m, 2H) 5.45 (s, 1H) 5.77 (br. s., 1H) 7.61 (d, J=7.35 Hz, 1H) 7.76 (dd, J=12.62, 7.54 Hz, 2H) 8.13 (d, J=7.72 Hz, 1H)

Intermediate 82: (2S,5R)-5-(N-(allyloxy)-2-nitrophenylsulfonamido)-1-(tert-butoxycarbonyl)-3-methyl-1,2,5,6-tetrahydropyridine-2-carboxylic acid

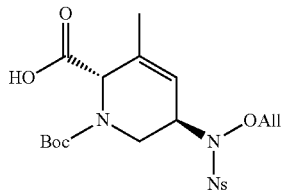

To a solution of periodic acid (4.10 g, 17.99 mmol) in wet acetonitrile (25 mL) (0.75% water by volume) at room temperature was added chromium(VI) oxide (0.490 g, 4.90 mmol). The mixture was stirred until complete dissolution was achieved.

To a solution of (2S,5R)-tert-butyl 5-(N-(allyloxy)-2-nitrophenylsulfonamido)-2-(hydroxymethyl)-3-methyl-5,6-dihydropyridine-1(2H)-carboxylate (Intermediate 81, 4.52 g, 9.35 mmol) in wet acetonitrile (25 mL) (0.75% by volume) at 0° C. was added dropwise the previously formed periodic acid/chromium oxide solution. The reaction was stirred o/n at rt. The reaction mixture was diluted with CHCl₃ and washed with conc. citric acid/water and then with brine (2×). The organics were dried over magnesium sulfate, filtered and concentrated to obtain the desired product (3.98 g, 86%) as a beige foam.

MS: 498 ES+ ($C_{21}H_{27}N_3O_9S$)

¹H NMR (300 MHz, CHLOROFORM-d) δ: 1.43 (s, 9H) 1.88 (br. s., 3H) 3.43 (d, J=15.07 Hz, 1H) 4.09-4.51 (m, 5H) 4.60-4.92 (m, 1H) 5.14-5.28 (m, 2H) 5.46 (br. s., 1H) 5.74 (br. s., 1H) 7.63 (d, J=6.03 Hz, 1H) 7.69-7.85 (m, 2H) 8.12 (d, J=7.72 Hz, 1H)

Intermediate 83: (2S,5R)-tert-butyl 5-(N-(allyloxy)-2-nitrophenylsulfonamido)-2-carbamoyl-3-methyl-5,6-dihydropyridine-1(2H)-carboxylate

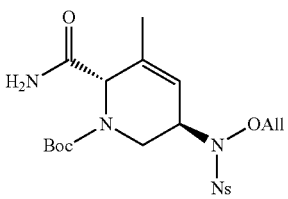

To a solution of (2S,5R)-5-(N-(allyloxy)-2-nitrophenylsulfonamido)-1-(tert-butoxycarbonyl)-3-methyl-1,2,5,6-tetrahydropyridine-2-carboxylic acid (Intermediate 82, 3.98 g, 8.00 mmol) in DMF (20 mL) at room temperature was added ammonia hydrochloride (0.856 g, 16.00 mmol), 2-(3H-[1,2,3]triazolo[4,5-b]pyridin-3-yl)-1,1,3,3-tetramethylisouronium hexafluorophosphate(V) (4.56 g, 12.00 mmol) and N-ethyl-N-isopropylpropan-2-amine (5.57 mL, 32.00 mmol). The reaction mixture was stirred at room temperature for 2 h. The reaction mixture was diluted with ethyl acetate and washed with saturated sodium bicarbonate and three times with 1:1 brine:water. The organics were dried over magnesium sulfate, filtered and concentrated. The crude product was purified with silica gel chromatography (220 g, 10%-80% ethyl acetate/hexanes) to yield the desired product (2.79 g, 70.2%) as an yellow foam.

MS: 497 ES+ ($C_{21}H_{28}N_4O_8S$)

$^1$H NMR (300 MHz, CHLOROFORM-d) δ: 1.40-1.48 (m, 9H) 1.81 (s, 3H) 3.34 (d, J=12.43 Hz, 1H) 4.19-4.53 (m, 4H) 4.84 (br. s., 1H) 5.14-5.38 (m, 3H) 5.52 (br. s., 1H) 5.74 (br. s., 1H) 6.45 (br. s., 1H) 7.58-7.64 (m, 1H) 7.76 (dtd, J=14.01, 7.69, 7.69, 6.22 Hz, 2H) 8.11 (d, J=7.72 Hz, 1H)

Intermediate 84: (2S,5R)-5-(N-(allyloxy)-2-nitrophenylsulfonamido)-3-methyl-1,2,5,6-tetrahydropyridine-2-carboxamide

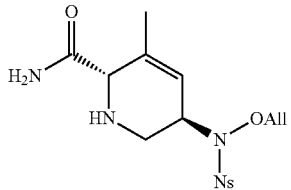

(2S,5R)-tert-butyl 5-(N-(allyloxy)-2-nitrophenylsulfonamido)-2-carbamoyl-3-methyl-5,6-dihydropyridine-1(2H)-carboxylate (Intermediate 83, 2.785 g, 5.61 mmol) and zinc(II) bromide (2.53 g, 11.22 mmol) was added DCM (10 mL) and stirred at rt overnight. The reaction mixture was diluted with dichloromethane and washed with saturated sodium bicarbonate and brine. The organics were dried over magnesium sulfate, filtered and concentrated to afford the desired product (2.015 g, 91%) as a beige foam.

MS: 397 ES+ ($C_{16}H_{20}N_4O_6S$)

$^1$H NMR (300 MHz, CHLOROFORM-d) δ: 1.97 (s, 3H) 2.96 (br. s., 2H) 3.77 (br. s., 1H) 4.29 (br. s., 1H) 4.34-4.52 (m, 2H) 5.21-5.44 (m, 4H) 5.55 (br. s., 1H) 5.75-5.94 (m, 1H) 7.13 (br. s., 1H) 7.63 (dd, J=7.82, 1.41 Hz, 1H) 7.70-7.88 (m, 2H) 8.15 (dd, J=7.72, 1.51 Hz, 1H)

Intermediate 85: (2S,5R)-5-(allyloxyamino)-3-methyl-1,2,5,6-tetrahydropyridine-2-carboxamide

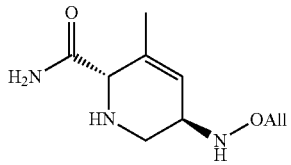

To (2S,5R)-5-(N-(allyloxy)-2-nitrophenylsulfonamido)-3-methyl-1,2,5,6-tetrahydropyridine-2-carboxamide (Intermediate 84, 2.01 g, 5.07 mmol) and potassium carbonate (2.172 g, 15.72 mmol) in acetonitrile (10 mL) was added benzenethiol (1.557 mL, 15.21 mmol) and stirred at rt for 2 h. The solvent was evaporated at 30° C., redissolved in DCM and a little bit MeOH, filtered and loaded onto silica gel at 30° C. The crude mixture was purified via flash chromatography (220 g column, 0-20% MeOH/DCM), the fractions were concentrated at 35° C. and dried under high-vacuum to obtain the desired product (0.759 g, 70.9%) as an off-white solid.

MS: 212 ES+ ($C_{10}H_{17}N_3O_2$)

$^1$H NMR (300 MHz, CHLOROFORM-d) δ: 1.94 (s, 3H) 2.93-3.09 (m, 2H) 3.40 (br. s., 1H) 3.78 (s, 1H) 4.17-4.23 (m, 2H) 5.19-5.25 (m, 1H) 5.25-5.33 (m, 1H) 5.37 (br. s., 1H) 5.53 (br. s., 1H) 5.94 (ddt, J=17.00, 10.60, 5.98, 5.98 Hz, 1H) 7.14 (br. s., 1H)

Intermediate 86: (2S,5R)-6-(allyloxy)-3-methyl-7-oxo-1,6-diazabicyclo[3.2.1]oct-3-ene-2-carboxamide

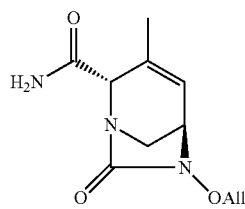

A solution of (2S,5R)-5-(allyloxyamino)-3-methyl-1,2,5,6-tetrahydropyridine-2-carboxamide (Intermediate 85, 0.758 g, 3.59 mmol) and N-ethyl-N-isopropylpropan-2-amine (2.507 mL, 14.35 mmol) in acetonitrile (350 mL) was cooled to below 0° C. in an ice-salt bath and added a solution of bis(trichloromethyl) carbonate (0.426 g, 1.44 mmol) in ACN (15 mL) at a rate of 0.1 mL/min. The reaction mixture was stirred at rt overnight. The solvents were evaporated at 30° C., and the crude mixture was redissolved in EtOAc. The crude organic solution was washed with sat. NaHCO$_3$, brine, dried over MgSO$_4$, and filtered. The organics were evaporated and the crude product was loaded onto silica gel at 30° C. and Purified via flash chromatography (80 g, 0-100% EtOAc/Hexanes), to obtain the desired product (0.700 g, 82%) as pale yellow oil.

MS: 238 ES+ ($C_{11}H_{15}N_3O_3$)

$^1$H NMR (300 MHz, CHLOROFORM-d) δ: 1.92 (d, J=0.75 Hz, 3H) 3.12-3.20 (m, 1H) 3.26-3.34 (m, 1H) 3.82 (dd, J=4.99, 2.73 Hz, 1H) 4.30 (s, 1H) 4.34-4.50 (m, 2H) 5.28-5.41 (m, 2H) 5.44 (br. s., 1H) 5.94-6.09 (m, 1H) 6.09-6.15 (m, 1H) 6.68 (br. s., 1H)

Intermediate 87: (E)-triphenyl(prop-1-enyl)phosphonium (2S,5R)-2-carbamoyl-3-methyl-7-oxo-1,6-diazabicyclo[3.2.1]oct-3-en-6-yl sulfate

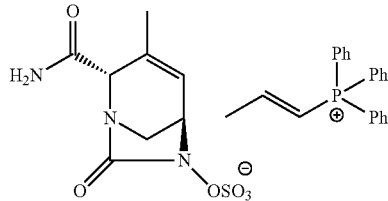

To a solution of (2S,5R)-6-(allyloxy)-3-methyl-7-oxo-1,6-diazabicyclo[3.2.1]oct-3-ene-2-carboxamide (Intermediate 86, 200 mg, 0.84 mmol) and AcOH (0.097 mL, 1.69 mmol) (dried over sodium sulfate) in CH$_2$Cl$_2$ (7 mL) at room temperature was added Pd(Ph$_3$P)$_4$ (450 mg, 0.39 mmol). The solution was stirred at rt for 45 min. To this reaction mixture was added pyridine (7.00 mL) and sulfur trioxide pyridine complex (496 mg, 3.12 mmol) and continued stirring under $N_2$ at rt overnight. The suspension was evaporated to dryness at 39° C. and then resuspended in DCM. The solids were filtered off through a 0.45 t nalgene filter. The filtrate was loaded onto column. Silica gel chromatography (80 g column, 0%-100% acetone/DCM) afforded the desired product (68.0 mg, 13.92%) as an off-white foam.

MS: 276 ES– ($C_{29}H_{30}N_3O_6PS$)

Example 11

(2S,5R)-2-carbamoyl-3-isopropyl-7-oxo-1,6-diazabicyclo[3.2.1]oct-3-en-6-yl sodium sulfate

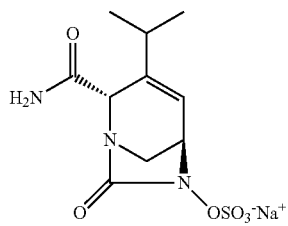

(2S,5R)-2-carbamoyl-3-methyl-7-oxo-1,6-diazabicyclo [3.2.1]oct-3-en-6-yl hydrogen sulfate (4.02 mg, 89%) was prepared a similar manner as described in Example 10 as a white solid, using (E)-triphenyl(prop-1-enyl)phosphonium (2S,5R)-2-carbamoyl-3-isopropyl-7-oxo-1,6-diazabicyclo [3.2.1]oct-3-en-6-yl sulfate (Intermediate 98, 9 mg, 0.12 mmol).

MS: 304 ES– ($C_{10}H_{14}N_3O_6SNa$)

$^1$H NMR (600 MHz, DEUTERIUM OXIDE) δ: 0.95 (d, J=7.15 Hz, 3H) 1.01 (d, J=6.78 Hz, 3H) 2.13 (spt, J=6.78 Hz, 1H) 3.38 (dd, J=11.29, 2.26 Hz, 1H) 3.54 (d, J=11.29 Hz, 1H) 4.27 (dd, J=5.27, 2.64 Hz, 1H) 4.49 (s, 1H) 6.26 (d, J=5.27 Hz, 1H)

Intermediate 88: (6S)-tert-butyl 6-((tert-butyldimethylsilyloxy)methyl)-5-isopropyl-3-(trimethylsilyloxy)-5,6-dihydropyridine-1(2H)-carboxylate

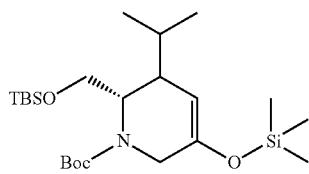 [SMILES: CC(C)C1C=C(O[Si](C)(C)C)CN(C(=O)OC(C)(C)C)[C@@H]1CO[Si](C)(C)C(C)(C)C]

(2S,5R)-2-carbamoyl-3-methyl-7-oxo-1,6-diazabicyclo [3.2.1]oct-3-en-6-yl hydrogen sulfate (theoretically 6.7 g) was prepared a similar manner as described in Intermediate 77 as a yellow oil, using (S)-tert-butyl 2-((tert-butyldimethylsilyloxy)methyl)-5-oxo-5,6-dihydropyridine-1(2H)-carboxylate (Intermediate 50, 5 g, 14.64 mmol) as a starting material.

MS: 330 ES+ ($C_{23}H_{47}NO_4Si_2$)

$^1$H NMR (300 MHz, CHLOROFORM-d) δ: 0.05-0.08 (m, 6H) 0.21 (br. s., 9H) 0.89 (br. s., 9H) 1.04 (d, J=6.40 Hz, 2H) 1.48 (s, 9H) 2.34 (br. s., 1H) 3.42 (br. s., 2H) 3.54 (dd, J=7.44, 3.67 Hz, 1H) 3.91-4.04 (m, 1H) 4.07-4.20 (m, 1H) 4.87 (br. s., 1H)

Intermediate 89: (S)-tert-butyl 2-((tert-butyldimethylsilyloxy)methyl)-3-isopropyl-5-oxo-5,6-dihydropyridine-1(2H)-carboxylate

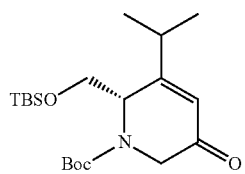 [SMILES: CC(C)C1=CC(=O)CN(C(=O)OC(C)(C)C)[C@@H]1CO[Si](C)(C)C(C)(C)C]

(S)-tert-butyl 2-((tert-butyldimethylsilyloxy)methyl)-3-isopropyl-5-oxo-5,6-dihydropyridine-1(2H)-carboxylate (804 mg, 14.32%) (over two steps) was prepared as described in Intermediate 78 as a yellow oil, using (6S)-tert-butyl 6-((tert-butyldimethylsilyloxy)methyl)-5-isopropyl-3-(trimethylsilyloxy)-5,6-dihydropyridine-1(2H)-carboxylate (Intermediate 88, theoretically 6.7 g, 14.64 mmol).

MS: 384 ES+ ($C_{20}H_{37}NO_4Si$)

$^1$H NMR (300 MHz, CHLOROFORM-d) δ: 0.01 (d, J=3.96 Hz, 6H) 0.84 (s, 9H) 1.14-1.23 (m, 6H) 1.49 (s, 9H) 2.35-2.50 (m, 1H) 3.77-3.94 (m, 2H) 3.96-4.05 (m, 1H) 4.32-4.85 (m, 2H) 6.05-6.14 (m, 1H)

Intermediate 90: (2S,5S)-tert-butyl 2-((tert-butyldimethylsilyloxy)methyl)-5-hydroxy-3-isopropyl-5,6-dihydropyridine-1(2H)-carboxylate

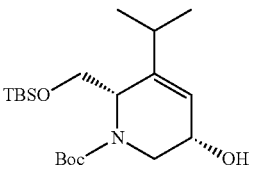 [SMILES: CC(C)C1=C[C@H](O)CN(C(=O)OC(C)(C)C)[C@@H]1CO[Si](C)(C)C(C)(C)C]

(2S,5S)-tert-butyl 2-((tert-butyldimethylsilyloxy) methyl)-5-hydroxy-3-isopropyl-5,6-dihydropyridine-1(2H)-carboxylate (0.732 g, 91%), was prepared a similar manner as described for Intermediate 79 as a colorless oil, using (S)-tert-butyl 2-((tert-butyldimethylsilyloxy)-methyl)-3-isopropyl-5-oxo-5,6-dihydropyridine-1(2H)-carboxylate (Intermediate 89, 804 mg, 2.10 mmol) and N-(allyloxy)-2-nitrobenzenesulfonamide (0.979 g, 3.79 mmol) as starting materials.

MS: 286 ES+ ($C_{20}H_{39}NO_4Si$)

$^1$H NMR (300 MHz, CHLOROFORM-d) δ: 0.06 (d, J=1.51 Hz, 6H) 0.89 (s, 9H) 1.09 (dd, J=10.55, 6.78 Hz, 6H) 1.48 (s, 9H) 2.13-2.26 (m, 1H) 2.86 (br. s., 1H) 3.36-3.52 (m, 1H) 3.60-3.78 (m, 2H) 3.82-4.42 (m, 3H) 5.73-5.91 (m, 1H)

Intermediate 91: (2S,5R)-tert-butyl 5-(N-(allyloxy)-2-nitrophenylsulfonamido)-2-((tert-butyldimethylsilyloxy)methyl)-3-isopropyl-5,6-dihydropyridine-1(2H)-carboxylate

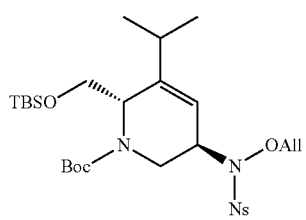

(2S,5R)-tert-butyl 5-(N-(allyloxy)-2-nitrophenylsulfonamido)-2-((tert-butyldimethylsilyloxy)methyl)-3-isopropyl-5,6-dihydropyridine-1(2H)-carboxylate (0.928 g, 78%) was prepared as described in Intermediate 80 as a pale yellow oil, using (2S,5S)-tert-butyl 2-((tert-butyldimethylsilyloxy)methyl)-5-hydroxy-3-isopropyl-5,6-dihydropyridine-1(2H)-carboxylate (Intermediate 90, 0.731 g, 1.90 mmol) as a starting material.

MS: 626 ES+ ($C_{29}H_{47}N_3O_8SSi$)

$^1$H NMR (300 MHz, CHLOROFORM-d) δ: 0.01 (s, 6H) 0.86 (s, 9H) 0.95-1.09 (m, 6H) 1.42 (br. s., 9H) 2.14-2.37 (m, 1H) 3.50 (dd, J=14.60, 4.43 Hz, 1H) 3.64-3.89 (m, 2H) 4.21-4.61 (m, 5H) 5.12-5.53 (m, 3H) 5.66-5.88 (m, 1H) 7.61 (d, J=7.72 Hz, 1H) 7.68-7.83 (m, 2H) 8.13 (d, J=8.10 Hz, 1H)

Intermediate 92: (2S,5R)-tert-butyl 5-(N-(allyloxy)-2-nitrophenylsulfonamido)-2-(hydroxymethyl)-3-isopropyl-5,6-dihydropyridine-1(2H)-carboxylate

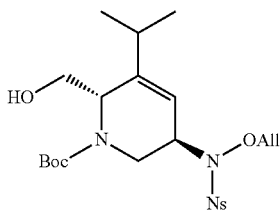

(2S,5R)-tert-butyl 5-(N-(allyloxy)-2-nitrophenylsulfonamido)-2-(hydroxymethyl)-3-isopropyl-5,6-dihydropyridine-1(2H)-carboxylate (660 mg, 87%) was prepared a similar manner as described in Intermediate 81 as a yellow oil, using (2S,5R)-tert-butyl 5-(N-(allyloxy)-2-nitrophenylsulfonamido)-2-((tert-butyldimethylsilyloxy)methyl)-3-isopropyl-5,6-dihydropyridine-1(2H)-carboxylate (Intermediate 91, 0.928 g, 1.48 mmol) as a starting material.

MS: 512 ES+ ($C_{23}H_{33}N_3O_8S$)

Intermediate 93: (2S,5R)-5-(N-(allyloxy)-2-nitrophenylsulfonamido)-1-(tert-butoxycarbonyl)-3-isopropyl-1,2,5,6-tetrahydropyridine-2-carboxylic acid

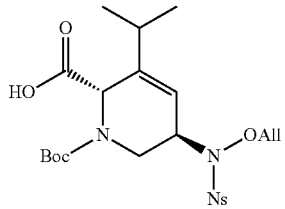

((2S,5R)-5-(N-(allyloxy)-2-nitrophenylsulfonamido)-1-(tert-butoxycarbonyl)-3-isopropyl-1,2,5,6-tetrahydropyridine-2-carboxylic acid (0.595 g, 87.76%) was prepared a similar manner as described in Intermediate 82 as a yellow oil, using (2S,5R)-tert-butyl 5-(N-(allyloxy)-2-nitrophenylsulfonamido)-2-(hydroxymethyl)-3-isopropyl-5,6-dihydropyridine-1(2H)-carboxylate (Intermediate 92, 660 mg, 1.29 mmol) as a starting material.

MS: 526 ES+ ($C_{23}H_{31}N_3O_9S$)

$^1$H NMR (300 MHz, DMSO-d$^6$) δ: 0.62-1.02 (m, 6H) 1.36 (br. s, 9H) 2.78-3.26 (m, 1H) 3.34-3.62 (m, 1H) 3.65-4.10 (m, 1H) 4.10-4.45 (m, 3H) 4.46-4.84 (m, 1H) 5.01-5.64 (m, 3H) 5.64-5.99 (m, 1H) 7.87-8.14 (m, 4H) 13.03 (br. s, 1H)

Intermediate 94: (2S,5R)-tert-butyl 5-(N-(allyloxy)-2-nitrophenylsulfonamido)-2-carbamoyl-3-isopropyl-5,6-dihydropyridine-1(2H)-carboxylate

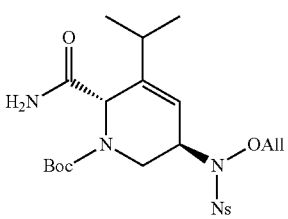

(2S,5R)-tert-butyl 5-(N-(allyloxy)-2-nitrophenylsulfonamido)-2-carbamoyl-3-isopropyl-5,6-dihydropyridine-1(2H)-carboxylate (0.260 g, 43.7%) was prepared a similar manner as described in Intermediate 83 as a pale yellow oil, using (2S,5R)-5-(N-(allyloxy)-2-nitrophenylsulfonamido)-1-(tert-butoxycarbonyl)-3-isopropyl-1,2,5,6-tetrahydropyridine-2-carboxylic acid (Intermediate 93, 0.595 g, 1.13 mmol) as a starting material.

MS: 525 ES+ ($C_{23}H_{32}N_4O_8S$)

$^1$H NMR (300 MHz, CHLOROFORM-d) δ: 1.02 (d, J=6.97 Hz, 6H) 1.44 (br. s., 9H) 2.24 (s, 1H) 3.29-3.40 (m, 1H) 4.18-4.50 (m, 4H) 5.02 (br. s., 1H) 5.15-5.28 (m, 3H) 5.73 (s, 2H) 6.44 (s, 1H) 7.60-7.64 (m, 1H) 7.76 (dqd, J=14.76, 7.54, 7.54, 7.54, 1.60 Hz, 2H) 8.11 (dd, J=7.91, 1.32 Hz, 1H)

Intermediate 95: (2S,5R)-5-(N-(allyloxy)-2-nitrophenylsulfonamido)-3-isopropyl-1,2,5,6-tetrahydropyridine-2-carboxamide

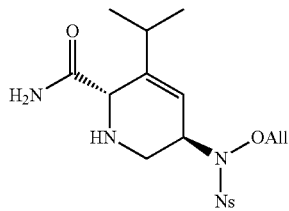

(2S,5R)-5-(N-(allyloxy)-2-nitrophenylsulfonamido)-3-isopropyl-1,2,5,6-tetrahydropyridine-2-carboxamide (160 mg, 86%) was prepared a similar manner as described in Intermediate 84 as a beige solid, using (2S,5R)-tert-butyl 5-(N-(allyloxy)-2-nitrophenylsulfonamido)-2-carbamoyl-3-isopropyl-5,6-dihydropyridine-1(2H)-carboxylate (Intermediate 94, 260 mg, 0.5 mmol) as a starting material.

MS: 425 ES+ ($C_{18}H_{24}N_4O_6S$)

$^1$H NMR (300 MHz, CHLOROFORM-d) δ: 1.01-1.12 (m, 6H) 2.64-2.77 (m, 1H) 2.82-3.06 (m, 2H) 3.93 (s, 1H) 4.33 (br. s., 1H) 4.35-4.55 (m, 2H) 5.21-5.31 (m, 3H) 5.59 (br. s., 1H) 5.76-5.93 (m, 1H) 7.04 (br. s., 1H) 7.62 (dd, J=7.54, 1.51 Hz, 1H) 7.71-7.85 (m, 2H) 8.14 (dd, J=7.82, 1.41 Hz, 1H)

Intermediate 96: (2S,5R)-5-(allyloxyamino)-3-isopropyl-1,2,5,6-tetrahydropyridine-2-carboxamide

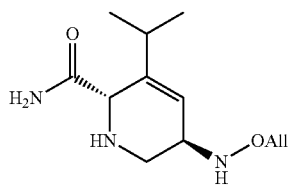

(2S,5R)-5-(allyloxyamino)-3-isopropyl-1,2,5,6-tetrahydropyridine-2-carboxamide (55.0 mg, 61.0%) was prepared a similar manner as described in Intermediate 85 as an off-white solid, using (2S,5R)-5-(N-(allyloxy)-2-nitrophenylsulfonamido)-3-isopropyl-1,2,5,6-tetrahydropyridine-2-carboxamide (Intermediate 95, 160 mg, 0.38 mmol) as a starting material.

MS: 340 ES+ ($C_{12}H_{21}N_3O_2$)

$^1$H NMR (300 MHz, CHLOROFORM-d) δ: 1.05 (d, J=6.97 Hz, 3H) 1.11 (d, J=6.78 Hz, 3H) 2.54-2.68 (m, 1H) 2.94-3.11 (m, 2H) 3.45 (br. s, 1H) 3.95 (br. s., 1H) 4.20 (d, J=5.84 Hz, 2H) 5.22 (d, J=10.36 Hz, 1H) 5.29 (dd, J=17.14, 1.51 Hz, 1H) 5.38 (br. s., 1H) 5.58 (d, J=3.58 Hz, 1H) 5.87-6.02 (m, 1H) 7.00 (br. s., 1H)

Intermediate 97: (2S,5R)-6-(allyloxy)-3-isopropyl-7-oxo-1,6-diazabicyclo[3.2.1]oct-3-ene-2-carboxamide

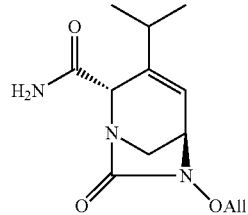

(2S,5R)-6-(allyloxy)-3-isopropyl-7-oxo-1,6-diazabicyclo[3.2.1]oct-3-ene-2-carboxamide (0.46 mg, 77%) was prepared a similar manner as described in Intermediate 86 as a pale yellow oil, using (2S,5R)-5-(allyloxyamino)-3-isopropyl-1,2,5,6-tetrahydropyridine-2-carboxamide (Intermediate 96, 0.54 mg, 0.23 mmol) as a starting material.

MS: 266 ES+ ($C_{13}H_{19}N_3O_3$)

$^1$H NMR (300 MHz, CHLOROFORM-d) δ: 1.02 (d, J=6.78 Hz, 3H) 1.10 (d, J=6.78 Hz, 3H) 2.60 (quin, J=6.69 Hz, 1H) 3.14-3.22 (m, 1H) 3.24-3.32 (m, 1H) 3.86 (dd, J=5.27, 2.83 Hz, 1H) 4.33-4.50 (m, 3H) 5.26-5.52 (m, 3H) 5.94-6.15 (m, 2H) 6.63 (br. s., 1H)

Intermediate 98: (E)-triphenyl(prop-1-enyl)phosphonium (2S,5R)-2-carbamoyl-3-isopropyl-7-oxo-1,6-diazabicyclo[3.2.1]oct-3-en-6-yl sulfate

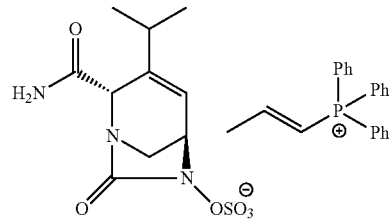

(E)-triphenyl(prop-1-enyl)phosphonium (2S,5R)-2-carbamoyl-3-isopropyl-7-oxo-1,6-diazabicyclo[3.2.1]oct-3-en-6-yl sulfate (9.00 mg, 8.73%) was prepared in a similar manner as described in Intermediate 87 as a colorless oil, using (2S,5R)-6-(allyloxy)-3-isopropyl-7-oxo-1,6-diazabicyclo[3.2.1]oct-3-ene-2-carboxamide (Intermediate 97, 45 mg, 0.17 mmol) as a starting material.

MS: 304 ES− ($C_{31}H_{34}N_3O_6PS$)

Example 12

(2S,5R)-4-carbamoyl-2-(methoxymethyl)-7-oxo-1,6-diazabicyclo[3.2.1]oct-3-en-6-yl hydrogen sulfate, monosodium salt

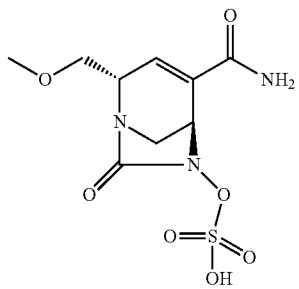 [SMILES: COC[C@@H]1C=C(C(N)=O)[C@@H]2CN1C(=O)N2OS(=O)(=O)O]

A stirred solution of (2S,5R)-6-hydroxy-2-(methoxymethyl)-7-oxo-1,6-diazabicyclo[3.2.1]oct-3-ene-4-carboxamide (Intermediate 116, 21 mg, 0.09 mmol) in pyridine (2 mL) was prepared and placed under a nitrogen atmosphere. To it was added Sulfur trioxide-Pyridine complex (6 eq, 88 mg, 0.55 mmol). This mixture was stirred overnight at ambient temperature; the mixture was then concentrated under reduced pressure and the residue dissolved in a small volume of water. A Dowex column was prepared as follows: Dowex® 50WX8-100, ion-exchange resin (16 g) was conditioned by stirring for 3 hours in 2N sodium hydroxide (34 mL). The resin was then loaded into a cartridge and washed with water until pH 7. It was then washed with (1/1) acetone/water, followed by water again. The aqueous solution of crude product was applied to the top of this column; the desired product was eluted with water. The fractions containing desired product were combined and lyophilized. The obtained material was triturated with methanol and the filtrate concentrated and freeze-dried again. The desired product was obtained as a white solid (19 mg, 62%).

MS: 308 ES+ ($C_9H_{13}N_3O_7S$)

$^1$H NMR (300 MHz, $D_2O$) δ: 3.37-3.50 (m, 4H) 3.51-3.63 (m, 2H) 3.72-3.88 (m, 3H) 4.26 (ddd, J=7.79, 4.67, 3.21 Hz, 1H) 4.77 (d, J=1.51 Hz, 1H) 6.61 (d, J=2.83 Hz, 1H)

Intermediate 99: (S)-tert-butyl 1-(tert-butyldimethylsilyloxy)but-3-en-2-yl(2-oxoethyl)carbamate

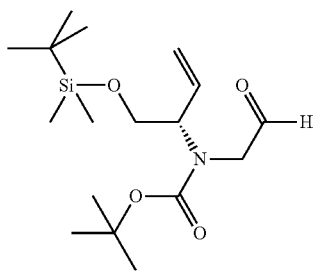 [SMILES: C=C[C@@H](CO[Si](C)(C)C(C)(C)C)N(CC=O)C(=O)OC(C)(C)C]

A stirred solution of (S)-tert-butyl 1-(tert-butyldimethylsilyloxy)but-3-en-2-yl(2-(methoxy(methyl)amino)-2-oxoethyl)carbamate (Intermediate 5, 28.36 g, 70.44 mmol) in methylene chloride (247 mL) was prepared, cooled in a dry ice/acetone bath, and placed under nitrogen. To it was added diisobutylaluminum hydride (1.0 M in methylene chloride) (106 mL, 105.66 mmol); the mixture was maintained at that temperature for about 2.5 hours. The reaction was monitored by TLC (25% ethyl acetate in hexanes). Upon complete conversion of starting material, the reaction was quenched with methanol. The resulting mixture was diluted with methylene chloride (about 400 mL) and washed with a 10% aqueous solution (w/w) of Rochelle's salt. The organic layer was separated and the aqueous layer was back-extracted with methylene chloride (about 250 mL). The two organic layers were combined, washed with brine, dried over sodium sulfate, filtered, and concentrated in vacuo. The desired product was isolated using normal-phase chromatography (330 g column, 45 minutes, 5-45% ethyl acetate in hexanes). The obtained product w as purified a second time by normal-phase chromatography (0-20% acetone in hexanes, 120-g column), affording a yellow oil, 16.1 g (66%).

$^1$H NMR (300 MHz, DMSO-$d_6$) δ: 0.03 (s, 6H) 0.84 (s, 9H) 1.30-1.46 (m, 9H) 3.65-3.91 (m, 4H) 4.43-4.73 (m, 1H) 5.17 (dt, J=8.12, 1.61 Hz, 1H) 5.21 (dd, J=1.70, 0.76 Hz, 1H) 5.69-5.87 (m, 1H) 9.38-9.50 (m, 1H)

Intermediate 100: methyl 4-(tert-butoxycarbonyl((S)-1-(tert-butyldimethylsilyloxy)but-3-en-2-yl)amino)-3-hydroxy-2-methylenebutanoate

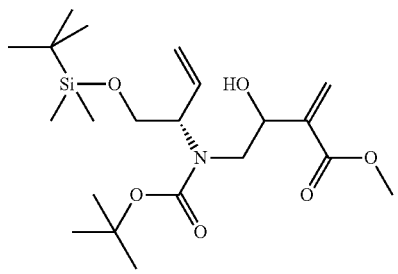 [SMILES: C=C[C@@H](CO[Si](C)(C)C(C)(C)C)N(CC(O)C(=C)C(=O)OC)C(=O)OC(C)(C)C]

To a stirred solution of (S)-tert-butyl 1-(tert-butyldimethylsilyloxy)but-3-en-2-yl(2-oxoethyl)carbamate (Intermediate 99, 16.1 g, 46.8 mmol), methyl acrylate (6.3 mL, 70 mmol), and methanol (about 2 mL), under nitrogen at ambient temperature, was added Quinuclidine (2.1 g, 19 mmol) as a solid. The mixture was then stirred for 1 day; analysis by TLC (15% ethyl acetate in hexanes) indicated incomplete conversion of starting material. Another 0.8 eq of quinuclidine was added every 24 hours; another 0.75 eq methyl acrylate and 1 mL methanol were added every two days. After 6 days total, the reaction was diluted with water and extracted with ethyl acetate. TLC indicated that only one extraction with about 250 mL ethyl acetate was needed to bring all the crude product into the organic layer, which was then washed with brine, dried over sodium sulfate, and concentrated under reduced pressure. Normal-phase chromatography (5-30% ethyl acetate in hexanes, 220-g column, 35 minutes) afforded the desired compound (16 g, 80%, pale oil) as a mixture of diastereomers, with about 10 mol % of starting aldehyde present according to proton NMR analysis. The material was taken forward in this state.

$^1$H NMR (300 MHz, DMSO-$d_6$) δ: 0.03 (s, 6H) 0.85 (s, 9H) 1.37 (s, 9H) 3.19-3.47 (m, 2H) 3.68 (s, 3H) 3.73-3.92 (m, 2H) 3.95-4.19 (m, 1H) 4.47-4.61 (m, 1H) 5.03-5.25 (m, 3H) 5.78-5.95 (m, 2H) 6.16 (br. s, 1H)

Intermediate 101: (2S,5S)-1-tert-butyl 4-methyl 2-((tert-butyldimethylsilyloxy)methyl)-5-hydroxy-5,6-dihydropyridine-1,4(2H)-dicarboxylate

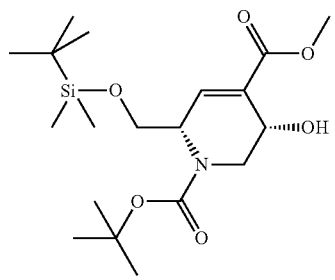 [SMILES: COC(=O)C1=C[C@@H](CO[Si](C)(C)C(C)(C)C)N(C(=O)OC(C)(C)C)C[C@H]1O]

A stirred solution of methyl 4-(tert-butoxycarbonyl((S)-1-(tert-butyldimethylsilyloxy)but-3-en-2-yl)amino)-3-hydroxy-2-methylenebutanoate (Intermediate 100, 16 g, 37 mmol) in toluene (about 300 mL), at ambient temperature in a heat-dried flask, was thoroughly degassed with argon and placed under a nitrogen atmosphere. To this was added Hoveyda-Grubbs Catalyst 2nd Generation (460 mg, 0.74 mmol). Analysis of the mixture 3.5 hours later by LCMS and TLC (15% ethyl acetate in hexanes) indicated very high conversion of starting material to two major products. The reaction mixture was concentrated in vacuo in the presence of enough silica gel to give a free-flowing powder upon reaching dryness. Normal-phase chromatography (0-100% ethyl acetate in hexanes, 330-g column, 45 minutes) was used to isolate the two compounds; the diastereomer shown above (6.4 g, 43%, dark oil) eluted first.

MS: 402 ES+ ($C_{19}H_{35}NO_6Si$)

$^1$H NMR (300 MHz, DMSO-$d_6$) δ: 0.01 (s, 6H) 0.83 (s, 9H) 1.41 (s, 9H) 2.81-3.10 (m, 1H) 3.68-3.78 (m, 5H) 3.93-4.15 (m, 1H) 4.34 (br. s., 1H) 4.42-4.64 (m, 1H) 4.99 (d, J=5.48 Hz, 1H) 6.94 (d, J=6.80 Hz, 1H)

Intermediate 102: (2S,5R)-1-tert-butyl 4-methyl 2-((tert-butyldimethylsilyloxy)methyl)-5-hydroxy-5,6-dihydropyridine-1,4(2H)-dicarboxylate

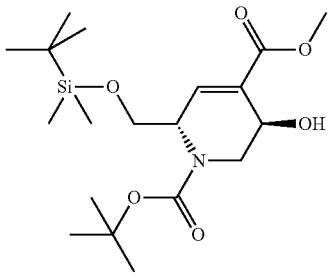 [SMILES: COC(=O)C1=C[C@@H](CO[Si](C)(C)C(C)(C)C)N(C(=O)OC(C)(C)C)C[C@@H]1O]

This product (6.6 g, 44%, dark oil) was prepared in the same reaction as Intermediate 101, and eluted second in the chromatographic purification described in that procedure.

MS: 402 ES+ ($C_{19}H_{35}NO_6Si$)

$^1$H NMR (300 MHz, DMSO-$d_6$) δ: 0.04 (s, 6H) 0.86 (s, 9H) 1.40 (s, 9H) 2.80 (br. s., 1H) 3.68 (s, 3H) 3.76 (d, J=5.67 Hz, 2H) 4.03 (m, J=7.20 Hz, 1H) 4.20-4.33 (m, 1H) 4.42 (br. s., 1H) 5.24 (d, J=5.85 Hz, 1H) 6.64 (br. d, J=1.00 Hz, 1H)

Intermediate 103: (3S,6S)-1-(tert-butoxycarbonyl)-6-((tert-butyldimethylsilyloxy)methyl)-3-hydroxy-1,2,3,6-tetrahydropyridine-4-carboxylic acid

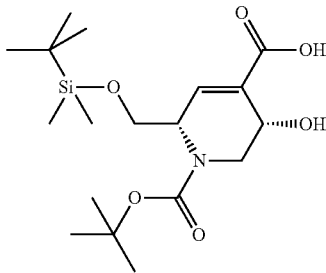 [SMILES: CC(C)(C)OC(=O)N1C[C@@H](O)C(C(=O)O)=C[C@H]1CO[Si](C)(C)C(C)(C)C]

A stirred solution of (2S,5S)-1-tert-butyl 4-methyl 2-((tert-butyldimethylsilyloxy)methyl)-5-hydroxy-5,6-dihydropyridine-1,4(2H)-dicarboxylate (Intermediate 101, 5.9 g, 15 mmol) in THF (55 mL) and water (18 mL) was prepared under ambient conditions. To it was added lithium hydroxide (700 mg, 29 mmol) as a solid. The mixture was stirred under an atmosphere of nitrogen at ambient temperature. The solid material dissolved within a few minutes. Analysis of the mixture by TLC (25% ethyl acetate in hexanes) at 30 minutes indicated complete consumption of starting material. About 20 mL of a 1N aq solution of HCl was added to the mixture as it stirred. A 10% aq solution of citric acid was used to bring the pH to the 4-5 range. The mixture was diluted with about 60 mL water and extracted twice with ethyl acetate. The organic extracts were combined, washed with brine, dried over sodium sulfate, filtered, and concentrated in vacuo. The dark brown, gummy residue (5.5 g, 96%, dark oil) was characterized by proton NMR and LCMS as desired product, and taken forward without further purification.

MS: 386 ES– ($C_{18}H_{33}NO_6Si$)

$^1$H NMR (300 MHz, DMSO-$d_6$) j 0.04 (s, 6H) 0.86 (s, 9H) 1.40 (s, 9H) 2.82 (br. s., 1H) 3.30 (br. s., 2H) 3.75 (d, J=6.04 Hz, 2H) 3.96-4.11 (m, 1H) 4.25 (t, J=7.55 Hz, 1H) 4.41 (br. s., 1H) 6.65 (d, J=3.59 Hz, 1H)

Intermediate 104: (2S,5S)-tert-butyl 2-((tert-butyldimethylsilyloxy)methyl)-4-carbamoyl-5-hydroxy-5,6-dihydropyridine-1(2H)-carboxylate

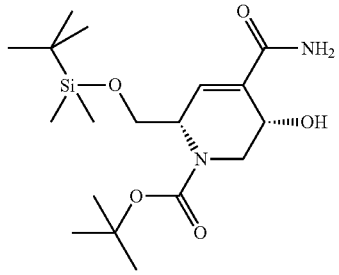 [SMILES: CC(C)(C)OC(=O)N1C[C@@H](O)C(C(N)=O)=C[C@H]1CO[Si](C)(C)C(C)(C)C]

A stirred solution of (3S,6S)-1-(tert-butoxycarbonyl)-6-((tert-butyldimethylsilyloxy)methyl)-3-hydroxy-1,2,3,6-tetrahydropyridine-4-carboxylic acid (Intermediate 103, 5.5 g, 14 mmol) and N,N-diisopropylethylamine (7.4 mL, 42 mmol) in DMF (about 50 mL) was prepared under ambient conditions. To this was added O-(7-Azabenzotriazol-1-yl)-N,N,N',N'-tetramethyluronium hexafluorophosphate (8.0 g, 21 mmol). The reaction vessel was purged with argon for one minute, and the dark, clear mixture was stirred under nitrogen for 5 minutes at ambient temperature. To the mixture was then added ammonium chloride (1.5 g, 22 mmol). The mixture was stirred under nitrogen at ambient temperature overnight. In the morning, analysis by LCMS indicated consumption of starting material and the presence of one major product with a longer retention time and desired mass. Aqueous workup using diethyl ether separated crude product from water-soluble materials. The organic phases were combined, washed with brine, dried over sodium sulfate, filtered, and concentrated in vacuo. Normal-phase chromatography (1-6% methanol in methylene chloride, 220-g, about 50 min) afforded the desired product (2.4 g, 44%, tan solid).

MS: 387 ES+ ($C_{18}H_{34}N_2O_5Si$)

$^1$H NMR (300 MHz, DMSO-$d_6$) δ: 0.04 (s, 6H) 0.86 (s, 9H) 1.40 (s, 9H) 2.74 (br. s., 1H) 3.72 (d, J=5.48 Hz, 2H) 4.09 (br. s., 1H) 4.18-4.32 (m, 1H) 4.40 (br. s., 1H) 5.59 (d, J=5.48 Hz, 1H) 6.54 (d, J=3.02 Hz, 1H) 7.15 (br. s., 1H) 7.36 (br. s., 1H)

Intermediate 105: (2S,5R)-tert-butyl 5-(N-(allyloxy)-2,4-dinitrophenylsulfonamido)-2-((tert-butyldimethylsilyloxy)methyl)-4-carbamoyl-5,6-dihydropyridine-1(2H)-carboxylate

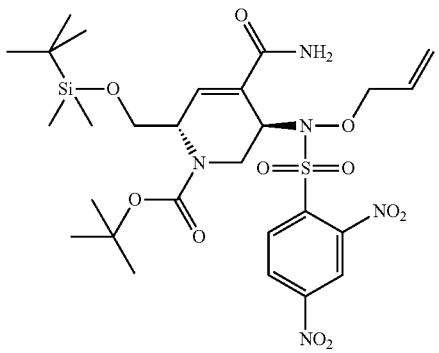 [SMILES: C=CCON([C@H]1CN(C(=O)OC(C)(C)C)[C@H](CO[Si](C)(C)C(C)(C)C)C=C1C(N)=O)S(=O)(=O)c1ccc([N+](=O)[O-])cc1[N+](=O)[O-]]

A solution of (2S,5S)-tert-butyl 2-((tert-butyldimethylsilyloxy)methyl)-4-carbamoyl-5-hydroxy-5,6-dihydropyridine-1(2H)-carboxylate (Intermediate 104, 1.4 g, 3.6 mmol) in toluene (35 mL) was prepared and stirred under nitrogen at ambient temperature. To it was added triphenylphosphine (1.1 g, 4.3 mmol) and N-(allyloxy)-2,4-dinitrobenzenesulfonamide (1.1 g, 3.6 mmol). Upon dissolution of these materials, the mixture was stirred for another ten minutes. To the mixture was then added diisopropyl azodicarboxylate (840 μl, 4.3 mmol) by syringe. Argon was blown over the top of the mixture and the mixture was then placed under nitrogen and stirred overnight. Analysis by LCMS in the morning and also by TLC (5% methanol in methylene chloride) indicated consumption of starting alcohol. The reaction mixture was adsorbed onto silica gel and normal phase chromatography (15-75% ethyl acetate in hexanes, 220-g column) afforded the desired product (orange solid; ~100% yield).

MS: 673 ES+ ($C_{27}H_{41}N_5O_{11}SSi$)

$^1$H NMR (300 MHz, DMSO-d$_6$) δ: 0.02 (s, 6H) 0.84 (s, 9H) 1.29-1.49 (m, 9H) 3.62-3.78 (m, 2H) 4.00 (s, 1H) 4.15-4.87 (m, 4H) 5.16-5.36 (m, 2H) 5.67-5.90 (m, 1H) 6.76-6.88 (m, 1H) 6.99-7.80 (m, 2H) 8.24-8.38 (m, 1H) 8.62 (ddd, J=8.64, 6.18, 2.36 Hz, 1H) 9.04 (d, J=2.27 Hz, 1H)

Intermediate 106: (3R,6S)-3-(N-(allyloxy)-2,4-dinitrophenylsulfonamido)-6-((tert-butyldimethylsilyloxy)methyl)-1,2,3,6-tetrahydropyridine-4-carboxamide

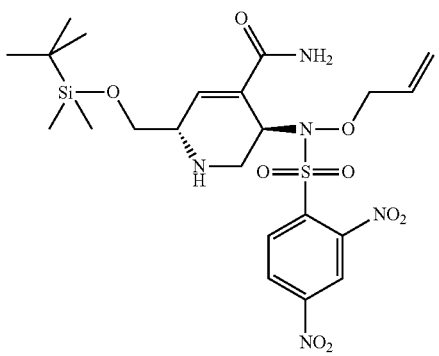 [SMILES: C=CCON([C@H]1CN[C@H](CO[Si](C)(C)C(C)(C)C)C=C1C(N)=O)S(=O)(=O)c1ccc([N+](=O)[O-])cc1[N+](=O)[O-]]

A stirred solution of (2S,5R)-tert-butyl 5-(N-(allyloxy)-2,4-dinitrophenylsulfonamido)-2-((tert-butyldimethylsilyloxy)methyl)-4-carbamoyl-5,6-dihydropyridine-1(2H)-carboxylate (Intermediate 105, 1.8 g, 2.6 mmol) in methylene chloride (about 25 mL) was prepared under ambient conditions; argon was blown over the solution for 30 seconds, and the solution was then stirred at ambient temperature. To it was added zinc bromide (4.1 g, 18 mmol). The mixture was stirred overnight. In the morning, solid, gummy, yellow material coated the bottom of the flask, and analysis by LCMS indicated incomplete conversion. A small amount of THF (about 2 mL) was added. The mixture became homogenous over the next 25 seconds. Analysis over the next few hours indicated increased reaction rate with little or no increase in by-product formation. More zinc bromide (another 5 g) was added in parts over that time. If addition of zinc bromide was followed by precipitation, another small volume of THF was added. By the end of the day, consumption of starting material was still incomplete but high. The reaction was carefully transferred into a saturated solution of sodium bicarbonate. A great deal of gas evolution was observed. Crude product was extracted using ethyl acetate until TLC (5% methanol in methylene chloride) indicated no UV-active material remained in the aqueous. The organic extracts were combined, washed with brine, dried over sodium sulfate, filtered, and concentrated. The residue was dissolved in methylene chloride for normal-phase chromatography (0-4% methanol in methylene chloride over 35 min, 80-g column), affording desired compound (1.1 g, 72%, pale yellow solid).

MS: 573 ES+ ($C_{22}H_{33}N_5O_9SSi$)

$^1$H NMR (300 MHz, DMSO-d$_6$) δ: -0.01-0.10 (m, 6H) 0.78-0.91 (m, 9H) 2.85 (br. s., 2H) 3.38-3.66 (m, 3H) 4.31-4.49 (m, 2H) 4.60 (br. s., 1H) 5.17-5.39 (m, 3H) 5.78-5.97 (m, 1H) 6.73-6.91 (m, 2H) 7.36 (br. s., 1H) 8.32 (d, J=8.69 Hz, 1H) 8.62 (dd, J=8.88, 2.27 Hz, 1H) 9.01 (d, J=2.27 Hz, 1H)

Intermediate 107: (3R,6S)-3-(allyloxyamino)-6-((tert-butyldimethylsilyloxy)methyl)-1,2,3,6-tetrahydropyridine-4-carboxamide

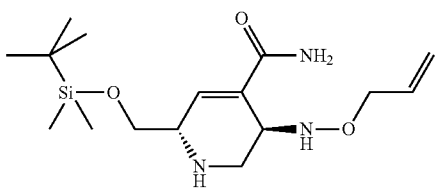 [SMILES: C=CCON[C@H]1CN[C@H](CO[Si](C)(C)C(C)(C)C)C=C1C(N)=O]

To a reddish-brown, stirred suspension of (3R,6S)-3-(N-(allyloxy)-2,4-dinitrophenylsulfonamido)-6-((tert-butyldimethylsilyloxy)methyl)-1,2,3,6-tetrahydropyridine-4-carboxamide (Intermediate 106, 1.1 g, 1.9 mmol) and cesium carbonate (3.1 g, 9.5 mmol) in THF (about 45 mL), at ambient temperature under a blanket of argon, was added benzenethiol (polymer-bound reagent, 1.55 mmol/g) (4.5 g, 7.0 mmol). This mixture was stirred overnight at ambient temperature. Analysis by LCMS in the morning indicated complete consumption of starting material, as did analysis by TLC (5% methanol in methylene chloride). The mixture was filtered and the filtered material was rinsed with THF until no material remained that was responsive to UV or I$_2$ stain on a silica plate. The red-orange solution obtained was concentrated and redissolved in methylene chloride. Normal-phase chromatography (0-6% methanol in methylene chloride, 80-g, 25 min.) afforded the desired compound (510 mg, 80%, orange-brown solid).

MS: 343 ES+ ($C_{16}H_{31}N_3O_3Si$)

$^1$H NMR (300 MHz, DMSO-$d_6$) δ: 0.04 (s, 6H) 0.87 (s, 9H) 2.39 (br. s., 1H) 2.74 (dd, J=12.84, 3.40 Hz, 1H) 2.94 (dd, J=12.84, 3.40 Hz, 1H) 3.31-3.37 (m, 1H) 3.49-3.57 (m, 2H) 3.57-3.66 (m, 1H) 4.11 (dt, J=5.62, 1.16 Hz, 2H) 5.13 (ddt, J=10.50, 2.10, 1.16, 1.16 Hz, 1H) 5.22 (dq, J=17.37, 1.70 Hz, 1H) 5.92 (ddt, J=17.37, 10.39, 5.67, 5.67 Hz, 1H) 6.41 (d, J=8.50 Hz, 1H) 6.68 (dd, J=3.21, 0.57 Hz, 1H) 6.98 (br. s., 1H) 7.36 (br. s., 1H)

Intermediate 108: (2S,5R)-6-(allyloxy)-2-((tert-butyldimethylsilyloxy)methyl)-7-oxo-1,6-diazabicyclo[3.2.1]oct-3-ene-4-carboxamide

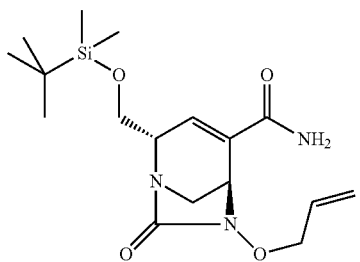 [SMILES: C=CCON1C(=O)N2C[C@H]1C(C(N)=O)=C[C@H]2CO[Si](C)(C)C(C)(C)C]

A stirred solution of (3R,6S)-3-(allyloxyamino)-6-((tert-butyldimethylsilyloxy)methyl)-1,2,3,6-tetrahydropyridine-4-carboxamide (Intermediate 107, 505 mg, 1.48 mmol) and N,N-diisopropylethylamine (1.03 mL, 5.91 mmol) in acetonitrile (150 mL) was prepared. Over this was blown argon for one minute. The solution was then placed under an argon atmosphere and cooled in an ice bath for 15 minutes. To it was added a solution of triphosgene (180 mg, 0.59 mmol) in acetonitrile (10 mL) via syringe using a syringe pump set to deliver 0.1 mL/min. During the course of the addition, temperature was kept at or near 0° C. Upon addition of all triphosgene, the orange solution was stirred at 0° C. for another 30 minutes. The ice bath was then removed and the mixture was stirred for another 30 minutes at ambient temperature. Analysis at that time by LCMS indicated conversion to desired product. The reaction mixture was concentrated in vacuo and the residue was dissolved in methylene chloride. Normal-phase chromatography (15-65% ethyl acetate in methylene chloride, 40-g column, 25 minutes) was used to isolate the desired product (454 mg, 84%, white solid).

MS: 349 ES+ ($C_{17}H_{29}N_3O_4Si$)

$^1$H NMR (300 MHz, DMSO-$d_6$) δ: 0.06 (s, 6H) 0.87 (s, 9H) 3.11-3.20 (m, 2H) 3.25-3.35 (m, 1H) 3.71-3.79 (m, 1H) 3.79-3.95 (m, 2H) 4.34 (dt, J=5.90, 1.20 Hz, 2H) 4.51 (d, J=2.83 Hz, 1H) 5.23 (ddt, J=10.43, 1.89, 1.01, 1.01 Hz, 1H) 5.33 (dq, J=17.30, 1.60 Hz, 1H) 5.80-6.00 (m, 1H) 6.49 (dd, J=2.83, 0.94 Hz, 1H) 7.08 (br. s., 1H) 7.51 (br. s., 1H)

Intermediate 109: (2S,5R)-6-(allyloxy)-2-(hydroxymethyl)-7-oxo-1,6-diazabicyclo[3.2.1]oct-3-ene-4-carboxamide

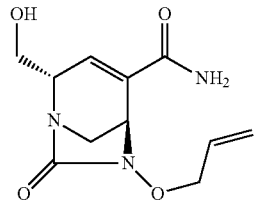 [SMILES: C=CCON1C(=O)N2C[C@H]1C(C(N)=O)=C[C@H]2CO]

(2S,5R)-6-(allyloxy)-2-((tert-butyldimethylsilyloxy)methyl)-7-oxo-1,6-diazabicyclo[3.2.1]oct-3-ene-4-carboxamide (Intermediate 108, 450 mg, 1.2 mmol) was dissolved in THF (about 7 mL); the atmosphere in the reaction vessel was evacuated and backfilled with argon, and the solution was stirred in an ice bath for ten minutes. To it was then added tetrabutylammonium fluoride (1 M in THF) (1.5 mL, 1.5 mmol) dropwise. After one hour, analysis of the mixture by LCMS indicated consumption of starting material and formation of one major product. The mixture was concentrated and dissolved in methylene chloride. Normal-phase chromatography (0-10% methanol in methylene chloride, 25-g column, 25 minutes) was used to isolate the desired product (284 mg, 92%, white solid).

MS: 254 ES+ ($C_{11}H_{15}N_3O_4$)

$^1$H NMR (300 MHz, DMSO-$d_6$) δ: 3.04-3.28 (m, 2H) 3.54-3.80 (m, 3H) 4.34 (dt, J=6.00, 1.16 Hz, 2H) 4.50 (d, J=2.83 Hz, 1H) 5.01-5.10 (m, 1H) 5.18-5.27 (m, 1H) 5.33 (dq, J=17.28, 1.54 Hz, 1H) 5.78-6.02 (m, 1H) 6.52 (d, J=1.70 Hz, 1H) 7.06 (br. s., 1H) 7.49 (br. s., 1H)

Intermediate 110: (2S,5R)-tert-butyl 5-(N-(allyloxy)-2-nitrophenylsulfonamido)-2-((tert-butyldimethylsilyloxy)methyl)-4-carbamoyl-5,6-dihydropyridine-1(2H)-carboxylate

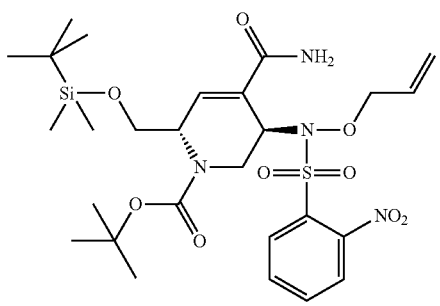 [SMILES: C=CCON([C@H]1CN(C(=O)OC(C)(C)C)[C@H](CO[Si](C)(C)C(C)(C)C)C=C1C(N)=O)S(=O)(=O)c1ccccc1[N+](=O)[O-]]

The title compound (4.0 g, 74%) was prepared from (2S,5S)-tert-butyl 2-((tert-butyldimethylsilyloxy)methyl)-4-carbamoyl-5-hydroxy-5,6-dihydropyridine-1(2H)-carboxylate (Intermediate 104, 3.36 g, 8.69 mmol) using the same procedure to prepare Intermediate 105 from Intermediate 104, but using N-(allyloxy)-2-nitrobenzenesulfonamide (Intermediate 9, 2.24 g, 8.69 mmol) as a reagent in place of N-(allyloxy)-2,4-dinitrobenzenesulfonamide.

MS: 627 ES+ ($C_{27}H_{42}N_4O_9SSi$)

$^1$H NMR (300 MHz, DMSO-$d_6$) δ: 0.02 (s, 6H) 0.84 (s, 9H) 1.36 (br. s., 9H) 2.84-3.22 (m, 1H) 3.59-3.77 (m, 2H)

4.10-4.46 (m, 3H) 4.64 (br. s., 1H) 4.82 (d, J=13.22 Hz, 1H) 5.08-5.42 (m, 2H) 5.63-5.93 (m, 1H) 6.72-6.83 (m, 1H) 7.37 (br. s., 1H) 7.49-7.71 (m, 1H) 7.85 (dt, J=8.21, 4.01 Hz, 1H) 7.97 (br. s., 2H) 8.00-8.11 (m, 1H)

Intermediate 111: (2S,5R)-tert-butyl 5-(N-(allyloxy)-2-nitrophenylsulfonamido)-4-carbamoyl-2-(hydroxymethyl)-5,6-dihydropyridine-1(2H)-carboxylate

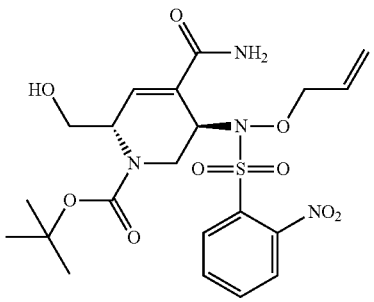 [SMILES: C=CCON([C@H]1CN(C(=O)OC(C)(C)C)[C@H](CO)C=C1C(N)=O)S(=O)(=O)c1ccccc1[N+](=O)[O-]]

The title compound (617 mg, 67%) was prepared from (2S,5R)-tert-butyl 5-(N-(allyloxy)-2-nitrophenylsulfonamido)-2-((tert-butyldimethylsilyloxy)methyl)-4-carbamoyl-5,6-dihydropyridine-1(2H)-carboxylate (Intermediate 110, 1.2 g, 1.80 mmol) using the same procedure to prepare Intermediate 109 from Intermediate 108.

MS: 513 ES+ ($C_{21}H_{28}N_4O_9S$)

$^1$H NMR (300 MHz, DMSO-$d_6$) δ: 1.19-1.56 (m, 9H) 2.86-3.20 (m, 1H) 3.44-3.55 (m, 2H) 3.89-4.65 (m, 4H) 4.82 (d, J=11.14 Hz, 1H) 4.94-5.07 (m, 1H) 5.12-5.36 (m, 2H) 5.57-5.92 (m, 1H) 6.70-7.10 (m, 2H) 7.36 (br. s., 1H) 7.78-7.89 (m, 1H) 7.96 (d, J=2.83 Hz, 2H) 8.00-8.14 (m, 1H)

Intermediate 112: (2S,5R)-tert-butyl 5-(N-(allyloxy)-2-nitrophenylsulfonamido)-4-carbamoyl-2-(methoxymethyl)-5,6-dihydropyridine-1(2H)-carboxylate

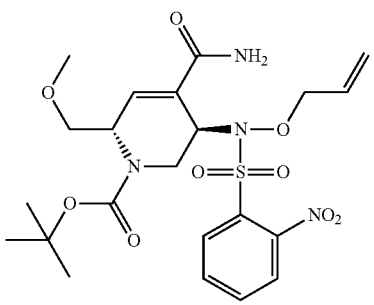 [SMILES: C=CCON([C@H]1CN(C(=O)OC(C)(C)C)[C@H](COC)C=C1C(N)=O)S(=O)(=O)c1ccccc1[N+](=O)[O-]]

A solution of Intermediate 111 (427 mg, 0.83 mmol) and methyl iodide (6 eq) (311 al, 5.00 mmol) in acetonitrile (~4 mL) was prepared under ambient conditions and placed under a nitrogen atmosphere. In this mixture was suspended silver oxide (1.1 eq) (212 mg, 0.92 mmol). The mixture was protected from light through the use of aluminum foil and stirred until analysis by TLC (1:1 acetonitrile:DCM) and LCMS indicated complete consumption of starting material, around 3 days. Filtration of the reaction mixture through a 0.45 filter gave a bronze solution. This was concentrated in vacuo and redissolved in methylene chloride. The crude mixture was purified by normal-phase chromatography (10-50% acetonitrile in DCM) to afford the desired product as a colorless residue (109 mg, 25%). The isolated material was lyophilized (white powder) for ease of characterization.

MS: 527 ES+ ($C_{22}H_{30}N_4O_9S$)

$^1$H NMR (300 MHz, DMSO-$d_6$) δ: 1.38 (d, J=6.99 Hz, 9H) 2.82-3.15 (m, 1H) 3.26 (s, 3H) 3.44 (d, J=3.02 Hz, 2H) 3.90-4.39 (m, 3H) 4.46-4.94 (m, 2H) 5.13-5.33 (m, 2H) 5.64-5.89 (m, 1H) 6.71-6.84 (m, 1H) 6.86-7.15 (m, 1H) 7.35 (br. s., 1H) 7.85 (t, J=8.03 Hz, 1H) 7.90-8.15 (m, 3H)

Intermediate 113: (3R,6S)-3-(N-(allyloxy)-2-nitrophenylsulfonamido)-6-(methoxymethyl)-1,2,3,6-tetrahydropyridine-4-carboxamide

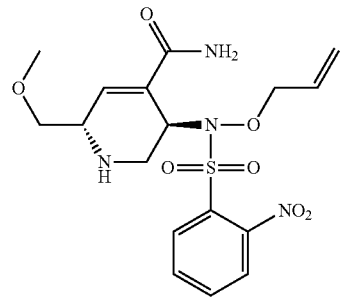 [SMILES: C=CCON([C@H]1CN[C@H](COC)C=C1C(N)=O)S(=O)(=O)c1ccccc1[N+](=O)[O-]]

To a solution of Intermediate 112 (729 mg, 1.38 mmol) in dichloromethane (10 mL) was added trifluoroacetic acid (2133 μl, 27.69 mmol). This solution was slightly darker after addition. The reaction was placed under a nitrogen atmosphere and stirred until LCMS analysis indicated consumption of starting material (~45 minutes). At that time, solvent was removed in vacuo. The residue was taken up in toluene and sonicated, and then toluene was removed in vacuo. This was repeated twice, affording an orange solid of high purity by proton NMR. The product was taken forward without further purification.

MS: 427 ES+ ($C_{17}H_{22}N_4O_7S$)

$^1$H NMR (300 MHz, DMSO-$d_6$) δ: 3.24-3.38 (m, 5H) 3.53-3.71 (m, 2H) 4.28 (m, J=11.10, 6.40 Hz, 2H) 4.34-4.44 (m, 1H) 5.11 (br. s., 1H) 5.20-5.35 (m, 2H) 5.84 (ddt, J=17.14, 10.43, 6.42, 6.42 Hz, 1H) 6.61 (d, J=1.70 Hz, 1H) 7.28 (br. s., 1H) 7.65 (br. s., 1H) 7.88-7.99 (m, 1H) 8.01-8.15 (m, 3H) 8.85-9.45 (m, 1H)

Intermediate 114: (3R,6S)-3-(allyloxyamino)-6-(methoxymethyl)-1,2,3,6-tetrahydro-pyridine-4-carboxamide

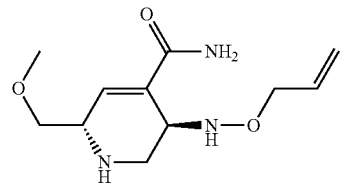 [SMILES: C=CCON[C@H]1CN[C@H](COC)C=C1C(N)=O]

This intermediate was prepared from (3R,6S)-3-(N-(allyloxy)-2-nitrophenylsulfonamido)-6-(methoxymethyl)-1,2,3, 6-tetrahydropyridine-4-carboxamide (Intermediate 113, 734 mg, 1.36 mmol) using the same procedure and isolation techniques to prepare Intermediate 107 from Intermediate 106. The title compound was an orange oil (173 mg, 53%).

MS: 242 ES+ ($C_{11}H_{19}N_3O_3$)

$^1$H NMR (300 MHz, DMSO-$d_6$) δ: 2.70-2.79 (m, 1H) 2.70-2.78 (m, 1H) 2.89-2.99 (m, 1H) 2.94 (dd, J=12.94, 3.30 Hz, 1H) 3.22-3.53 (m, 4H) 3.26 (s, 3H) 3.61 (br. s., 1H) 4.11 (dt, J=5.62, 1.25 Hz, 2H) 5.09-5.29 (m, 2H) 5.92 (ddt, J=17.33, 10.48, 5.74, 5.74 Hz, 1H) 6.34-6.49 (m, 1H) 6.65 (dd, J=3.21, 0.76 Hz, 1H) 7.00 (br. s., 1H) 7.39 (br. s., 1H)

Intermediate 115: (2S,5R)-6-(allyloxy)-2-(methoxymethyl)-7-oxo-1,6-diazabicyclo[3.2.1]oct-3-ene-4-carboxamide

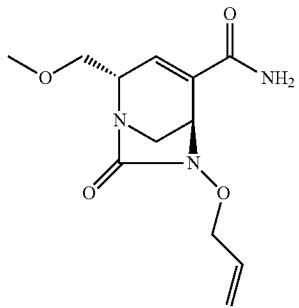 [SMILES: C=CCON1C(=O)N2C[C@H]1C(C(N)=O)=C[C@H]2COC]

A solution of (3R,6S)-3-(allyloxyamino)-6-(methoxymethyl)-1,2,3,6-tetrahydro-pyridine-4-carboxamide (Intermediate 114, 125 mg, 0.52 mmol) and triethylamine (210 mg, 2.07 mmol) in acetonitrile (45 mL) was prepared. Over this was blown argon for one minute. The solution was then placed under an argon atmosphere and cooled in an ice bath for 15 minutes. To it was slowly added a solution of diphosgene (56 mg, 0.28 mmol) in 5 mL acetonitrile via syringe pump at a rate of 0.1 mL/min. Once the addition was complete, the reaction was stirred at room temperature overnight. The reaction mixture was then concentrated in vacuo. The residue was dissolved in methylene chloride and subjected to normal-phase chromatography (0-7% methanol in DCM) to afford 60 mg (43%) of a pale yellow foam upon application of high vacuum.

MS: 268 ES+ ($C_{12}H_{17}N_3O_4$)

$^1$H NMR (300 MHz, DMSO-$d_6$) δ: 3.27-3.42 (m, 5H) 3.59-3.77 (m, 2H) 4.07-4.15 (m, 1H) 4.36-4.55 (m, 3H) 5.27-5.31 (m, 1H) 5.32-5.36 (m, 1H) 5.38-5.70 (m, 2H) 5.92-6.13 (m, 1H) 6.39 (dd, J=3.02, 1.13 Hz, 1H)

Intermediate 116: (2S,5R)-6-hydroxy-2-(methoxymethyl)-7-oxo-1,6-diazabicyclo[3.2.1]oct-3-ene-4-carboxamide

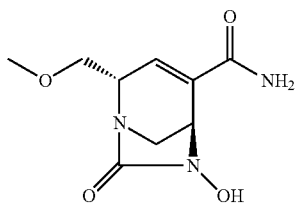 [SMILES: COC[C@@H]1C=C(C(N)=O)[C@@H]2CN1C(=O)N2O]

A stirred solution of Intermediate 115 (60 mg, 0.22 mmol) in dichloromethane (2 mL) was prepared and placed under a nitrogen atmosphere. To it was added acetic acid (25.7 μl, 0.45 mmol) followed by tetrakis(triphenylphosphine)palladium(0) (259 mg, 0.22 mmol). The mixture was stirred under nitrogen at ambient temperature for about 60 minutes. Upon complete consumption of starting material as indicated by LCMS analysis, the solvent was removed in vacuo. Addition of MeCN precipitated a tan solid, which was filtered and discarded. The filtrate was adsorbed onto Celite, and the desired product (21 mg, 41%, white solid) was isolated using reverse-phase chromatography (100% water) followed by freeze-drying.

MS: 228 ES+ ($C_9H_{13}N_3O_4$)

$^1$H NMR (300 MHz, METHANOL-$d_4$) δ: 3.38 (dt, J=3.26, 1.68 Hz, 2H) 3.46 (s, 3H) 3.68-3.83 (m, 2H) 4.05 (td, J=5.76, 3.02 Hz, 1H) 4.38-4.44 (m, 1H) 6.58 (dd, J=2.93, 1.04 Hz, 1H)

Example 13

(2S,5R)-2,4-bis(methoxymethyl)-7-oxo-1,6-diazabicyclo[3.2.1]oct-3-en-6-yl sulfate Sodium salt

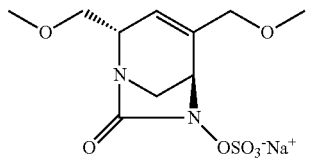

To a solution of Intermediate 124 (100 mg, 0.37 mmol) in DCM (3 mL) was added acetic acid (0.043 mL, 0.75 mmol) (dried over $Na_2SO_4$) and Pd(PPh$_3$)$_4$ (215 mg, 0.19 mmol) under argon at room temperature. The yellow solution was stirred at room temperature for 1 hr. TLC and LCMS showed complete conversion of starting material to product. The reaction mixture was concentrated and dried under vacuum. Then it was diluted with 5 mL 10% $CH_3CN$ in water and loaded onto 30 g ISCO gold C18 column, and eluted with 0% $CH_3CN$ for 5 minutes, followed by 0-50% $CH_3CN/H_2O$ over 15 minutes. The first few fractions were collected and lypholized to give an yellow oil (126 mg). The oil was dissolved in pyridine (3 mL) at rt. Then $SO_3$—Pyr (353 mg, 2.22 mmol) was added as solid. The mixture was then stirred at rt overnight. LCMS showed the completion of the reaction. The reaction solution was concentrated to dryness and azetropic with 2×5 mL toluene. The crude was then applied to ~30 g pretreated dowex resin (200 mL 2N NaOH for 2 hrs, then packed and washed with $H_2O$ til neutral pH). And purified using a gravity column with $H_2O$, collecting every 10 mL. Fractions containing the desired compound were combined and lypholized to give a white solid, which was then purified by RP-HPLC to give ~20 mg white solid.

MS: 309 ES+ ($C_{10}H_{16}N_2O_7S$)

$^1$H NMR (300 MHz, $D_2O$) δ: 3.31 (s, 3H) 3.40 (s, 3H) 3.44 (s, 2H) 3.57-3.77 (m, 2H) 3.96-4.12 (m, 3H) 4.24 (s, 1H) 5.62 (br. s., 1H)

Intermediate 117: (S)-tert-butyl 2-((tert-butyldimethylsilyloxy)methyl)-4-(hydroxymethyl)-5-oxo-5,6-dihydropyridine-1(2H)-carboxylate

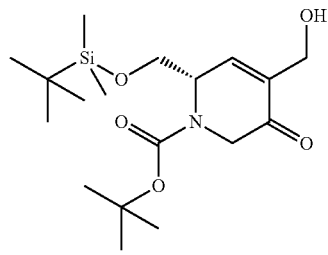 [SMILES: CC(C)(C)OC(=O)N1CC(=O)C(CO)=C[C@H]1CO[Si](C)(C)C(C)(C)C]

To a solution of (S)-tert-butyl 2-((tert-butyldimethylsilyloxy)methyl)-5-oxo-5,6-dihydropyridine-1(2H)-carboxylate (Intermediate 7, 18 g, 52.71 mmol) in a mixture of DCM (900 mL) and MeOH (350 mL) was added successively formaldehyde (42.8 mL, 527.06 mmol) and tributylphosphine (0.692 mL, 3.16 mmol) at rt. The solution was stirred at room temperature for 2-3 hr until TLC (4:1 Hex/EA) showed that the reaction was complete. It was concentrated under reduced pressure and purified by 120 g silica gel column (0-50% Hex/EA) to afford the title compound (20.00 g, 102%) as an oil.

MS: 372 ES+ ($C_{18}H_{33}NO_5Si$)

$^1$H NMR (300 MHz, DMSO-d6) δ: −0.13-0.08 (m, 6H) 0.73-0.97 (m, 9H) 1.43 (s, 9H) 3.87 (m, 3H) 4.11 (m, 2H) 4.22-4.39 (m, 1H) 4.69-4.86 (m, 1H) 5.01 (m, 1H) 6.92-7.07 (m, 1 H).

Intermediate 118: (S)-tert-butyl 2-((tert-butyldimethylsilyloxy)methyl)-5-hydroxy-4-(methoxymethyl)-5,6-dihydropyridine-1(2H)-carboxylate

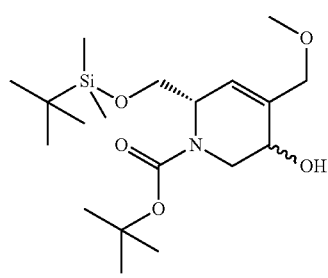 [SMILES: COCC1=C[C@@H](CO[Si](C)(C)C(C)(C)C)N(C(=O)OC(C)(C)C)CC1O]

To a stirred solution of Intermediate 117 (7.3 g, 19.65 mmol) in DCM (180 mL) was added N1,N1,N8,N8-tetramethylnaphthalene-1,8-diamine (25.3 g, 117.89 mmol). Then it was cooled to 0° C. and trimethyloxonium tetrafluoroborate (8.72 g, 58.94 mmol) was added. The reaction was then stirred at rt for several hours until LCMS showed the starting material was all consumed. Then it was concentrated under reduced pressure. The residue was then taken up in 100 mL Et$_2$O and filtered, washed with 100 mL Et$_2$O. The organic layer was then washed with 10% citric acid, aq NaHCO$_3$, brine, dried over MgSO$_4$, filtered and concentrated. The residue was then taken up in MeOH (180 mL), cooled to 0° C. and cerium(III) chloride (7.32 g, 19.65 mmol) was added to give a clear solution. Then NaBH$_4$ (0.743 g, 19.65 mmol) was added as solid, and the mixture was stirred from 0° C. to rt for 1 hr. The reaction mixture was concentrated in vacuo. The white solid was redissolved in 200 mL Et$_2$O and washed with 10% citric acid, NaHCO$_3$, brine, dried over MgSO$_4$, filtered and concentrated. The residue was purified by silica gel column (20-80% Hex/EA, 80 g) to afford the title compound (6.20 g, 81%) as a colorless oil (~3.8:1 mixture of 2 diastereomers).

MS: 388 ES+ ($C_{19}H_{37}NO_5Si$)

Intermediate 119: (S)-tert-butyl 5-(N-(allyloxy)-2-nitrophenylsulfonamido)-2-((tert-butyldimethylsilyloxy)methyl)-4-(methoxymethyl)-5,6-dihydropyridine-1(2H)-carboxylate

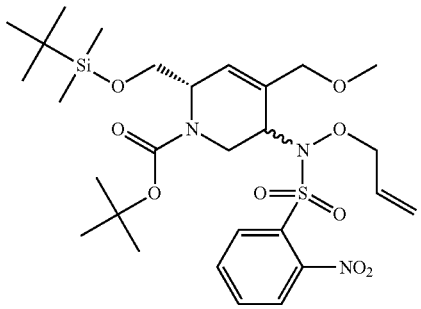 [SMILES: C=CCON(C1CN(C(=O)OC(C)(C)C)[C@H](CO[Si](C)(C)C(C)(C)C)C=C1COC)S(=O)(=O)c1ccccc1[N+](=O)[O-]]

To a stirred solution of Intermediate 118 (6.2 g, 16.00 mmol), N-(allyloxy)-2-nitrobenzenesulfonamide (4.34 g, 16.80 mmol) and triphenylphosphine (5.03 g, 19.20 mmol) in toluene (140 mL), was added (E)-diisopropyl diazene-1,2-dicarboxylate (3.67 g, 17.60 mmol) at rt. The reaction was stirred at rt over the weekend. The mixture was then concentrated and the residue was purified by silica gel column (120 g, 0-100% Hex/EA) to give the title compound (8.80 g, 88%) as an oil MS: 628 ES+ ($C_{28}H_{45}N_3O_9SSi$)

Intermediate 120: (S)—N-(allyloxy)-N-(6-((tert-butyldimethylsilyloxy)methyl)-4-(methoxymethyl)-1,2,3,6-tetrahydropyridin-3-yl)-2-nitrobenzenesulfonamide

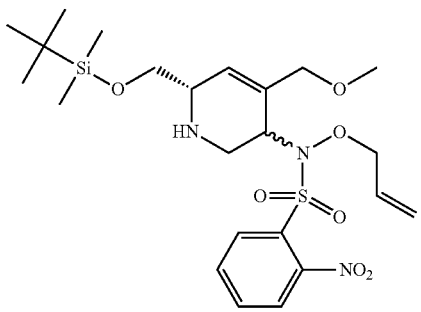 [SMILES: C=CCON(C1CN[C@H](CO[Si](C)(C)C(C)(C)C)C=C1COC)S(=O)(=O)c1ccccc1[N+](=O)[O-]]

A solution of Intermediate 119 (8.8 g, 14.02 mmol) in DCM (120 mL) at room temperature was added to zinc bromide (9.47 g, 42.05 mmol). The reaction mixture was stirred under N$_2$ at room temperature overnight. LCMS showed reaction was completed to give the secondary amine. It was filtered and washed DCM. The DCM layer was washed with aq NaHCO$_3$, brine, dried over MgSO$_4$, filtered and concentrated to give a residue, which was adsorbed onto silica gel and purified by silica gel column (40 g, 20-80% hex/EA) to afford the title compound (5.00 g, 67.6%) as an oil.

MS: 528 ES+ ($C_{23}H_{37}N_3O_7SSi$)

Intermediate 121: (S)—O-allyl-N-(6-((tert-butyldimethylsilyloxy)methyl)-4-(methoxymethyl)-1,2,3,6-tetrahydropyridin-3-yl)hydroxylamine

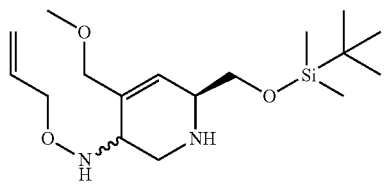 [SMILES: C=CCONC1CN[C@H](CO[Si](C)(C)C(C)(C)C)C=C1COC]

To a stirred suspension of Intermediate 120 (5 g, 9.47 mmol) and $K_2CO_3$ (7.86 g, 56.85 mmol) in acetonitrile (100 mL), PhSH (3.90 mL, 37.90 mmol) was added. The reaction was stirred at rt overnight. It was filtered and concentrated, then diluted with DCM and filtered through disposal filter. The filtrate was concentrated and purified by silica gel column (0-100% Hex/EA, 80 g ISCO) to afford the title compound (2.04 g, 63%) as an oil.

MS: 343 ES+ ($C_{17}H_{34}N_2O_3Si$)

Intermediate 122: (S)-6-(allyloxy)-2-((tert-butyldimethylsilyloxy)methyl)-4-(methoxymethyl)-1,6-diazabicyclo[3.2.1]oct-3-en-7-one

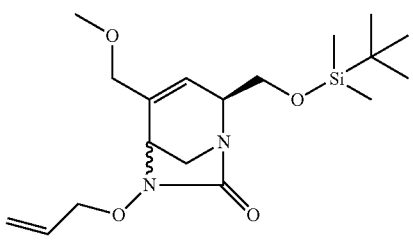 [SMILES: C=CCON1C(=O)N2CC1C(COC)=C[C@H]2CO[Si](C)(C)C(C)(C)C]

To a stirred solution of Intermediate 121 (2.04 g, 5.96 mmol) in acetonitrile (500 mL), N-ethyl-N-isopropylpropan-2-amine (4.15 mL, 23.82 mmol) was added triphosgene (0.721 g, 2.38 mmol) as a solution in 20 mL $CH_3CN$ via syringe pump (0.1 ml/min) at 0° C. The reaction was stirred and allowed to warm from 0° C. to rt overnight. LCMS showed complete conversion to product. The solution was concentrated to give a residue, which was then taken up in 150 mL EtOAc and washed with 5% citric acid, $NaHCO_3$, brine, dried over $MgSO_4$, filtered and concentrated. The residue was purified by silica gel column (40 g, 0-60% Hex/EA) to afford the title compound (1.700 g, 77%) as an oil.

MS: 369 ES+ ($C_{18}H_{32}N_2O_4Si$)

Intermediate 123: (S)-6-(allyloxy)-2-(hydroxymethyl)-4-(methoxymethyl)-1,6-diazabicyclo[3.2.1]oct-3-en-7-one

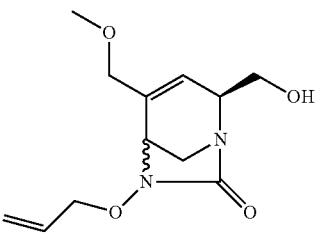 [SMILES: C=CCON1C(=O)N2CC1C(COC)=C[C@H]2CO]

To a stirred solution of Intermediate 122 (1.7 g, 4.61 mmol) in THF (40 mL), TBAF (6.92 mL, 6.92 mmol) was added at 0° C. The reaction mixture was stirred at 0° C. for 1 hr. LCMS indicated the disappearance of starting material and formation of the desired product. The mixture was concentrated and purified by silica gel column (40 g, 50-100% Hex/EA) to give the title compound (1.050 g, 90%) as a white solid.

MS: 255 ES+ ($C_{12}H_{18}N_2O_4$)

Intermediate 124: (S)-6-(allyloxy)-2,4-bis(methoxymethyl)-1,6-diazabicyclo[3.2.1]oct-3-en-7-one

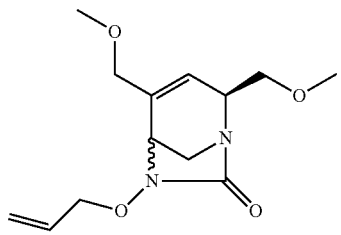 [SMILES: C=CCON1C(=O)N2CC1C(COC)=C[C@H]2COC]

To a stirred solution of Intermediate 123 (0.3 g, 1.18 mmol) in ACN (12 mL) was added iodomethane (0.734 mL, 11.80 mmol) and silver oxide (1.094 g, 4.72 mmol). The reaction was stirred at rt with aluminum foil wrapped around overnight. LCMS showed product. The mixture was filtered and concentrated. The residue was then purified by silica gel column (40 g, 0-100% Hex/EA) to afford the title compound (0.100 g, 31.6%) as an oil.

MS: 269 ES+ ($C_{13}H_{20}N_2O_4$)

Example 14

(2S,5R)-2-(1-(tert-butoxycarbonyl)piperidin-4-ylcarbamoyl)-7-oxo-1,6-diazabicyclo[3.2.1]oct-3-en-6-yl sulfate sodium salt

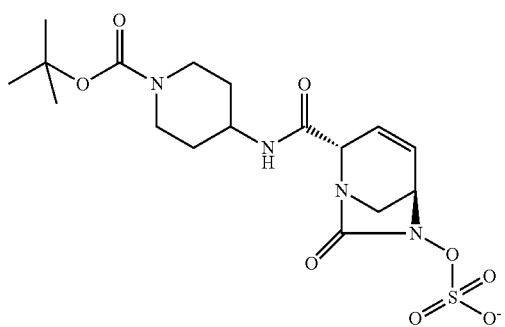 [SMILES: CC(C)(C)OC(=O)N1CCC(NC(=O)[C@@H]2C=C[C@@H]3CN2C(=O)N3OS(=O)(=O)[O-])CC1]

In a beaker, the DOWEX resin 50WX8 (15 g) was conditioned by stirring it for 20 min in 2N sodium hydroxide (39.3 mL, 78.69 mmol), loaded onto a cartridge, washed with water until pH equaled 7, and then was rinsed with acetone/water (1/1) followed by water again. The phosphonium salt (Intermediate 132, 140 mg) was loaded using water and a minimum amount of acetone and eluted with water. The fractions were directly frozen and lyophilized to give the desired sodium salt as a white solid (39 mg).

MS: 445 (M-H) ($C_{17}H_{26}N_4O_8S.[Na^+]$)

$^1$H NMR (300 MHz, DMSO-d) δ: 1.31-1.40 (m, 2H) 1.40-1.45 (s, 9H) 1.70 (m., 2H) 2.79-2.86 (m, 2H) 3.21 (d, 1H) 3.85 (dd, 2H) 3.75 (m, 1H) 3.80-3.93 (m, 2H) 4.01-4.12 (m, 1H) 4.25 (s, 1H) 5.82 (d, 1H) 6.30-6.36 (m, 1H)

Intermediate 125: (2S,5S)-tert-butyl 2-((tert-butyldimethylsilyloxy)methyl)-5-hydroxy-5,6-dihydropyridine-1(2H)-carboxylate

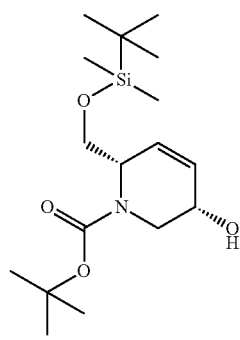 [SMILES: CC(C)(C)OC(=O)N1C[C@@H](O)C=C[C@H]1CO[Si](C)(C)C(C)(C)C]

To a stirred solution of cerious chloride (4.36 g, 11.71 mmol) and (S)-tert-butyl 2-((tert-butyldimethylsilyloxy)methyl)-5-oxo-5,6-dihydropyridine-1(2H)-carboxylate (Intermediate 50, 4.00 g, 11.71 mmol) in 50 mL MeOH at 0° C., NaBH$_4$ (0.443 g, 11.71 mmol) was added as a solid. The mixture was stirred at ambient temp for 15 minutes. The mixture was concentrated and diluted with 10% citric acid (aq), H$_2$O and ethyl acetate. The organic layer was separated and washed with brine, dried over MgSO$_4$, filtered and concentrated to give a residue which was purified by silica gel column (25 g, 20-40% Hex/EA) to give the desired product (2.6 g) as a colorless oil.

MS: 344 ES+ ($C_{17}H_{33}NO_4Si$)

$^1$H NMR (300 MHz, DMSO-d6) δ: −0.10-0.07 (m, 6H) 0.65-0.88 (m, 9H) 1.25 (br. s., 6H) 3.60 (d, J=5.67 Hz, 3H) 5.08 (d, J=5.10 Hz, 1H) 5.67 (br. s., 1H) 5.72-5.86 (m, 1H)

Intermediate 126: (2S,5R)-tert-butyl 5-(N-(allyloxy)-2,4-dinitrophenylsulfonamido)-2-((tert-butyldimethylsilyloxy)methyl)-5,6-dihydropyridine-1(2H)-carboxylate

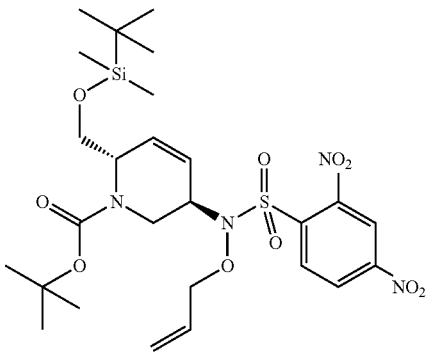 [SMILES: C=CCON([C@@H]1C=C[C@@H](CO[Si](C)(C)C(C)(C)C)N(C(=O)OC(C)(C)C)C1)S(=O)(=O)c1ccc([N+](=O)[O-])cc1[N+](=O)[O-]]

To a stirred solution of (2S,5S)-tert-butyl 2-((tert-butyldimethylsilyloxy)methyl)-5-hydroxy-5,6-dihydropyridine-1(2H)-carboxylate (Intermediate 125, 17.50 g, 50.94 mmol), phosphorus triphenyl (14.70 g, 56.04 mmol), N-(allyloxy)-2,4-dinitrobenzenesulfonamide (16.22 g, 53.49 mmol) in toluene (380 mL) was added diisopropyl azodicarboxylate (11.03 ml, 56.04 mmol) at room temperature. The reaction mixture was stirred at rt overnight. The mixture was concentrated and the residue was purified by silica gel column (220 g, 0-40% Hex/EA) to give the desired product (30.8 g) as a yellow gum.

MS: 429 ES+ ($C_{26}H_{40}N_4O_{10}SSi$)

$^1$H NMR (300 MHz, DMSO-d$_6$) δ: −0.10-0.07 (m, 6H) 0.65-0.88 (m, 9H) 1.25 (br. s., 6H) 1.32 (s, 4H) 5.14 (d, J=10.01 Hz, 2H) 8.01 (dd, J=9.25, 1.89 Hz, 4H) 8.10 (s, 1H)

Intermediate 127: N-(allyloxy)-N-((3R,6S)-6-((tert-butyldimethylsilyloxy)methyl)-1,2,3,6-tetrahydropyridin-3-yl)-2,4-dinitrobenzenesulfonamide

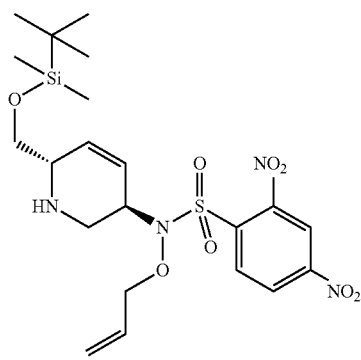 [SMILES: C=CCON([C@@H]1C=C[C@@H](CO[Si](C)(C)C(C)(C)C)NC1)S(=O)(=O)c1ccc([N+](=O)[O-])cc1[N+](=O)[O-]]

To a stirred solution of (2S,5R)-tert-butyl 5-(N-(allyloxy)-2,4-dinitrophenylsulfonamido)-2-((tert-butyldimethylsilyloxy)methyl)-5,6-dihydropyridine-1(2H)-carboxylate (Intermediate 126, 19.5 g, 31.01 mmol) in DCM (250 mL) under nitrogen at rt, zinc bromide (20.95 g, 93.04 mmol) was added. The reaction mixture was stirred at rt for 6 hs, (1 cms indicated the reaction was a clean one) and diluted with 50 mL DCM and washed with sat. NaHCO$_3$, brine, dried over MgSO$_4$, filtered and concentrated to give the desired product as an orange oil (17.5 g).

MS: 529 ES+ (C$_{21}$H$_{32}$N$_4$O$_8$SSi)

$^1$H NMR (300 MHz, CHLOROFORM-d) δ: −0.17-0.11 (m, 6H) 0.65-0.87 (m, 9H) 3.1 (m, 2H), 3.75 (m, 3H) 4.6 (m 3H) 5.26 (d, J=8.69 Hz, 2H) 5.86 (m, J=8.69 Hz, 3H) 8.17-8.57 (m, 3H)

Intermediate 128: O-allyl-N-((3R,6S)-6-((tert-butyldimethylsilyloxy)methyl)-1,2,3,6-tetrahydropyridin-3-yl)hydroxylamine

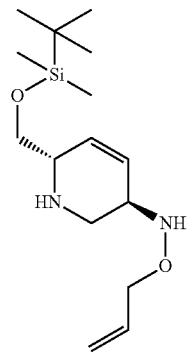 [SMILES: C=CCON[C@@H]1C=C[C@@H](CO[Si](C)(C)C(C)(C)C)NC1]

To a stirred suspension of N-(allyloxy)-N-((3R,6S)-6-((tert-butyldimethylsilyloxy)methyl)-1,2,3,6-tetrahydropyridin-3-yl)-2,4-dinitrobenzenesulfonamide (Intermediate 127, 17.50 g, 33.10 mmol) and potassium carbonate (13.73 g, 99.31 mmol) in acetonitrile (700 mL), benzenethiol (5.10 ml, 49.65 mmol) was added. The reaction mixture was stirred at rt for 2.5 hours. LCMS showed the completion of the reaction. The reaction was concentrated, the diluted with EtOAc and filtered through a disposal filter. The filtrate was concentrated and the crude product was purified on silica gel column (0-4% MeOH in DCM) to get the desired product as a yellow oil (5.6 g).

MS: 299 ES+ (C$_{15}$H$_{30}$N$_2$O$_2$Si)

$^1$H NMR (300 MHz, DMSO-d$_6$) δ: −0.08-0.09 (m, 6H) 0.75-0.92 (m, 9H) 2.53-2.62 (m, 1H) 3.03 (dd, J=11.71, 4.72 Hz, 1H) 3.15-3.25 (m, 1H) 3.29 (s, 1H) 3.37 (td, J=4.58, 2.36 Hz, 1H) 3.41-3.49 (m, 2H) 4.08 (dt, J=5.57, 1.37 Hz, 2H) 5.04-5.27 (m, 2H) 5.61-5.80 (m, 2H) 5.80-6.00 (m, 1H) 6.40 (d, J=7.37 Hz, 1H)

Intermediate 129: (2S,5R)-6-(allyloxy)-2-((tert-butyldimethylsilyloxy)methyl)-1,6-diazabicyclo[3.2.1]oct-3-en-7-one

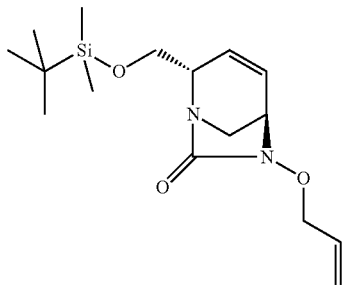 [SMILES: C=CCON1C(=O)N2C[C@H]1C=C[C@H]2CO[Si](C)(C)C(C)(C)C]

To a stirred solution of O-allyl-N-((3R,6S)-6-((tert-butyldimethylsilyloxy)methyl)-1,2,3,6-tetrahydropyridin-3-yl)hydroxylamine (Intermediate 128, 2.0 g, 6.70 mmol) in acetonitrile (560 mL), N-ethyl-N-isopropylpropan-2-amine (4.67 ml, 26.80 mmol) was added. Bis(trichloromethyl)carbonate (0.795 g, 2.68 mmol) dissolved in 40 mL CH$_3$CN was added via a syringe pump (at a rate 0.1 ml/min) at 0° C. The reaction mixture was stirred at 0° C. for 1 hr. It was then allowed to stir at room temperature overnight. The mixture was then concentrated and diluted with EtOAc (50 mL). The organic layer was washed with water, brine, dried over MgSO$_4$, filtered and concentrated. The residue was purified by silica gel column (12 g, 0-25% Hex/EA) to give the desired product as a colorless oil (1.64 g).

MS: 325 ES+ (C$_{16}$H$_{28}$N$_2$O$_3$Si)

$^1$H NMR (300 MHz, DMSO-d$_6$) δ: −0.05-0.07 (m, 6H) 0.67-0.87 (m, 9H) 2.92-3.08 (m, 1H) 3.32 (d, J=11.14 Hz, 1H) 3.48-3.62 (m, 1H) 3.68-3.82 (m, 2H) 3.87 (dd, J=5.00, 2.74 Hz, 1H) 4.29 (dt, J=6.00, 1.25 Hz, 2H) 5.09-5.39 (m, 2H) 5.50-6.02 (m, 2H) 6.11-6.39 (m, 1H)

Intermediate 130: (2S,5R)-6-(allyloxy)-2-(hydroxymethyl)-1,6-diazabicyclo[3.2.1]oct-3-en-7-one

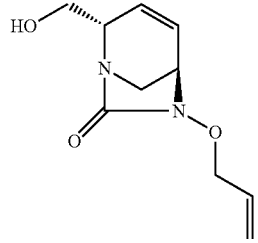

To a stirred solution of (2S,5R)-6-(allyloxy)-2-((tert-butyldimethylsilyloxy)methyl)-1,6-diazabicyclo[3.2.1]oct-3-en-7-one (Intermediate 129, 1.64 g, 5.05 mmol) in THF (40 mL), tetrabutylammonium fluoride (6.06 ml, 6.06 mmol) was added at 0° C. The reaction mixture was stirred at 0° C. for 1 hr. The mixture was concentrated and purified by silica gel column (40 g, 50-100% Hex/EA) to give the desired product (1.03 g) as an yellow oil.

MS: 211 ES+ (C$_{10}$H$_{14}$N$_2$O$_3$)

$^1$H NMR (300 MHz, CHLOROFORM-d) δ: 3.31-3.37 (m, 2H) 3.69-3.81 (m, 2H) 3.88 (dd, J=4.34, 1.51 Hz, 1H) 3.97-4.11 (m, 1H) 4.46 (ddt, J=7.86, 6.63, 1.06, 1.06 Hz, 2H) 5.24-5.45 (m, 2H) 5.56-5.72 (m, 1H) 5.92-6.18 (m, 1H) 6.30-6.49 (m, 1H)

Intermediate 131: tert-butyl 4-((2S,5R)-6-(allyloxy)-7-oxo-1,6-diazabicyclo[3.2.1]oct-3-enecarboxamido)piperidine-1-carboxylate

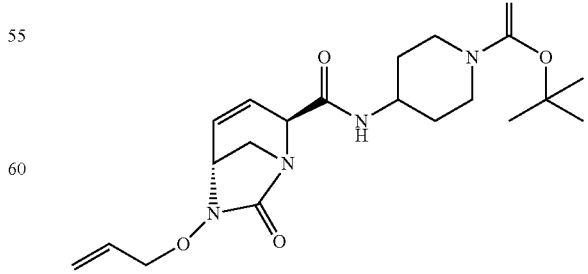

To a solution of periodic acid (6 g, 31.26 mmol) in wet acetonitrile (60 mL) (0.75% water by volume) at room temperature was added chromium(VI) oxide (10 mg, 0.10 mmol). The mixture was stirred until complete dissolution was achieved. This orthoperiodic acid solution was used in the next step.

To a stirred solution of (2S,5R)-6-(allyloxy)-2-(hydroxymethyl)-1,6-diazabicyclo[3.2.1]oct-3-en-7-one (Intermediate 130, 216 mg, 1.03 mmol) in wet $CH_3CN$ (10 mL) (0.75% water by volume) at rt, 9 mL previously formed orthoperiodic acid solution was added dropwise. The mixture was then stirred at rt for 50 minutes, when 50 mL of EtOAc was added. The organic solution was washed with small amount of water and brine then dried over $MgSO_4$, filtered, concentrated to give a light yellow oil as the crude acid (200 mg). To a solution of the crude acid in DMF (5 mL) at 0° C. was added, tert-butyl 4-aminopiperidine-1-carboxylate (214 mg, 1.07 mmol), O-(7-azabenzotriazol-1-yl)-N,N,N',N'-tetramethyluronium hexafluorophosphate (509 mg, 1.34 mmol) and TEA (497 μl, 3.57 mmol). The reaction was stirred at 0° C. for 35 min, then the mixture was diluted with ethyl acetate and washed with brine and water. The combined aqueous washes were extracted once with ethyl acetate. The combined organic extracts were dried over magnesium sulfate, filtered and concentrated. Silica gel chromatography (12 g column, 50%-100% EtOAc) afforded the desired product as a colorless oil (110 mg).

MS: 407 ES+ ($C_{20}H_{30}N_4O_5$)

$^1$H NMR (300 MHz, CHLOROFORM-d) δ: 1.31-1.43 (m, 2H) 1.42-1.51 (m, 9H) 1.90 (br. s., 2H) 2.79-2.96 (m, 2H) 3.01 (d, J=10.39 Hz, 1H) 3.38 (dd, J=10.48, 1.61 Hz, 1H) 3.85 (dd, J=5.00, 3.12 Hz, 1H) 3.89-3.98 (m, 1H) 4.01-4.12 (m, 2H) 4.35-4.52 (m, 3H) 5.22-5.45 (m, 2H) 5.93-6.08 (m, 1H) 6.15 (dd, J=9.35, 3.30 Hz, 1H) 6.32-6.50 (m, 1H) 6.84 (d, J=7.55 Hz, 1H)

Intermediate 132: (E)-triphenyl(prop-1-enyl)phosphonium (2S,5R)-2-(1-(tert-butoxycarbonyl)piperidin-4-ylcarbamoyl)-7-oxo-1,6-diazabicyclo[3.2.1]oct-3-en-6-yl sulfate

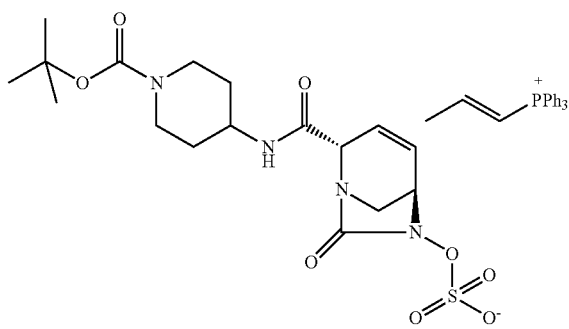

To a solution of tert-butyl 4-((2S,5R)-6-(allyloxy)-7-oxo-1,6-diazabicyclo[3.2.1]oct-3-enecarboxamido)piperidine-1-carboxylate (Intermediate 131, 110 mg, 0.52 mmol) in DCM (5 mL) was added AcOH (59.2 μl, 1.03 mmol) (dried over $Na_2SO_4$) and tetrakis(triphenyl-phosphine)palladium(0) (597 mg, 0.52 mmol) under nitrogen at room temperature. The yellow solution was stirred at room temperature for 1 hr. To the mixture was added pyridine (10 mL), followed by pyridine/sulfur trioxide complex (493 mg, 3.10 mmol). The suspension was stirred at room temperature overnight under nitrogen. The reaction mixture was concentrated to dryness (≤30° C.) and then purified on silica gel column (acetone in hexane (5 to 100%)) to yield an off-white solid (140 mg).

Example 15

(2S,5R)-4-(dimethylcarbamoyl)-2-(methoxymethyl)-7-oxo-1,6-diazabicyclo[3.2.1]oct-3-en-6-yl sulfate sodium salt

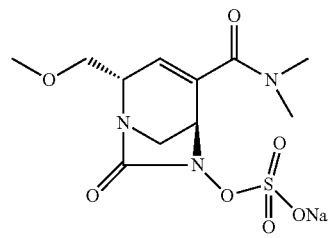

Dowex® 50WV8, 100-200 mesh, ion exchange resin (0.63 g, 9.41 mol) was conditioned by stirring for 3 hours in 2N NaOH (1.6 mL, 3.20 mmol). The resin was then loaded into a cartridge and washed with water until the pH was 7. It was then washed with (1/1) acetone/water, followed by water. (E)-triphenyl(prop-1-enyl)phosphonium (2S,5R)-4-(dimethylcarbamoyl)-2-(methoxymethyl)-7-oxo-1,6-diazabicyclo[3.2.1]oct-3-en-6-yl sulfate (Intermediate 144, 6 mg, 9.41 μmol) was taken up in water. The yellow solution was loaded on the resin and washed through with water. The product was collected. Dried on lyophilizer to obtain the desired product (3.3 mg, 98%) as an off-white solid.

MS: 334 ES− ($C_{11}H_{16}N_3O_7SNa$)

$^1$H NMR (300 MHz, $D_2O$) δ: 2.99 (s, 7H) 3.13 (s, 7H) 3.44 (s, 6H) 3.56 (d, J=1.70 Hz, 4H) 3.65-3.79 (m, 5H) 4.24 (ddd, J=8.34, 4.47, 3.01 Hz, 2H) 4.47 (s, 2H) 5.97 (d, J=1.88 Hz, 2H)

Intermediate 133: (2S,5R)-tert-butyl 2-((tert-butyldimethylsilyloxy)methyl)-4-(dimethylcarbamoyl)-5-hydroxy-5,6-dihydropyridine-1 (2H)-carboxylate

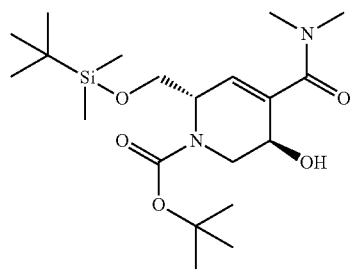 [SMILES: CN(C)C(=O)C1=C[C@@H](CO[Si](C)(C)C(C)(C)C)N(C(=O)OC(C)(C)C)C[C@@H]1O]

A dry, two-necked, round-bottomed flask equipped with a reflux condenser fitted with a nitrogen inlet at its top, a rubber septum, and a magnetic stirring bar was charged with toluene (7.5 mL) and flushed briefly with nitrogen after which trimethylaluminum in hexanes (3.5 mL, 7.0 mmol) was injected through the septum into the flask. The solution was stirred and cooled in an ice-salt bath at −10° to −15°, and dimethylamine in THF (3.36 mL, 6.72 mmol) was added slowly with a syringe. Twenty minutes after the addition was completed, the cooling bath was removed, and the contents of the flask were allowed to stir and warm slowly to room temperature over a 45-minute period. A solution of (2S,5R)-1-tert-butyl 4-methyl 2-((tert-butyldimethylsilyloxy)methyl)-5-hydroxy-5,6-dihydropyridine-1,4(2H)-dicarboxylate (Intermediate 102, 2.25 g, 5.60 mmol) in toluene (3 mL) was prepared and injected into two-necked flask through the septum under nitrogen, immediate bubbling was observed. The resulting solution was stirred overnight at rt. LCMS showed a tiny amount of starting material left. Another batch of $Me_2AlNMe_2$ was prepared using 0.6 mL amine and 0.6 mL $AlMe_3$ in 1 mL toluene and transferred into reaction mix. The reaction was stirred for 3 more hours. The reaction was then hydrolyzed by slow, cautious addition of 7.82 mL (7.82 mmole) of 1M HCl. The mixture was then stirred for 30 minutes to ensure complete hydrolysis. The upper organic layer was separated, and the aqueous layer was extracted with three 50 mL portions of EtOAc. The organic extracts were combined, washed with brine, dried with anhydrous $Na_2SO_4$ and evaporated under reduced pressure to obtain the desired product (2.194 g, 94%) as a clear brown oil.

MS: 415 ES+ ($C_{20}H_{38}N_2O_5Si$)

$^1$H NMR (300 MHz, DMSO-d6) δ: 0.01 (s, 6H) 0.83-0.86 (m, 9H) 1.40-1.44 (m, 9H) 2.91 (br. s., 7H) 3.66-3.73 (m, 2H) 4.04 (m, J=7.00 Hz, 1H) 4.15-4.22 (m, 1H) 4.33-4.51 (m, 1H) 4.98 (d, J=6.22 Hz, 1H) 5.88 (d, J=3.58 Hz, 1H)

Intermediate 134: (S)-tert-butyl 2-((tert-butyldimethylsilyloxy)methyl)-4-(dimethylcarbamoyl)-5-oxo-5,6-dihydropyridine-1(2H)-carboxylate

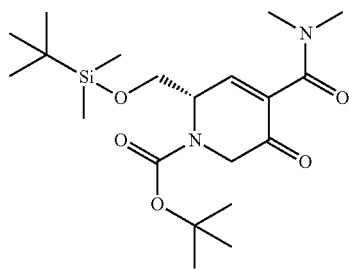 [SMILES: CN(C)C(=O)C1=C[C@@H](CO[Si](C)(C)C(C)(C)C)N(C(=O)OC(C)(C)C)CC1=O]

(2S,5R)-tert-butyl 2-((tert-butyldimethylsilyloxy)methyl)-4-(dimethylcarbamoyl)-5-hydroxy-5,6-dihydropyridine-1(2H)-carboxylate (Intermediate 133, 2.194 g, 5.29 mmol) in DCM (65 mL) was cooled in an ice-bath then Dess-Martin periodinane in DCM (26.5 mL, 7.94 mmol) was added and the reaction was stirred at rt overnight. The organic solution was washed with sat.

$Na_2S_2O_3$, sat. $NaHCO_3$, brine, dried over $MgSO_4$, filtered and evaporated. The crude product was purified via flash chromatography (10-75% EA/EtOAc) to obtain the desired product (1.050 g, 48.1%).

MS: 413 ES+ ($C_{20}H_{36}N_2O_5Si$)

$^1$H NMR (300 MHz, DMSO-d6) δ: 0.02 (s, 6H) 0.83 (s, 9H) 1.44 (s, 9H) 2.81 (s, 3H) 2.89 (s, 3H) 3.79-4.02 (m, 3H) 4.30-4.48 (m, 1H) 4.72-4.87 (m, 1H) 7.10-7.22 (m, 1H)

Intermediate 135: (2S,5S)-tert-butyl 2-((tert-butyldimethylsilyloxy)methyl)-4-(dimethylcarbamoyl)-5-hydroxy-5,6-dihydropyridine-1 (2H)-carboxylate

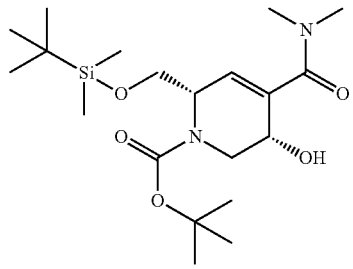 [SMILES: CN(C)C(=O)C1=C[C@@H](CO[Si](C)(C)C(C)(C)C)N(C(=O)OC(C)(C)C)C[C@H]1O]

To a stirred solution of cerium(III) chloride heptahydrate (0.948 g, 2.54 mmol) and (S)-tert-butyl 2-((tert-butyldimethylsilyloxy)methyl)-4-(dimethylcarbamoyl)-5-oxo-5,6-dihydropyridine-1(2H)-carboxylate (Intermediate 134, 1.05 g, 2.54 mmol) in 1 mL MeOH at 0° C., sodium tetrahydroborate (0.096 g, 2.54 mmol) was added as a solid. The mixture was stirred at ambient temp for 15 minutes. The mixture was concentrated and diluted with $NH_4Cl$(aq), $H_2O$ and ether. The ether layer was separated and washed with brine, dried over $Na_2SO_4$, filtered and concentrated to give the desired product (1.034 g, 98%) as a beige solid.

MS: 415 ES+ ($C_{20}H_{38}N_2O_5Si$)

$^1$H NMR (300 MHz, DMSO-$d_6$) j 0.03 (s, 6H) 0.76-0.92 (m, 9H) 1.30-1.48 (m, 9H) 2.71-3.05 (m, 7H) 3.74 (d, J=4.71 Hz, 2H) 4.18 (br. s., 3H) 5.34 (d, J=5.46 Hz, 1H) 5.66 (br. s., 1H)

Intermediate 136: (3S,6S)-1-(tert-butoxycarbonyl)-6-((tert-butyldimethylsilyloxy)methyl)-3-hydroxy-1,2,3,6-tetrahydropyridine-4-carboxylic acid

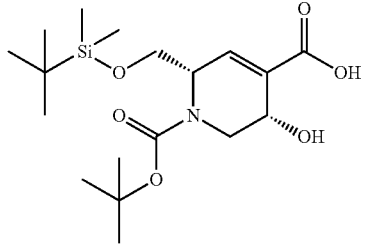 [SMILES: CC(C)(C)OC(=O)N1C[C@@H](O)C(C(=O)O)=C[C@H]1CO[Si](C)(C)C(C)(C)C]

(2S,5S)-1-tert-butyl 4-methyl 2-((tert-butyldimethylsilyloxy)methyl)-5-hydroxy-5,6-dihydropyridine-1,4(2H)-dicarboxylate (Intermediate 101, 4.22 g, 10.51 mmol) was dissolved in THF (64.0 mL) and water (32 mL) and then LiOH (0.277 g, 11.56 mmol) was added and stirred at rt overnight. The reaction mixture was acidified with 1N HCl, extracted with EtOAc, washed with brine, dried over $Na_2SO_4$, filtered and concentrated to obtain the desired product (4.07 g, 100%) as a transparent oil.

MS: 386 ES− ($C_{18}H_{33}NO_6Si$)

$^1$H NMR (300 MHz, DMSO-$d_6$) δ: 0.04 (s, 6H) 0.84-0.90 (m, 9H) 1.40 (s, 9H) 2.73-2.88 (m, 1H) 3.75 (d, J=5.46 Hz, 2H) 4.25 (t, J=7.16 Hz, 1H) 4.41 (br. s., 1H) 5.15 (br. s., 1H) 6.65 (d, J=3.96 Hz, 1H) 12.46 (br. s., 1H)

Intermediate 137: (2S,5S)-tert-butyl 2-((tert-butyldimethylsilyloxy)methyl)-4-(dimethylcarbamoyl)-5-hydroxy-5,6-dihydropyridine-1(2H)-carboxylate

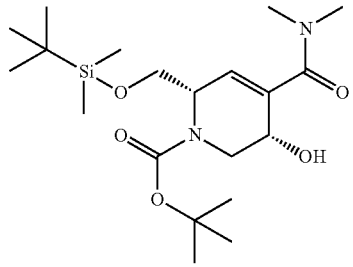 [SMILES: CN(C)C(=O)C1=C[C@@H](CO[Si](C)(C)C(C)(C)C)N(C(=O)OC(C)(C)C)C[C@H]1O]

To a solution of (3S,6S)-1-(tert-butoxycarbonyl)-6-((tert-butyldimethylsilyloxy)methyl)-3-hydroxy-1,2,3,6-tetrahydropyridine-4-carboxylic acid (Intermediate 136, 4.07 g, 10.50 mmol) in DMF (20 mL) at room temperature was added 2M dimethylamine in THF (5.25 mL, 10.50 mmol), HATU (5.99 g, 15.75 mmol) and then DIEA (5.50 mL, 31.51 mmol). The reaction mixture was stirred at room temperature. The reaction ran until the starting material was consumed, then it was quenched with water and extracted with EtOAc. The organic solutions was then washed with brine, and purified via flash chromatography (35-100% EA/Hex) to isolate the desired product (3.05 g, 70.0%) as a pink glassy solid.

MS: 415 ES+ ($C_{20}H_{38}N_2O_5Si$)

$^1$H NMR (300 MHz, DMSO-$d_6$) δ: 0.03 (s, 6H) 0.76-0.92 (m, 9H) 1.30-1.48 (m, 9H) 2.71-3.05 (m, 7H) 3.74 (d, J=4.71 Hz, 2H) 4.18 (br. s., 3H) 5.34 (d, J=5.46 Hz, 1H) 5.66 (br. s., 1H)

Intermediate 138: (2S,5R)-tert-butyl 5-(N-(allyloxy)-2-nitrophenylsulfonamido)-2-((tert-butyldimethylsilyloxy)methyl)-4-(dimethylcarbamoyl)-5,6-dihydropyridine-1(2H)-carboxylate

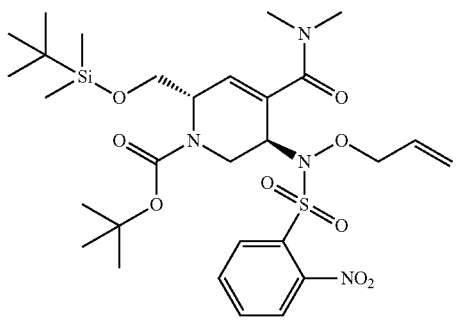 [SMILES: C=CCON([C@H]1CN(C(=O)OC(C)(C)C)[C@H](CO[Si](C)(C)C(C)(C)C)C=C1C(=O)N(C)C)S(=O)(=O)c1ccccc1[N+](=O)[O-]]

A stirred suspension of (2S,5S)-tert-butyl 2-((tert-butyldimethylsilyloxy)methyl)-4-(dimethylcarbamoyl)-5-hydroxy-5,6-dihydropyridine-1(2H)-carboxylate (Intermediate 137, 3.09 g, 7.45 mmol), N-(allyloxy)-2-nitrobenzenesulfonamide (2.348 g, 9.09 mmol) and triphenylphosphine (2.150 g, 8.20 mmol) in toluene (65 mL) was cooled in a salt-ice-bath and then (E)-diisopropyl diazene-1,2-dicarboxylate (1.588 mL, 8.20 mmol) was added dropwise. The reaction was let warm up to rt and was stirred for an additional 2 h. The solvent was removed and the crude product was loaded onto silica gel, purified via flash chromatography (25-75% EA/Hex) to obtain the desired product (4.0 g, 82%) as an off-white solid.

MS: 655 ES+ ($C_{29}H_{46}N_4O_9SSi$)

$^1$H NMR (300 MHz, DMSO-$d_6$) δ: −0.01 (s, 6H) 0.82 (s, 9H) 1.37 (d, J=12.24 Hz, 9H) 2.56-3.06 (m, 6H) 3.06-3.25 (m, 1H) 3.60-3.81 (m, 2H) 4.07-4.41 (m, 3H) 4.41-4.68 (m, 1H) 4.73 (br. s., 1H) 5.14-5.33 (m, 2H) 5.70-5.92 (m, 1H) 6.18-6.31 (m, 1H) 7.83-8.09 (m, 4H)

Intermediate 139: (2S,5R)-tert-butyl 5-(N-(allyloxy)-2-nitrophenylsulfonamido)-4-(dimethylcarbamoyl)-2-(hydroxymethyl)-5,6-dihydropyridine-1(2H)-carboxylate

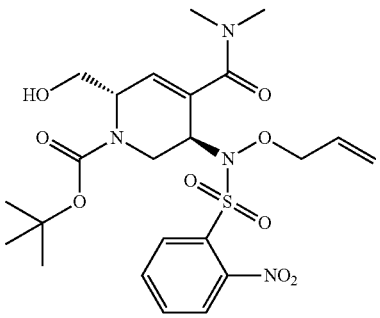 [SMILES: C=CCON([C@H]1CN(C(=O)OC(C)(C)C)[C@H](CO)C=C1C(=O)N(C)C)S(=O)(=O)c1ccccc1[N+](=O)[O-]]

(2S,5R)-tert-butyl 5-(N-(allyloxy)-2-nitrophenylsulfonamido)-2-((tert-butyldimethyl-silyloxy)methyl)-4-(dimethylcarbamoyl)-5,6-dihydropyridine-1(2H)-carboxylate (Intermediate 138, 4 g, 6.11 mmol) in THF (20 mL) was charged with nitrogen and cooled in an ice-bath. To this solution was added 1M TBAF in THF (7.33 mL, 7.33 mmol) dropwise and stirred for 1 h. The solvent was then removed and the crude product loaded onto silica gel and purified via flash chromatography (0-20% MeOH-DCM) to obtain the desired product (2.98 g, 90%) as a beige solid.

MS: 541 ES+ ($C_{23}H_{32}N_4O_9S$)

$^1$H NMR (300 MHz, DMSO-$d_6$) δ: 1.38 (d, J=6.03 Hz, 9H) 2.85 (br. s., 6H) 3.04-3.27 (m, 1H) 3.51 (br. s., 2H) 4.27 (br. s., 3H) 4.39-4.64 (m, 1H) 4.75 (br. s., 1H) 4.87-4.99 (m, 1H) 5.24 (t, J=3.96 Hz, 2H) 5.73-5.91 (m, 1H) 6.18-6.35 (m, 1H) 8.00 (br. s., 4H)

Intermediate 140: (2S,5R)-tert-butyl 5-(N-(allyloxy)-2-nitrophenylsulfonamido)-4-(dimethylcarbamoyl)-2-(methoxymethyl)-5,6-dihydropyridine-1(2H)-carboxylate

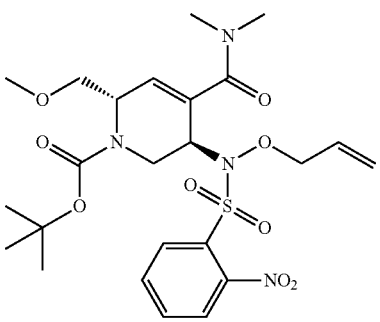 [SMILES: C=CCON([C@H]1CN(C(=O)OC(C)(C)C)[C@H](COC)C=C1C(=O)N(C)C)S(=O)(=O)c1ccccc1[N+](=O)[O-]]

(2S,5R)-tert-butyl 5-(N-(allyloxy)-2-nitrophenylsulfonamido)-4-(dimethylcarbamoyl)-2-(hydroxymethyl)-5,6-dihydropyridine-1(2H)-carboxylate (Intermediate 139, 1.64 g, 3.03 mmol) and silver oxide (2.81 g, 12.13 mmol) were dissolved in acetonitrile (40 mL). To this solution was added iodomethane (1.897 mL, 30.34 mmol) under $N_2$ and stirred over for 5 days protected from the light. The reaction mixture was then filtered through Celite, rinsed with EtOAc, and the crude product was loaded onto silica gel. The product was purified by flash chromatography (0-20% MeOH/DCM) to yield the desired product (1.643 g, 98%) as an off-white solid.

MS: 555 ES+ ($C_{24}H_{34}N_4O_9S$)

$^1$H NMR (300 MHz, DMSO-$d_6$) j 1.38 (d, J=7.35 Hz, 9H) 2.57-3.20 (m, 7H) 3.22 (s, 3H) 3.44 (d, J=3.58 Hz, 2H) 4.08-4.35 (m, 3H) 4.57-4.82 (m, 2H) 5.17-5.31 (m, 2H) 5.73-5.90 (m, 1H) 6.16-6.32 (m, 1H) 7.82-7.92 (m, 1H) 7.99 (d, J=6.22 Hz, 3H)

Intermediate 141: (3R,6S)-3-(N-(allyloxy)-2-nitrophenylsulfonamido)-6-(methoxymethyl)-N,N-dimethyl-1,2,3,6-tetrahydropyridine-4-carboxamide

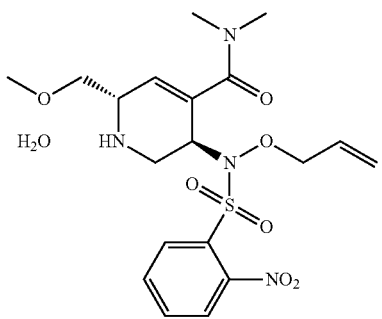

To a solution of (2S,5R)-tert-butyl 5-(N-(allyloxy)-2-nitrophenylsulfonamido)-4-(dimethylcarbamoyl)-2-(methoxymethyl)-5,6-dihydropyridine-1 (2H)-carboxylate (Intermediate 140, 1.642 g, 2.96 mmol) in DCM (8 mL) was added trifluoroacetic acid (4.33 mL, 56.25 mmol) and stirred at rt for 30 minutes. Upon addition, the color of the solution immediately turned pink. Then the solvents were evaporated and the crude product redissolved in DCM and washed with 0.5N NaOH, brine, filtered and concentrated to obtain the desired product (1.346 g, 100%) as a beige foam.

MS: 455 ES+ ($C_{19}H_{26}N_4O_7S$)

$^1$H NMR (300 MHz, DMSO-$d_6$) δ: 2.62-3.03 (m, 9H) 3.20-3.28 (m, 5H) 3.55 (br. s., 1H) 4.31-4.44 (m, 1H) 4.48 (d, J=6.97 Hz, 1H) 4.65 (br. s., 1H) 5.19-5.33 (m, 2H) 5.81-5.97 (m, 1H) 6.12 (s, 1H) 7.86-7.92 (m, 1H) 7.95-8.09 (m, 2H)

Intermediate 142: (3R,6S)-3-(allyloxyamino)-6-(methoxymethyl)-N,N-dimethyl-1,2,3,6-tetrahydropyridine-4-carboxamide

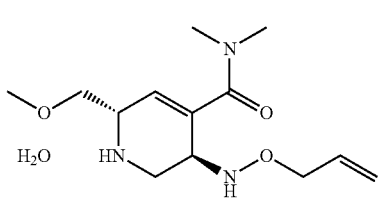

To a solution of (3R,6S)-3-(N-(allyloxy)-2-nitrophenylsulfonamido)-6-(methoxymethyl)-N,N-dimethyl-1,2,3,6-tetrahydropyridine-4-carboxamide (Intermediate 141, 1.346 g, 2.96 mmol) and potassium carbonate (2.456 g, 17.77 mmol) in acetonitrile (50 mL) was added benzenethiol (1.825 mL, 17.77 mmol) and stirred at rt overnight. The solvent was evaporated then the crude mixture was redissolved in DCM and a little bit MeOH, filtered, loaded onto silica gel. The crude product was purified via flash chromatography (0-20% MeOH/DCM) and dried under high-vacuum to obtain the desired product (0.725 g, 91%) as a pale yellow oil.

MS: 270 ES+ ($C_{13}H_{23}N_3O_3$)

$^1$H NMR (300 MHz, DMSO-$d_6$) δ: 2.78-3.00 (m, 9H) 3.20-3.28 (m, 5H) 3.46 (br. s., 1H) 3.58 (d, J=8.10 Hz, 1H) 4.02 (dt, J=5.51, 1.39 Hz, 2H) 5.08-5.23 (m, 2H) 5.79-5.92 (m, 2H) 6.36-6.41 (m, 1H)

Intermediate 143: (2S,5R)-6-(allyloxy)-2-(methoxymethyl)-N,N-dimethyl-7-oxo-1,6-diazabicyclo[3.2.1]oct-3-ene-4-carboxamide

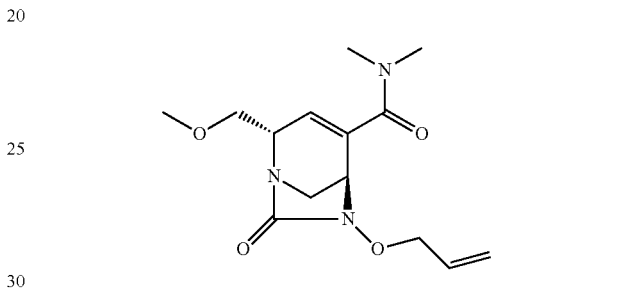

A solution of (3R,6S)-3-(allyloxyamino)-6-(methoxymethyl)-N,N-dimethyl-1,2,3,6-tetrahydropyridine-4-carboxamide (Intermediate 142, 725 mg, 2.69 mmol) and Hunig's Base (1.880 mL, 10.77 mmol) in acetonitrile (350 mL) was cooled to below 0° C. in an ice-salt bath and then a solution of triphosgene (320 mg, 1.08 mmol) in ACN (22 mL) was added at a rate of 0.1 mL/min. The reaction was stirred overnight at rt. Upon completion of the reaction, the solvents were removed and the crude mixture was redissolved in EtOAc, washed with sat. NaHCO$_3$ and brine, dried over MgSO$_4$, filtered and concentrated to obtain the desired product (658 mg, 83%) as a pale yellow oil.

MS: 296 ES+ ($C_{14}H_{21}N_3O_4$)

$^1$H NMR (300 MHz, DMSO-$d_6$) δ: 2.92 (br. s., 6H) 3.16-3.22 (m, 1H) 3.28 (s, 3H) 3.32-3.38 (m, 1H) 3.51-3.65 (m, 2H) 3.92 (ddd, J=6.40, 4.99, 2.92 Hz, 1H) 4.16 (d, J=2.64 Hz, 1H) 4.34 (dd, J=5.84, 1.32 Hz, 2H) 5.20-5.35 (m, 2H) 5.80 (dd, J=2.92, 1.04 Hz, 1H) 5.81-5.95 (m, 1H)

Intermediate 144: (E)-triphenyl(prop-1-enyl)phosphonium (2S,5R)-4-(dimethylcarbamoyl)-2-(methoxymethyl)-7-oxo-1,6-diazabicyclo[3.2.1]oct-3-en-6-yl sulfate

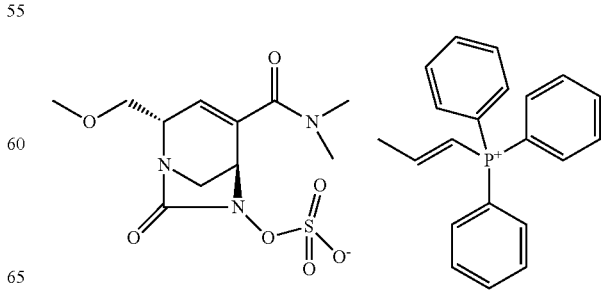

To a solution of (2S,5R)-6-(allyloxy)-2-(methoxymethyl)-N,N-dimethyl-7-oxo-1,6-diazabicyclo[3.2.1]oct-3-ene-4-carboxamide (Intermediate 143, 115 mg, 0.39 mmol) and AcOH (0.045 mL, 0.78 mmol) (dried over sodium sulfate) in CH$_2$Cl$_2$ (3 mL) at room temperature was added Pd(Ph$_3$P)$_4$ (450 mg, 0.39 mmol) under a nitrogen atmosphere. The solution was astirred at rt for 1 h. To this reaction was added pyridine (3.00 mL) and sulfur trioxide pyridine complex (496 mg, 3.12 mmol) and continued stirring under N$_2$ at rt overnight. The desired mass was observed by LC/MS in the reaction mixture. The suspension was evaporated to dryness and then resuspended in DCM. The solids were filtered off through a 0.2 nalgene filter. The filtrate was concentrated to afford a yellow oil. The 80 mg crude was purified using prep HPLC using Water/Formic Acid. The product was then lyophilized to obtain 6 mg slightly impure product which was kept under inert atmosphere until next step.

Example 16

(2S,5R)-2-(hydroxymethyl)-4-methyl-7-oxo-1,6-diazabicyclo[3.2.1]oct-3-en-6-yl hydrogen sulfate Sodium Salt

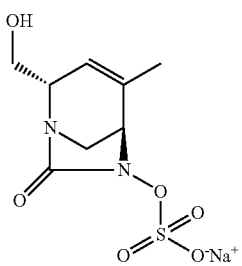

In a 150 mL of beaker, the DOWEX resin 50WX8 (50 g) was conditioned by stirring it for 20 min in 2N sodium hydroxide (40 mL), loaded onto a cartridge, washed with water until pH was 7, then washed with acetone/water (1/1) and water again. (2S,5R)-2-((tert-butyldimethylsilyloxy)methyl)-4-methyl-7-oxo-1,6-diazabicyclo[3.2.1]oct-3-en-6-yl sulfate-(E)-triphenyl(prop-1-enyl)phosphonium (Intermediate 145, 190 mg) was loaded using water and a minimum amount of acetone and eluted with water. The fractions were directly frozen and lyophilized to give the compound as a white solid (130 mg), which was purified by a reversed phase chromatography (MeCN in water: 0-4%) to give a white solid as the desired product (31 mg).

MS: 263 ES− (C$_8$H$_{12}$N$_2$O$_6$S.[Na+])

$^1$H NMR (300 MHz, DMSO-d$_6$) δ: 1.76 (t, J=1.70 Hz, 3H) 3.02-3.14 (m, 1H) 3.15-3.25 (m, 1H) 3.41-3.52 (m, 1H) 3.52-3.62 (m, 2H) 3.92 (d, J=2.83 Hz, 1H) 4.72-4.89 (m, 1H) 5.27 (s, 1H)

Intermediate 145: (2S,5R)-2-((tert-butyldimethylsilyloxy)methyl)-4-methyl-7-oxo-16-diazabicyclo[3.2.1]oct-3-en-6-yl sulfate-(E)-triphenyl(prop-1-enyl)phosphonium

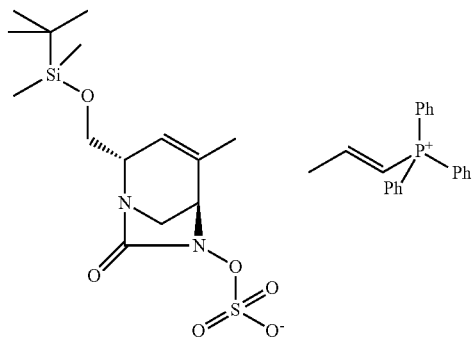 [SMILES: CC1=C[C@@H](CO[Si](C)(C)C(C)(C)C)N2C[C@@H]1N(OS(=O)(=O)[O-])C2=O ; C/C=C/[P+](c1ccccc1)(c1ccccc1)c1ccccc1]

To a solution of (2S,5R)-6-(allyloxy)-2-((tert-butyldimethylsilyloxy)methyl)-4-methyl-1,6-diazabicyclo[3.2.1]oct-3-en-7-one (Intermediate 13, 0.40 g, 1.18 mmol) in DCM (20 mL) was added dried acetic acid (0.135 mL, 2.36 mmol) and tetrakis(triphenylphosphine)palladium(0) (1.365 g, 1.18 mmol) under nitrogen at room temperature. The yellow solution was stirred at room temperature for 4 hours, LC/MS indicated the starting material was gone. Then to the mixture was added pyridine (20 ml), followed by pyridine-sulfurtrioxide (1.128 g, 7.09 mmol). The suspension was stirred at room temperature overnight under nitrogen. The mixture was concentrated to dryness (<=30° C.), redissolved in DCM and filtered. The crude product was purified on silica gel column (Acetone in DCM: 10-40%) to give a white solid (190 mg) as the desired product.

MS: 377 ES− (C$_{14}$H$_{25}$N$_2$O$_6$SSi)

$^1$H NMR (300 MHz, DMSO-d$_6$) δ: ppm −0.11-0.09 (m, 6H) 0.73-0.88 (m, 9H) 1.21-1.22 (m, 0H) 1.71 (t, J=1.89 Hz, 3H) 2.06-2.19 (m, 2H) 3.03 (dd, J=11.05, 2.93 Hz, 1H) 3.42-3.57 (m, 1H) 3.60-3.79 (m, 2H) 3.88 (d, J=3.02 Hz, 1H) 5.20 (dt, J=2.74, 1.46 Hz, 1H) 6.44-6.73 (m, 1H) 7.08-7.36 (m, 1H) 7.51-7.79 (m, 10H) 7.80-7.98 (m, 3H)

Example 17

(2S,5R)-3-methyl-7-oxo-2-(piperidin-1-ium-4-ylcarbamoyl)-1,6-diazabicyclo[3.2.1]oct-3-en-6-yl sulfate

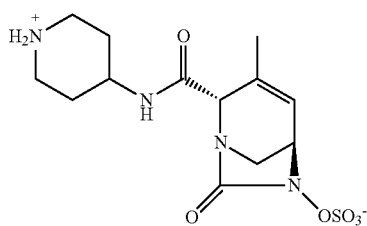

To a solution of (E)-triphenyl(prop-1-en-1-yl)phosphonium (2S,5R)-2-((1-(tert-butoxycarbonyl)piperidin-4-yl)carbamoyl)-3-methyl-7-oxo-1,6-diazabicyclo[3.2.1]oct-3-en-6-yl sulfate (Intermediate 152, 0.2 g, 0.26 mmol) in DCM (3 mL) at 0° C. was added TFA (0.5 mL). The reaction mixture was stirred for 30 minutes and concentrated to afford a yellow oil. The residue was redissolved in DCM and extracted with water. The aqueous was lyophilized. Purification was done on reverse phase HPLC (0%-20% acetonitrile in water, Synergi Polar RP 21.2 mm×100 mm, 4 m coupled with YMC C30, 20 mm×150 mm, 5 μm) to afford the title compound as a white solid (18.7 mg, 20%).

Optical Rotation: (0.16 g/dL, DMSO)=−291

MS: 359 ES− ($C_{13}H_{20}N_4O_6S$)

$^1$H NMR (300 MHz, $D_2O$) δ: 1.74 (m, 3H); 1.82 (m, 2H); 2.19 (m, 2H); 3.15 (m, 2H); 3.47 (m, 3H); 3.61 (m, 1H); 4.05 (m, 1H); 4.29 (m, 1H); 4.39 (m, 1H); 6.30 (m, 1H).

Intermediate 146: N-[(3R,6S)-6-[[(tert-butyldimethylsilyl)oxy]methyl]-5-methyl-1,2,3,6-tetrahydropyridin-3-yl]-2-nitro-N-(prop-2-en-1-yloxy)benzene-1-sulfonamide

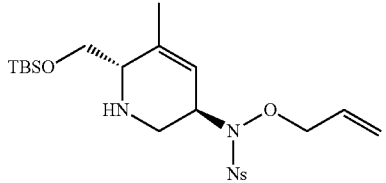

Into a 250-mL round-bottom flask purged and maintained with an inert atmosphere of nitrogen, was placed a solution of tert-butyl (3R,6S)-6-[[(tert-butyldimethylsilyl)oxy]methyl]-5-methyl-3-[N-(prop-2-en-1-yloxy)(2-nitrobenzene)sulfonamido]-1,2,3,6-tetrahydropyridine-1-carboxylate (Intermediate 80, 13.6 g, 22.75 mmol, 1.00 equiv) in dichloromethane (100 mL). This was followed by the addition of $ZnBr_2$ (10.2 g, 45.29 mmol, 2.00 equiv) in several batches. The resulting solution was stirred overnight at room temperature. The resulting solution was diluted with 500 mL of dichloromethane. The resulting mixture was washed with 2×200 mL of sodium bicarbonate(aq) and 2×200 mL of $NH_4Cl$(aq). The mixture was dried over anhydrous sodium sulfate and concentrated under vacuum. This resulted in 12 g (crude product) of the title compound as yellow oil.

MS: 498 ES+ ($C_{22}H_{35}N_3O_6SSi$)

Intermediate 147: (3R,6S)-6-[[(tert-butyldimethylsilyl)oxy]methyl]-5-methyl-N-(prop-2-en-1-yloxy)-1,2,3,6-tetrahydropyridin-3-amine

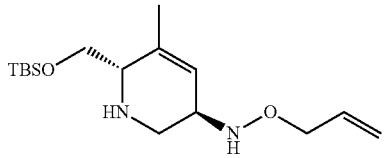 [SMILES: C=CCON[C@@H]1C=C(C)[C@@H](CO[Si](C)(C)C(C)(C)C)NC1]

Into a 250-mL round-bottom flask purged and maintained with an inert atmosphere of nitrogen, was placed a solution of N-[(3R,6S)-6-[[(tert-butyldimethylsilyl)oxy]methyl]-5-methyl-1,2,3,6-tetrahydropyridin-3-yl]-2-nitro-N-(prop-2-en-1-yloxy)benzene-1-sulfonamide (Intermediate 146, 12 g, 24.11 mmol, 1.00 equiv) in N,N-dimethylformamide (100 mL), 2-sulfanylacetic acid (4.4 g, 47.77 mmol, 2.00 equiv). This was followed by the addition of LiOH (5.8 g, 242.17 mmol, 10.00 equiv), in portions. The resulting solution was stirred for 2 h at room temperature. The resulting solution was diluted with 500 mL of water. The resulting solution was extracted with 5×200 mL of ethyl acetate and the organic layers combined. The resulting mixture was washed with 3×200 mL of brine and 2×200 mL of sodium bicarbonate (aq.). The mixture was dried over anhydrous sodium sulfate and concentrated under vacuum. This resulted in 8.4 g (crude product) of the title compound as yellow oil.

MS: 313 ES+ ($C_{16}H_{32}N_2O_2Si$)

Intermediate 148: (2S,5R)-2-[[(tert-butyldimethylsilyl)oxy]methyl]-3-methyl-6-(prop-2-en-1-yloxy)-1,6-diazabicyclo[3.2.1]oct-3-en-7-one

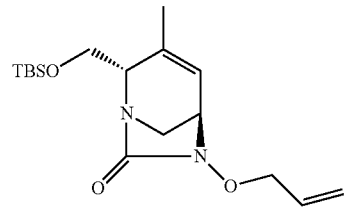 [SMILES: C=CCON1C(=O)N2C[C@H]1C=C(C)[C@H]2CO[Si](C)(C)C(C)(C)C]

Into a 2000-mL 3-necked round-bottom flask purged and maintained with an inert atmosphere of nitrogen, was placed a solution of (3R,6S)-6-[[(tert-butyldimethylsilyl)oxy]methyl]-5-methyl-N-(prop-2-en-1-yloxy)-1,2,3,6-tetrahydropyridin-3-amine (Intermediate 147, 8.4 g, 26.88 mmol, 1.00 equiv) in acetonitrile (1600 mL), N,N-Diisopropylethylamine (14.2 g, 109.87 mmol, 4.00 equiv). This was followed by the addition of a solution of ditrichloromethyl carbonate (2.9 g, 9.77 mmol, 0.40 equiv) in acetonitrile (100 mL) dropwise with stirring at −15° C. in 3 hr. The resulting solution was stirred overnight at room temperature. The resulting mixture was concentrated under vacuum. The resulting solution was diluted with 500 mL of ethyl acetate. The resulting mixture was washed with 2×400 mL of $NH_4Cl$ (aq.) and 2×400 mL of brine. The resulting mixture was concentrated under vacuum. The residue was applied onto a silica gel column with ethyl acetate/petroleum ether (1:10). This resulted in 3.9 g (43%) of the title compound as yellow oil.

MS: 339 ES+ ($C_{17}H_{30}N_2O_3Si$)

Intermediate 149: (2S,5R)-2-(hydroxymethyl)-3-methyl-6-(prop-2-en-1-yloxy)-1,6-diazabicyclo[3.2.1]oct-3-en-7-one

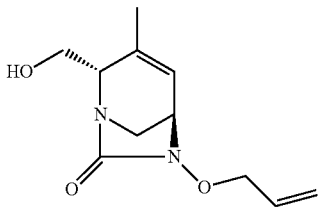 [SMILES: C=CCON1C(=O)N2C[C@H]1C=C(C)[C@H]2CO]

Into a 100-mL round-bottom flask, was placed tetrahydrofuran (30 mL), (2S,5R)-2-[[(tert-butyldimethylsilyl)oxy]methyl]-3-methyl-6-(prop-2-en-1-yloxy)-1,6-diazabicyclo[3.2.1]oct-3-en-7-one (Intermediate 148, 3.2 g, 9.45 mmol, 1.00 equiv) and it was cooled to 0° C., then TBAF (14.2 mL 1N in THF, 1.50 equiv) was added dropwise. The resulting solution was stirred for 1 h at 0° C. in a water/ice bath. The resulting mixture was concentrated under vacuum. The residue was applied onto a silica gel column with ethyl acetate/petroleum ether (1:5-1:2). This resulted in 1.6 g (75%) of the title compound as a light yellow solid.

MS: 225 ES+ ($C_{11}H_{16}N_2O_3$)

$^1$H NMR (300 MHz, CDCl$_3$) δ 1.63 (3H, d), 3.20 (2H, d), 3.62-3.84 (2H, m), 3.85-3.90 (2H, m), 4.35-4.48 (2H, m), 5.28-5.39 (2H, m), 5.95-6.08 (2H, m).

Intermediate 150: 2S,5R)-3-methyl-7-oxo-6-(prop-2-en-1-yloxy)-1,6-diazabicyclo[3.2.1]oct-3-ene-2-carboxylic acid

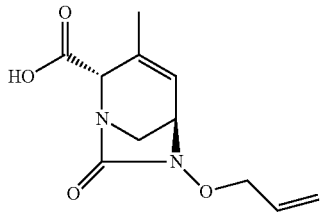 [SMILES: C=CCON1C(=O)N2C[C@H]1C=C(C)[C@H]2C(=O)O]

To a solution of H$_5$IO$_6$(12.93 g, 56.71 mmol) in wet CH$_3$CN (150 mL, 0.75% H$_2$O v/v) at r.t. was added CrO$_3$ (128 mg, 1.28 mmol). The mixture was stirred until complete dissolved was achieved. Into a 100-mL round-bottom flask, was placed wet acetonitrile (35 mL), (2S,5R)-2-(hydroxymethyl)-3-methyl-6-(prop-2-en-1-yloxy)-1,6-diazabicyclo[3.2.1]oct-3-en-7-one (Intermediate 149, 740 mg, 3.30 mmol, 1.00 equiv) and it was cooled to 0° C., then the above oxidation solution (35 mL, 3.00 equiv) was added dropwise during 30 min at 0° C. The resulting solution was stirred for 1 h at 0° C. in a water/ice bath and monitor by TLC until the material was consumed completely. Then it was diluted with 200 mL of chloroform and 50 mL of citric acid solution (25%). Separating the organic layer and the organic layer was washed by 3×50 mL of brine, dried over anhydrous sodium sulfate and concentrated under vacuum. This resulted in 0.700 g crude of the title compound as yellow oil.

MS: 239 ES+ ($C_{11}H_{16}N_2O_4$)

Intermediate 151: tert-butyl 4-[(2S,5R)-3-methyl-7-oxo-6-(prop-2-en-1-yloxy)-1,6-diazabicyclo[3.2.1]oct-3-ene-2-amido]piperidine-1-carboxylate

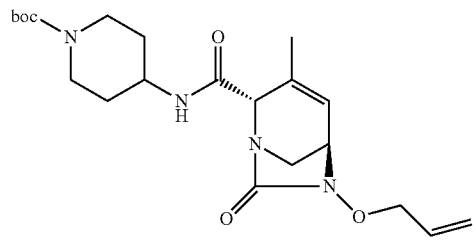

Into a 100-mL round-bottom flask, was placed N,N-dimethylformamide (20 mL), crude of (2S,5R)-3-methyl-7-oxo-6-(prop-2-en-1-yloxy)-1,6-diazabicyclo[3.2.1]oct-3-ene-2-carboxylic acid (Intermediate 150, 700 mg, 2.94 mmol, 1.00 equiv), tert-butyl 4-aminopiperidine-1-carboxylate (1.17 g, 5.84 mmol, 1.99 equiv), HATU (1.67 g, 4.39 mmol, 1.49 equiv), DIEA (1.51 g, 11.68 mmol, 3.98 equiv) at 0° C. The resulting solution was stirred for 12 h at 25° C. The resulting solution was diluted with 150 mL of ethyl acetate and it was washed with 3×100 mL of brine, dried over anhydrous sodium sulfate and concentrated under vacuum. The residue was applied onto a silica gel column with ethyl acetate/petroleum ether (1:5-1:2). This resulted in 0.500 g (40%) of the title compound as a white solid.

MS: =421 ES+ ($C_{21}H_{32}N_4O_5$)

$^1$H NMR (300 MHz, CDCl$_3$) δ 1.36 (2H, m), 1.46 (9H, s), 1.88-2.05 (5H, m), 2.90 (2H, m), 3.07 (1H, m), 3.24 (1H, m), 3.79-3.92 (2H, m), 4.06 (2H, m), 4.23 (1H, m), 4.44 (2H, m), 5.29-5.39 (2H, m), 5.96-6.10 (2H, m), 6.73 (1H, d).

Intermediate 152: (E)-triphenyl(prop-1-en-1-yl) phosphonium (2S,5R)-2-((1-(tert-butoxycarbonyl) piperidin-4-yl)carbamoyl)-3-methyl-7-oxo-1,6-diazabicyclo[3.2.1]oct-3-en-6-yl sulfate

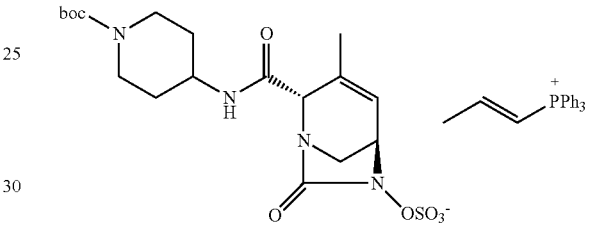

The title compound was prepared from tert-butyl 4-((2S, 5R)-6-(allyloxy)-3-methyl-7-oxo-1,6-diazabicyclo[3.2.1] oct-3-ene-2-carboxamido)piperidine-1-carboxylate (Intermediate 151, 0.763 g, 1.81 mmol) following the procedure described for Intermediate 17. Silica gel chromatography (0%-5% methanol/dichloromethane) afforded the desired product as a yellow foam (1.22 g, 88%).

MS: 459 ES−, 303 ES+ ($C_{18}H_{27}N_4O_8S$, $C_{21}H_{20}P$)

Example 18

(2S,5R)-2-carbamoyl-3-(hydroxymethyl)-7-oxo-1,6-diazabicyclo[3.2.1]oct-3-en-6-yl hydrogen sulfate sodium salt

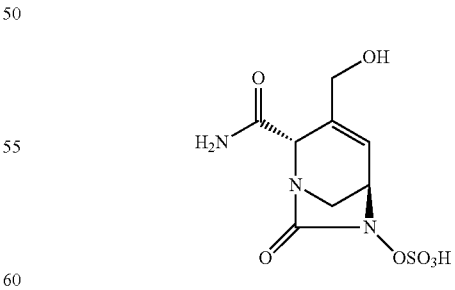

The title compound was prepared from hydrogen (2S,5R)-2-carbamoyl-3-(hydroxymethyl)-7-oxo-1,6-diazabicyclo [3.2.1]oct-3-en-6-yl sulfate (Intermediate 167, solution from ion exchange column) according to the procedure for Example 1. The desired product was obtained as an off-white fluffy solid, 5.6 mg.

The route described in this example may be used to synthesize other compounds of the invention, such as the compound described in Example 10.

MS: 292 ES− ($C_8H_{10}N_3O_7S$)

$^1$H NMR (300 MHz, DEUTERIUM OXIDE-d) δ: 3.44-3.58 (m, 2H) 4.14 (s, 2H) 4.37 (d, J=5.09 Hz, 1H) 4.63 (s, 1H) 6.52 (d, J=4.90 Hz, 1H).

The intermediates for Example 18 were prepared as follows:

Intermediate 153: tert-butyl benzyloxycarbamate

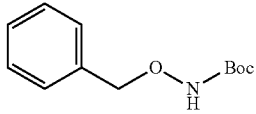 [SMILES: CC(C)(C)OC(=O)NOCc1ccccc1]

To a solution of O-benzylhydroxylamine hydrochloride (225 g, 1.44 mol) in dichloromethane (300 mL) was added a solution of sodium bicarbonate (261 g, 3.11 mol, 300 ml). After 1 hour the di-tert-butyl dicarbonate (375 g, 1.72 mol) was added at 0° C. The resulting solution was stirred for 60 min at 0° C. in a water/ice bath and then the reaction was stirred for 16 h at room temperature. The reaction was then quenched by the addition of 300 mL of aqueous sodium bicarbonate. The aqueous phase was extracted with 3×500 mL of dichloromethane and the organic layers were combined and dried over anhydrous sodium sulfate and concentrated under vacuum. Flash chromatograph on silica gel (PE:EA=10:1) afforded 220 g (69%) of the title compound as a yellow oil.

$^1$H NMR (300 MHz, CDCl$_3$) δ: 1.43 (9H, s), 4.85 (2H, s), 7.19-7.21 (1H, brs), 7.30-7.40 (5H, m).

Intermediate 154: (R)-tert-butyl benzyloxy(1-hydroxybut-3-en-2-yl)carbamate

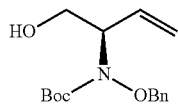

In a 3 L RBF, a solution of tert-butyl benzyloxycarbamate (Intermediate 153, 86.9 g, 389.22 mmol), N,N(1S,2S)-cyclohexane-1,2-diyl)bis(2-(diphenylphosphino)-1-naphthamide) (18.5 g, 23.39 mmol), Pd$_2$(dba)$_3$-CHCl$_3$ (8.05 g, 7.78 mmol) and TBAB (150.5 g, 466.81 mmol) in acetonitrile (1.8 L) was bubbled with N$_2$ for 30 minutes and the flask was closed with a rubber septum. The solution was then kept in a −20° C. freezer for 2 hrs. 2-vinyloxirane (30 g, 428.02 mmol, 1.10 equiv) was added and the mixture was stirred in the freezer (~20-25° C.) for 3 days. The mixture was filtered and the filtrate was evaporated. The residue was purified by silica gel column eluted with EtOAc/hexane (0-40%) to give the title compound (106 g, 93%) as a pale yellow oil.

MS: 194 ES+ ($C_{16}H_{23}NO_4$)

Intermediate 155: (R)-tert-butyl benzyloxy(1-(1,3-dioxoisoindolin-2-yl)but-3-en-2-yl)carbamate

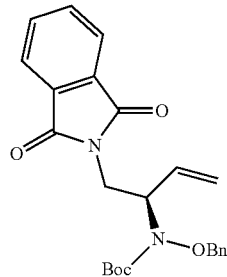 [SMILES: C=C[C@H](CN1C(=O)c2ccccc2C1=O)N(OCc1ccccc1)C(=O)OC(C)(C)C]

A suspension of (R)-tert-butyl benzyloxy(1-hydroxybut-3-en-2-yl)carbamate (Intermediate 154, 74 g, 252.25 mmol), phthalimide (66.8 g, 454.02 mmol) and triphenylphosphine (119 g, 453.70 mmol) in toluene/THF (200/200 mL) was cooled under nitrogen with ice. DIAD (91.8 g, 453.98 mmol) was added dropwise over 20 minutes and the mixture was stirred at 0° C. for 20 minutes, without cooling for 2 hr. The mixture was filtered and the filtrate was evaporated. The residue was taken up in ether and filtered. The filtrate was evaporated and the residue was purified by silica gel column and eluted with EtOAc/hexane (0-50%) to give the title compound (74 g, 79%) as a colorless oil.

MS: 323 ES+ ($C_{24}H_{26}N_2O_5$)

Intermediate 156: (R)-tert-butyl 1-aminobut-3-en-2-yl(benzyloxy)carbamate

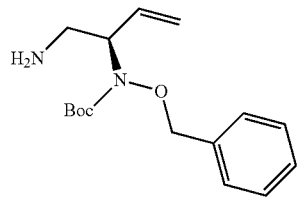 [SMILES: C=C[C@H](CN)N(OCc1ccccc1)C(=O)OC(C)(C)C]

A solution of (R)-tert-butyl benzyloxy(1-(1,3-dioxoisoindolin-2-yl)but-3-en-2-yl)carbamate (Intermediate 155, 80 g, 189.36 mmol) and hydrazine hydrate (47.4 g, 946.86 mmol) in MeOH (800 mL) was stirred at rt overnight. The mixture was diluted with ether and filtered. The filtrate was evaporated and the residue was purified by silica gel column and eluted with MeOH/DCM (0-10%) to give the title compound (44.3 g, 80%) as a colorless oil.

$^1$H NMR (300 MHz, METHANOL-d) δ: 7.36-7.40 (m, 5H), 5.76-5.88 (m, 1H), 5.14-5.21 (m, 2H), 4.83 (q, 2H), 4.27-4.30 (m, 1H), 2.81-2.88 (m, 1H), 2.67-2.73 (m, 1H), 1.45 (s, 9H).

Intermediate 157: 2-(((tert-butyldimethylsilyl)oxy)methyl)prop-2-en-1-ol

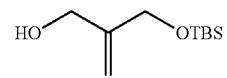

To a dry flask containing sodium hydride (2.270 g, 56.75 mmol) in THF (150 mL) under $N_2$ at 0° C. was added slowly 2-methylenepropane-1,3-diol (5 g, 56.75 mmol). The reaction was warmed to room temperature and stirred 45 min. TBS-Cl (8.55 g, 56.75 mmol) was added in one batch and stirring was continued for another 45 min, until complete by TLC. To the reaction was added water and the mixture was extracted three times with EtOAc and washed with brine. The organics were dried over magnesium sulfate, filtered and concentrated at ~10-15° C. Silica gel chromatography (20%-50% EtOAc/Hex) afforded the title compound (11.36 g, 99%) as a clear oil.

$^1$H NMR (300 MHz, DMSO-$d_6$) δ: 0.03 (s, 6H) 0.88 (s, 10H) 3.91 (d, J=5.65 Hz, 2H) 4.10 (s, 2H) 4.74 (t, J=5.46 Hz, 1H) 5.00 (t, J=1.51 Hz, 2H).

Intermediate 158: 2-(((tert-butyldimethylsilyl)oxy)methyl)acrylaldehyde

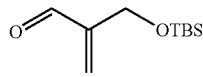

To a solution of 2-(((tert-butyldimethylsilyl)oxy)methyl)prop-2-en-1-ol (Intermediate 157, 11.35 g, 56.09 mmol) in DCM (150 mL) was added manganese dioxide (activated, 5) (28.7 g, 280.43 mmol). The reaction mixture was stirred at room temperature for three days. More $MnO_2$ was added and continued stirring until TLC shows minimum starting material. The reaction mixture was filtered through a pad of silica, evaporated at ~15° C. and purified on silica gel column (5-20%, EA/Hex) to afford the title compound (6.70 g, 59.6%) as a colorless oil.

$^1$H NMR (300 MHz, CHLOROFORM-d) δ: 0.06-0.13 (m, 6H) 0.89-0.97 (m, 9H) 4.41 (t, J=2.07 Hz, 2H) 6.11 (q, J=1.88 Hz, 1H) 6.50-6.56 (m, 1H) 9.63 (s, 1H).

Intermediate 159: tert-butyl ((2R)-1-((((9H-fluoren-9-yl)methoxy)carbonyl)(2-(((tert-butyldimethylsilyl)oxy)methyl)-1-cyanoallyl)amino)but-3-en-2-yl)(benzyloxy)carbamate

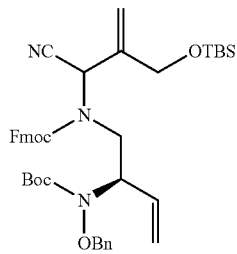

2-(((tert-butyldimethylsilyl)oxy)methyl)acrylaldehyde (Intermediate 158, 4.76 g, 23.76 mmol) was added to a solution of (R)-tert-butyl (1-aminobut-3-en-2-yl)(benzyloxy)carbamate (Intermediate 156, 5.79 g, 19.80 mmol) in THF (100 mL), followed by addition of trimethylsilyl cyanide (10.62 mL, 79.19 mmol). The mixture was stirred at room temperature overnight. More TMS-CN was added and stirred longer until less starting material seen by LCMS. $MgSO_4$ was added to the reaction mixture and stirred for 1 hr. Sodium bicarbonate (3.33 g, 39.58 mmol) was added, followed by (9H-fluoren-9-yl)methyl carbonochloridate (7.68 g, 29.69 mmol). The resulting mixture was stirred at room temperature overnight. 0.3 eq more FmocCl was added and stirred 5 h more. The mixture was filtered and the filtrate was evaporated. The residue was purified on silica gel column (0-22%, EtOAc/hexane) to afford the title compound (3.32 g, 23.18%) as a pale yellow thick oil.

MS: 724 ES+ ($C_{42}H_{53}N_3O_6Si$)

Intermediate 160: (5R)-(9H-fluoren-9-yl)methyl 5-((benzyloxy)(tert-butoxycarbonyl)amino)-3-(((tert-butyldimethylsilyl)oxy)methyl)-2-cyano-5,6-dihydropyridine-1(2H)-carboxylate

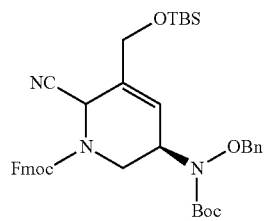

A solution of tert-butyl ((2R)-1-((((9H-fluoren-9-yl)methoxy)carbonyl)(2-(((tert-butyldimethylsilyl)oxy)methyl)-1-cyanoallyl)amino)but-3-en-2-yl)(benzyloxy)carbamate (Intermediate 159, 3.32 g, 4.59 mmol) in toluene (150 mL) was bubbled with nitrogen for 15 minutes. Hoveyda-Grubbs Catalyst 2nd Generation (0.288 g, 0.46 mmol) was added and the mixture was bubbled with nitrogen for an additional 15 minutes. The resulting solution was heated under nitrogen at 90° C. for 2 days. The reaction mixture was evaporated. The residue was purified on silica gel column (0-30% EtOAc/hexane) to afford the title compound (1.300 g, 40.7%) as a light brown film.

MS: 596 ES+ ($C_{40}H_{49}N_3O_6Si$)

Intermediate 161: (5R)-(9H-fluoren-9-yl)methyl 5-((benzyloxy)(tert-butoxycarbonyl)amino)-3-(((tert-butyldimethylsilyl)oxy)methyl)-2-carbamoyl-5,6-dihydropyridine-1(2H)-carboxylate

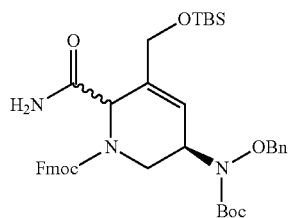

Preparation of copper(II) chloride on 4 Å molecular sieves: 4 Å Molecular sieves (2 g, 2.00 mmol) was added to a solution of copper(II) chloride dihydrate (0.341 g, 2.00 mmol) in water (200 mL) and the suspension was stirred overnight. The solid was filtered, washed with water and acetone, and dried in an oven at 140° C. for 1 hr to obtain 2.104 g of blue solid. The material needed to be activated by putting into 140° C. over for a couple hours and cooled to room temperature in a desicator prior to use.

A mixture of (5R)-(9H-fluoren-9-yl)methyl 5-((benzyloxy)(tert-butoxycarbonyl)amino)-3-(((tert-butyldimethylsilyl)oxy)methyl)-2-cyano-5,6-dihydropyridine-1(2H)-carboxylate (Intermediate 160, 1.3 g, 1.87 mmol), acetaldehyde oxime (0.569 mL, 9.34 mmol) and newly activated copper (II) chloride on 4 Å MS (187 mg, 0.15 mmol) (used 100 mg $CuCl_2$/mol sieves per 1 mmol substrate) in MeOH (5 mL) was stirred under nitrogen at 65° C. for 6 h. The mixture was filtered and evaporated. The residue was purified on silica gel column (0-60%, EtOAc/hexanes). The two diastereomers were combined together to afford the title compound (1.190 g, 89%) as a pale yellow foamy solid.

MS: 714 ES+ ($C_{40}H_{51}N_3O_7Si$)

Intermediate 162: (5R)-(9H-fluoren-9-yl)methyl 5-((benzyloxy)amino)-3-(((tert-butyldimethylsilyl)oxy)methyl)-2-carbamoyl-5,6-dihydropyridine-1(2H)-carboxylate

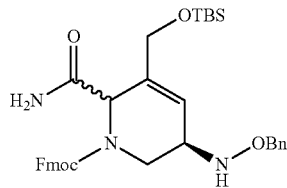

To a solution of (5R)-(9H-fluoren-9-yl)methyl 5-((benzyloxy)(tert-butoxycarbonyl)amino)-3-(((tert-butyldimethylsilyl)oxy)methyl)-2-carbamoyl-5,6-dihydropyridine-1(2H)-carboxylate (Intermediate 161, 1.19 g, 1.67 mmol) in DCM (20 mL) at room temperature was added zinc bromide (1.502 g, 6.67 mmol). The reaction mixture was stirred at room temperature for 2 h. The reaction mixture was diluted with dichloromethane and washed with saturated sodium bicarbonateand. The aqueous wash was extracted three to four times more with DCM. The organics were washed with brine, dried over magnesium sulfate, filtered and concentrated to afford the title compound (0.970 g, 95%) as an off white foam.

MS: 614 ES+ ($C_{35}H_{43}N_3O_5Si$)

Intermediate 163: (5R)-5-((benzyloxy)amino)-3-(((tert-butyldimethylsilyl)oxy)methyl)-1,2,5,6-tetrahydropyridine-2-carboxamide

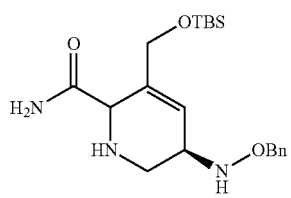 [SMILES: CC(C)(C)[Si](C)(C)OCC1=C[C@@H](NOCc2ccccc2)CNC1C(N)=O]

Diethylamine (0.824 mL, 7.89 mmol) was added to a solution of (5R)-(9H-fluoren-9-yl)methyl 5-((benzyloxy)amino)-3-(((tert-butyldimethylsilyl)oxy)methyl)-2-carbamoyl-5,6-dihydropyridine-1(2H)-carboxylate (Intermediate 162, 0.968 g, 1.58 mmol) in DCM (20 mL) and the resulting solution was allowed to stir at room temperature overnight. The volatiles were removed by evaporation and the residue was purified on silica gel (0-12%, MeOH/DCM, UV 220 nm) to afford the title compound (0.564 g, 91%) as a yellow film.

MS: 392 ES+ ($C_{20}H_{33}N_3O_3Si$)

Intermediate 164: (2S,5R)-6-(benzyloxy)-3-(((tert-butyldimethylsilyl)oxy)methyl)-7-oxo-1,6-diazabicyclo[3.2.1]oct-3-ene-2-carboxamide

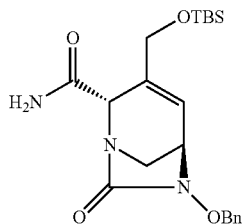 [SMILES: CC(C)(C)[Si](C)(C)OCC1=C[C@@H]2CN(C(=O)N2OCc2ccccc2)[C@@H]1C(N)=O]

To a solution of (5R)-5-((benzyloxy)amino)-3-(((tert-butyldimethylsilyl)oxy)methyl)-1,2,5,6-tetrahydropyridine-2-carboxamide (Intermediate 163, 0.562 g, 1.44 mmol) and diisopropylethyl amine (1.000 mL, 5.74 mmol) in acetonitrile (200 mL) at 0° C. was added triphosgene (0.145 g, 0.49 mmol) as a solution in acetonitrile (6 mL). The triphosgene solution was added at a rate of 4 mL/hour. Once addition was complete the reaction was stirred at 0° C. overnight. The reaction mixture was diluted with ethyl acetate and washed with saturated sodium bicarbonate. The aqueous layer was extracted again with EtOAc and then DCM. The combined organic extracts were washed with brine, dried over magnesium sulfate, filtered and concentrated. Silica gel chromatography (0%-100, ethyl acetate/hexanes) afforded the title compound (0.225 g, 37.5%) as a colorless film.

MS: 418 ES+ ($C_{21}H_{31}N_3O_4Si$)

$^1$H NMR (300 MHz, CHLOROFORM-d) δ: −0.08 (s, 6H) 0.76 (s, 9H) 2.89-3.00 (m, 1H) 3.04-3.13 (m, 1H) 3.32 (dd, J=5.09, 2.45 Hz, 1H) 4.01-4.09 (m, 1H) 4.19-4.28 (m, 1H) 4.30 (s, 1H) 4.67-4.76 (m, 1H) 4.83-4.93 (m, 1H) 5.51 (br. s., 1H) 6.09-6.21 (m, 1H) 6.63 (br. s., 1H) 7.19-7.36 (m, 5H).

Intermediate 165: trimethylammonium (2S,5R)-3-(((tert-butyldimethylsilyl)oxy)methyl)-2-carbamoyl-7-oxo-1,6-diazabicyclo[3.2.1]oct-3-en-6-yl sulfate

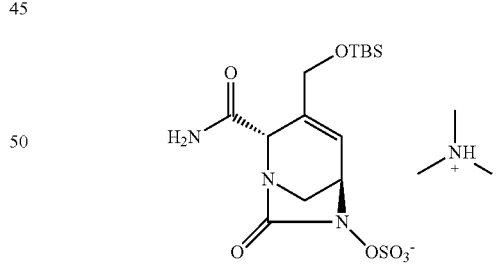

To a solution of (2S,5R)-6-(benzyloxy)-3-(((tert-butyldimethylsilyl)oxy)methyl)-7-oxo-1,6-diazabicyclo[3.2.1]oct-3-ene-2-carboxamide (Intermediate 164, 30 mg, 0.07 mmol) in EtOAc (1.33 mL), water (1.995 mL) and EtOH (0.660 mL) was added Pd/C (wet, degussa type E101 NE/W) (7.65 mg, 7.18 mol), $SO_3$.TMA (12.00 mg, 0.09 mmol) and TEA (2.003 al, 0.01 mmol) under $N_2$ atmosphere. The reaction mixture was degassed and filled with $H_2$ using a balloon. The reaction mixture was stirred at room temperature under a $H_2$ balloon for 5 hours. The $H_2$ balloon was removed and the reaction mixture was stirred overnight. The reaction mixture was filtered and the organics evaporated. The remaining aqueous mixture was lyophilized and the resulting residue was purified by preparative HPLC (Synergi Polar RP 21.2 mm×100 mm 4 m coupled with YMC C30 20 mm×100 mm 5 μm) to afford the title compound as a white solid, 5 mg, 15%.

MS: 406 ES– ($C_{14}H_{24}N_3O_7SSi$)

Intermediate 166: (2S,5R)-2-carbamoyl-3-(hydroxymethyl)-7-oxo-1, 6-diazabicyclo[3.2.1]oct-3-en-6-yl hydrogen sulfate sodium salt

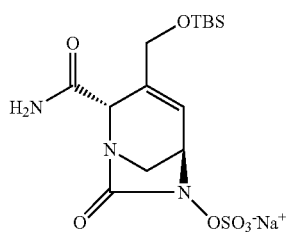

Dowex 50WX8, 100-200 mesh (0.75 g, 0.01 mmol) was conditioned by stirring for 3 hours in 2N NaOH (1.8 mL, 3.60 mmol). The resin was then loaded into a cartridge and washed with water until the pH was 7. It was then washed with (1/1) acetone/water, followed by water. (2S,5R)-3-(((tert-butyldimethylsilyl)oxy)methyl)-2-carbamoyl-7-oxo-1,6-diazabicyclo[3.2.1]oct-3-en-6-yl sulfate (Intermediate 165, 5 mg, 0.01 mmol) in water was passed through the resin 5 times and then lyophilized to afford the title compound (3.00 mg, 56.7%).

MS: 406 ES+ ($C_{14}H_{24}N_3O_7SSi$)

Intermediate 167: (2S,5R)-2-carbamoyl-3-(hydroxymethyl)-7-oxo-1,6-diazabicyclo[3.2.1]oct-3-en-6-yl hydrogen sulfate

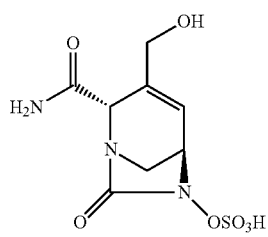

Dowex 50WX8, 100-200 mesh (0.48 g, 6.43 mol) resin in 2 mL water was loaded into a cartridge and let water run off. Trimethylammonium (2S,5R)-3-(((tert-butyldimethylsilyl)oxy)methyl)-2-carbamoyl-7-oxo-1,6-diazabicyclo[3.2.1] oct-3-en-6-yl sulfate sodium salt (Intermediate 166, 3 mg, 6.43 mol) in water was passed through the resin 2 times (pH is ~3). The solution was carried forward to the final ion exchange column, see Example 18.

Example 19

(2S,5R)-4-(2-amino-2-oxoethyl)-2-carbamoyl-7-oxo-1,6-diazabicyclo[3.2.1]oct-3-en-6-yl hydrogen sulfate sodium salt

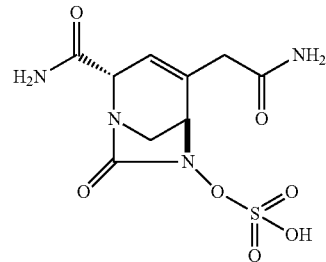 [SMILES: NC(=O)CC1=C[C@@H](C(N)=O)N2C[C@@H]1N(OS(=O)(=O)O)C2=O]

The title compound was prepared from (2S,5R)-2-carbamoyl-4-(hydroxymethyl)-7-oxo-1,6-diazabicyclo[3.2.1] oct-3-en-6-yl sulfate (Intermediate 179, 34 mg, 0.04 mmol) according to the procedure described for Example 1. It was further purified on reverse phase HPLC using Synergi Polar RP (21.2 mm×100 mm 4 μm) coupled with YMC C30 (20×150 mm 5 μm) (Mobile Phase A 100% H₂O, Mobile Phase B 100% Acetonitrile), yielding a pale yellow solid, 1.6 mg, 3%.

MS: 343 ES+ ($C_9H_{12}N_4NaO_7S$)

¹H NMR (300 MHz, D₂O) δ: 3.17 (s, 2H); 3.37 (d, 1H); 3.70 (dd, 1H); 4.23 (d, 1H); 4.64 (d, 1H); 5.93 (d, 1H).

The intermediates for Example 19 were prepared as follows:

Intermediate 168: (S)-tert-butyl 2-(((tert-butyldimethylsilyl)oxy)methyl)-4-(((4-methoxybenzyl)-oxy)methyl)-5-oxo-5,6-dihydropyridine-1(2H)-carboxylate

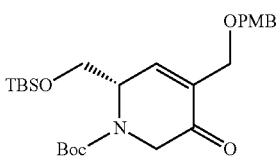

To a solution of (2S)-tert-butyl 5-hydroxy-4-(hydroxymethyl)-2-(isopropyldimethylsilyl)oxy)methyl)-5,6-dihydropyridine-1(2H)-carboxylate (Intermediate 117, 13.0 g, 34.99 mmol) in toluene (150 mL) was added 4-methoxybenzyl 2,2,2-trichloroacetimidate (7.65 mL, 10.42 g, 36.74 mmol) and La(OTf)₃ (205 mg, 0.35 mmol). The mixture was stirred at 50° C. for 4 h. Aqueous work-up with ethyl acetate and the organic layer was dried over MgSO₄ to afford the crude product.

MS: 492 ES+ ($C_{26}H_{41}NO_6Si$)

Intermediate 169: (2S)-tert-butyl 2-(((tert-butldimethylsilyl)oxy)methyl)-5-hydroxy-4-(((4-methoxybenzyl)oxy)methyl)-5,6-dihydropyridine-1(2H)-carboxylate

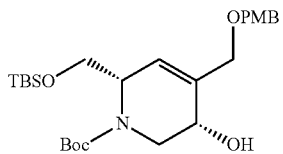

The title compound was prepared from (S)-tert-butyl 2-(((tert-butyldimethylsilyl)oxy)methyl)-4-(((4-methoxybenzyl)oxy)methyl)-5-oxo-5,6-dihydropyridine-1(2H)-carboxylate (Intermediate 168, 34.99 mmol) according to the procedure for Intermediate 8. The reaction mixture was concentrated and the white solid was redissolved in 200 mL EtOAc and washed with satd. NaHCO₃, brine, dried over MgSO₄, filtered and concentrated. The residue was purified by silica gel column eluting with 0-100% ethyl acetate/hexanes to afford a colorless oil. 17.10 g, 99% over 2 steps.

MS: 494 ES+ ($C_{26}H_{43}NO_6Si$)

¹H NMR (300 MHz, CDCl₃) δ: 0.01 (s, 6H); 0.83 (s, 9H); 1.41 (s, 9H); 3.62 (m, 1H); 3.75 (s, 3H); 3.75 (m, 1H); 4.14 (m, 4H); 4.34 (m, 1H); 4.41 (s, 2H); 5.70 (d, 1H); 6.83 (d, 2H); 7.21 (d, 2H).

Intermediate 170: (2S)-tert-butyl 5-(N-(allyloxy)-2-nitrophenylsulfonamido)-2-(((tert-butyldimethylsilyl)-oxy)methyl)-4-(((4-methoxybenzyl)oxy)methyl)-5,6-dihydropyridine-1(2H)-carboxylate

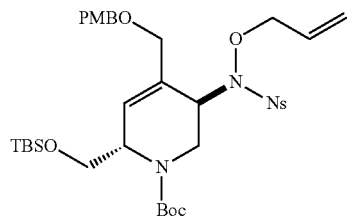

The title compound was prepared from (S)-tert-butyl 2-(((tert-butyldimethylsilyl)oxy)methyl)-4-(((4-methoxybenzyl)-oxy)methyl)-5-oxo-5,6-dihydropyridine-1 (2H)-carboxylate (Intermediate 169, 17.10 g, 34.78 mmol) and N-(allyloxy)-2-nitrobenzenesulfonamide (Intermediate 9, 9.88 g, 38.26 mmol) according to the procedure described for Intermediate 10. Desired product was obtained as a pale yellow oil, 18.70 g, 74%.

MS: 734 ES+ ($C_{35}H_{51}N_3O_{10}SSi$)

¹H NMR (300 MHz, CDCl₃) δ: 0.05 (s, 6H); 0.87 (s, 9H); 1.26 (s, 9H); 3.71 (m, 2H); 3.81 (s, 3H); 4.45 (m, 4H); 4.57 (d, 2H); 5.28 (m, 2H); 5.32 (m, 2H); 5.71 (m, 1H); 5.93 (m, 2H); 6.12 (d, 1H); 6.86 (m, 2H); 7.70 (m, 5H); 8.13 (m, 1H).

Intermediate 171: (2S)-tert-butyl 5-(N-(allyloxy)-2-nitrophenylsulfonamido)-2-(((tert-butyldimethylsilyl)oxy)methyl)-4-(hydroxymethyl)-5,6-dihydropyridine-1(2H)-carboxylate

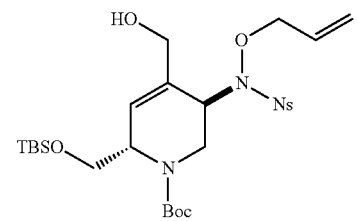

To a stirred solution of (2S)-tert-butyl 5-(N-(allyloxy)-2-nitrophenylsulfonamido)-2-(((tert-butyldimethylsilyl)oxy)methyl)-4-(((4-methoxybenzyl)oxy)methyl)-5,6-dihydropyridine-1(2H)-carboxylate (Intermediate 170, 18.70 g, 25.48 mmol) in DCM/water (180 mL/20 mL), was added DDQ (6.94 g, 30.57 mmol) at 0° C. The mixture was stirred at room temperature for 1 hour before it was concentrated. The residue was purified on silica gel column eluting with 0-100% ethyl acetate/hexanes to give a pale yellow oil, 12.38 g, 79%.

MS: 614 ES+ ($C_{27}H_{43}N_3O_9SSi$)

¹H NMR (300 MHz, CDCl₃) δ: 0.05 (s, 6H); 0.87 (s, 9H); 1.40 (s, 9H); 1.81 (bs, 1H); 3.63 (d, 1H); 3.70 (m, 2H); 4.27 (m, 6H); 4.60 (m, 1H); 5.18 (m, 2H); 5.71 (m, 1H); 6.09 (m, 1H); 7.60 (t, 1H); 7.77 (m, 2H); 8.14 (t, 1H).

Intermediate 172: (2S)-tert-butyl 5-(N-(allyloxy)-2-nitrophenylsulfonamido)-2-(((tert-butyldimethylsilyl)oxy)methyl)-4-(cyanomethyl)-5,6-dihydropyridine-1(2H)-carboxylate

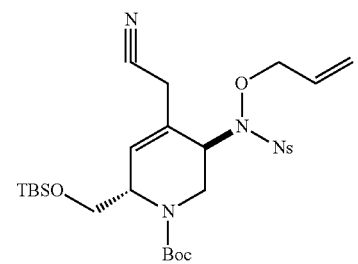

To a stirred solution of (2S)-tert-butyl 5-(N-(benzyloxy)-2-nitrophenylsulfonamido)-2-(((tert-butyldimethylsilyl)oxy)methyl)-4-(hydroxymethyl)-5,6-dihydropyridine-1 (2H)-carboxylate (Intermediate 171, 12.38 g, 20.17 mmol) in DCM (200 mL) at 0° C., pyridine (2.39 g, 30.25 mmol) and N,N-dimethylpyridin-4-amine (123 mg, 1.01 mmol) was added. Then methanesulfonic anhydride (4.22 g, 24.20 mmol) was added. The mixture was then stirred from 0° C. to room temperature for 2 hours. It was diluted with DCM (100 mL) and washed with brine, dried over MgSO₄, filtered and concentrated to give the crude as a pale yellow oil. It was used directly for the next step.

To a stirred solution of sodium cyanide (4.94 g, 100.85 mmol) in water (20.0 mL) was added (2S)-tert-butyl 5-(N-(allyloxy)-2-nitrophenylsulfonamido)-2-(((tert-butyldimethylsilyl)oxy)methyl)-4-((((methylsulfonyl)oxy)methyl)-5, 6-dihydropyridine-1(2H)-carboxylate (crude, 20.17 mmol) in DMF (100 mL). The mixture was then stirred at room temperature for 15 h. It became a dark orange solution. It was then diluted with sat. NaHCO₃ and water and extracted with ethyl acetate, dried over MgSO₄. The crude was subjected to silica gel column eluting with 0-100% ethyl acetate/hexanes to give a pale yellow oil, 5.92 g, 47.1%.

MS: 623 ES+ ($C_{28}H_{42}N_4O_8SSi$)

¹H NMR (300 MHz, CDCl₃) δ: 0.05 (s, 6H); 0.88 (s, 9H); 1.41 (s, 9H); 3.12 (m, 1H); 3.32 (m, 1H); 3.74 (m, 2H); 4.21 (m, 5H); 4.65 (s, 1H); 5.18 (m, 2H); 5.69 (m, 1H); 6.31 (bs, 1H); 7.65 (m, 1H); 7.81 (m, 2H); 8.15 (d, 1H).

Intermediate 173: (2S)-tert-butyl 5-(N-(allyloxy)-2-nitrophenylsulfonamido)-4-(2-amino-2-oxoethyl)-2-(((tert-butyldimethylsilyl)oxy)methyl)-5,6-dihydropyridine-1(2H)-carboxylate

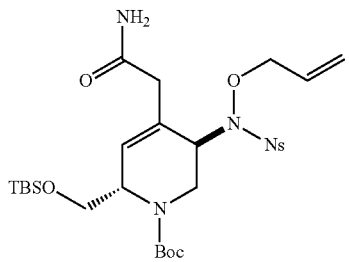

Preparation of the catalyst: 4 Å molecular sieves (MS-4 Å) were impregnated with the corresponding metal salt (CuCl₂-2H₂O) as follows: 1 mmol of the salts was dissolved in 100 ml of deionized H₂O and stirred with 1 g of MS-4 Å at room temperature for 6 h. The solid was filtered, washed with deionized H₂O and acetone, and dried in an oven at 150° C. for 1 h. (2S)-tert-butyl 5-(N-(allyloxy)-2-nitrophenylsulfonamido)-2-(((tert-butyldimethylsilyl)oxy)methyl)-4-(cyanomethyl)-5,6-dihydropyridine-1(2H)-carboxylate (Intermediate 172, 3.60 g, 5.78 mmol), Cu(II)Cl₂-4 Å catalyst (200 mg), acetaldoxime (1.762 mL, 28.90 mmol, 5.0 eq) and MeOH (40.0 mL) were stirred at 60° C. for 15 h. The solid was filtered, washed with MeOH and the filtrate was evaporated to afford crude product.

MS: 641 ES+ ($C_{28}H_{42}N_4O_8SSi$)

Intermediate 174: (2S)-tert-butyl 5-(N-(allyloxy)-2-nitrophenylsulfonamido)-4-(2-amino-2-oxoethyl)-2-(hydroxymethyl)-5,6-dihydropyridine-1(2H)-carboxylate

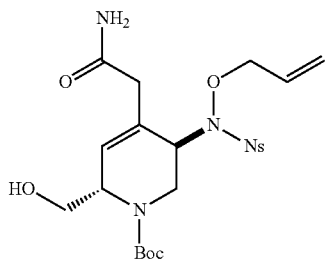

The title compound was prepared from (2S)-tert-butyl 5-(N-(allyloxy)-2-nitrophenylsulfonamido)-4-(2-amino-2-oxoethyl)-2-(((tert-butyldimethylsilyl)oxy)methyl)-5,6-dihydropyridine-1(2H)-carboxylate (Intermediate 173, crude, 5.78 mmol) following the procedure described for Intermediate 18. Silica column eluting with 0-100% ethyl acetate/hexanes gave a pale yellow solid. 2.61 g, 86%.

MS: 527 ES+ ($C_{22}H_{30}N_4O_9S$)

¹H NMR (300 MHz, CDCl₃) δ: 1.39 (s, 9H); 3.03 (m, 2H); 3.33 (m, 2H); 3.70 (m, 2H); 4.20 (m, 1H); 4.35 (m, 2H); 4.68 (bs, 1H); 5.17 (m, 2H); 5.72 (m, 2H); 6.00 (s, 1H); 6.08 (bs, 1H); 6.32 (bs, 1H); 7.65 (d, 1H); 7.80 (m, 2H); 8.15 (d, 1H).

Intermediate 175: (2S)-tert-butyl 5-(N-(allyloxy)-2-nitrophenylsulfonamido)-4-(2-amino-2-oxoethyl)-2-carbamoyl-5,6-dihydropyridine-1 (2H)-carboxylate

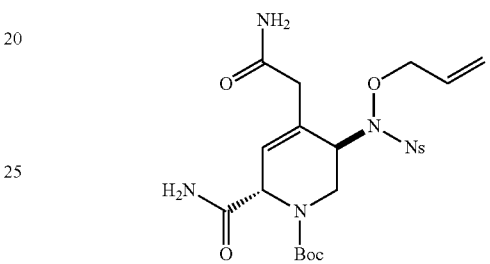

Stock solution: 240 mg conc. HNO₃ and 80 mg Na₂Cr₂O₇-2H₂O was dissolved in 16 mL H₂O at rt.

To the solution of (2S)-tert-butyl 5-(N-(allyloxy)-2-nitrophenylsulfonamido)-4-(2-amino-2-oxoethyl)-2-(((tert-butyldimethylsilyl)oxy)methyl)-5,6-dihydropyridine-1(2H)-carboxylate (Intermediate 174, 2.61 g, 4.96 mmol) in acetonitrile (50 mL) was added sodium periodate (4.66 g, 21.81 mmol) and catalytic solution of NaCr₂O₇/HNO₃ solution (6.0 mL) at room temperature and stirred for 15 h. The mixture was diluted with 100 mL ethyl acetate, 25 mL 1M pH 7 buffer, 25 mL 2M NaHSO₃. The aqueous solution was extracted with 50 mL ethyl acetate. The ethyl acetate layer was then washed with brine and dried over MgSO₄, filtered and concentrated to afford (2S)-5-(N-(allyloxy)-2-nitrophenylsulfonamido)-4-(2-amino-2-oxoethyl)-1-(tert-butoxycarbonyl)-1,2,5,6-tetrahydropyridine-2-carboxylic acid, which was used directly in the next step without further purification. Pale yellow solid, crude, 2.79 g, 104%.

MS: 541 ES+ ($C_{22}H_{28}N_4O_{10}S$)

To a stirred solution of (2S)-5-(N-(allyloxy)-2-nitrophenylsulfonamido)-4-(2-amino-2-oxoethyl)-1-(tert-butoxycarbonyl)-1,2,5,6-tetrahydropyridine-2-carboxylic acid (crude, 2.79 g, 5.16 mmol), ammonium chloride (552 mg, 10.32 mmol), HATU (3.93 g, 10.32 mmol) in DMF (20 mL) at 0° C., was added DIPEA (2.67 g, 20.65 mmol). After stirring at room temperature for 1 hr, 50 mL EtOAc and 50 mL water was added. The organic layer was washed with water, brine and dried over MgSO₄, filtered and concentrated to give a residue, which was purified on silica gel column eluting with 0-100% ethyl acetate/hexanes to afford an off-white solid, 1.36 g, 49%.

MS: 540 ES+ ($C_{22}H_{29}N_5O_9S$)

¹H NMR (300 MHz, CDCl₃) δ: 1.38 (s, 9H); 3.08 (m, 2H); 4.24 (m, 1H); 4.40 (m, 2H); 5.17 (m, 2H); 5.68 (m, 1H); 6.02 (m, 2H); 6.20 (m, 2H); 6.40 (bs, 1H); 6.51 (bs, 1H); 7.64 (d, 1H); 7.78 (m, 2H); 8.14 (d, 1H).

Intermediate 176: (2S)-tert-butyl 5-((allyloxy)amino)-4-(2-amino-2-oxoethyl)-2-carbamoyl-5,6-dihydropyridine-1(2H)-carboxylate

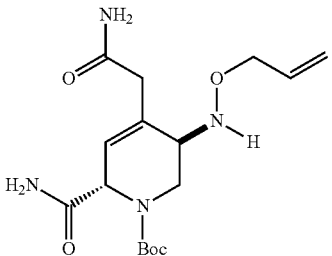 [SMILES: C=CCON[C@H]1CN(C(=O)OC(C)(C)C)[C@H](C(N)=O)C=C1CC(N)=O]

To a solution of (2S)-tert-butyl 5-(N-(allyloxy)-2-nitrophenylsulfonamido)-4-(2-amino-2-oxoethyl)-2-carbamoyl-5,6-dihydropyridine-1(2H)-carboxylate (Intermediate 175, 1.36 g, 2.52 mmol) and potassium carbonate (1.742 g, 12.60 mmol) in acetonitrile (20.0 mL) at 0° C. was added benzenethiol (1.389 g, 12.60 mmol). The mixture was stirred at room temperature for 15 hours. The reaction mixture was concentrated and the resulting residue was triturated with DCM.

The solids were removed by filtration. The filtrate was concentrated to a pale yellow film, which was subjected to silica gel column eluting with 0-50% MeOH/DCM to give a pale yellow solid. 330 mg, 36.9%.

MS: 355 ES+ ($C_{16}H_{26}N_4O_5$)

$^1$H NMR (300 MHz, CDCl$_3$) δ: 1.50 (s, 9H); 3.05 (m, 2H); 3.20 (m, 1H); 3.45 (bs, 1H); 4.23 (d, 2H); 4.500 (m, 1H); 5.03 (m, 1H); 5.24 (m, 2H); 5.88 (m, 2H); 5.94 (m, 2H); 6.57 (bs, 1H); 6.76 (bs, 1H).

Intermediate 177: (R)-5-(allyloxyamino)-4-(2-amino-2-oxoethyl)-1,2,5,6-tetrahydropyridine-2-carboxamide

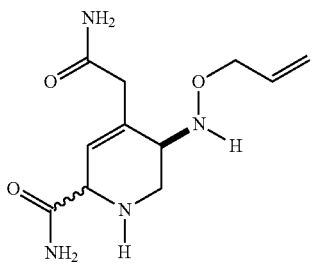 [SMILES: C=CCON[C@H]1CNC(C(N)=O)C=C1CC(N)=O]

To a solution of (2S)-tert-butyl 5-((allyloxy)amino)-4-(2-amino-2-oxoethyl)-2-carbamoyl-5,6-dihydropyridine-1(2H)-carboxylate (Intermediate 176, crude, 330 mg, 0.93 mmol) in DCM (5.0 mL) at 0° C. was added HCl (4.0M in dioxane, 0.233 mL, 0.93 mmol). The mixture was stirred from 0° C. to room temperature for 2 h. Then 0.233 mL more HCl was added to the mixture and stirred for 2 h. It was neutralized by K$_2$CO$_3$ and TEA, filtered and the solvent was removed under vacuum. The crude was subjected to silica column eluting with 0-50% MeOH/DCM to give the desired diastereomeric products as white solids. 100 mg, diastereomer 1. 32 mg, diastereomer 2. 56% yield.

Diastereomer 1:
MS: 255 ES+ ($C_{11}H_{18}N_4O_3$)
$^1$H NMR (300 MHz, CD$_3$OD) δ: 3.22 (m, 1H); 3.38 (m, 2H); 3.61 (m, 2H); 3.82 (m, 1H); 4.27 (d, 2H); 4.75 (m, 1H); 5.30 (m, 2H); 6.03 (m, 1H); 6.15 (d, 1H).

Diastereomer 2:
MS: 255 ES+ ($C_{11}H_{18}N_4O_3$)
$^1$H NMR (300 MHz, CD3OD) δ: 3.16 (m, 2H); 3.33 (m, 2H); 3.58 (m, 2H); 4.16 (m, 2H); 4.38 (bs, 1H); 5.19 (m, 2H); 5.89 (d, 1H); 5.95 (m, 1H).

Intermediate 178: (2S,5R)-6-(allyloxy)-4-(2-amino-2-oxoethyl)-7-oxo-1,6-diazabicyclo[3.2.1]oct-3-ene-2-carboxamide

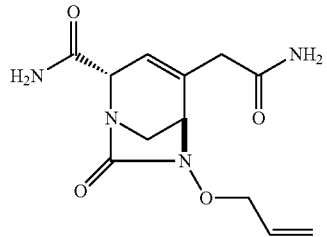 [SMILES: C=CCON1C(=O)N2C[C@H]1C(CC(N)=O)=C[C@H]2C(N)=O]

The title compound was prepared from (R)-5-(allyloxyamino)-4-(2-amino-2-oxoethyl)-1,2,5,6-tetrahydropyridine-2-carboxamide (Intermediate 177, 132 mg, 0.52 mmol) following the procedure described for Intermediate 16. The reaction mixture was stirred at 0° C. for 2 h. The volatile was removed under vacuum and the crude was subjected to silica column eluting with 0-100% ethyl acetate/hexanes and then 95% ethyl acetate/5% MeOH to give a pale yellow solid. 62 mg, 43%.

MS: 281 ES+ ($C_{12}H_{16}N_4O_4$)

$^1$H NMR (300 MHz, CD$_3$Cl) δ: 3.13 (m, 3H); 3.43 (dd, 1H); 4.10 (d, 1H); 4.43 (m, 3H); 5.35 (m, 2H); 5.57 (bs, 1H); 5.80 (m, 2H); 5.90 (d, 1H); 6.01 (m, 1H); 6.86 (bs, 1H).

Intermediate 179: (2S,5R)-4-(2-amino-2-oxoethyl)-2-carbamoyl-7-oxo-1,6-diazabicyclo[3.2.1]oct-3-en-6-yl sulfate

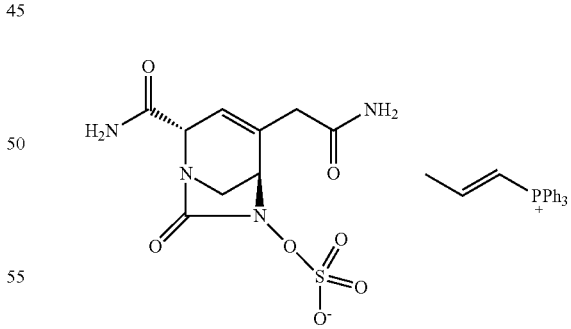

The title compound was prepared from (2S,5R)-6-(allyloxy)-4-(2-amino-2-oxoethyl)-7-oxo-1,6-diazabicyclo[3.2.1]oct-3-ene-2-carboxamide (Intermediate 178, 62 mg, 0.22 mmol) following the procedure described for Intermediate 17. The desired product was obtained as a pale yellow oil. 34 mg, 48%.

MS: 304; 320 ($C_{21}H_{20}P$; $C_9H_{11}N_4O_7S$).

$^1$H NMR (300 MHz, CD$_3$Cl) δ: 2.31 (m, 1H); 2.64 (s, 3H); 3.15 (m, 4H); 3.63 (dd, 1H); 4.22 (d, 1H); 4.45 (bs,

1H); 5.62 (bs, 1H); 5.96 (d, 1H); 6.01 (bs, 1H); 6.64 (bs, 1H); 6.96 (bs, 1H); 7.68 (m, 15H); 8.60 (bs, 1H).

Example 20

(2S,5R)-4-carbamoyl-2-(hydroxymethyl)-7-oxo-1,6-diazabicyclo[3.2.1]oct-3-en-6-yl hydrogen sulfate sodium Salt

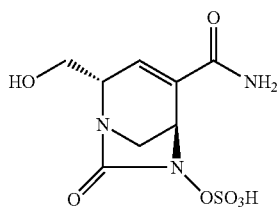

The DOWEX resin 50WX8 (50 g) was conditioned by stirring for 20 min in 2N sodium hydroxide (40 ml). The DOWEX was loaded into a cartridge, washed with water until pH=7, then washed with acetone/water (1/1) and water again. The compound (Intermediate 180, 0.31 g, 0.76 mmol) was loaded using water and a minimum amount of acetone and eluted with water. The fractions were reloaded onto the cartridge and washed though with water again. This load and wash process was repeated five times, then the final round of fractions was directly frozen and lyophilized to give a white solid (130 mg). Reversed phase chromatography (0%-4% MeCN in water) afforded the title compound as a white solid (31 mg).

MS: 292 ES− ($C_8H_{10}N_3O_7S$)

$^1$H NMR (600 MHz, DEUTERIUM OXIDE) δ: 3.56 (d, J=11.67 Hz, 1H); 3.64 (br. s., 1H); 3.69-3.81 (m, 1H); 3.97 (d, J=6.40 Hz, 2H); 4.18 (br. s., 1H); 4.84 (br. s., 1H); 6.73 (br. s., 1H).

The intermediates for Example 20 were prepared as follows:

Intermediate 180: (2S,5R)-2-(((tert-butyldimethylsilyl)oxy)methyl)-4-carbamoyl-7-oxo-1,6-diazabicyclo[3.2.1]oct-3-en-6-yl sulfate-(E)-triphenyl(prop-1-en-1-yl)phosphonium

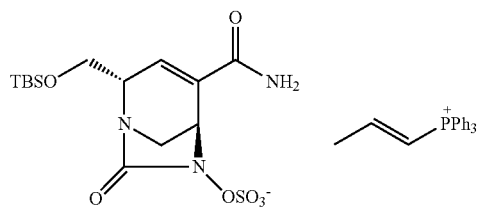

To a solution of (2S,5R)-6-(allyloxy)-2-(((tert-butyldimethylsilyl)oxy)methyl)-7-oxo-1,6-diazabicyclo[3.2.1]oct-3-ene-4-carboxamide (Intermediate 108, 0.32 g, 0.87 mmol) in DCM (15 mL) was added acetic acid (dried over sodium sulfate) (0.100 mL, 1.74 mmol) and tetrakis(triphenylphosphine)palladium(0) (1.006 g, 0.87 mmol) under nitrogen at room temperature. The yellow solution was stirred at room temperature for 3.5 hours. To the mixture was added pyridine (10 ml), followed by sulfur trioxide pyridine complex (0.832 g, 5.22 mmol). The suspension was stirred at room temperature overnight under nitrogen. The reaction mixture was concentrated to dryness (≤30° C.), suspended in DCM, filtered, concentrated and purified on a silica gel column (0%-100% MeOH in DCM) to afford the title compound as a white solid (0.31 g).

MS: 406 ES− ($C_{14}H_{24}N_3O_7SSi$)

$^1$H NMR (300 MHz, DMSO-d$_6$) δ: −0.07-0.05 (m, 6H); 0.71-0.86 (m, 9H); 2.10 (dt, J=6.28, 2.05 Hz, 3H); 3.03-3.18 (m, 1H); 3.22-3.32 (m, 1H); 3.60-3.73 (m, 1H); 3.79 (d, J=6.42 Hz, 2H); 4.48 (d, J=3.02 Hz, 1H); 6.40 (dd, J=2.93, 1.04 Hz, 1H); 6.43-6.70 (m, 1H); 7.17 (br. s., 2H); 7.56-7.96 (m, 16H).

Example 21

(2S,5R)-2-carbamoyl-3,4-dimethyl-7-oxo-1,6-diazabicyclo[3.2.1]oct-3-en-6-yl hydrogen sulfate sodium salt

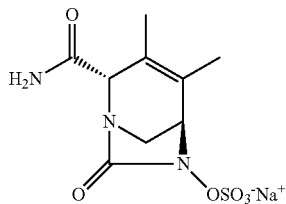

The title compound was prepared from (E)-triphenyl (prop-1-enyl)phosphonium (2S,5R)-2-carbamoyl-3,4-dimethyl-7-oxo-1,6-diazabicyclo[3.2.1]oct-3-en-6-yl sulfate (Intermediate 199, 0.22 g, 0.37 mmol) following the procedure described for Example 1. The desired product was obtained as a white solid (99.6 mg, 86%).

Optical rotation: (0.2 g/dL, MeOH)=−228

MS: 290.0 ES− ($C_9H_{13}N_3O_6S$)

$^1$H NMR (300 MHz, DMSO-d6) δ: 1.51 (s, 3H); 1.75 (s, 3H); 3.03 (dd, J=10.76, 3.02 Hz, 1H); 3.70 (d, J=10.76 Hz, 1H); 3.88-4.06 (m, 2H); 7.23 (br. s., 1H); 7.76 (br. s., 1H).

The intermediates for Example 21 were prepared as follows:

Intermediate 181: (R)-3-tert-butyl 4-methyl 2,2-dimethyloxazolidine-3,4-dicarboxylate

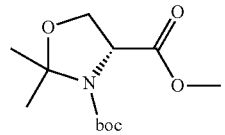

A solution of (R)-methyl 2-(tert-butoxycarbonylamino)-3-hydroxypropanoate (Aldrich, 9.26 mL, 45.61 mmol) in dichloromethane (18.10 mL) was cooled to 0° C. in an ice-water bath. After 20 minutes 2,2-dimethoxypropane (Aldrich, 28.6 mL, 232.63 mmol) and para-toluene sulfonic acid monohydrate (1.301 g, 6.84 mmol) were added at 0° C. and stirred overnight at 25° C. After 24 hours observed starting material still present, added additional 270 mg of para-toluene sulfonic acid monohydrate and let reaction mixture stir at 25° C. for 3 hours. The reaction mixture was poured into saturated aqueous NaHCO$_3$ solution and the resulting solution was extracted with ether. The combined organic layers were washed with sodium bicarbonate solution and brine. The resulting organic layers were dried over magnesium sulfate, filtered, and concentrated. Silica gel chromatography (0%-70% ethyl acetate/hexanes) afforded a colorless oily solid (9.53 g, 81%).

MS: 260.1 ES+ ($C_{12}H_{21}NO_5$)

$^1$H NMR (300 MHz, CHLOROFORM-d) δ: 1.37-1.57 (m, 12H); 1.62-1.71 (m, 3H); 3.70-3.81 (m, 3H); 3.98-4.22 (m, 2H); 4.33-4.54 (m, 1H).

Intermediate 182: (R)-tert-butyl 4-formyl-2,2-dimethyloxazolidine-3-carboxylate

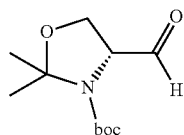

To a −78° C. solution of (R)-3-tert-butyl 4-methyl 2,2-dimethyloxazolidine-3,4-dicarboxylate (Intermediate 181, 18.80 g, 72.50 mmol) in toluene (153 mL) was dropwise (via addition funnel) added DIBAL-H (1.0 M in toluene) (116 ml, 116.01 mmol) over 1.5 hours. The reaction mixture was stirred at −78° C. for 2 hours under nitrogen atmosphere. The cold reaction mixture was treated with 38 mL MeOH (~1.91 M) and then poured 750 mL cold 1N HCl (~0.09M) into reaction mixture, removed reaction mixture from −78° C. bath, transferred to separatory funnel and extracted with ethyl acetate. The organic layers were dried over magnesium sulfate, filtered, concentrated. Due to a difficult separation required two silica gel chromatography columns (0%-50% ethyl acetate/hexanes) to afford the title compound as a colorless oily solid (10.2 g, 61%).

$^1$H NMR (300 MHz, CHLOROFORM-d) δ: 1.36-1.74 (m, 15H); 3.95-4.49 (m, 3H); 9.45-9.68 (m, 1H).

Intermediate 183: (R)-tert-butyl 4-(1-hydroxyethyl)-2,2-dimethyloxazolidine-3-carboxylate

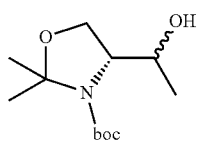

To a solution of (R)-tert-butyl 4-formyl-2,2-dimethyloxazolidine-3-carboxylate (Intermediate 182, 10.18 g, 44.40 mmol) in THF (188 mL) at −78° C. was added methyl magnesium bromide (16.28 mL, 48.84 mmol) dropwise. The reaction mixture was allowed to warm to room temperature and stir overnight under nitrogen atmosphere. Re-cooled reaction mixture to −78° C. and added dropwise additional 13 mL (0.9 eq, to bring total to 2 eq) of methyl magnesium bromide. Allowed reaction mixture to stir at −78° C. for 3 hours and warm to room temperature. The reaction mixture was quenched with water and diluted with ethyl acetate saturated sodium chloride (brine). The resulting emulsion was filtered thru celite and the layers separated. The organic layers were dried over magnesium sulfate, filtered, concentrated. Silica gel chromatography (0%-20% ethyl acetate/hexanes) afforded the title compound as a colorless oily solid (8.42 g, 77%).

$^1$H NMR (300 MHz, CHLOROFORM-d) δ: 1.09-1.22 (m, 3H); 1.36-1.64 (m, 15H); 3.70-4.27 (m, 4H).

Intermediate 184: (R)-tert-butyl 4-acetyl-2,2-dimethyloxazolidine-3-carboxylate

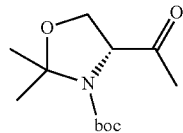

The title compound was prepared from (R)-tert-butyl 4-(1-hydroxyethyl)-2,2-dimethyloxazolidine-3-carboxylate (Intermediate 183, 8.42 g, 34.32 mmol) following the procedure for Intermediate 231. Silica gel chromatography (0%-50% ethyl acetate/hexanes) afforded the desired product as a colorless oily solid (8.16 g, 98%).

$^1$H NMR (300 MHz, CHLOROFORM-d) δ: 1.37-1.57 (m, 12H); 1.61-1.77 (m, 3H); 2.20 (br. s., 3H); 3.89-4.03 (m, 1H); 4.07-4.21 (m, 1H); 4.24-4.47 (m, 1H).

Intermediate 185: (S)-tert-butyl 2,2-dimethyl-4-(prop-1-en-2-yl)oxazolidine-3-carboxylate

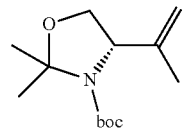

The title compound was prepared from (R)-tert-butyl 4-acetyl-2,2-dimethyloxazolidine-3-carboxylate (Intermediate 184, 8.16 g, 33.54 mmol) following the procedure for JC75. Silica gel chromatography (0%-20% ethyl acetate/hexanes) afforded the desired product as a colorless oily solid (7.25 g, 90%).

$^1$H NMR (300 MHz, CHLOROFORM-d) δ: 1.37-1.54 (m, 12H); 1.66 (br. s., 3H); 1.74 (s, 3H); 3.75 (dd, J=9.06, 3.02 Hz, 1H); 4.02-4.19 (m, 1H); 4.20-4.44 (m, 1H); 4.86 (br. s., 2H).

Intermediate 186: (S)-tert-butyl 1-(tert-butyldimethylsilyloxy)-3-methylbut-3-en-2-ylcarbamate

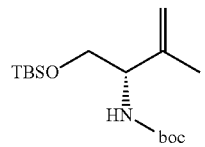

The title compound was prepared from (S)-tert-butyl 2,2-dimethyl-4-(prop-1-en-2-yl)oxazolidine-3-carboxylate (Intermediate 185, 6.92 g, 28.67 mmol) following the procedure for JC76. Silica gel chromatography (0%-10% ethyl acetate/hexanes) afforded the desired product as a colorless oil (8.28 g, 92%).

MS: 316.3 ES+ ($C_{16}H_{33}NO_3Si$)

$^1$H NMR (300 MHz, CHLOROFORM-d) δ: 0.05 (d, J=2.27 Hz, 6H); 0.84-0.93 (m, 9H); 1.45 (s, 9H); 1.76 (s, 3H); 3.59-3.81 (m, 2H); 4.06 (d, J=6.99 Hz, 1H); 4.81-5.05 (m, 2H).

Intermediate 187: (S)-1-(tert-butyldimethylsilyloxy)-3-methylbut-3-en-2-amine

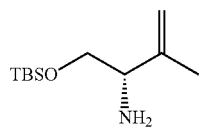

The title compound was prepared from (S)-tert-butyl 1-(tert-butyldimethylsilyloxy)-3-methylbut-3-en-2-ylcarbamate (Intermediate 186, 8.28 g, 26.24 mmol) following the procedure for Intermediate 234. The organic layers were dried over magnesium sulfate, filtered and concentrated to afford the title compound as an off-white solid (5.57 g, 99%).

MS: 216.2 ES+ ($C_{11}H_{25}NOSi$)

$^1$H NMR (300 MHz, CHLOROFORM-d) δ: 0.06-0.15 (m, 6H); 0.88-0.96 (m, 9H); 1.78-1.88 (m, 3H); 3.00 (br. s., 2H); 3.53-3.64 (m, 1H); 3.66-3.79 (m, 1H); 3.91 (dd, J=10.29, 3.30 Hz, 1H); 4.97-5.11 (m, 2H).

Intermediate 188: (S)-tert-butyl 1-(tert-butyldimethylsilyloxy)-3-methylbut-3-en-2-yl(2-(methoxy(methyl)amino)-2-oxoethyl)carbamate

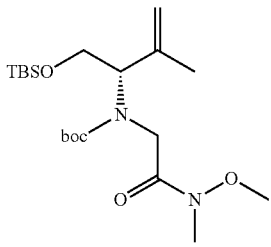

The title compound was prepared from (S)-1-(tert-butyldimethylsilyloxy)-3-methylbut-3-en-2-amine (Intermediate 187, 5.57 g, 25.86 mmol) and 2-bromo-N-methoxy-N-methylacetamide (Intermediate 4, 4.28 g, 23.53 mmol) following the procedure described for Intermediate 5. Silica gel chromatography (0%-20% ethyl acetate/hexanes) afforded the desired product as a colorless oil (4.24 g, 39%).

MS: 417.3 ES+ ($C_{20}H_{40}N_2O_5Si$)

$^1$H NMR (300 MHz, CHLOROFORM-d) δ: −0.03-0.15 (m, 6H); 0.81-0.97 (m, 9H); 1.41-1.63 (m, 9H); 1.72-1.82 (m, 3H); 3.55-3.79 (m, 2H); 3.92-4.23 (m, 1H); 4.85-5.02 (m, 2H).

Intermediate 189: (S)-tert-butyl 1-(tert-butyldimethylsilyloxy)-3-methylbut-3-en-2-yl(3-methyl-2-oxobut-3-enyl)carbamate

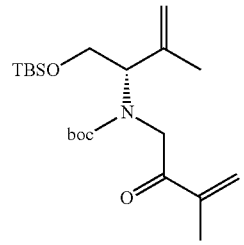

The title compound was prepared from (S)-tert-butyl 1-(tert-butyldimethylsilyloxy)-3-methylbut-3-en-2-yl(2-(methoxy(methyl)amino)-2-oxoethyl)carbamate (Intermediate 188, 4.24 g, 10.18 mmol) following the procedure described for Intermediate 6 substituting the relevant isoprenyl magnesium bromide (0.5 M in THF) (204 mL, 101.77 mmol). Silica gel chromatography (0%-20% ethyl acetate/hexanes) afforded the desired product as a light yellow oil (3.72 g, 92%).

MS: 398.3 ES+ ($C_{21}H_{39}NO_4Si$)

$^1$H NMR (300 MHz, CHLOROFORM-d) δ: −0.02-0.08 (m, 6H); 0.82-0.90 (m, 9H); 1.35-1.51 (m, 9H); 1.78 (s, 3H); 1.90 (s, 3H); 3.68-3.99 (m, 2H); 4.23-4.75 (m, 3H); 4.84-5.01 (m, 2H); 5.84-5.98 (m, 2H).

Intermediate 190: (S)-tert-butyl 2-((tert-butyldimethylsilyloxy)methyl)-3,4-dimethyl-5-oxo-5,6-dihydropyridine-1(2H)-carboxylate

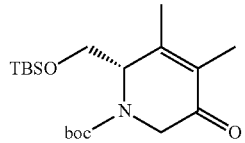

The title compound was prepared from (S)-tert-butyl 1-(tert-butyldimethylsilyloxy)-3-methylbut-3-en-2-yl(3-methyl-2-oxobut-3-enyl)carbamate (Intermediate 189, 3.72 g, 9.36 mmol) following the procedure described for Intermediate 7 except the reaction mixture was heated at 110-120° C. for 48 hours and doubling the catalyst loading (0.6 equivalents). Silica gel chromatography (0%-15% ethyl acetate/hexanes) afforded the desired product as a light tan oily solid (2.39 g, 69%).

Optical rotation: (1 g/dL, MeOH)=−40

MS: 370.3 ES+ ($C_{19}H_{35}NO_4Si$)

$^1$H NMR (300 MHz, CHLOROFORM-d) δ: 0.00 (d, J=7.93 Hz, 6H); 0.82 (s, 9H); 1.48 (s, 9H); 1.79-1.87 (m, 3H); 1.98 (s, 3H); 3.79-4.06 (m, 4H); 4.36-4.58 (m, 1H).

Intermediate 191: (2S,5S)-tert-butyl 2-((tert-butyldimethylsilyloxy)methyl)-5-hydroxy-3,4-dimethyl-5,6-dihydropyridine-1(2H)-carboxylate

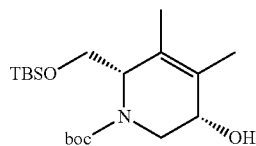

The title compound was prepared from (S)-tert-butyl 2-((tert-butyldimethylsilyloxy)methyl)-3,4-dimethyl-5-oxo-5,6-dihydropyridine-1(2H)-carboxylate (Intermediate 190, 2.39 g, 6.47 mmol) following the procedure described for Intermediate 8. Silica gel chromatography (0%-20% ethyl acetate/hexanes) afforded the desired product as a colorless oily solid (1.73 g, 72%).

MS: 372.3 ES+ ($C_{19}H_{37}NO_4Si$)

$^1$H NMR (300 MHz, CHLOROFORM-d) δ: 0.01-0.12 (m, 6H); 0.83-0.94 (m, 9H); 1.48 (s, 9H); 1.69 (s, 3H); 1.84 (s, 3H); 3.34 (d, J=12.84 Hz, 1H); 3.68 (d, J=8.12 Hz, 2H); 3.87 (br. s., 1H); 4.00-4.29 (m, 2H).

Intermediate 192: (2S,5R)-tert-butyl 5-(N-(allyloxy)-2-nitrophenylsulfonamido)-2-((tert-butyldimethylsilyloxy)methyl)-3,4-dimethyl-5,6-dihydropyridine-1(2H)-carboxylate

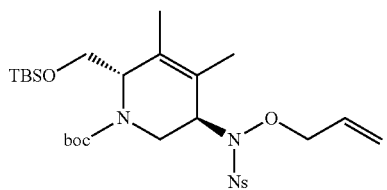

The title compound was prepared from (2S,5S)-tert-butyl 2-((tert-butyldimethylsilyloxy)methyl)-5-hydroxy-3,4-dimethyl-5,6-dihydropyridine-1(2H)-carboxylate (Intermediate 191, 1.73 g, 4.66 mmol) and N-(allyloxy)-2-nitrobenzenesulfonamide (Intermediate 9, 1.26 g, 4.89 mmol) following the procedure described for Intermediate 10. Silica gel chromatography (0%-20% ethyl acetate/hexanes) afforded the desired product as an off-white solid (3.15 g, 100%).

MS: 612.3 ES+ ($C_{28}H_{45}N_3O_8SSi$)

$^1$H NMR (300 MHz, CHLOROFORM-d) δ: −0.05-0.08 (m, 6H); 0.78-0.91 (m, 9H); 1.31-1.89 (m, 15H); 3.17-3.86 (m, 4H); 4.17-4.31 (m, 1H); 4.39 (br. s., 1H); 4.57 (dt, J=6.23, 1.23 Hz, 2H); 5.05-5.43 (m, 2H); 5.94 (ddt, J=17.09, 10.48, 6.33, 6.33 Hz, 1H); 7.50-7.64 (m, 1H); 7.66-8.00 (m, 1H); 8.02-8.32 (m, 2H).

Intermediate 193: (2S,5R)-tert-butyl 5-(N-(allyloxy)-2-nitrophenylsulfonamido)-2-(hydroxymethyl)-3,4-dimethyl-5,6-dihydropyridine-1(2H)-carboxylate

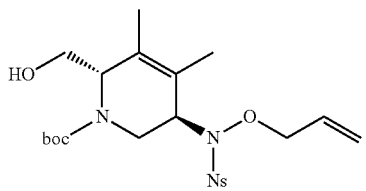

The title compound was prepared from (2S,5R)-tert-butyl 5-(N-(allyloxy)-2-nitrophenylsulfonamido)-2-((tert-butyldimethylsilyloxy)methyl)-3,4-dimethyl-5,6-dihydropyridine-1(2H)-carboxylate (Intermediate 192, 3.15 g, 5.15 mmol) following the procedure described for Intermediate 18. Two silica gel chromatography (0%-100% ethyl acetate/hexanes) afforded the desired product as a white foamy solid (1.68 g, 65.6%).

MS: 498.2 ES+ ($C_{22}H_{31}N_3O_8S$)

$^1$H NMR (300 MHz, CHLOROFORM-d) δ: 1.15-1.92 (m, 15H); 2.98-3.46 (m, 1H); 3.55-3.96 (m, 3H); 4.01-4.35 (m, 3H); 4.57 (d, J=6.80 Hz, 1H); 5.09-5.35 (m, 2H); 5.54-5.91 (m, 1H); 7.61 (d, J=7.37 Hz, 1H); 7.67-7.85 (m, 2H); 8.08-8.22 (m, 1H).

Intermediate 194: (2S,5R)-5-(N-(allyloxy)-2-nitrophenylsulfonamido)-1-(tert-butoxycarbonyl)-3,4-dimethyl-1,2,5,6-tetrahydropyridine-2-carboxylic acid

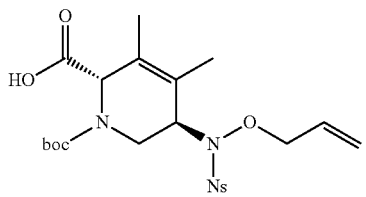

The title compound was prepared from (2S,5R)-tert-butyl 5-(N-(allyloxy)-2-nitrophenylsulfonamido)-2-(hydroxymethyl)-3,4-dimethyl-5,6-dihydropyridine-1(2H)-carboxylate (Intermediate 193, 1.68 g, 3.38 mmol) following the procedure described for Intermediate 19. The workup yielded organics that were dried over magnesium sulfate, filtered and concentrated crude material to afford a light orange foam (1.48 g, 86%).

MS: 512.2 ES+ ($C_{22}H_{29}N_3O_9S$)

$^1$H NMR (300 MHz, CHLOROFORM-d) δ: 1.22-1.61 (m, 12H); 1.86 (s, 3H); 3.15-3.42 (m, 1H); 3.82-4.07 (m, 1H); 4.09-4.34 (m, 2H); 4.92 (s, 1H); 5.09-5.24 (m, 2H); 5.31 (s, 1H); 5.56-5.84 (m, 1H); 7.52-7.67 (m, 1H); 7.69-7.91 (m, 2H); 8.13 (dd, J=7.84, 1.42 Hz, 1H).

Intermediate 195: (2S,5R)-tert-butyl 5-(N-(allyloxy)-2-nitrophenylsulfonamido)-2-carbamoyl-3,4-dimethyl-5,6-dihydropyridine-1(2H)-carboxylate

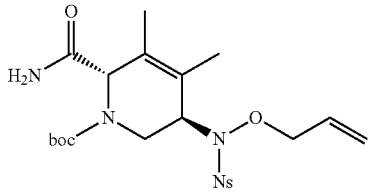

The title compound was prepared from (2S,5R)-5-(N-(allyloxy)-2-nitrophenylsulfonamido)-1-(tert-butoxycarbonyl)-3,4-dimethyl-1,2,5,6-tetrahydropyridine-2-carboxylic acid (Intermediate 194, 1.48 g, 2.89 mmol) following the procedure described for Intermediate 20. Silica gel chromatography (0%-80% ethyl acetate/hexanes) afforded the desired product as a light yellow foamy solid (1.41 g, 95%).

Optical rotation: (0.4 g/dL, MeOH)=−51

MS: 511.2 ES+ ($C_{22}H_{30}N_4O_8S$)

$^1$H NMR (300 MHz, CHLOROFORM-d) δ: 1.15-1.48 (m, 9H); 1.51-1.85 (m, 6H); 2.93-3.36 (m, 2H); 4.02-4.34 (m, 2H); 4.83 (br. s., 1H); 5.04-5.40 (m, 3H); 5.51-5.77 (m, 1H); 7.60 (d, J=7.36 Hz, 1H); 7.65-7.85 (m, 2H); 7.99-8.18 (m, 1H).

Intermediate 196: (2S,5R)-5-(N-(allyloxy)-2-nitrophenlsulfonamido)-3,4-dimethyl-1,2,5,6-tetrahydropyridine-2-carboxamide

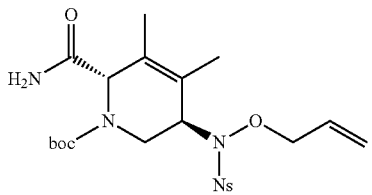

The title compound was prepared from (2S,5R)-tert-butyl 5-(N-(allyloxy)-2-nitrophenylsulfonamido)-2-carbamoyl-3,4-dimethyl-5,6-dihydropyridine-1(2H)-carboxylate (Intermediate 195, 1.36 g, 2.66 mmol) following the procedure described for Intermediate 21. The workup yielded an organic layer that was dried over magnesium sulfate, filtered and concentrated to afford the desired product as a light pink solid (0.82 g, 75%).

MS: 411.1 ES+ ($C_{17}H_{22}N_4O_6S$)

$^1$H NMR (300 MHz, CHLOROFORM-d) δ: 1.87 (s, 3H); 1.98 (s, 3H); 2.67-2.89 (m, 2H); 3.66 (s, 1H); 3.92-4.31 (m, 2H); 4.51 (dd, J=11.33, 6.04 Hz, 1H); 5.15-5.34 (m, 2H); 5.67-5.93 (m, 1H); 7.61 (dd, J=7.84, 1.42 Hz, 1H); 7.68-7.94 (m, 2H); 8.05-8.18 (m, 1H).

Intermediate 197: (2S,5R)-5-(allyloxyamino)-3,4-dimethyl-1,2,5,6-tetrahydropyridine-2-carboxamide

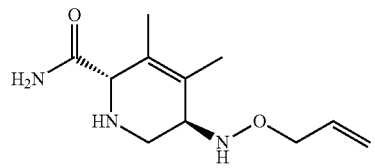 [SMILES: C=CCON[C@H]1CN[C@H](C(N)=O)C(C)=C1C]

The title compound was prepared from (2S,5R)-5-(N-(allyloxy)-2-nitrophenylsulfonamido)-3,4-dimethyl-1,2,5,6-tetrahydropyridine-2-carboxamide (Intermediate 196, 0.82 g, 2.00 mmol) following the procedure described for Intermediate 12. Silica gel chromatography (0%-10% methanol/dichloromethane) afforded the desired product as a white solid (0.31 g, 68.9%).

MS: 226.2 ES+ ($C_{11}H_{19}N_3O_2$)

$^1$H NMR (300 MHz, CHLOROFORM-d) δ: 1.80 (s, 3H); 1.86 (s, 3H); 2.83-2.97 (m, 1H); 3.12 (br. s., 1H); 3.22 (d, J=13.79 Hz, 1H); 3.76 (br. s., 1H); 4.20 (dt, J=6.00, 1.25 Hz, 2H); 5.16-5.35 (m, 2H); 5.42 (br. s., 1H); 5.95 (ddt, J=17.28, 10.34, 6.02, 6.02 Hz, 1H); 7.06-7.20 (m, 1H).

Intermediate 198: (2S,5R)-6-(allyloxy)-3,4-dimethyl-7-oxo-1,6-diazabicyclo[3.2.1]oct-3-ene-2-carboxamide

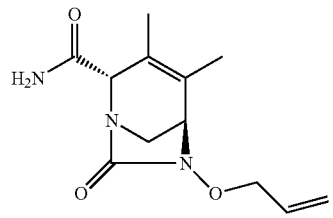 [SMILES: C=CCON1C(=O)N2C[C@H]1C(C)=C(C)[C@H]2C(N)=O]

The title compound was prepared from (2S,5R)-5-(allyloxyamino)-3,4-dimethyl-1,2,5,6-tetrahydropyridine-2-carboxamide (Intermediate 197, 0.31 g, 1.38 mmol) following the procedure described for Intermediate 13. Silica gel chromatography (0%-70% ethyl acetate/hexanes) afforded the desired product as a white solid (0.23 g, 66.5%).

MS: 252.2 ES+ ($C_{12}H_{17}N_3O_3$)

$^1$H NMR (300 MHz, CHLOROFORM-d) δ: 1.76-1.82 (m, 3H); 1.83-1.90 (m, 3H); 3.10-3.33 (m, 1H); 3.66 (d, J=2.64 Hz, 1H); 4.23 (s, 1H); 4.42 (qdt, J=12.20, 12.20, 12.20, 6.35, 1.09, 1.09 Hz, 2H); 5.24-5.51 (m, 3H); 6.02 (ddt, J=17.00, 10.53, 6.35, 6.35 Hz, 1H); 6.61 (br. s., 2H).

Intermediate 199: (E)-triphenyl(prop-1-enyl)phosphonium (2S,5R)-2-carbamoyl-3,4-dimethyl-7-oxo-1,6-diazabicyclo[3.2.1]oct-3-en-6-yl sulfate

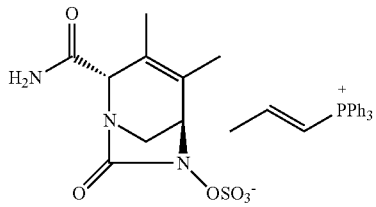

The title compound was prepared from (2S,5R)-6-(allyloxy)-3,4-dimethyl-7-oxo-1,6-diazabicyclo[3.2.1]oct-3-ene-2-carboxamide (Intermediate 198, 0.227 g, 0.9 mmol) following the procedure described for Intermediate 17. Silica gel chromatography (0%-100% acetone/dichloromethane) afforded the desired product as a light yellow oily solid (0.5 g, 93%).

MS: 290 ES−, 303 ES+ ($C_9H_{12}N_3O_6S$, $C_{21}H_{20}P$)

$^1$H NMR (300 MHz, CHLOROFORM-d) δ: 1.77 (s, 3H); 1.86-1.95 (m, 3H); 2.28-2.39 (m, 3H); 3.14 (d, J=10.76 Hz, 1H); 3.46 (dd, J=10.76, 3.02 Hz, 1H); 4.29 (d, J=2.83 Hz, 1H); 5.38 (br. s., 1H); 6.51-6.80 (m, 1H); 7.20-7.54 (m, 6H); 7.58-7.91 (m, 10H).

Example 22

(2S,5R)-2-carbamoyl-3-ethyl-7-oxo-1,6-diazabicyclo[3.2.1]oct-3-en-6-yl hydrogen sulfate sodium salt

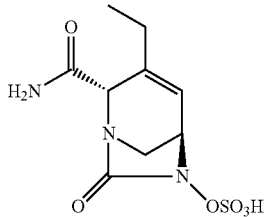

The title compound was prepared from (E)-triphenyl(prop-1-en-1-yl)phosphonium (2S,5R)-2-carbamoyl-3-ethyl-7-oxo-1,6-diazabicyclo[3.2.1]oct-3-en-6-yl sulfate (Intermediate 216, 0.77 g, 1.30 mmol) according to the procedure for Example 1. Fractions 5-7 were combined and lyophilized separately from fractions 8-17 which were yellow. The title compound was obtained from fractions 5-7 (0.275 g, 67.5%) as an off-white solid.

MS: 292 ES+ ($C_9H_{13}N_3O_6S$)

$^1$H NMR (300 MHz, DMSO-d6) δ: 0.94 (t, J=7.54 Hz, 3H) 1.59-2.19 (m, 2H) 3.07 (dd, J=10.93, 1.88 Hz, 1H) 3.73 (d, J=10.55 Hz, 1H) 4.06 (dd, J=4.52, 2.26 Hz, 1H) 4.15 (s, 1H) 6.03 (d, J=4.52 Hz, 1H) 7.29 (br. s., 1H) 7.83 (br. s., 1H).

The intermediates for Example 22 were prepared as follows:

Intermediate 200: (R)-tert-butyl 4-(3-hydroxypentan-3-yl)-2,2-dimethyloxazolidine-3-carboxylate

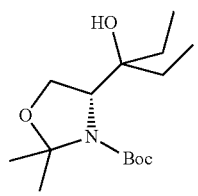 [SMILES: CCC(O)(CC)[C@H]1COC(C)(C)N1C(=O)OC(C)(C)C]

A suspension of cerium (III) chloride (119 g, 482.07 mmol) in THF (350 mL) at room temperature was stirred vigorously for 2 hours. The suspension was cooled to −78° C. and ethylmagnesium bromide (482 mL, 482.07 mmol) was added dropwise. The mixture was stirred at −78° C. for 1.5 hours. (R)-3-tert-butyl 4-methyl 2,2-dimethyloxazolidine-3,4-dicarboxylate (Aldrich, 25 g, 96.41 mmol) in THF (100 mL) was then added dropwise at −78° C. The reaction was stirred at −78° C. for 30 minutes and then warmed to 0° C. for 15 minutes. The reaction was quenched with saturated $NH_4Cl$, diluted further with water and extracted twice with ether. The organics were dried over magnesium sulfate, filtered and concentrated. Silica gel chromatography (0%-20% ethyl acetate/hexanes) afforded the title compound (26.4 g, 95%) as a colorless oil.

MS: 288 ES+ ($C_{15}H_{29}NO_4$)

$^1$H NMR (300 MHz, CHLOROFORM-d) δ: 0.77-0.98 (m, 6H) 1.24-1.81 (m, 19H) 3.86 (d, J=8.29 Hz, 1H) 3.95-4.07 (m, 1H) 4.17 (d, J=7.35 Hz, 1H) 4.97 (br. s., 1H).

Intermediate 201: (S)-tert-butyl 2,2-dimethyl-4-(pent-2-en-3-yl)oxazolidine-3-carboxylate

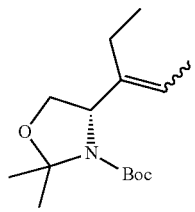

To a solution of (R)-tert-butyl 4-(3-hydroxypentan-3-yl)-2,2-dimethyloxazolidine-3-carboxylate (Intermediate 200, 26.4 g, 91.86 mmol) in dichloromethane (350 mL) at 0° C. was added triethylamine (128 mL, 918.60 mmol) and then slowly added methanesulfonyl chloride (35.8 mL, 459.30 mmol). The yellow reaction mixture was warmed to room temperature and stirred overnight for ~16 h. The reaction mixture was diluted with diethyl ether and poured into water. The organic layer was washed with 10% citric acid, saturated sodium bicarbonate, saturated sodium chloride, dried over sodium sulfate, filtered, and concentrated under reduced pressure to give a brown oil. Purification by flash column chromatography (0-20% ethyl acetate/hexanes) afforded the title compound (17.70 g, 71.5%) as very pale yellow oil.

MS: 270 ES+ ($C_{15}H_{27}NO_3$)

$^1$H NMR (300 MHz, CHLOROFORM-d) δ: 1.02 (q, J=7.47 Hz, 3H) 1.38-1.54 (m, 12H) 1.61-1.73 (m, 6H) 1.83-2.29 (m, 2H) 3.59-3.75 (m, 1H) 4.03-4.16 (m, 1H) 4.18-5.01 (m, 1H) 5.32 (br. s., 1H).

Intermediate 202: (S)-tert-butyl 3-ethyl-1-hydroxypent-3-en-2-ylcarbamate

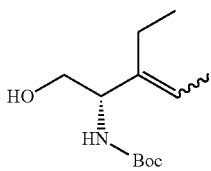

A solution of (S)-tert-butyl 2,2-dimethyl-4-(pent-2-en-3-yl)oxazolidine-3-carboxylate (Intermediate 201, 15.815 g, 58.71 mmol) and p-toluenesulfonic acid monohydrate (3.35 g, 17.61 mmol) in methanol (100 mL) was heated to 85° C. for 3 h. The reaction mixture was cooled to room temperature and triethylamine (8.18 mL, 58.71 mmol) and di-tert-butyl dicarbonate (6.82 mL, 29.35 mmol) were added. The reaction mixture was stirred at room temperature overnight. The reaction mixture was concentrated under reduced pressure to give a yellow oil. Purification by flash column chromatography (0-100% ethyl acetate/hexanes) afforded the title compound (10.12 g, 75%) as a white solid.

MS: 230 ES+ ($C_{12}H_{23}NO_3$)

$^1$H NMR (300 MHz, CHLOROFORM-d) δ: 0.99-1.08 (m, 3H) 1.46 (q, J=2.07 Hz, 9H) 1.64-1.75 (m, 3H) 1.92-2.22 (m, 3H) 3.54-3.76 (m, 2H) 4.15-4.89 (m, 2H) 5.43 (q, J=6.84 Hz, 1H).

Intermediate 203: (S,E)-tert-butyl 1-(tert-butyldimethylsilyloxy)-3-ethylpent-3-en-2-ylcarbamate

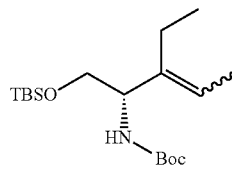

To a solution of (S)-tert-butyl 3-ethyl-1-hydroxypent-3-en-2-ylcarbamate (Intermediate 202, 11.855 g, 51.70 mmol) in DCM (120 mL) was added imidazole (5.28 g, 77.55 mmol), DMAP (1.263 g, 10.34 mmol) and TBDMS-Cl (9.35 g, 62.04 mmol). The reaction mixture was stirred at room temperature overnight. The reaction mixture was diluted with ethyl ether and washed with brine. The organic layer was dried over sodium sulfate, filtered, and concentrated under reduced pressure. Purification by flash column chromatography (0-50% ethyl acetate/hexanes) afforded the title compound (17.20 g, 97%) as a clear oil.

MS: 344 ES+ ($C_{18}H_{37}NO_3Si$)

$^1$H NMR (300 MHz, CHLOROFORM-d) δ: 0.06 (d, J=1.13 Hz, 6H) 0.89 (dd, J=2.83, 1.32 Hz, 9H) 0.96-1.08 (m, 3H) 1.45 (s, 9H) 1.54-1.76 (m, 3H) 1.89-2.20 (m, 2H) 3.50-3.76 (m, 2H) 3.93-4.71 (m, 1H) 4.87 (br. s., 1H) 5.27-5.46 (m, 1H).

Intermediate 204: (S)-1-(tert-butyldimethylsilyloxy)-3-ethylpent-3-en-2-amine

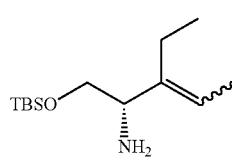

To a solution of (S)-tert-butyl 1-(tert-butyldimethylsilyloxy)-3-ethylpent-3-en-2-ylcarbamate (Intermediate 203, 17.2 g, 50.06 mmol) in DCM (300 mL) at room temperature was added zinc bromide (45.1 g, 200.25 mmol). The reaction mixture was stirred for 2 days. The reaction mixture was filtered through fritted funnel and washed with saturated sodium bicarbonate. The aqueous layer was extracted two more times with DCM and the organics were combined, dried over magnesium sulfate, filtered and concentrated to afford the title compound (12.19 g, 100%) as a yellow oil.

MS: 244 ES+ ($C_{13}H_{29}NOSi$)

$^1$H NMR (300 MHz, CHLOROFORM-d) δ: 0.02-0.12 (m, 6H) 0.86-0.94 (m, 9H) 0.95-1.05 (m, 3H) 1.60-1.72 (m, 3H) 1.87-2.22 (m, 2H) 3.29-3.57 (m, 2H) 3.58-4.00 (m, 1H) 5.24-5.51 (m, 1H).

Intermediate 205: (S)-tert-butyl 1-(tert-butyldimethylsilyloxy)-3-ethylpent-3-en-2-yl(2-(methoxy(methyl)amino)-2-oxoethyl)carbamate

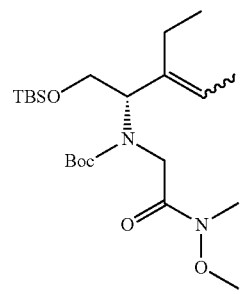

A mixture of (S)-1-(tert-butyldimethylsilyloxy)-3-ethylpent-3-en-2-amine (Intermediate 204, 14.14 g, 58.08 mmol) and cesium carbonate (18.92 g, 58.08 mmol) in DMF (140 mL) was stirred at room temperature for 1 hour. 2-bromo-N-methoxy-N-methylacetamide (Intermediate 4, 9.61 g, 52.80 mmol) was added and the reaction mixture was stirred at room temperature for 6 hours. Di-tert-butyl dicarbonate (12.74 mL, 55.44 mmol) was added and the reaction mixture was stirred at room temperature overnight.

The reaction mixture was diluted with ethyl acetate and filtered to remove the inorganic salts. The filtrate was concentrated and the residue was taken up in ether and washed with aqueous saturated sodium bicarbonate, water, aqueous 5% citric acid, water and brine. The organics were dried over magnesium sulfate, filtered and concentrated. Silica gel chromatography (0%-30% ethyl acetate/hexanes) afforded the title compound (13.71 g, 58.4%) as a light yellow oil.

MS: 445 ES+ ($C_{22}H_{44}N_2O_5Si$)

$^1$H NMR (300 MHz, DMSO-d6) δ: −0.05-0.05 (m, 6H) 0.83 (s, 9H) 0.87-0.98 (m, 3H) 1.27-1.43 (m, 9H) 1.59 (dd, J=8.57, 7.06 Hz, 3H) 1.84-2.15 (m, 2H) 3.01-3.11 (m, 3H) 3.63 (d, J=6.03 Hz, 3H) 3.69-3.92 (m, 3H) 3.98-4.22 (m, 1H) 4.43-4.91 (m, 1H) 5.27-5.42 (m, 1H).

Intermediate 206: (S)-tert-butyl 1-(tert-butyldimethylsilyloxy)-3-ethylpent-3-en-2-yl(2-oxopent-3-enyl)carbamate

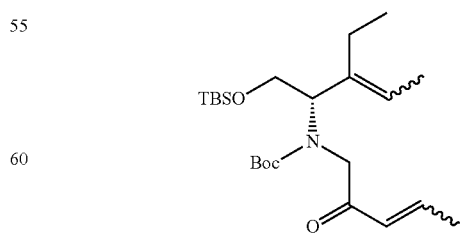

The title compound was prepared from (S)-tert-butyl 1-(tert-butyldimethylsilyloxy)-3-ethylpent-3-en-2-yl(2-(methoxy(methyl)amino)-2-oxoethyl)carbamate (Intermediate 205, 13.7 g, 30.81 mmol) according to the procedure described for Intermediate 236. The reaction was quenched with saturated NH₄Cl, diluted further with water and extracted twice with ether. The organics were dried over magnesium sulfate, filtered and concentrated. Silica gel chromatography (0%-45% ethyl acetate/hexanes) afforded the title compound (10.95 g, 83%) as a colorless oil.

MS: 426 ES+ ($C_{23}H_{43}NO_4Si$)

¹H NMR (300 MHz, CHLOROFORM-d) δ: −0.02-0.07 (m, 6H) 0.83-0.91 (m, 9H) 1.00 (t, J=7.35 Hz, 3H) 1.33-1.51 (m, 9H) 1.57-1.74 (m, 3H) 1.82-1.92 (m, 3H) 1.92-2.21 (m, 2H) 3.65-3.97 (m, 3H) 3.97-4.34 (m, 1H) 4.54-5.08 (m, 1H) 5.25-5.44 (m, 1H) 6.12-6.35 (m, 1H) 6.79-7.00 (m, 1H).

Intermediate 207: (S)-tert-butyl 2-((tert-butyldimethylsilyloxy)methyl)-3-ethyl-5-oxo-5,6-dihydropyridine-1 (2H)-carboxylate

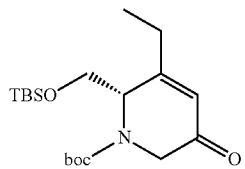

The title compound was prepared from (S)-tert-butyl 1-(tert-butyldimethylsilyloxy)-3-ethylpent-3-en-2-yl(2-oxopent-3-enyl)carbamate (Intermediate 206, 10.95 g, 25.72 mmol) according to the procedure described for Intermediate 7, except the reaction was heated at 86° C. for 6 days. Silica gel chromatography (0-10% ethyl acetate/hexanes) afforded the title compound (5.15 g, 54.1%) as a light yellow oil.

MS: 370 ES+ ($C_{19}H_{35}NO_4Si$)

¹H NMR (300 MHz, CHLOROFORM-d) δ: −0.18-0.09 (m, 6H) 0.70-0.94 (m, 9H) 1.17 (t, J=7.35 Hz, 3H) 1.48 (s, 9H) 2.19-2.43 (m, 2H) 3.68-4.06 (m, 3H) 4.28-4.78 (m, 2H) 6.08 (s, 1H).

Intermediate 208: (2S,5S)-tert-butyl 2-((tert-butyldimethylsilyloxy)methyl)-3-ethyl-5-hydroxy-5,6-dihydropyridine-1(2H)-carboxylate

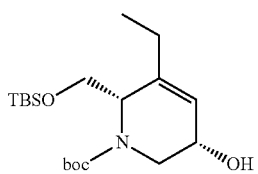

The title compound was prepared from (S)-tert-butyl 2-((tert-butyldimethylsilyloxy)methyl)-3-ethyl-5-oxo-5,6-dihydropyridine-1(2H)-carboxylate (Intermediate 207, 5.146 g, 13.92 mmol) according to the procedure described for Intermediate 8, except the mixture was stirred at ambient temperature for 1 h. The mixture was concentrated and diluted with aqueous NH₄Cl, water and EtOAc. The organic layer was separated and washed three times with brine, dried over Na₂SO₄, filtered and concentrated to afford the title compound (5.19 g, 100%) as a cloudy oil.

MS: 372 ES+ ($C_{19}H_{37}NO_4Si$)

¹H NMR (300 MHz, CHLOROFORM-d) δ: 0.06 (s, 6H) 0.80-0.93 (m, 9H) 1.05-1.14 (m, 3H) 1.48 (s, 9H) 1.98-2.17 (m, 2H) 2.83-3.53 (m, 2H) 3.74 (d, J=11.30 Hz, 2H) 4.06-4.35 (m, 3H) 5.82 (br. s., 1H).

Intermediate 209: (2S,5R)-tert-butyl 5-(N-(allyloxy)-2-nitrophenylsulfonamido)-2-((tert-butyldimethylsilyloxy)methyl)-3-ethyl-5,6-dihydropyridine-1 (2H)-carboxylate

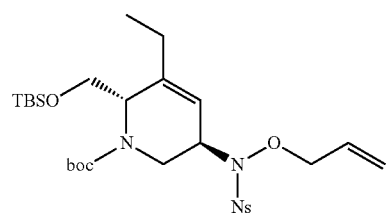

To a stirred suspension of (2S,5S)-tert-butyl 2-((tert-butyldimethylsilyloxy)methyl)-3-ethyl-5-hydroxy-5,6-dihydropyridine-1(2H)-carboxylate (Intermediate 208, 6.36 g, 17.12 mmol), N-(allyloxy)-2-nitrobenzenesulfonamide (Intermediate 9) (8.84 g, 34.23 mmol) and triphenylphosphine (13.47 g, 51.35 mmol) in toluene (25 mL) at 0° C. was added dropwise (E)-diisopropyl diazene-1,2-dicarboxylate (9.95 ml, 51.35 mmol). The reaction mixture was warmed to room temperature and stirred for 30 minutes. Silica gel chromatography (0-40% ethyl acetate/hexanes) afforded the title compound (7.00 g, 66.8%) as a yellow oil.

MS: 612 ES+ ($C_{28}H_{45}N_3O_8SSi$)

Intermediate 210: (2S,5R)-tert-butyl 5-(N-(allyloxy)-2-nitrophenylsulfonamido)-3-ethyl-2-(hydroxymethyl)-5,6-dihydropyridine-1(2H)-carboxylate

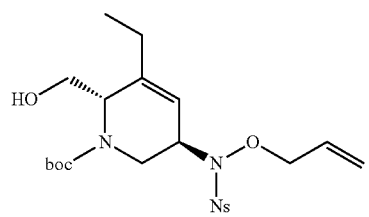

The title compound was prepared from (2S,5R)-tert-butyl 5-(N-(allyloxy)-2-nitrophenylsulfonamido)-2-((tert-butyldimethylsilyloxy)methyl)-3-ethyl-5,6-dihydropyridine-1 (2H)-carboxylate (Intermediate 209, 7 g, 11.44 mmol) following the procedure described for Intermediate 18. Silica gel chromatography (30%-90% ethyl acetate/hexanes) afforded the title compound (4.93 g, 87%) as an tan foam.

MS: 498 ES+ ($C_{22}H_{31}N_3O_8S$)

Intermediate 211: (2S,5R)-5-(N-(allyloxy)-2-nitrophenylsulfonamido)-1-(tert-butoxycarbonyl)-3-ethyl-1,2,56-tetrahydropyridine-2-carboxylic acid

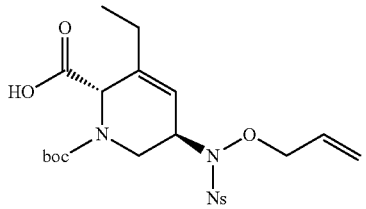

The title compound was prepared from (2S,5R)-tert-butyl 5-(N-(allyloxy)-2-nitrophenylsulfonamido)-3-ethyl-2-(hydroxymethyl)-5,6-dihydropyridine-1(2H)-carboxylate (Intermediate 210, 2.35 g, 4.72 mmol) following the procedure described for Intermediate 19. The title compound was obtained as a tan foam (1.89 g, 78%).
MS: 512 ES+ ($C_{22}H_{29}N_3O_9S$)

Intermediate 212: (2S,5R)-tert-butyl 5-(N-(allyloxy)-2-nitrophenylsulfonamido)-2-carbamoyl-3-ethyl-5,6-dihydropyridine-1(2H)-carboxylate

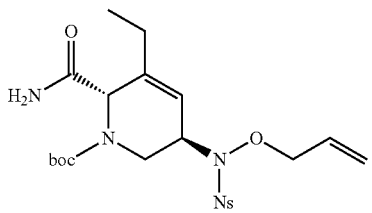

The title compound was prepared from (2S,5R)-5-(N-(allyloxy)-2-nitrophenylsulfonamido)-1-(tert-butoxycarbonyl)-3-ethyl-1,2,5,6-tetrahydropyridine-2-carboxylic acid (Intermediate 211, 1.89 g, 3.69 mmol) following the procedure described for Intermediate 20. Silica gel chromatography (0%-80% ethyl acetate/hexanes) afforded the title compound (1.445 g, 77%) as a beige foam.
MS: 511 ES+ ($C_{22}H_{29}N_3O_9S$)

Intermediate 213: (2S,5R)-5-(N-(allyloxy)-2-nitrophenylsulfonamido)-3-ethyl-1,2,5,6-tetrahydropyridine-2-carboxamide

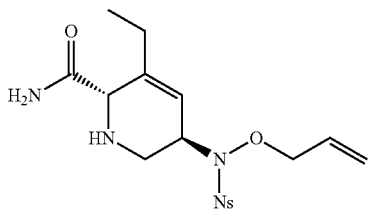

The title compound was prepared from (2S,5R)-tert-butyl 5-(N-(allyloxy)-2-nitrophenylsulfonamido)-2-carbamoyl-3-ethyl-5,6-dihydropyridine-1(2H)-carboxylate (Intermediate 212, 1.44 g, 2.82 mmol) following the procedure described for Intermediate 21, except the reaction mixture was stirred over the weekend at room temperature. The reaction mixture was diluted with dichloromethane and washed with saturated sodium bicarbonate. An emulsion formed and the aqueous was extracted three to four more times with DCM. The organics were washed with brine, dried over magnesium sulfate, filtered and concentrated to afford the title compound (0.870 g, 75%) as a yellow foam.
MS: 411 ES+ ($C_{17}H_{22}N_4O_6S$)
$^1$H NMR (300 MHz, CHLOROFORM-d) δ: 1.04 (t, J=7.54 Hz, 3H) 2.17-2.35 (m, 1H) 2.35-2.52 (m, 1H) 2.94 (d, J=5.27 Hz, 2H) 3.79 (s, 1H) 4.29 (d, J=3.01 Hz, 1H) 4.35-4.56 (m, 2H) 5.18-5.39 (m, 3H) 5.55 (br. s., 1H) 5.74-5.94 (m, 1H) 7.04 (br. s., 1H) 7.55-7.67 (m, 1H) 7.69-7.86 (m, 2H) 8.06-8.23 (m, 1H).

Intermediate 214: (R)-5-(allyloxyamino)-3-ethyl-1,2,5,6-tetrahydropyridine-2-carboxamide

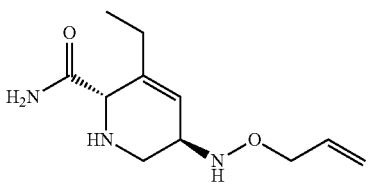 [SMILES: C=CCON[C@@H]1C=C(CC)[C@@H](C(N)=O)NC1]

The title compound was prepared from (2S,5R)-5-(N-(allyloxy)-2-nitrophenylsulfonamido)-3-ethyl-1,2,5,6-tetrahydropyridine-2-carboxamide (Intermediate 213, 0.87 g, 2.12 mmol) following the procedure described for Intermediate 12. Silica gel chromatography (0%-8% methanol/dichloromethane) afforded the title compound (0.355 g, 74.3%) as an off-white solid upon drying on high-vacuum.
MS: 226 ES+ ($C_{11}H_{19}N_3O_2$)
$^1$H NMR (300 MHz, CHLOROFORM-d) δ: 1.07 (t, J=7.54 Hz, 3H) 2.10-2.48 (m, 3H) 2.90-3.08 (m, 2H) 3.43 (d, J=2.26 Hz, 1H) 3.84 (s, 1H) 4.21 (dd, J=6.78, 1.51 Hz, 2H) 5.16-5.67 (m, 5H) 5.95 (ddt, J=17.14, 10.74, 6.03, 6.03 Hz, 1H) 7.08 (br. s., 1H).

Intermediate 215: (2S,5R)-6-(allyloxy)-3-ethyl-7-oxo-1,6-diazabicyclo[3.2.1]oct-3-ene-2-carboxamide

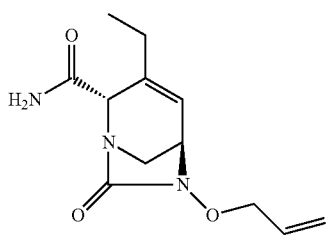 [SMILES: C=CCON1C(=O)N2C[C@H]1C=C(CC)[C@H]2C(N)=O]

To a solution of (R)-5-(allyloxyamino)-3-ethyl-1,2,5,6-tetrahydropyridine-2-carboxamide (Intermediate 214, 0.35 g, 1.55 mmol) and diisopropylethyl amine (1.082 mL, 6.21 mmol) in acetonitrile (110 mL) at 0° C. was added triphosgene (0.157 g, 0.53 mmol) as a solution in acetonitrile (4 mL). The triphosgene solution was added at a rate of 4 mL/hour. Once addition was complete the reaction was stirred at 0° C. for ~1 hour. The reaction mixture was diluted with ethyl acetate, then washed with saturated sodium bicarbonate and brine. The aqueous washes were extracted once with dichloromethane. The combined organic extracts were dried over magnesium sulfate, filtered and concentrated. Silica gel chromatography (0%-100% ethyl acetate/hexanes) afforded the title compound (0.340 g, 87%) as a colorless oil.

MS: 252 ES+ ($C_{12}H_{17}N_3O_3$)

$^1$H NMR (300 MHz, CHLOROFORM-d) δ: 1.05 (t, J=7.16 Hz, 3H) 2.08-2.47 (m, 2H) 3.15-3.34 (m, 2H) 3.85 (dd, J=5.27, 3.01 Hz, 1H) 4.31-4.50 (m, 3H) 5.27-5.51 (m, 3H) 5.93-6.15 (m, 2H) 6.65 (br. s., 1H).

Intermediate 216: (E)-triphenyl(prop-1-enyl)phosphonium (2S,5R)-2-carbamoyl-3-ethyl-7-oxo-1,6-diazabicyclo[3.2.1]oct-3-en-6-yl sulfate

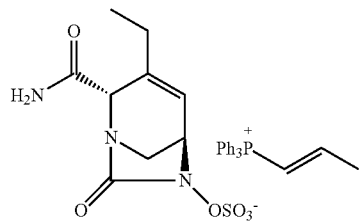

The title compound was prepared from (2S,5R)-6-(allyloxy)-3-ethyl-7-oxo-1,6-diazabicyclo[3.2.1]oct-3-ene-2-carboxamide (Intermediate 215, 340 mg, 1.35 mmol) following the procedure described for Intermediate 17. Silica gel chromatography (0%-100% acetone/DCM) afforded the title compound (770 mg, 96%) as a yellow foam.

MS: 303 ES+ ($C_{21}H_{20}P$) and 290 ES− ($C_9H_{12}N_3O_6S$)

$^1$H NMR (300 MHz, CHLOROFORM-d) δ: 0.99 (t, J=7.16 Hz, 3H) 2.05-2.16 (m, 1H) 2.07-2.16 (m, 1H) 2.34 (td, J=4.33, 1.88 Hz, 3H) 2.36-2.47 (m, 1H) 3.13 (d, J=10.55 Hz, 1H) 3.45-3.55 (m, 1H) 4.31 (s, 1H) 4.42 (dd, J=5.27, 3.01 Hz, 1H) 5.40 (br. s., 1H) 6.18 (d, J=5.27 Hz, 1H) 6.53-6.81 (m, 2H) 7.35-7.47 (m, 2H) 7.62-7.87 (m, 13H).

Example 23

(2S,5R)-4-(2-aminoethyl)-2-carbamoyl-7-oxo-16-diazabicyclo[3.2.1]oct-3-en-6-yl hydrogen sulfate

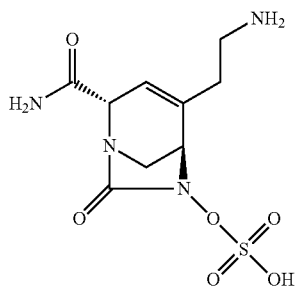 [SMILES: NCCC1=C[C@@H](C(N)=O)N2C[C@@H]1N(OS(=O)(=O)O)C2=O]

To a suspension of (2S,5R)-4-(2-(tert-butoxycarbonylamino)ethyl)-2-carbamoyl-7-oxo-1,6-diazabicyclo[3.2.1]oct-3-en-6-yl hydrogen sulfate (Intermediate 229, 0.060 g, 0.15 mmol) in dichloromethane (2 mL) at 0° C. was added trifluoroacetic acid (0.100 mL). After 15 minutes the solvent was removed in vacuo and the residue was dried under high vacuum. Purified by reverse phase chromatogry using acetonitrile/water to afford the title compound as a white solid after lyophilization (0.006 g, 13%).

MS: 305 ES− ($C_9H_{14}N_4O_6S$)

$^1$H NMR (300 MHz, DMSO-$d_6$) j 2.19-2.33 (m, 2H) 2.71-2.87 (m, 1H) 2.93 (d, J=9.80 Hz, 1H) 3.13 (br. s., 2H) 3.89-4.14 (m, 2H) 5.49 (br. s., 1H) 7.27 (br. s., 1H) 7.52 (d, J=11.30 Hz, 3H).

The intermediates for Example 23 were prepared as follows:

Intermediate 217: (2S,5S)-tert-butyl 2-((tert-butyldimethylsilyloxy)methyl)-5-hydroxy-4-(hydroxymethyl)-5,6-dihydropyridine-1(2H)-carboxylate

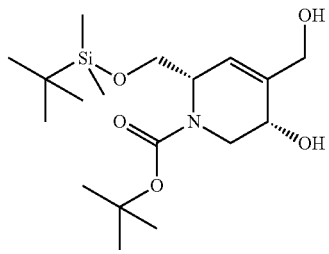 [SMILES: CC(C)(C)OC(=O)N1C[C@@H](O)C(CO)=C[C@H]1CO[Si](C)(C)C(C)(C)C]

The title compound was prepared as a colorless oil (13.7 g, 88%), according to the procedure described for Intermediate 79, from (S)-tert-butyl 2-((tert-butyldimethylsilyloxy)methyl)-4-(hydroxymethyl)-5-oxo-5,6-dihydropyridine-1(2H)-carboxylate (Intermediate 117).

MS: 374 ES+ ($C_{18}H_{35}NO_5Si$)

$^1$H NMR (300 MHz, DMSO-$d_6$) δ: 0.00 (s, 6H) 0.75-0.89 (m, 9H) 1.37 (s, 9H) 3.59 (d, J=5.27 Hz, 2H) 3.88-4.00 (m, 3H) 4.15-4.36 (m, 1H) 4.57 (t, J=5.65 Hz, 1H) 5.00 (d, J=5.27 Hz, 1H) 5.62 (d, J=2.26 Hz, 1H).

Intermediate 218: (2S,5S)-tert-butyl 2-((tert-butyldimethylsilyloxy)methyl)-4-((ethoxycarbonyloxy)methyl)-5-hydroxy-5,6-dihydropyridine-1(2H)-carboxylate

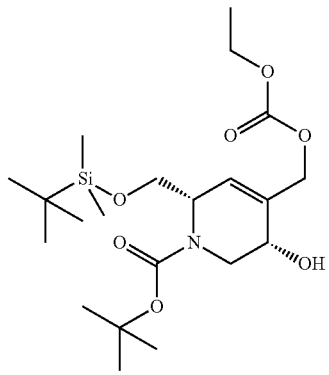 [SMILES: CCOC(=O)OCC1=C[C@@H](CO[Si](C)(C)C(C)(C)C)N(C(=O)OC(C)(C)C)C[C@H]1O]

To a solution of (2S,5S)-tert-butyl 2-((tert-butyldimethylsilyloxy)methyl)-5-hydroxy-4-(hydroxymethyl)-5,6-dihydropyridine-1(2H)-carboxylate (Intermediate 217, 13.7 g, 36.67 mmol) in dichloromethane (20 mL) at 0° C. was added pyridine (5.93 mL, 73.35 mmol) followed by dropwise addition of ethyl chloroformate (3.87 mL, 40.34 mmol). The reaction was allowed to warm to room temperature over 3 hours. Diluted with dichloromethane and washed with saturated NH$_4$Cl. Extracted with dichloromethane three times, combined and dried over Na$_2$SO$_4$. Removed solvent to give title compound as a yellow oil (14.5 g, 89%).

MS: 446 ES+ (C$_{21}$H$_{39}$NO$_7$Si)

Intermediate 219: (2S,5S)-tert-butyl 2-((tert-butyldimethylsilyloxy)methyl)-5-hydroxy-4-(2-nitroethyl)-5,6-dihydropyridine-1(2H)-carboxylate

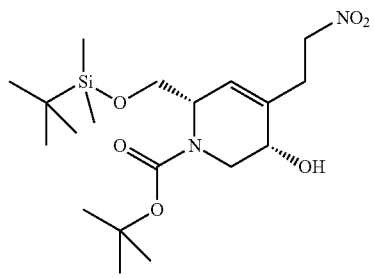 [SMILES: CC(C)(C)OC(=O)N1C[C@@H](O)C(CC[N+](=O)[O-])=C[C@H]1CO[Si](C)(C)C(C)(C)C]

(2S,5S)-tert-butyl 2-((tert-butyldimethylsilyloxy)methyl)-4-((ethoxycarbonyloxy)methyl)-5-hydroxy-5,6-dihydropyridine-1(2H)-carboxylate (Intermediate 218, 14.5 g, 32.54 mmol) was taken up in nitromethane (100 ml, 1854.52 mmol) and degassed for 5 minutes. Pd$_2$(dba)$_3$ (1.49 g, 1.63 mmol) was added and the reaction mixture was stirred under nitrogen at room temperature for 18 hrs. Reaction mixture was dried directly onto silica and purified by flash chromatography using 0-50% EtOAc/Hexanes. The title compound was obtained as a yellow oil (6 g, 44.3%).

MS: 417 ES+ (C$_{19}$H$_{36}$N$_2$O$_6$Si)

Intermediate 220: (2S,5R)-tert-butyl 5-(N-(benzyloxy)-2-nitrophenylsulfonamido)-2-((tert-butyldimethylsilyloxy)methyl)-4-(2-nitroethyl)-5,6-dihydropyridine-1(2H)-carboxylate

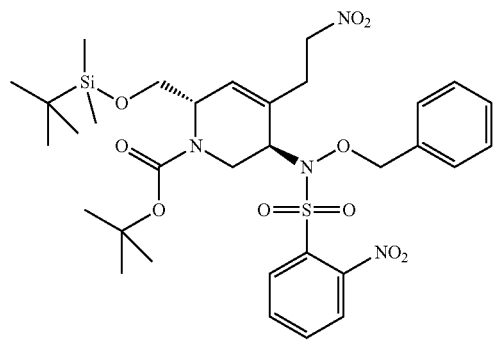 [SMILES: CC(C)(C)OC(=O)N1C[C@H](N(OCc2ccccc2)S(=O)(=O)c2ccccc2[N+](=O)[O-])C(CC[N+](=O)[O-])=C[C@H]1CO[Si](C)(C)C(C)(C)C]

The title compound was prepared as a pale yellow oil (5 g, 30%) according to the procedure described for Intermediate 80, from (2S,5S)-tert-butyl 2-((tert-butyldimethylsilyloxy)methyl)-5-hydroxy-4-(2-nitroethyl)-5,6-dihydropyridine-1(2H)-carboxylate (Intermediate 219, 6.73 g, 16.3 mmol) and N-(benzyloxy)-2-nitrobenzenesulfonamide (7.40 g, 24.00 mmol).

MS: 707 ES+ (C$_{32}$H$_{46}$N$_4$O$_{10}$SSi)

Intermediate 221: (2S,5R)-tert-butyl 5-(N-(benzyloxy)-2-nitrophenylsulfonamido)-2-(hydroxymethyl)-4-(2-nitroethyl)-5,6-dihydropyridine-1(2H)-carboxylate

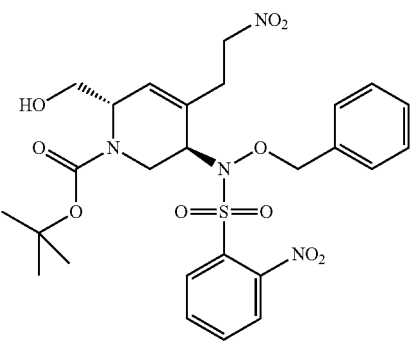 [SMILES: CC(C)(C)OC(=O)N1C[C@H](N(OCc2ccccc2)S(=O)(=O)c2ccccc2[N+](=O)[O-])C(CC[N+](=O)[O-])=C[C@H]1CO]

(2S,5R)-tert-butyl 5-(N-(benzyloxy)-2-nitrophenylsulfonamido)-2-((tert-butyldimethylsilyloxy)methyl)-4-(2-nitroethyl)-5,6-dihydropyridine-1(2H)-carboxylate (Intermediate 220, 5 g, 7.07 mmol) was taken up in methanol (150 mL) cooled to 0° C. and acetyl chloride (0.075 mL, 1.06 mmol) added. The reaction mixture was stirred for 3 hours at 0° C. The solvent was removed in vacuo and the residue was taken up in EtOAc, washed with saturated sodium bicarbonate, dried over Na$_2$SO$_4$, filtered and concentrated to afford the title compound as an oil (4.1 g, 98%).

MS: 593 ES+ (C$_{26}$H$_{32}$N$_4$O$_{10}$S)

Intermediate 222: (2S,5R)-5-(N-(benzyloxy)-2-nitrophenylsulfonamido)-1-(tert-butoxycarbonyl)-4-(2-nitroethyl)-1,2,5,6-tetrahydropyridine-2-carboxylic acid

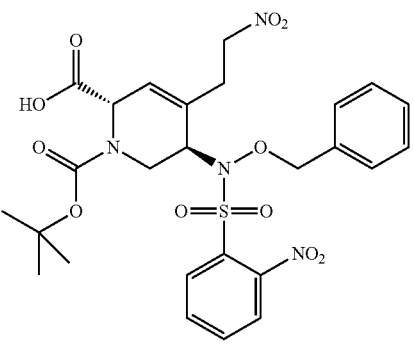 [SMILES: CC(C)(C)OC(=O)N1C[C@H](N(OCc2ccccc2)S(=O)(=O)c2ccccc2[N+](=O)[O-])C(CC[N+](=O)[O-])=C[C@H]1C(=O)O]

The title compound was prepared from (2S,5R)-tert-butyl 5-(N-(benzyloxy)-2-nitrophenylsulfonamido)-2-(hydroxymethyl)-4-(2-nitroethyl)-5,6-dihydropyridine-1(2H)-carboxylate (Intermediate 221, 4.1 g, 6.92 mmol) according to the procedure described for Intermediate 19. The desired product was obtained as an off-white foam (4.0 g, 98%).

MS: 606 ES+ (C$_{26}$H$_{30}$N$_4$O$_{11}$S)

Intermediate 223: (2S,5R)-tert-butyl 5-(N-(benzyloxy)-2-nitrophenylsulfonamido)-2-carbamoyl-4-(2-nitroethyl)-5,6-dihydropyridine-1(2H)-carboxylate

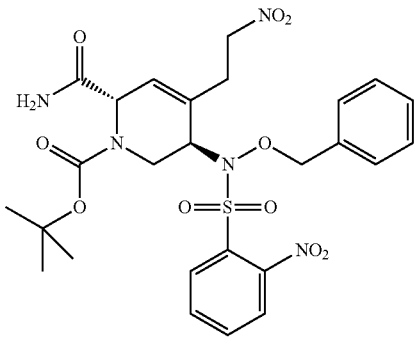 [SMILES: CC(C)(C)OC(=O)N1C[C@H](N(OCc2ccccc2)S(=O)(=O)c2ccccc2[N+](=O)[O-])C(CC[N+](=O)[O-])=C[C@H]1C(N)=O]

The title compound was prepared from (2S,5R)-5-(N-(benzyloxy)-2-nitrophenylsulfonamido)-1-(tert-butoxycarbonyl)-4-(2-nitroethyl)-1,2,5,6-tetrahydropyridine-2-carboxylic acid (Intermediate 222, 4.0 g, 6.59 mmol) according to the procedure described for Intermediate 20. The desired product was obtained as an off-white foam (2 g, 50%).

MS: 606 ES+ ($C_{26}H_{31}N_5O_{10}S$)

Intermediate 224: (2S,5R)-tert-butyl 5-(benzyloxyamino)-2-carbamoyl-4-(2-nitroethyl)-5,6-dihydropyridine-1(2H)-carboxylate

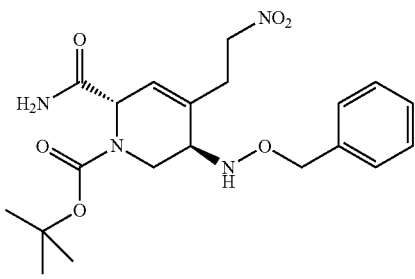 [SMILES: CC(C)(C)OC(=O)N1C[C@H](NOCc2ccccc2)C(CC[N+](=O)[O-])=C[C@H]1C(N)=O]

The desired product was prepared from (2S,5R)-tert-butyl 5-(N-(benzyloxy)-2-nitrophenylsulfonamido)-2-carbamoyl-4-(2-nitroethyl)-5,6-dihydropyridine-1(2H)-carboxylate (Intermediate 223, 2 g, 3.30 mmol) following the procedure described for Intermediate 22. The desired product was obtained as yellow oil (0.8 g, 68%).

MS: 421 ES+ ($C_{20}H_{28}N_4O_6$)

Intermediate 225: (2S,5R)-5-(benzyloxyamino)-4-(2-nitroethyl)-1,2,56-tetrahydropyridine-2-carboxamide

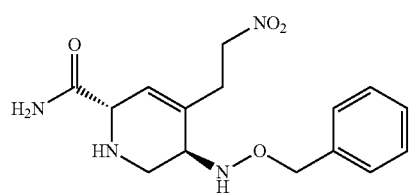 [SMILES: NC(=O)[C@@H]1C=C(CC[N+](=O)[O-])[C@@H](NOCc2ccccc2)CN1]

The title compound was prepared from (2S,5R)-tert-butyl 5-(benzyloxyamino)-2-carbamoyl-4-(2-nitroethyl)-5,6-dihydropyridine-1(2H)-carboxylate (Intermediate 224, 0.800 g, 3.30 mmol) according to the procedure described for Intermediate 21. The desired product was obtained as a yellow oil (0.6 g, 98%).

MS: 321 ES+ ($C_{15}H_{20}N_4O_4$)

Intermediate 226: (2S,5R)-6-(benzyloxy)-4-(2-nitroethyl)-7-oxo-1,6-diazabicyclo[3.2.1]oct-3-ene-2-carboxamide

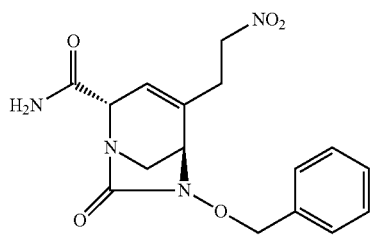 [SMILES: NC(=O)[C@@H]1C=C(CC[N+](=O)[O-])[C@@H]2CN1C(=O)N2OCc1ccccc1]

The title compound was prepared from (2S,5R)-5-(benzyloxyamino)-4-(2-nitroethyl)-1,2,5,6-tetrahydropyridine-2-carboxamide (Intermediate 225, 0.600 g, 1.87 mmol) according to the procedure described for Intermediate 16. The desired product was obtained as a light yellow oil (0.510 g, 79%).

MS: 347 ES+ ($C_{16}H_{18}N_4O_5$)

$^1$H NMR (300 MHz, DMSO-$d_6$) δ: 2.69 (t, J=6.78 Hz, 2H) 3.17 (s, 2H) 3.88 (s, 1H) 4.09-4.18 (m, 1H) 4.55-4.70 (m, 2H) 4.91 (d, J=3.01 Hz, 2H) 5.56 (br. s., 1H) 7.30 (br. s., 1H) 7.35-7.46 (m, 5H) 7.50 (br. s., 1H).

Intermediate 227: tert-butyl 2-((2S,5R)-6-(benzyloxy)-2-carbamoyl-7-oxo-1,6-diazabicyclo[3.2.1]oct-3-en-4-yl)ethylcarbamate

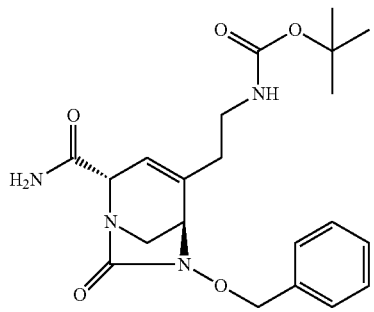 [SMILES: CC(C)(C)OC(=O)NCCC1=C[C@@H](C(N)=O)N2C[C@@H]1N(OCc1ccccc1)C2=O]

(2S,5R)-6-(benzyloxy)-4-(2-nitroethyl)-7-oxo-1,6-diazabicyclo[3.2.1]oct-3-ene-2-carboxamide (Intermediate 226, 0.420 g, 1.21 mmol) was taken up in ethanol (absolute, 99.5%) (20 mL), and zinc dust (1.983 g, 30.32 mmol) was added followed by acetic acid (2.78 mL, 48.51 mmol). The reaction mixture was stirred at ambient temperature for 1 hour. DIPEA (2.118 mL, 12.13 mmol) was added followed by BOC-anhydride (0.845 mL, 3.64 mmol). The reaction mixture was stirred for 2 hours, then diluted with DCM, washed with saturated bicarbonate and concentrated to dryness. Flash chromatography, 0-10% MeOH/DCM, afforded the title compound as a clear oil (0.31 g, 61%).

MS: 417 ES+ ($C_{21}H_{28}N_4O_5$)

$^1$H NMR (300 MHz, DMSO-d$_6$) j 1.10-1.26 (m, 3H) 1.28-1.46 (m, 9H) 2.17 (d, J=6.03 Hz, 1H) 2.79-3.16 (m, 2H) 3.18-3.26 (m, 1H) 3.55 (br. s., 1H) 4.21 (br. s., 1H) 4.71 (s, 3H) 4.76-4.95 (m, 2H) 5.53 (d, J=2.26 Hz, 1H) 7.23-7.46 (m, 4H).

Intermediate 228: tert-butyl 2-((2S,5R)-2-carbamoyl-6-hydroxy-7-oxo-1,6-diazabicyclo[3.2.1]oct-3-en-4-yl)ethylcarbamate

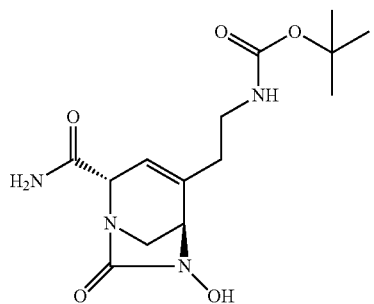 [SMILES: CC(C)(C)OC(=O)NCCC1=C[C@@H](C(N)=O)N2C[C@@H]1N(O)C2=O]

To a solution of tert-butyl 2-((2S,5R)-6-(benzyloxy)-2-carbamoyl-7-oxo-1,6-diazabicyclo[3.2.1]oct-3-en-4-yl)ethylcarbamate (Intermediate 227, 0.300 g, 0.72 mmol) in EtOAc (5 mL) was added 10% Pd/C (0.077 g, 0.72 mmol). The reaction mixture was stirred under hydrogen for 30 minutes. The reaction mixtured was filtered through celite and washed with EtOAc. The solvent was removed in vacuo to give the title compound as a white solid (0.23 g, 98%).

MS: 327 ES+ ($C_{14}H_{22}N_4O_5$)

Intermediate 229: (2S,5R)-4-(2-(tert-butoxycarbonylamino)ethyl)-2-carbamoyl-7-oxo-1,6-diazabicyclo[3.2.1]oct-3-en-6-yl hydrogen sulfate

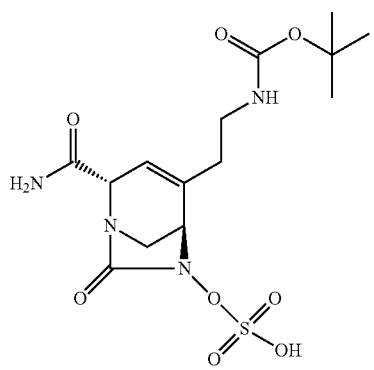 [SMILES: CC(C)(C)OC(=O)NCCC1=C[C@@H](C(N)=O)N2C[C@@H]1N(OS(=O)(=O)O)C2=O]

To a solution of tert-butyl 2-((2S,5R)-2-carbamoyl-6-hydroxy-7-oxo-1,6-diazabicyclo[3.2.1]oct-3-en-4-yl)ethylcarbamate (Intermediate 228, 0.230 g, 0.70 mmol) in pyridine (5 mL) was added pyridine/sulfur trioxide complex (0.673 g, 4.23 mmol). The reaction was stirred overnight at room temperature. The solvent was removed in vacuo, and the residue was purified by reverse phase chromatography using acetonitrile/water. Desired fractions were combined and lypholized to afford the title compound as a while solid (0.23 g, 80%) as a white solid.

MS: 405 ES– ($C_{14}H_{22}N_4O_8S$)

$^1$H NMR (300 MHz, DMSO-d$_6$) δ: 1.36 (s, 9H) 2.17 (t, J=6.40 Hz, 2H) 2.90-3.27 (m, 4H) 4.08 (d, J=18.84 Hz, 2H) 5.43 (d, J=2.26 Hz, 1H) 6.61 (br. s., 1H) 7.25 (br. s., 1H) 7.47 (br. s., 1H) 7.80-7.95 (m, 1H) 8.38 (t, J=7.54 Hz, 1H) 8.83 (d, J=5.27 Hz, 1H).

Example 24

(2S,5R)-2-carbamoyl-3-cyclopropyl-7-oxo-1,6-diazabicyclo[3.2.1]oct-3-en-6-yl hydrogen sulfate sodium salt

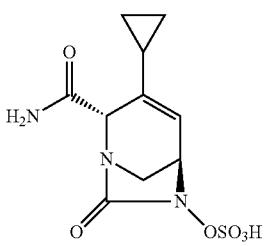

The title compound was prepared from (E)-triphenyl (prop-1-enyl)phosphonium (2S,5R)-2-carbamoyl-3-cyclopropyl-7-oxo-1,6-diazabicyclo[3.2.1]oct-3-en-6-yl sulfate (Intermediate 246, 0.39 g, 0.64 mmol) following the procedure described for Example 1. The desired product was obtained as an off-white solid (158 mg, 75%).

Optical rotation: (0.1 g/dL, MeOH)=–50

MS: 302 ES– ($C_{10}H_{13}N_3O_6S$)

$^1$H NMR (300 MHz, DMSO-d$_6$) δ: 0.38 (m, 2H); 0.59 (m, 2H); 1.19 (m, 1H); 3.03 (m, 1H); 3.78 (m, 1H); 4.02 (m, 1H); 4.20 (m, 1H); 5.91 (m, 1H); 7.28 (bs, 1H); 7.85 (bs, 1H).

The intermediates for Example 24 were prepared as follows:

Intermediate 230: (R)-tert-butyl 4-(cyclopropyl(hydroxy)methyl)-2,2-dimethyloxazolidine-3-carboxylate

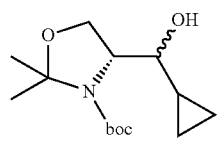

To a solution of (R)-tert-butyl 4-formyl-2,2-dimethyloxazolidine-3-carboxylate (Aldrich, 12.44 g, 54.26 mmol) in THF (150 mL) at –78° C. was added cyclopropylmagnesium bromide (217 mL, 108.52 mmol) dropwise. The reaction mixture was allowed to warm to room temperature and stir overnight. The reaction was quenched with water and diluted with ethyl acetate and brine. The resulting emulsion was filtered through celite and the layers separated. The organics were dried over magnesium sulfate, filtered and concentrated. Silica gel chromatography (0%-20% ethyl acetate/hexanes) afforded the title compound as a light yellow oil (12.47 g, 85%).

¹H NMR (300 MHz, DMSO-d₆) δ: 0.16 (m, 2H); 0.37 (m, 2H); 0.82 (m, 1H); 1.45 (m, 15H); 2.87 (m, 1H); 3.86 (m, 2H); 3.97 (m, 1H); 4.74 (m, 1H).

Intermediate 231: (R)-tert-butyl 4-(cyclopropanecarbonyl)-2,2-dimethyloxazolidine-3-carboxylate

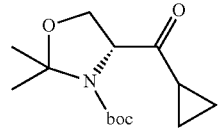

To a solution of (R)-tert-butyl 4-(cyclopropyl(hydroxy)methyl)-2,2-dimethyloxazolidine-3-carboxylate (Intermediate 230, 12.47 g, 45.95 mmol) in DCM (300 mL) at room temperature was added Dess-Martin periodinane (29.2 g, 68.93 mmol). The reaction mixture was stirred overnight then diluted with ethyl acetate and washed with saturated sodium bicarbonate. An emulsion formed and was filtered through celite. The layers were separated and the organics washed with brine. The organics were dried over magnesium sulfate, filtered and concentrated. Silica gel chromatography (0%-20% ethyl acetate/hexanes) afforded the title compound as a colorless oil (11.15 g, 90%).

¹H NMR (300 MHz, DMSO-d₆) δ: 0.90 (m, 4H); 1.38 (m, 12H); 1.54 (m, 3H); 2.12 (m, 1H); 3.94 (m, 1H); 4.18 (m, 1H); 4.56 (m, 1H).

Intermediate 232: (S)-tert-butyl 4-(1-cyclopropylvinyl)-2,2-dimethyloxazolidine-3-carboxylate

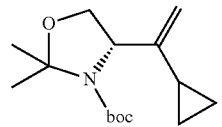

To a suspension of potassium tert-butoxide (9.29 g, 82.80 mmol) in ether (250 mL) at room temperature was added methyltriphenylphosphonium bromide (29.6 g, 82.80 mmol). The mixture turned bright yellow and was heated to 40° C. for 1 hour. The mixture was cooled to room temperature and a solution of (R)-tert-butyl 4-(cyclopropanecarbonyl)-2,2-dimethyloxazolidine-3-carboxylate (Intermediate 231, 11.15 g, 41.40 mmol) in ether (30 mL) was added and the reaction mixture was stirred for 2 hours. The reaction was quenched with water (10 mL) and the layers were separated. The aqueous was extracted once with ether. The combined organic extracts were dried over magnesium sulfate, filtered and concentrated. Silica gel chromatography (0%-15% ethyl acetate/hexanes) afforded the title compound as a colorless oil (9.84 g, 89%).

¹H NMR (300 MHz, DMSO-d₆) δ: 0.42 (m, 2H); 0.65 (m, 2H); 1.43 (m, 16H); 3.76 (m, 1H); 4.09 (m, 1H); 4.27 (m, 1H); 4.66 (m, 2H).

Intermediate 233: (S)-tert-butyl 1-(tert-butyldimethylsilyloxy)-3-cyclopropylbut-3-en-2-ylcarbamate

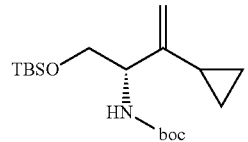

To a solution of (S)-tert-butyl 4-(1-cyclopropylvinyl)-2,2-dimethyloxazolidine-3-carboxylate (Intermediate 232, 8.25 g, 30.86 mmol) in methanol (100 mL) at room temperature was added p-toluenesulfonic acid monohydrate (1.174 g, 6.17 mmol). The reaction mixture was heated to 80° C. overnight. Another 0.2 eq of p-toluenesulfonic acid monohydrate was added. Continue heating at 80° C. for 2 hours. The reaction mixture was cooled to room temperature. Triethylamine (4.29 mL, 30.86 mmol) and di-tert-butyl dicarbonate (3.37 g, 15.43 mmol) were added. The reaction mixture was stirred over the weekend then concentrated. The residue was dissolved in ethyl acetate and washed once with saturated sodium bicarbonate. The combined organic extracts were dried over magnesium sulfate, filtered and concentrated. The resulting oil was dissolved in DCM (100 mL). Imidazole (2.73 g, 40.11 mmol), 4-dimethylaminopyridine (0.754 g, 6.17 mmol) and tert-butyldimethylsilyl chloride (4.65 g, 30.86 mmol) were added and the reaction mixture was stirred overnight at room temperature. The reaction mixture was filtered to remove solids and washed with brine twice. The organic layer was dried over magnesium sulfate, filtered and concentrated. Silica gel chromatography (0%-10% ethyl acetate/hexanes) afforded the title compound as a colorless oil (6.77 g, 64%).

MS: 342 ES+ (C₁₈H₃₅NO₃Si)

¹H NMR (300 MHz, DMSO-d₆) δ: 0.04 (s, 6H); 0.39 (m, 2H); 0.63 (m, 2H); 0.85 (s, 9H); 1.32 (m, 1H); 1.37 (m, 9H); 3.55 (m, 1H); 3.67 (m, 1H); 3.99 (m, 1H); 4.63 (s, 1H); 4.78 (s, 1H); 6.80 (m, 1H).

Intermediate 234: (S)-1-(tert-butyldimethylsilyloxy)-3-cyclopropylbut-3-en-2-amine

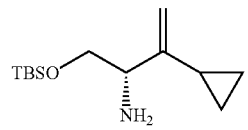

To a solution of (S)-tert-butyl 1-(tert-butyldimethylsilyloxy)-3-cyclopropylbut-3-en-2-ylcarbamate (Intermediate 233, 6.77 g, 19.82 mmol) in DCM (100 mL) at room temperature was added zinc bromide (17.86 g, 79.28 mmol). The reaction mixture was stirred overnight at room temperature. Another 1 eq of zinc bromide was added. After several hours the reaction mixture was filtered and washed with saturated sodium bicarbonate. The resulting emulsion was filtered through a nylon filter and the layers were separated. The organics were dried over magnesium sulfate, filtered and concentrated to afford the title compound as a yellow oil (4.61 g, 96%).

¹H NMR (300 MHz, DMSO-d₆) δ: 0.04 (s, 6H); 0.39 (m, 2H); 0.63 (m, 2H); 0.87 (s, 9H); 1.35 (m, 1H); 1.81 (m, 2H); 3.33 (m, 1H); 3.45 (m, 1H); 3.67 (m, 1H); 4.59 (s, 1H); 4.83 (m, 1H).

Intermediate 235: (S)-tert-butyl 1-(tert-butyldimethylsilyloxy)-3-cyclopropylbut-3-en-2-yl(2-(methoxy(methyl)amino)-2-oxoethyl)carbamate

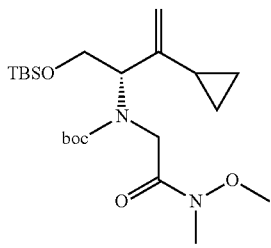

The title compound was prepared from (S)-1-(tert-butyldimethylsilyloxy)-3-cyclopropylbut-3-en-2-amine (Intermediate 234, 4.61 g, 19.09 mmol) and 2-bromo-N-methoxy-N-methylacetamide (Intermediate 4, 3.16 g, 17.36 mmol) following the procedure described for Intermediate 5. The desired product was obtained as a light yellow oil (4.94 g, 64%).

MS: 443 ES+ ($C_{22}H_{42}N_2O_5Si$)

¹H NMR (300 MHz, DMSO-d₆) δ: 0.03 (m, 6H); 0.35 (m, 1H); 0.48 (m, 1H); 0.61 (m, 2H); 0.83 (m, 9H); 1.35 (m, 9H); 3.07 (m, 3H); 3.65 (m, 3H); 3.84 (m, 2H); 4.02 (m, 2H); 4.54 (m, 1H); 4.83 (m, 2H).

Intermediate 236: (S)-tert-butyl 1-(tert-butyldimethylsilyloxy)-3-cyclopropylbut-3-en-2-yl(2-oxopent-3-enyl)carbamate

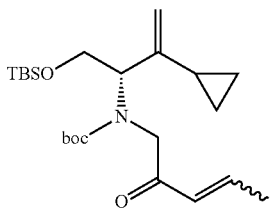

A suspension of cerium (III) chloride (27.8 g, 112.95 mmol) in THF (100 mL) at room temperature was stirred vigorously for 2 hours. The suspension was cooled to −78° C. and (E)-prop-1-enylmagnesium bromide (0.5 M in THF) (226 mL, 112.95 mmol) was added dropwise. The mixture was stirred at −78° C. for 1.5 hours. (S)-tert-butyl 1-(tert-butyldimethylsilyloxy)-3-cyclopropylbut-3-en-2-yl(2-(methoxy(methyl)amino)-2-oxoethyl)carbamate (Intermediate 235, 5 g, 11.30 mmol) in THF (20 mL) was then added dropwise at −78° C. The reaction was stirred at −78° C. for 30 minutes and then warmed to 0° C. for 15 minutes. The reaction was quenched with 10% citric acid, diluted further with water and extracted twice with ether. The organics were washed once with brine, dried over magnesium sulfate, filtered and concentrated. Silica gel chromatography (0%-20% ethyl acetate/hexanes) afforded the title compound as a light yellow oil (4.0 g, 84%).

MS: 424 ES+ ($C_{23}H_{41}NO_4Si$)

¹H NMR (300 MHz, DMSO-d₆) δ: 0.03 (m, 6H); 0.43 (m, 2H); 0.61 (m, 2H); 0.83 (m, 9H); 1.34 (m, 10H); 1.84 (m, 2H); 2.04 (m, 1H); 3.74 (m, 1H); 3.84 (m, 2H); 4.03 (m, 1H); 4.57 (m, 1H); 4.79 (m, 2H); 6.28 (m, 1H); 6.84 (m, 1H).

Intermediate 237: (S)-tert-butyl 2-((tert-butyldimethylsilyloxy)methyl)-3-cyclopropyl-5-oxo-5,6-dihydropyridine-1(2H)-carboxylate

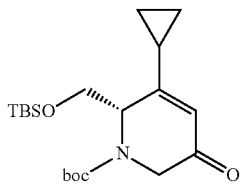

The title compound was prepared from (S,E)-tert-butyl 1-(tert-butyldimethylsilyloxy)-3-cyclopropylbut-3-en-2-yl (2-oxopent-3-enyl)carbamate (Intermediate 236, 4 g, 9.44 mmol) following the procedure described for Intermediate 7, except the reaction mixture was heated at 110° C. overnight. The desired product was obtained as a light brown oil (2.97 g, 82%).

MS: 382 ES+ ($C_{20}H_{35}NO_4Si$)

¹H NMR (300 MHz, DMSO-d₆) δ: 0.01 (m, 6H); 0.62 (m, 1H); 0.80 (s, 9H); 1.00 (m, 3H); 1.42 (s, 9H); 1.61 (m, 1H); 3.80 (m, 1H); 3.95 (m, 2H); 4.19 (m, 1H); 4.75 (m, 1H); 5.72 (s, 1H).

Intermediate 238: (2S,5S)-tert-butyl 2-((tert-butyldimethylsilyloxy)methyl)-3-cyclopropyl-5-hydroxy-5,6-dihydropyridine-1(2H)-carboxylate

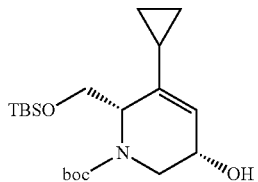

The title compound was prepared from (S)-tert-butyl 2-((tert-butyldimethylsilyloxy)methyl)-3-cyclopropyl-5-oxo-5,6-dihydropyridine-1(2H)-carboxylate (Intermediate 237, 2.97 g, 7.78 mmol) following the procedure described for Intermediate 8. The desired product was obtained as a tan oil (2.74 g, 92%).

MS: 384 ES+ ($C_{20}H_{37}NO_4Si$)

¹H NMR (300 MHz, DMSO-d₆) δ: 0.02 (m, 6H); 0.34 (m, 1H); 0.47 (m, 1H); 0.64 (m, 2H); 0.85 (m, 9H); 1.26 (m, 1H); 1.39 (s, 9H); 2.65 (m, 1H); 3.89 (m, 3H); 4.05 (m, 1H); 4.95 (m, 1H); 5.34 (m, 1H).

Intermediate 239: (2S,5R)-tert-butyl 5-(N-(allyloxy)-2-nitrophenylsulfonamido)-2-((tert-butyldimethylsilyloxy)methyl)-3-cyclopropyl-5,6-dihydropyridine-1 (2H)-carboxylate

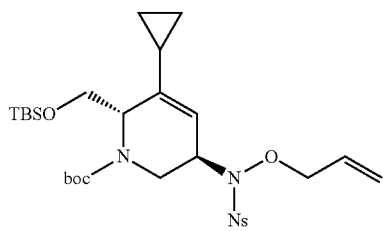

The title compound was prepared from (2S,5S)-tert-butyl 2-((tert-butyldimethylsilyloxy)methyl)-3-cyclopropyl-5-hydroxy-5,6-dihydropyridine-1 (2H)-carboxylate (Intermediate 238, 2.74 g, 7.14 mmol) and N-(allyloxy)-2-nitrobenzenesulfonamide (Intermediate 9, 1.85 g, 7.14 mmol) following the procedure described for Intermediate 10. The desired product was obtained as a light yellow oil (3.19 g, 71%).

MS: 624 ES+ ($C_{29}H_{45}N_3O_8SSi$)

$^1$H NMR (300 MHz, DMSO-$d_6$) δ: 0.00 (m, 6H); 0.34 (m, 1H); 0.63 (m, 2H); 0.83 (m, 9H); 1.37 (m, 9H); 3.30 (m, 1H); 3.84 (m, 2H); 4.30 (m, 4H); 5.18 (m, 2H); 5.75 (m, 1H); 8.04 (m, 4H).

Intermediate 240: (2S,5R)-tert-butyl 5-(N-(allyloxy)-2-nitrophenylsulfonamido)-3-cyclopropyl-2-(hydroxymethyl)-5,6-dihydropyridine-1(2H)-carboxylate

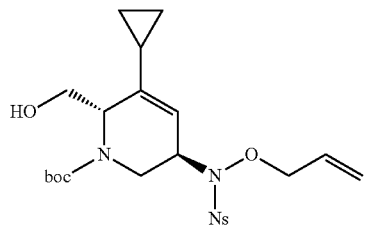

The title compound was prepared from (2S,5R)-tert-butyl 5-(N-(allyloxy)-2-nitrophenylsulfonamido)-2-((tert-butyldimethylsilyloxy)methyl)-3-cyclopropyl-5,6-dihydropyridine-1(2H)-carboxylate (Intermediate 239, 3.19 g, 5.11 mmol) following the procedure described for Intermediate 18. The desired product was obtained as a tan foam (2.35 g, 90%).

MS: 510 ES+ ($C_{23}H_{31}N_3O_8S$)

$^1$H NMR (300 MHz, DMSO-$d_6$) δ: 0.32 (m, 2H); 0.62 (m, 2H); 1.35 (m, 9H); 3.30 (m, 1H); 3.67 (m, 2H); 4.27 (m, 4H); 4.71 (m, 1H); 5.19 (m, 2H); 5.71 (m, 1H); 8.04 (m, 4H).

Intermediate 241: (2S,5R)-5-(N-(allyloxy)-2-nitrophenylsulfonamido)-1-(tert-butoxycarbonyl)-3-cyclopropyl-1,2,5,6-tetrahydropyridine-2-carboxylic acid

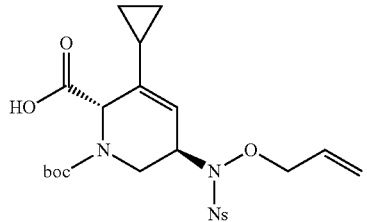

The title compound was prepared from (2S,5R)-tert-butyl 5-(N-(allyloxy)-2-nitrophenylsulfonamido)-3-cyclopropyl-2-(hydroxymethyl)-5,6-dihydropyridine-1(2H)-carboxylate (Intermediate 240, 2.35 g, 4.61 mmol) following the procedure described for Intermediate 19. The desired product was obtained as an orange foam (2.28 g, 94%).

MS: 524 ES+ ($C_{23}H_{29}N_3O_9S$)

Intermediate 242: (2S,5R)-tert-butyl 5-(N-(allyloxy)-2-nitrophenylsulfonamido)-2-carbamoyl-3-cyclopropyl-5,6-dihydropyridine-1(2H)-carboxylate

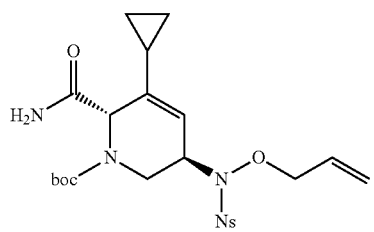

The title compound was prepared from (2S,5R)-5-(N-(allyloxy)-2-nitrophenylsulfonamido)-1-(tert-butoxycarbonyl)-3-cyclopropyl-1,2,5,6-tetrahydropyridine-2-carboxylic acid (Intermediate 241, 2.28 g, 4.35 mmol) following the procedure described for Intermediate 20. The desired product was obtained as an orange foam (1.07 g, 47%).

MS: 523 ES+ ($C_{23}H_{30}N_4O_8S$)

$^1$H NMR (300 MHz, DMSO-$d_6$) δ: 0.23 (m, 2H); 0.59 (m, 2H); 1.35 (m, 9H); 3.58 (m, 1H); 4.23 (m, 3H); 4.72 (m, 1H); 5.19 (m, 2H); 5.71 (m, 1H); 7.18 (m, 1H); 7.59 (m, 1H); 8.04 (m, 4H).

Intermediate 243: (2S,5R)-5-(N-(allyloxy)-2-nitrophenylsulfonamido)-3-cyclopropyl-1,2,5,6-tetrahydropyridine-2-carboxamide

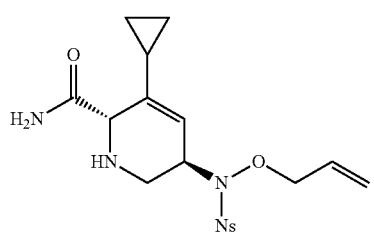

The title compound was prepared from (2S,5R)-tert-butyl 5-(N-(allyloxy)-2-nitrophenylsulfonamido)-2-carbamoyl-3-cyclopropyl-5,6-dihydropyridine-1(2H)-carboxylate (Intermediate 242, 0.932 g, 1.78 mmol) following the procedure described for Intermediate 21. The desired product was obtained as an orange foam (0.518 g, 68%).

MS: 423 ES+ ($C_{18}H_{22}N_4O_6S$)

$^1$H NMR (300 MHz, DMSO-$d_6$) δ: 0.18 (m, 2H); 0.53 (m, 2H); 1.29 (m, 1H); 2.30 (m, 1H); 2.58 (m, 1H); 2.95 (m, 1H); 3.72 (m, 1H); 4.22 (m, 1H); 4.36 (m, 2H); 4.96 (m, 1H); 5.24 (m, 2H); 5.80 (m, 1H); 7.07 (bs, 1H); 7.39 (bs, 1H); 8.04 (m, 4H).

Intermediate 244: (R)-5-(allyloxyamino)-3-cyclopropyl-1,2,5,6-tetrahydropyridine-2-carboxamide

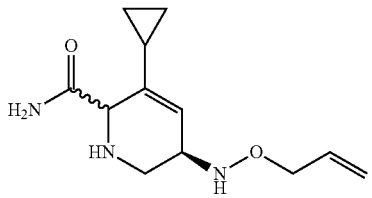 [SMILES: C=CCON[C@@H]1C=C(C2CC2)C(C(N)=O)NC1]

The title compound was prepared from (2S,5R)-5-(N-(allyloxy)-2-nitrophenylsulfonamido)-3-cyclopropyl-1,2,5,6-tetrahydropyridine-2-carboxamide (Intermediate 243, 0.518 g, 1.23 mmol) following the procedure described for Intermediate 12. The desired product was obtained as a light yellow oil (0.171 g, 59%). The product is a mixture of diastereomers.

MS: 238 ES+ ($C_{12}H_{19}N_3O_2$)

$^1$H NMR (300 MHz, DMSO-$d_6$) δ: 0.28 (m, 2H); 0.41 (m, 2H); 0.54 (m, 2H); 1.33 (m, 1H); 2.49 (m, 1H); 2.64 (m, 1H); 2.93 (m, 1H); 3.23 (m, 1H); 3.65 (m, 1H); 4.07 (m, 2H); 5.19 (m, 3H); 5.89 (m, 1H); 6.26 (m, 1H); 6.97 (bs, 1H); 7.34 (bs, 1H).

Intermediate 245: (2S,5R)-6-(allyloxy)-3-cyclopropyl-7-oxo-1,6-diazabicyclo[3.2.1]oct-3-ene-2-carboxamide

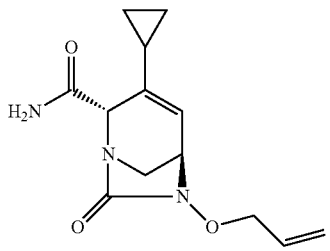 [SMILES: C=CCON1C(=O)N2C[C@H]1C=C(C1CC1)[C@H]2C(N)=O]

The title compound was prepared from (R)-5-(allyloxyamino)-3-cyclopropyl-1,2,5,6-tetrahydropyridine-2-carboxamide (Intermediate 244, 0.316 g, 1.33 mmol) following the procedure described for Intermediate 16. The desired product was obtained as a colorless oil (0.261 g, 74%).

MS: 264 ES+ ($C_{13}H_{17}N_3O_3$)

$^1$H NMR (300 MHz, DMSO-$d_6$) δ: 0.37 (m, 2H); 0.60 (m, 2H); 1.20 (m, 1H); 2.98 (m, 1H); 3.79 (m, 1H); 3.92 (m, 1H); 4.20 (m, 1H); 4.33 (m, 2H); 5.28 (m, 2H); 5.93 (m, 2H); 7.30 (bs, 1H); 7.86 (bs, 1H).

Intermediate 246: (E)-triphenyl(prop-1-enyl)phosphonium (2S,5R)-2-carbamoyl-3-cyclopropyl-7-oxo-1,6-diazabicyclo[3.2.1]oct-3-en-6-yl sulfate

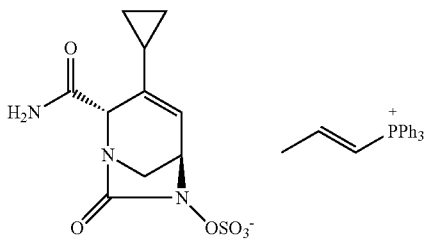

The title compound was prepared from (2S,5R)-6-(allyloxy)-3-cyclopropyl-7-oxo-1,6-diazabicyclo[3.2.1]oct-3-ene-2-carboxamide (Intermediate 245, 0.261 g, 0.99 mmol) following the procedure described for Intermediate 17. The desired product was obtained as a yellow foam (0.39 g, 65%).

MS: 302 ES−, 303 ES+ ($C_{10}H_{12}N_3O_6S$—.$C_{21}H_{20}P+$)

$^1$H NMR (300 MHz, DMSO-$d_6$) δ: 0.39 (m, 2H); 0.58 (m, 2H); 1.18 (m, 2H); 2.16 (m, 3H); 3.03 (m, 1H); 3.78 (m, 1H); 4.01 (m, 1H); 4.20 (m, 1H); 5.91 (m, 1H); 6.65 (m, 1H); 7.38 (m, 2H); 7.78 (m, 15H).

Example 25

(2S,5R)-4-(2-acetamidoethyl)-2-carbamol-7-oxo-1,6-diazabicyclo[3.2.1]oct-3-en-6-yl sulfate sodium salt

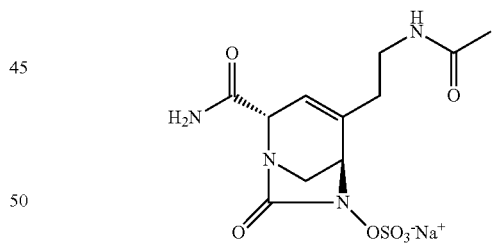

The title compound was prepared from pyridine (2S,5R)-4-(2-acetamidoethyl)-2-carbamoyl-7-oxo-1,6-diazabicyclo[3.2.1]oct-3-en-6-yl sulfate (Intermediate 248, 0.007 g, 0.020 mmol) according to the procedure described for Example 1. The desired product was obtained as a white solid (3 mg, 58%).

MS: 347 ES− ($C_{11}H_{16}N_4O_7S$)

$^1$H NMR (300 MHz, DMSO-$d_6$) δ: 0.85 (d, J=6.78 Hz, 1H) 1.70-1.84 (m, 3H) 2.18 (t, J=6.78 Hz, 1H) 3.12-3.21 (m, 2H) 3.97-4.17 (m, 2H) 5.42 (br. s., 1H) 7.27 (br. s., 1H) 7.49 (s, 1H) 7.71 (s, 1H).

The intermediates for Example 25 were prepared as follows:

Intermediate 247: (2S,5R)-4-(2-acetamidoethyl)-6-(benzyloxy)-7-oxo-1,6-diazabicyclo[3.2.1]oct-3-ene-2-carboxamide

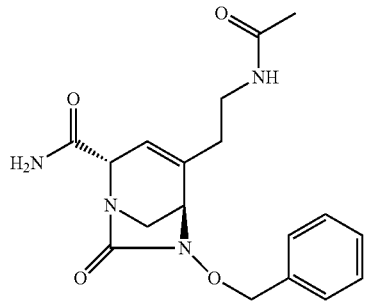 [SMILES: CC(=O)NCCC1=C[C@@H](C(N)=O)N2C[C@@H]1N(OCc1ccccc1)C2=O]

To a solution of (2S,5R)-6-(benzyloxy)-4-(2-nitroethyl)-7-oxo-1,6-diazabicyclo[3.2.1]oct-3-ene-2-carboxamide (Intermediate 226, 0.300 g, 0.87 mmol) in ethanol (10 mL) was added zinc dust (1.416 g, 21.66 mmol) and acetic acid (1.984 mL, 34.65 mmol). The reaction mixture was stirred at ambient temperature for 1 hour. Then DIPEA (2.118 mL, 12.13 mmol) was added to reaction mixture followed by acetic anhydride (0.245 mL, 2.60 mmol). The reaction mixture was stirred for an additional 2 hours, then diluted with DCM, washed with saturated bicarbonate and concentrated to dryness. Flash chromatography, 0%-10% MeOH/DCM, afforded the title compound as a clear oil (0.31 g, 61%).

MS: 359 ES+ ($C_{18}H_{22}N_4O_4$)

$^1$H NMR (300 MHz, DMSO-$d_6$) δ 1.75 (s, 3H) 2.08-2.21 (m, 2H) 2.92-3.05 (m, 1H) 3.09-3.24 (m, 3H) 3.72 (s, 1H) 4.12 (br. s., 1H) 4.89 (s, 2H) 5.44 (br. s., 1H) 7.29 (br. s., 1H) 7.34-7.51 (m, 6H) 7.70 (br. s., 1H).

Intermediate 248: (2S,5R)-4-(2-acetamidoethyl)-6-hydroxy-7-oxo-1,6-diazabicyclo[3.2.1]oct-3-ene-2-carboxamide

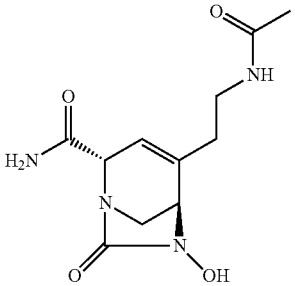 [SMILES: CC(=O)NCCC1=C[C@@H](C(N)=O)N2C[C@@H]1N(O)C2=O]

To a solution of 4-(2-acetamidoethyl)-6-(benzyloxy)-7-oxo-1,6-diazabicyclo[3.2.1]oct-3-ene-2-carboxamide (Intermediate 247, 0.120 g, 0.33 mmol) in EtOAc (20 mL) and ethanol (6.67 mL) was added Pd/C (0.036 g, 0.33 mmol). The reaction mixture was stirred under hydrogen at 1atm for 1 hour, then filtered through celite and concentrated to dryness to afford the title compound as a white solid (0.09 g, 100%).

Intermediate 249: pyridine (2S,5R)-4-(2-acetamidoethyl)-2-carbamoyl-7-oxo-1,6-diazabicyclo[3.2.1]oct-3-en-6-yl sulfate

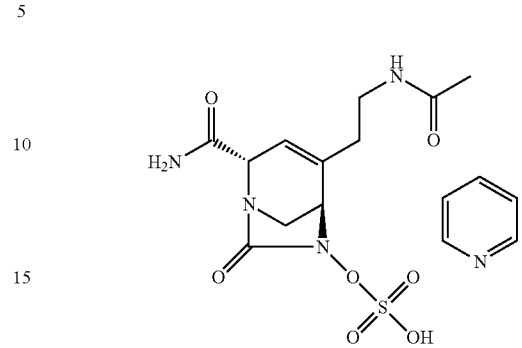

To a solution of (2S,5R)-4-(2-acetamidoethyl)-6-hydroxy-7-oxo-1,6-diazabicyclo[3.2.1]oct-3-ene-2-carboxamide (Intermediate 248, 0.090 g, 0.34 mmol) in pyridine (5 mL) was added pyridine/sulfur trioxide complex (0.320 g, 2.01 mmol). The reaction mixture was stirred overnight at room temperature. The solvent was removed in vacuo and the residue was purified by reverse phase HPLC. The title compound was obtained as a white solid after lypholization (0.007 g, 6%).

MS: 347 ES– ($C_{11}H_{16}N_4O_7S$)

$^1$H NMR (300 MHz, DMSO-$d_6$) δ: 0.85 (d, J=6.78 Hz, 1H) 1.68-1.82 (m, 3H) 2.18 (t, J=7.16 Hz, 2H) 3.06 (dt, J=12.81, 6.40 Hz, 1H) 3.47 (d, J=6.78 Hz, 1H) 3.99-4.17 (m, 3H) 5.42 (d, J=1.51 Hz, 1H) 7.28 (br. s., 1H) 7.49 (br. s., 1H) 7.72 (t, J=5.27 Hz, 1H) 7.91-8.02 (m, 1H) 8.48 (t, J=7.91 Hz, 1H) 8.89 (br. s., 1H).

Example 26

(2S,5R)-2-(methoxymethyl)-4-(methylcarbamoyl)-7-oxo-1,6-diazabicyclo[3.2.1]oct-3-en-6-yl hydrogen sulfate sodium salt

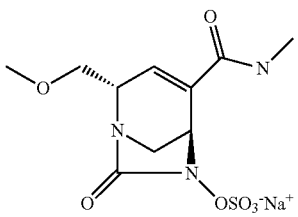

The title compound (0.08 g, 44%) was prepared according to the procedure described for Example 1, starting from (E)-triphenyl(prop-1-enyl)phosphonium (2S,5R)-2-(methoxymethyl)-4-(methylcarbamoyl)-7-oxo-1,6-diazabicyclo[3.2.1]oct-3-en-6-yl sulfate (Intermediate 260, 0.33 g).

Optical rotation: (0.1 g/dL, MeOH)=–136

MS: 320 ES– ($C_{10}H_{15}N_3O_7S$)

$^1$H NMR (300 MHz, DMSO-$d_6$) δ: 2.65 (d, J=4.52 Hz, 3H) 3.19-3.29 (m, 6H) 3.53-3.69 (m, 2H) 3.89 (td, J=5.75, 3.01 Hz, 1H) 4.50-4.61 (m, 1H) 6.38 (dd, J=3.01, 0.94 Hz, 1H) 7.76 (d, J=4.52 Hz, 1H).

The intermediates for Example 26 were prepared as follows:

Intermediate 250: (S)-tert-butyl 1-hydroxybut-3-en-2-yl(2-(methoxy(methyl)amino)-2-oxoethyl)carbamate

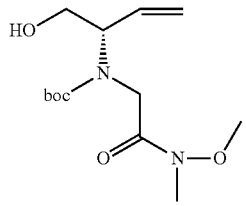

To a solution of (S)-tert-butyl 1-(tert-butyldimethylsilyloxy)but-3-en-2-yl(2-(methoxy(methyl)amino)-2-oxoethyl)carbamate (Intermediate 5, 10.7 g, 26.58 mmol) in THF (25 mL) was added TBAF (31.9 mL, 31.89 mmol) at 0° C. After 1 hour the reaction mixture was concentrated and purified by silica gel chromatography (hexanes/ethyl acetate) to afford the product as a light yellow oil (5.9 g, 77%).

MS: 289 ES+ ($C_{13}H_{24}N_2O_5$)

$^1$H NMR (300 MHz, CDCl$_3$) δ: 1.36-1.61 (m, 10H) 3.25 (s, 3H) 3.35-3.52 (m, 1H) 3.57-3.72 (m, 2H) 3.72-3.82 (m, 3H) 4.26-4.56 (m, 1H) 4.83 (ddd, J=8.24, 4.19, 2.07 Hz, 2H) 5.10-5.34 (m, 2H) 5.57-5.84 (m, 1H).

Intermediate 251: (S)-tert-butyl 2-(methoxy(methyl)amino)-2-oxoethyl(1-methoxybut-3-en-2-yl)carbamate

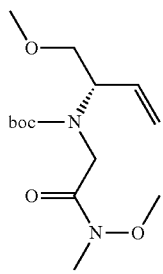

To a solution of (S)-tert-butyl 1-hydroxybut-3-en-2-yl(2-(methoxy(methyl)amino)-2-oxoethyl)carbamate (Intermediate 250, 7 g, 24.28 mmol) in THF (75 mL) at 0° C. was added dimethyl sulfate (2.436 mL, 25.49 mmol) followed by LiHMDS (26.7 mL, 26.70 mmol). The reaction mixture was allowed to warm slowly to room temperature and stirred for two hours. The reaction mixture was then partitioned between ethyl acetate and water. The layers were separated and the organics were washed with saturated sodium bicarbonate, water and brine. The organics were dried over magnesium sulfate, filtered and concentrated. Silica gel chromatography (5%-30% ethyl acetate/hexanes) afforded the title compound as a clear oil (6.89 g, 91%).

MS: 303 ES+ ($C_{14}H_{264}N_2O_5$)

$^1$H NMR (300 MHz, CDCl$_3$) δ: 1.18-1.42 (m, 9H) 3.02 (s, 3H) 3.14 (d, J=6.03 Hz, 3H) 3.41-3.64 (m, 5H) 3.76-4.13 (m, 2H) 4.57-4.82 (m, 1H) 4.93-5.13 (m, 2H) 5.60-5.90 (m, 1H).

Intermediate 252: (S)-tert-butyl 1-methoxybut-3-en-2-yl(2-oxoethyl)carbamate

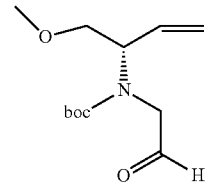

To a solution of (S)-tert-butyl 2-(methoxy(methyl)amino)-2-oxoethyl(1-methoxybut-3-en-2-yl)carbamate (Intermediate 251, 3.35 g, 11.08 mmol) in dichloromethane (60 ml) at −78° C. under nitrogen was added diisobutylaluminum hydride (1.5 eq, 1.0M in dichloromethane) (16.62 ml, 16.62 mmol). The reaction mixture was stirred at that temperature for two hours. The reaction was quenched with slow addition of methanol at the low temperature and slowly warmed to ambient temperature. The reaction mixture was diluted with dichloromethane and washed with 10% aqueous potassium sodium tartrate twice, followed by water and brine. The organics were dried over sodium sulfate, filtered and concentrated. Silica gel chromatography (0%-50% ethyl acetate/hexanes) afforded the title compound as a clear oil (1.8 g, 68%).

$^1$H NMR (300 MHz, CDCl$_3$) δ 1.46 (s, 9H) 3.31 (s, 3H) 3.46-3.65 (m, 2H) 3.65-3.80 (m, 1H) 3.80-4.05 (m, 1H) 4.65-5.01 (m, 1H) 5.13-5.36 (m, 2H) 5.64-5.90 (m, 1H) 9.49 (s, 1H).

Intermediate 253: methyl 4-(tert-butoxycarbonyl((S)-1-methoxybut-3-en-2-yl)amino)-3-hydroxy-2-methylenebutanoate

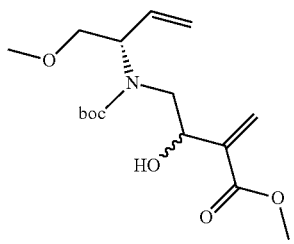

To a solution of (S)-tert-butyl 1-methoxybut-3-en-2-yl(2-oxoethyl)carbamate (Intermediate 252, 1.475 g, 6.06 mmol) and methyl acrylate (0.82 ml, 9.09 mmol) in MeOH (0.2 ml) under nitrogen at room temperature was added quinuclidine (0.337 g, 3.03 mmol). The reaction mixture was stirred at that temperature overnight. Another 100 mg of quinuclidine was added and the reaction was stirred for another 24 hours. The reaction mixture was then partitioned between water and ethyl acetate. The layers were separated and the organics were washed with water and brine, then dried over magnesium sulfate, filtered and concentrated. Silica gel chromatography (0%-30% ethyl acetatae/hexanes) afforded the title compound as a clear oil (1.28 g, 65%). The product is a mixture of two distereomers.

MS: 330 ES+ ($C_{16}H_{27}NO_6$)

Intermediate 254: (2S,5S)-1-tert-butyl 4-methyl 5-hydroxy-2-(methoxymethyl)-5,6-dihydropyridine-1,4(2H)-dicarboxylate

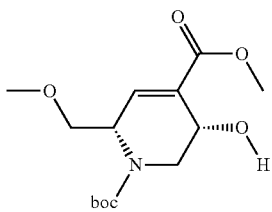

The title compound (0.45 g, 40%) was prepared according to the procedure described for Intermediate 101 starting from methyl 4-(tert-butoxycarbonyl((S)-1-methoxybut-3-en-2-yl)amino)-3-hydroxy-2-methylenebutanoate (Intermediate 253, 1.22 g).

MS: 302 ES+ ($C_{14}H_{23}NO_6$)

$^1$H NMR (300 MHz, CDCl$_3$) δ: 1.49 (s, 9H) 2.96-3.18 (m, 1H) 3.39 (s, 3H) 3.52-3.73 (m, 2H) 3.88 (s, 3H) 3.99-4.19 (m, 1H) 4.19-4.38 (m, 1H) 4.52-4.59 (m, 1H) 4.59-4.81 (m, 1H) 7.01 (d, J=4.14 Hz, 1H).

Intermediate 255: (2S,5S)-tert-Butyl 5-hydroxy-2-(methoxymethyl)-4-(methylcarbamoyl)-5,6-dihydropyridine-1(2H)-carboxylate

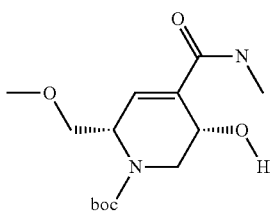

A dry 2 necked round bottomed flask was equipped with a magnetic stirrer and it was flushed with nitrogen twice. Then trimethylaluminum (0.191 ml, 0.38 mmol) was added followed by toluene (0.5 ml). The solution was cooled down to −10° C. and methanamine (0.183 ml, 0.37 mmol) was added slowly. The reaction mixture was stirred at that temperature for 20 minutes. A solution of (2S,5S)-1-tert-butyl 4-methyl 5-hydroxy-2-(methoxymethyl)-5,6-dihydropyridine-1,4(2H)-dicarboxylate (Intermediate 254, 100 mg, 0.33 mmol) in toluene (0.5 ml) was added slowly at room temperature. After stirring overnight the reaction was quenched with 1M HCl and allowed to stir for 15 minutes to complete the hydrolysis. The reaction mixture was extracted with ethyl acetate. The organics were washed with saturated sodium bicarbonate, dried over magnesium sulfate, filtered and concentrated. Silica gel chromatography (MeOH/DCM) afforded the title compound as a clear oil (53 mg).

MS: 302 ES+ ($C_{14}H_{24}N_2O_5$)

$^1$H NMR (300 MHz, CDCl$_3$) δ 1.48 (s, 9H) 1.69 (br. s., 2H) 2.57-2.94 (m, 3H) 3.08 (dd, J=13.00, 9.04 Hz, 1H) 3.36 (s, 3H) 3.40-3.56 (m, 1H) 3.51-3.72 (m, 1H) 4.13 (dd, J=13.00, 4.71 Hz, 1H) 4.47 (t, J=6.78 Hz, 1H) 4.60-4.66 (m, 1H) 6.60 (d, J=4.14 Hz, 1H).

Intermediate 256: (2S,5R)-tert-butyl 5-(N-(allyloxy)-2-nitrophenylsulfonamido)-2-(methoxymethyl)-4-(methylcarbamoyl)-5,6-dihydropyridine-1(2H)-carboxylate

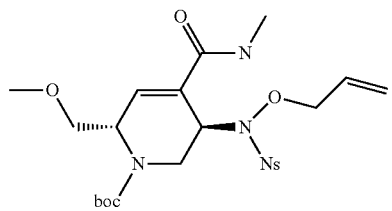

The title compound, as an off-white solid (1 g, 63%), was prepared according to the procedure for Intermediate 10 starting from (2S,5S)-tert-Butyl 5-hydroxy-2-(methoxymethyl)-4-(methylcarbamoyl)-5,6-dihydropyridine-1(2H)-carboxylate (Intermediate 255, 0.87 g).

MS: 541 ES+ ($C_{23}H_{32}N_4O_9S$)

Intermediate 257: (3R,6S)-3-(N-(allyloxy)-2-nitrophenylsulfonamido)-6-(methoxymethyl)-N-methyl-1,2,3,6-tetrahydropyridine-4-carboxamide

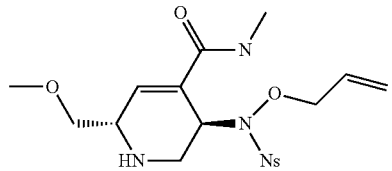

To a solution of (2S,5R)-tert-butyl 5-(N-(allyloxy)-2-nitrophenylsulfonamido)-2-(methoxymethyl)-4-(methylcarbamoyl)-5,6-dihydropyridine-1(2H)-carboxylate (Intermediate 256, 1 g, 1.85 mmol) in dioxane (10 ml) at room temperature was added 4M HCl in Dioxane (2 ml, 57.16 mmol). The reaction mixture was stirred at that temperature for 4-5 hours. The reaction mixture was concentrated and the crude was taken up in 2M NaOH and extracted with dichloromethane. The combined organic extracts were washed with brine, dried over sodium sulfate, filtered and concentrated. Silica gel chromatography (increasing percentage of methanol in dichloromethane) afforded the title compound as a thick oil (0.56 g, 69%).

MS: 441 ES+ ($C_{18}H_{24}N_4O_7S$)

$^1$H NMR (300 MHz, DMSO-d$_6$) δ: 2.58 (d, J=3.96 Hz, 3H); 2.77 (br. s., 1H); 3.14-3.26 (m, 2H); 3.24 (s, 3H) 3.48 (d, J=4.52 Hz, 1H) 4.16-4.42 (m, 2H) 4.66 (br. s., 1H) 5.12-5.33 (m, 2H) 5.83 (dd, J=17.24, 10.46 Hz, 1H) 6.63 (d, J=2.26 Hz, 1H) 7.77-7.94 (m, 2H) 7.94-8.02 (m, 2H) 8.08 (d, J=7.91 Hz, 1H) (2H peaks buried underneath water peak).

Intermediate 258: (3R,6S)-3-(allyloxyamino)-6-(methoxymethyl)-N-methyl-1,2,3,6-tetrahydropyridine-4-carboxamide

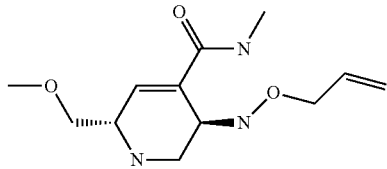 [SMILES: C=CCON[C@H]1CN[C@H](COC)C=C1C(=O)NC]

To a mixture of (3R,6S)-3-(N-(allyloxy)-2-nitrophenylsulfonamido)-6-(methoxymethyl)-N-methyl-1,2,3,6-tetrahydropyridine-4-carboxamide (Intermediate 257, 561 mg, 1.27 mmol) and potassium carbonate (880 mg, 6.37 mmol) in acetonitrile (15 mL) at room temperature was added benzenethiol (0.654 mL, 6.37 mmol). The resulting mixture was stirred at room temperature overnight. The reaction mixture was concentrated onto silica gel. Silica gel chromatography (0%-20% methanol/dichloromethane) afforded the title compound as an off-white solid (0.26 g, 81%).

MS: 256 ES+ ($C_{12}H_{21}N_3O_3$)

$^1$H NMR (300 MHz, DMSO-$d_6$) δ: 2.64 (d, J=4.71 Hz, 3H) 2.73 (d, J=9.04 Hz, 1H) 2.94 (dd, J=12.90, 3.11 Hz, 1H) 3.20-3.28 (m, 2H) 3.26 (s, 3H) 3.37-3.52 (m, 1H) 3.54-3.68 (m, 1H) 4.12 (dt, J=5.70, 1.39 Hz, 2H) 5.00-5.30 (m, 2H) 5.79-6.04 (m, 1H) 6.43 (d, J=8.48 Hz, 1H) 6.53-6.65 (m, 1H) 7.86 (d, J=4.52 Hz, 1H) (1H peak buried underneath water peak).

Intermediate 259: (2S,5R)-6-(allyloxy)-2-(methoxymethyl)-N-methyl-7-oxo-1,6-diazabicyclo[3.2.1]oct-3-ene-4-carboxamide

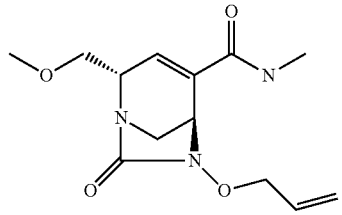 [SMILES: C=CCON1C(=O)N2C[C@H]1C(C(=O)NC)=C[C@H]2COC]

The title compound (0.28 g, 68%) was prepared according to the procedure described for Intermediate 13, starting from (3R,6S)-3-(allyloxyamino)-6-(methoxymethyl)-N-methyl-1,2,3,6-tetrahydropyridine-4-carboxamide (Intermediate 258, 0.52 g)

MS: 282 ES+ ($C_{13}H_{19}N_3O_4$)

$^1$H NMR (300 MHz, CDCl$_3$) δ: 2.88 (d, J=4.90 Hz, 3H) 3.27-3.38 (m, 2H) 3.40 (s, 3H) 3.49-3.79 (m, 2H) 4.11 (td, J=5.79, 2.92 Hz, 1H) 4.36-4.41 (m, 1H) 4.41-4.56 (m, 2H) 5.14-5.46 (m, 2H) 5.94 (br. s., 1H) 5.96-6.14 (m, 1H) 6.26 (d, J=2.26 Hz, 1H).

Intermediate 260: (E)-triphenyl(prop-1-enyl)phosphonium (2S,5R)-2-(methoxymethyl)-4-(methylcarbamoyl)-7-oxo-1,6-diazabicyclo[3.2.1]oct-3-en-6-yl sulfate

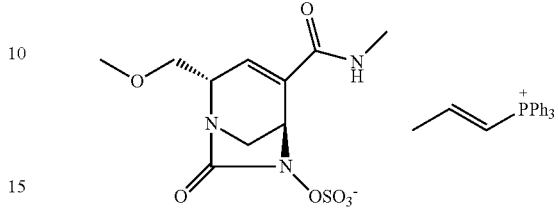

The title compound (0.33 g, 79%) was prepared according to the procedure described for Intermediate 17, starting from (2S,5R)-6-(allyloxy)-2-(methoxymethyl)-N-methyl-7-oxo-1,6-diazabicyclo[3.2.1]oct-3-ene-4-carboxamide (Intermediate 259, 0.19 g).

MS: 319 ES–, 303 ES+ ($C_{10}H_{15}N_3O_7S$, $C_{21}H_{20}P$)

$^1$H NMR (300 MHz, DMSO-$d_6$) δ: 2.17 (dt, J=6.36, 2.00 Hz, 4H) 2.65 (d, J=4.71 Hz, 3H) 3.17-3.28 (m, 4H) 3.51-3.69 (m, 2H) 3.89 (td, J=5.79, 3.11 Hz, 1H) 4.57 (d, J=1.13 Hz, 1H) 6.38 (dd, J=2.92, 1.04 Hz, 1H) 6.54-6.78 (m, 1H) 7.18-7.41 (m, 1H) 7.63-7.84 (m, 14H) 7.85-8.00 (m, 3H).

Example 27

(2S,5R)-2-carbamoyl-4-cyclopropyl-7-oxo-1,6-diazabicyclo[3.2.1]oct-3-en-6-yl hydrogen sulfate sodium salt

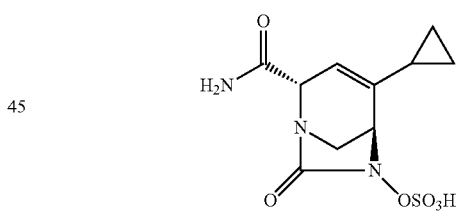

The title compound was prepared from (E)-triphenyl(prop-1-enyl)phosphonium (2S,5R)-2-carbamoyl-4-cyclopropyl-7-oxo-1,6-diazabicyclo[3.2.1]oct-3-en-6-yl sulfate (Intermediate 272, 0.305 g, 0.50 mmol) following the procedure described for Example 1. The desired product was obtained as a white solid (66.4 mg, 40%) after HPLC purification (Synergi Polar RP 19 mm×100 mm 5 μm).

Optical rotation: (0.1 g/dL, MeOH)=–229

MS: 302 ES– ($C_{10}H_{13}N_3O_6S$)

$^1$H NMR (300 MHz, D$_2$O: 0.56 (m, 1H); 0.78 (m, 3H); 1.56 (m, 1H); 3.28 (d, 1H); 3.59 (m, 1H); 4.07 (m, 1H); 4.51 (m, 1H); 5.63 (m, 1H).

The intermediates for Example 27 were prepared as follows:

Intermediate 261: (E)-N'-(1-cyclopropylethylidene)-2,4,6-triisopropylbenzenesulfonohydrazide

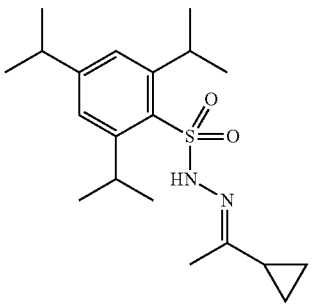 [SMILES: C/C(=N\NS(=O)(=O)c1c(C(C)C)cc(C(C)C)cc1C(C)C)C1CC1]

The title compound was prepared from 2,4,6-triisopropylbenzenesulfonyl hydrazide (Aldrich, 20 g, 67.01 mmol) and 1-cyclopropylethanone (Aldrich, 6.28 mL, 67.01 mmol) following the procedure described for Intermediate 33. The desired product was obtained as a white solid (15 g, 61%).

MS: 365 ES+ ($C_{20}H_{32}N_2O_2S$)

$^1$H NMR (300 MHz, DMSO-$d_6$) δ: 0.56 (m, 3H); 0.75 (m, 1H); 1.17 (m, 18H); 1.47 (m, 1H); 1.61 (s, 3H); 2.91 (m, 1H); 4.25 (m, 2H); 7.20 (s, 2H); 9.97 (s, 1H).

Intermediate 262: (S)-tert-butyl 1-(tert-butyldimethylsilyloxy)but-3-en-2-yl(3-cyclopropyl-2-oxobut-3-enyl)carbamate

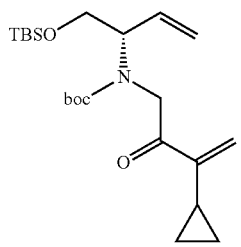

The title compound was prepared from (E)-N'-(1-cyclopropylethylidene)-2,4,6-triisopropylbenzenesulfonohydrazide (Intermediate 261, 17.58 g, 48.22 mmol) and (S)-tert-butyl 1-(tert-butyldimethylsilyloxy)but-3-en-2-yl(2-(methoxy(methyl)amino)-2-oxoethyl)carbamate (Intermediate 5, 9.71 g, 24.11 mmol) following the procedure described for Intermediate 34. The desired product was obtained as a light yellow oil (4.86 g, 49%).

MS: 410 ES+ ($C_{22}H_{39}NO_4Si$)

$^1$H NMR (300 MHz, DMSO-$d_6$) δ: 0.02 (m, 6H); 0.45 (m, 2H); 0.75 (m, 2H); 0.83 (m, 10H); 1.32 (m, 9H); 0.70 (m, 1H); 3.71 (m, 2H); 4.35 (m, 2H); 5.18 (m, 2H); 5.46 (m, 1H); 5.78 (m, 1H); 5.88 (m, 1H).

Intermediate 263: (S)-tert-butyl 2-((tert-butyldimethylsilyloxy)methyl)-4-cyclopropyl-5-oxo-5,6-dihydropyridine-1(2H)-carboxylate

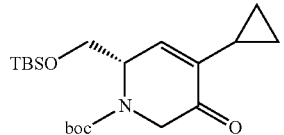

The title compound was prepared from (S)-tert-butyl 1-(tert-butyldimethylsilyloxy)but-3-en-2-yl(3-cyclopropyl-2-oxobut-3-enyl)carbamate (Intermediate 262, 5.16 g, 12.60 mmol) following the procedure described for Intermediate 7, except the reaction mixture was heated at 85° C. overnight. The desired product was obtained as a light yellow oil (3.82 g, 79%).

MS: 382 ES+ ($C_{20}H_{35}NO_4Si$)

$^1$H NMR (300 MHz, DMSO-$d_6$) δ: 0.02 (m, 6H); 0.45 (m, 2H); 0.75 (m, 1H); 0.83 (m, 10H); 1.28 (m, 1H); 1.41 (m, 9H); 1.71 (m, 1H); 3.85 (m, 2H); 4.05 (m, 1H); 4.66 (m, 1H); 6.56 (m, 1H).

Intermediate 264: (2S,5S)-tert-butyl 2-((tert-butyldimethylsilyloxy)methyl)-4-cyclopropyl-5-hydroxy-5,6-dihydropyridine-1(2H)-carboxylate

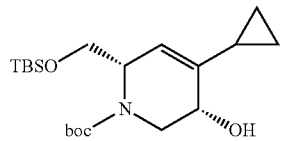

The title compound was prepared from (S)-tert-butyl 2-((tert-butyldimethylsilyloxy)methyl)-4-cyclopropyl-5-oxo-5,6-dihydropyridine-1(2H)-carboxylate (Intermediate 263, 3.82 g, 10.01 mmol) following the procedure described for Intermediate 8. The desired product was obtained as a colorless oil (3 g, 78%).

MS: 384 ES+ ($C_{20}H_{37}NO_4Si$)

$^1$H NMR (300 MHz, DMSO-$d_6$) δ: 0.02 (s, 6H); 0.22 (m, 1H); 0.57 (m, 3H); 0.85 (s, 9H); 1.38 (s, 9H); 1.57 (m, 1H); 2.69 (m, 1H); 3.58 (m, 2H); 3.93 (m, 1H); 4.17 (m, 1H); 5.11 (d, 1H); 5.22 (m, 1H).

Intermediate 265: (2S,5R)-tert-butyl 5-(N-(allyloxy)-2-nitrophenylsulfonamido)-2-((tert-butyldimethylsilyloxy)methyl)-4-cyclopropyl-5,6-dihydropyridine-1(2H)-carboxylate

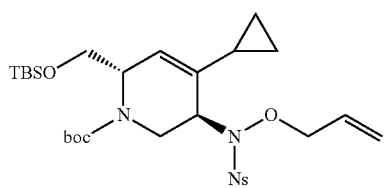

The title compound was prepared from (2S,5S)-tert-butyl 2-((tert-butyldimethylsilyloxy)methyl)-4-cyclopropyl-5-hydroxy-5,6-dihydropyridine-1 (2H)-carboxylate (Intermediate 264, 3 g, 7.82 mmol) and N-(allyloxy)-2-nitrobenzenesulfonamide (Intermediate 9, 2.020 g, 7.82 mmol) following the procedure described for Intermediate 10. The desired product was obtained as a yellow oil (3.62 g, 74%).

MS: 624 ES+ ($C_{29}H_{45}N_3O_8SSi$)

$^1$H NMR (300 MHz, DMSO-$d_6$) δ: 0.01 (s, 6H); 0.40 (m, 3H); 0.83 (s, 9H); 1.31 (m, 9H); 3.14 (m, 1H); 3.57 (m, 2H); 4.10 (m, 4H); 4.43 (m, 1H); 5.20 (m, 2H); 5.70 (m, 2H); 8.02 (m, 4H).

Intermediate 266: (2S,5R)-tert-butyl 5-(N-(allyloxy)-2-nitrophenylsulfonamido)-4-cyclopropyl-2-(hydroxymethyl)-5,6-dihydropyridine-1(2H)-carboxylate

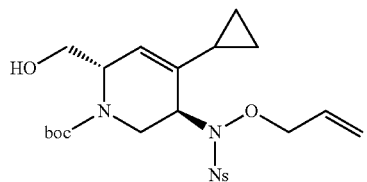

The title compound was prepared from (2S,5R)-tert-butyl 5-(N-(allyloxy)-2-nitrophenylsulfonamido)-2-((tert-butyldimethylsilyloxy)methyl)-4-cyclopropyl-5,6-dihydropyridine-1(2H)-carboxylate (Intermediate 265, 3.62 g, 5.80 mmol) in THF (30 mL) following the procedure described for Intermediate 18. The desired product was obtained as an off-white foam (2.64 g, 89%).

MS: 510 ES+ ($C_{23}H_{31}N_3O_8S$)

$^1$H NMR (300 MHz, DMSO-$d_6$) δ: 0.46 (m, 3H); 1.34 (m, 9H); 3.07 (m, 1H); 3.38 (m, 2H); 4.05 (m, 2H); 4.29 (m, 3H); 4.73 (m, 1H); 5.20 (m, 2H); 5.69 (m, 2H); 8.04 (m, 4H).

Intermediate 267: (2S,5R)-5-(N-(allyloxy)-2-nitrophenylsulfonamido)-1-(tert-butoxycarbonyl)-4-cyclopropyl-1,2,5,6-tetrahydropyridine-2-carboxylic acid

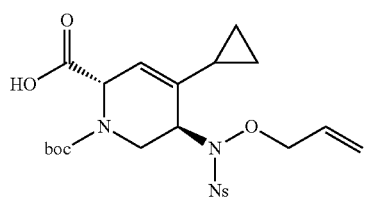

The title compound was prepared from (2S,5R)-tert-butyl 5-(N-(allyloxy)-2-nitrophenylsulfonamido)-4-cyclopropyl-2-(hydroxymethyl)-5,6-dihydropyridine-1(2H)-carboxylate (Intermediate 266, 2.64 g, 5.18 mmol) following the procedure described for Intermediate 19. The desired product was obtained as an orange foam (2.33 g, 86%).

MS: 524 ES+ ($C_{23}H_{29}N_3O_9S$)

$^1$H NMR (300 MHz, DMSO-$d_6$) δ: 0.46 (m, 3H); 1.28 (m, 9H); 3.10 (m, 1H); 3.90 (m, 1H); 4.29 (m, 3H); 4.78 (m, 1H); 5.19 (m, 2H); 5.69 (m, 2H); 8.04 (m, 4H).

Intermediate 268: (2S,5R)-tert-butyl 5-(N-(allyloxy)-2-nitrophenylsulfonamido)-2-carbamoyl-4-cyclopropyl-5,6-dihydropyridine-1(2H)-carboxylate

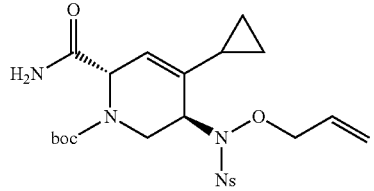

The title compound was prepared from (2S,5R)-5-(N-(allyloxy)-2-nitrophenylsulfonamido)-1-(tert-butoxycarbonyl)-4-cyclopropyl-1,2,5,6-tetrahydropyridine-2-carboxylic acid (Intermediate 267, 2.33 g, 4.45 mmol) following the procedure described for Intermediate 20. The desired product was obtained as a tan foam (1.47 g, 63%).

MS: 523 ES+ ($C_{23}H_{30}N_4O_8S$)

$^1$H NMR (300 MHz, DMSO-$d_6$) δ: 0.53 (m, 4H); 1.28 (m, 9H); 3.15 (m, 1H); 3.93 (m, 1H); 4.27 (m, 3H); 4.73 (m, 1H); 5.19 (m, 2H); 5.73 (m, 2H); 7.03 (m, 1H); 7.43 (m, 1H); 8.05 (m, 4H).

Intermediate 269: (2S,5R)-5-(N-(allyloxy)-2-nitrophenylsulfonamido)-4-cyclopropyl-1,2,5,6-tetrahydropyridine-2-carboxamide

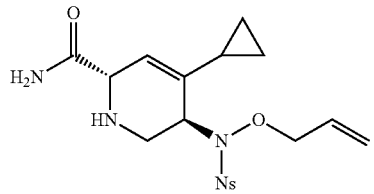

The title compound was prepared from (2S,5R)-tert-butyl 5-(N-(allyloxy)-2-nitrophenylsulfonamido)-2-carbamoyl-4-cyclopropyl-5,6-dihydropyridine-1(2H)-carboxylate (Intermediate 268, 1.47 g, 2.81 mmol) following the procedure described for Intermediate 21. The desired product was obtained as a light yellow foam (0.95 g, 80%).

MS: 423 ES+ ($C_{18}H_{22}N_4O_6S$)

$^1$H NMR (300 MHz, DMSO-$d_6$) δ: 0.30 (m, 1H); 0.50 (m, 2H); 0.81 (m, 1H); 1.28 (m, 1H); 2.70 (m, 2H); 3.75 (m, 1H); 4.07 (m, 1H); 4.37 (m, 2H); 5.24 (m, 2H); 5.84 (m, 2H); 7.02 (m, 1H); 7.28 (m, 1H); 8.04 (m, 4H).

Intermediate 270: (R)-5-(allyloxyamino)-4-cyclopropyl-1,2,5,6-tetrahydropyridine-2-carboxamide

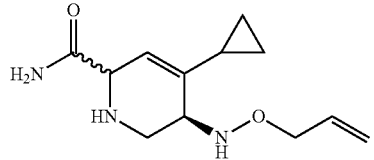 [SMILES: C=CCON[C@H]1CNC(C(N)=O)C=C1C1CC1]

The title compound was prepared from (2S,5R)-5-(N-(allyloxy)-2-nitrophenylsulfonamido)-4-cyclopropyl-1,2,5,6-tetrahydropyridine-2-carboxamide (Intermediate 269, 0.95 g, 2.25 mmol) following the procedure described for Intermediate 22. The desired product was obtained as a light yellow oil (0.307 g, 57%).

MS: 238 ES+ ($C_{12}H_{19}N_3O_2$)

$^1$H NMR (300 MHz, DMSO-$d_6$) δ: 0.52 (m, 4H); 1.43 (m, 2H); 2.46 (m, 1H); 3.04 (m, 2H); 3.59 (m, 1H); 4.13 (m, 2H); 5.20 (m, 2H); 5.39 (m, 1H); 5.92 (m, 1H); 6.39 (m, 1H); 7.00 (m, 1H); 7.34 (bs, 1H).

Intermediate 271: (2S,5R)-6-(allyloxy)-4-cyclopropyl-7-oxo-1,6-diazabicyclo[3.2.1]oct-3-ene-2-carboxamide

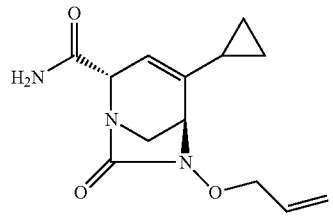 [SMILES: C=CCON1C(=O)N2C[C@H]1C(C1CC1)=C[C@H]2C(N)=O]

The title compound was prepared from (R)-5-(allyloxyamino)-4-cyclopropyl-1,2,5,6-tetrahydropyridine-2-carboxamide (Intermediate 270, 0.307 g, 1.29 mmol) following the procedure described for Intermediate 16. The desired product was obtained as a yellow oil (0.168 g, 49%).

MS: 264 ES+ ($C_{13}H_{17}N_3O_3$)

$^1$H NMR (300 MHz, DMSO-$d_6$) δ: 0.56 (m, 4H); 1.43 (m, 1H); 3.17 (m, 2H); 3.71 (m, 1H); 4.11 (m, 1H); 4.36 (m, 2H); 5.34 (m, 3H); 5.94 (m, 1H); 7.27 (bs, 1H); 7.49 (bs, 1H).

Intermediate 272: (E)-triphenyl(prop-1-enyl)phosphonium (2S,5R)-2-carbamoyl-4-cyclopropyl-7-oxo-1,6-diazabicyclo[3.2.1]oct-3-en-6-yl sulfate

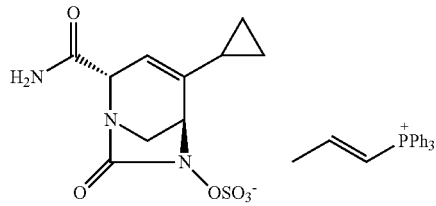

The title compound was prepared from (2S,5R)-6-(allyloxy)-4-cyclopropyl-7-oxo-1,6-diazabicyclo[3.2.1]oct-3-ene-2-carboxamide (Intermediate 271, 0.168 g, 0.64 mmol) following the procedure described for Intermediate 17. The desired product was obtained as a yellow foam (0.305 g, 79%).

MS: 302 ES−, 303 ES+ ($C_{10}H_{12}N_3O_6S$—.$C_{21}H_{20}P+$)

$^1$H NMR (300 MHz, DMSO-$d_6$) δ: 0.56 (m, 3H); 0.85 (m, 1H); 1.42 (m, 1H); 2.16 (m, 3H); 3.18 (m, 2H); 3.71 (m, 1H); 4.10 (m, 1H); 5.44 (m, 1H); 6.65 (m, 1H); 7.25 (m, 2H); 7.51 (m, 1H); 7.79 (m, 15H).

Example 28

(2S,5R)-3-(2-methoxyethyl)-2-(methoxymethyl)-7-oxo-1,6-diazabicyclo[3.2.1]oct-3-en-6-yl hydrogen sulfate sodium salt

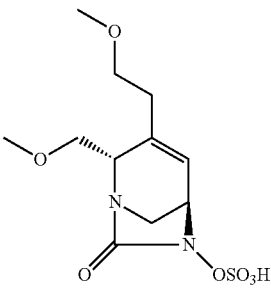

The title compound was prepared from (E)-triphenyl(prop-1-en-1-yl)phosphonium (2S,5R)-3-(2-methoxyethyl)-2-(methoxymethyl)-7-oxo-1,6-diazabicyclo[3.2.1]oct-3-en-6-yl sulfate (Intermediate 288, 0.328 g, 0.53 mmol) following the procedure described for Example 1. The desired product was obtained as an off-white solid (146 mg, 81%).

Optical Rotation: (0.22 g/dL, DMSO)=−263

MS: 321 ES− ($C_{11}H_{18}N_2O_7S$)

$^1$H NMR (300 MHz, DMSO-$d_6$) δ: 2.13 (m, 2H); 3.07 (m, 1H); 3.22 (s, 3H); 3.28 (s, 3H); 3.36 (m, 3H); 3.68 (m, 3H); 4.00 (m, 1H); 6.03 (m, 1H).

The intermediates for Example 28 were prepared as follows:

Intermediate 273: ((3-bromobut-3-en-1-yl)oxy)(tert-butyl)dimethylsilane

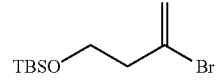

To a solution of 3-bromobut-3-en-1-ol (ACROS, 15.18 g, 100.53 mmol) in DCM (300 mL) at room temperature was added imidazole (8.90 g, 130.69 mmol), 4-dimethylaminopyridine (2.456 g, 20.11 mmol) and tert-butyldimethylsilyl chloride (16.67 g, 110.58 mmol). The reaction mixture was stirred at room temperature for 3 hours, then filtered to remove solids and washed with brine. The organics were dried over magnesium sulfate, filtered and concentrated. Silica gel chromatography (0%-15% ethyl acetate/hexanes) afforded the title compound (24.67 g, 93%) as a colorless oil.

$^1$H NMR (300 MHz, CDCl$_3$) δ 0.08 (s, 3H), 0.90 (s, 9H), 2.63 (t, 2H), 3.80 (t, 2H), 5.46 (m, 1H), 5.64 (m, 1H).

Intermediate 274: (S,E)-N-(2-((tert-butyldimethylsilyl)oxy)ethylidene)-2-methylpropane-2-sulfinamide

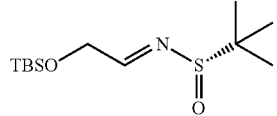 [SMILES: CC(C)(C)[S@](=O)/N=C/CO[Si](C)(C)C(C)(C)C]

To a solution of 2-((tert-butyldimethylsilyl)oxy)acetaldehyde (Aldrich, 15 g, 86.05 mmol) in DCM (200 mL) at room temperature was added copper(II) sulfate (41.2 g, 258.16 mmol) and (S)-2-methylpropane-2-sulfinamide (Aldrich, 15.64 g, 129.08 mmol). The reaction mixture was stirred overnight at room temperature, then filtered through celite, washed with DCM and concentrated to afford an oil. Silica gel chromatography (0%-25% ethyl acetate/hexanes) afforded the title compound (14.73 g, 61.7%) as a colorless oil.

$^1$H NMR (300 MHz, CDCl$_3$) δ 0.11 (s, 6H), 0.93 (s, 9H), 1.22 (s, 9H), 4.55 (d, 2H), 8.07 (t, 1H).

Intermediate 275: (S)-2-methyl-N—((S)-2,2,3,3,11,11,12,12-octamethyl-7-methylene-4,10-dioxa-3,11-disilatridecan-6-yl)propane-2-sulfinamide

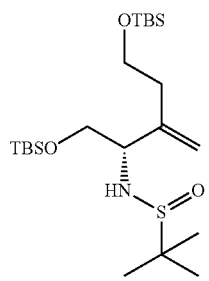 [SMILES: C=C(CCO[Si](C)(C)C(C)(C)C)[C@@H](CO[Si](C)(C)C(C)(C)C)NS(=O)C(C)(C)C]

To a solution of ((3-bromobut-3-en-1-yl)oxy)(tert-butyl)dimethylsilane (Intermediate 273, 24.66 g, 92.97 mmol) in THF (200 mL) at –78° C. was added tert-butyllithium (1.7M in pentane) (120 mL, 204.54 mmol) dropwise via cannula. The reaction mixture was stirred for 45 minutes at –78° C. The (S,E)-N-(2-((tert-butyldimethylsilyl)oxy)ethylidene)-2-methylpropane-2-sulfinamide (Intermediate 274, 17.2 g, 61.98 mmol) in THF (50 mL) was added dropwise. The reaction mixture was stirred for ~1.5 hours at –78° C. The reaction was quenched with saturated sodium bicarbonate and extracted twice with ether. The combined organic extracts were dried over magnesium sulfate, filtered and concentrated. Silica gel chromatography (0%-15% ethyl acetate/hexanes) afforded the title compound (21.07 g, 73.3%) as a colorless oil.

$^1$H NMR (300 MHz, CDCl$_3$) δ 0.06 (m, 12H), 0.90 (m, 18H), 1.24 (s, 9H), 2.25 (m, 2H), 3.57 (m, 1H); 3.73 (m, 3H); 3.95 (m, 2H); 5.04 (m, 1H); 5.19 (m, 1H).

Intermediate 276:
(S)-2-amino-3-methylenepentane-1,5-diol hydrochloride

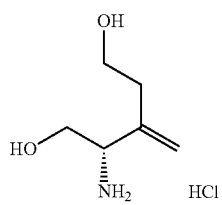

To a solution of 2-methyl-N—((S)-2,2,3,3,11,11,12,12-octamethyl-7-methylene-4,10-dioxa-3,11-disilatridecan-6-yl)propane-2-sulfinamide (Intermediate 275, 21.07 g, 45.42 mmol) in methanol (100 mL) at 0° C. was added hydrochloric acid (4M in dioxane) (22.71 mL, 90.85 mmol). The reaction mixture was stirred at 0° C. for ~20 minutes. LC/MS shows no remaining starting material. The reaction mixture was concentrated to afford an oil (7.6 g, 100%).

MS: 132 ES+ (C$_6$H$_{13}$NO$_2$)

Intermediate 277: (S)-2,2,3,3,11,11,12,12-octamethyl-7-methylene-4,10-dioxa-3,11-disilatridecan-6-amine

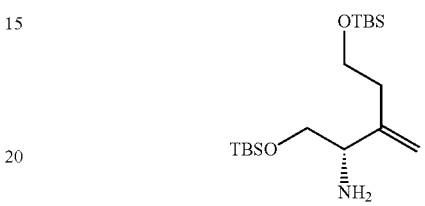

To a solution of (S)-2-amino-3-methylenepentane-1,5-diol, HCl (Intermediate 276, 7.6 g, 45.34 mmol) in DCM (200 mL) at room temperature was added imidazole (12.35 g, 181.35 mmol), 4-dimethylaminopyridine (2.77 g, 22.67 mmol) and tert-butyldimethylsilyl chloride (20.50 g, 136.01 mmol). The reaction mixture was stirred at room temperature overnight, then filtered to remove the solids and washed with brine. The organics were dried over magnesium sulfate, filtered and concentrated. Silica gel chromatography (0%-5% methanol/dichloromethane) afforded the title compound (14.34 g, 88%) as a yellow oil.

MS: 359 ES+ (C$_{18}$H$_{41}$NO$_2$Si$_2$)

$^1$H NMR (300 MHz, CDCl$_3$) δ 0.06 (m, 12H), 0.90 (m, 18H), 2.30 (m, 2H), 3.41 (m, 2H); 3.72 (m, 3H); 4.90 (m, 1H); 5.09 (m, 1H).

Intermediate 278: (S)-tert-butyl (2-(methoxy(methyl)amino)-2-oxoethyl)(2,2,3,3,11,11,12,12-octamethyl-7-methylene-4,10-dioxa-3, 1-disilatridecan-6-yl)carbamate

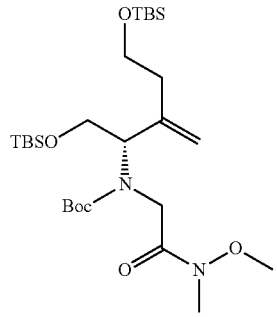 [SMILES: C=C(CCO[Si](C)(C)C(C)(C)C)[C@@H](CO[Si](C)(C)C(C)(C)C)N(CC(=O)N(C)OC)C(=O)OC(C)(C)C]

A mixture of (S)-2,2,3,3,11,11,12,12-octamethyl-7-methylene-4,10-dioxa-3,11-disilatridecan-6-amine (14.34 g, 39.87 mmol) and potassium carbonate (Intermediate 277, 5.51 g, 39.87 mmol) in DMF (300 mL) was stirred at room temperature for 1 hour. 2-bromo-N-methoxy-N-methylacetamide (Intermediate 4, 7.26 g, 39.87 mmol) was added and the reaction mixture was stirred at room temperature overnight. The reaction mixture was diluted with ethyl acetate and washed with saturated sodium bicarbonate. An emulsion formed and was filtered to remove the solids. The layers were separated and the organics were washed with 1:1 brine:water. The organics were dried over magnesium sulfate, filtered and concentrated. The resulting yellow oil was dissolved in THF (100 mL) and di-tert-butyl dicarbonate (17.40 g, 79.73 mmol) was added. The reaction mixture was stirred at room temperature for 4 hours, then at 50° C. for ~4 hours, then room temperature over the weekend. The reaction mixture was diluted with ethyl acetate and washed with saturated sodium bicarbonate. The layers were separated and the organics were washed twice with 1:1 brine:water, dried over magnesium sulfate, filtered and concentrated.

Silica gel chromatography (0%-30% ethyl acetate/hexanes) afforded the title compound (13.55 g, 60.6%) as a light yellow oil.

MS: 561 ES+ ($C_{27}H_{56}N_2O_6Si_2$)

$^1$H NMR (300 MHz, CDCl$_3$) δ 0.06 (m, 12H), 0.88 (m, 18H), 1.45 (m, 9H), 2.32 (m, 2H); 3.16 (s, 3H); 3.69 (m, 5H); 3.80 (m, 2H); 3.02 (m, 2H); 4.64 (m, 1H); 5.04 (m, 2H).

Intermediate 279: (S)-tert-butyl (2,2,3,3,11,11,12,12-octamethyl-7-methylene-4,10-dioxa-3,11-disilatridecan-6-yl)(2-oxopent-3-en-1-yl)carbamate

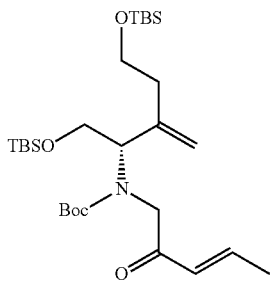 [SMILES: C=C(CCO[Si](C)(C)C(C)(C)C)[C@@H](CO[Si](C)(C)C(C)(C)C)N(CC(=O)/C=C/C)C(=O)OC(C)(C)C]

A suspension of cerium (III) chloride (47.6 g, 193.26 mmol) in THF (200 mL) 3 at room temperature was stirred vigorously for 2 hours. The suspension was cooled to −78° C. and (E)-prop-1-enylmagnesium bromide (0.5 M in THF) (387 mL, 193.26 mmol) was added dropwise. The mixture was stirred at −78° C. for 1.5 hours. (S)-tert-butyl (2-(methoxy(methyl)amino)-2-oxoethyl)(2,2,3,3,11,11,12,12-octamethyl-7-methylene-4,10-dioxa-3,11-disilatridecan-6-yl)carbamate (Intermediate 278, 13.55 g, 24.16 mmol) in THF (50 mL) was then added dropwise at −78° C. The reaction was stirred at −78° C. for 1 hour and then warmed to 0° C. for 30 minutes. The reaction was quenched with 10% citric acid, diluted further with water and extracted twice with ether. The organics were dried over magnesium sulfate, filtered and concentrated. Silica gel chromatography (0%-20% ethyl acetate/hexanes) afforded the title compound (10 g, 76%) as a yellow oil.

MS: 542 ES+ ($C_{28}H_{55}NO_5Si_2$)

$^1$H NMR (300 MHz, DMSO-d$_6$) δ 0.03 (m, 12H), 0.85 (m, 18H), 1.33 (m, 9H), 1.84 (m, 2H); 2.18 (m, 2H); 3.71 (m, 6H); 4.56 (m, 1H); 4.93 (m, 2H); 6.20 (m, 1H); 6.85 (m, 1H).

Intermediate 280: (S)-tert-butyl 3-(2-((tert-butyldimethylsilyl)oxy)ethyl)-2-(((tert-butyldimethylsilyl)oxy)methyl)-5-oxo-5,6-dihydropyridine-1(2H)-carboxylate

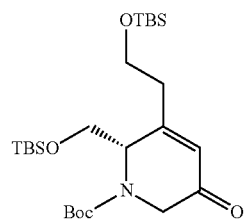 [SMILES: CC(C)(C)OC(=O)N1CC(=O)C=C(CCO[Si](C)(C)C(C)(C)C)[C@H]1CO[Si](C)(C)C(C)(C)C]

A solution of (S,E)-tert-butyl (2,2,3,3,11,11,12,12-octamethyl-7-methylene-4,10-dioxa-3,11-disilatridecan-6-yl)(2-oxopent-3-en-1-yl)carbamate (Intermediate 279, 10 g, 18.45 mmol) in toluene (400 mL) was purged with nitrogen for 15 minutes. The Hoveyda-Grubbs Catalyst 2nd Generation (2.320 g, 3.69 mmol) was then added. The reaction was heated at 100° C. overnight. Another 0.05 eq of catalyst was added and the reaction mixture was heated at 100° C. for another 2 hours. The reaction mixture was concentrated onto silica gel. Silica gel chromatography (0%-15% ethyl acetate/hexanes) afforded the title compound (8.55 g, 93%) as a light brown oil.

MS: 500 ES+ ($C_{25}H_{49}NO_5Si_2$)

$^1$H NMR (300 MHz, DMSO-d$_6$) δ 0.01 (m, 12H), 0.81 (m, 18H), 1.42 (s, 9H), 2.50 (m, 2H); 3.79 (m, 5H); 4.20 (m, 1H); 4.67 (m, 1H); 6.07 (s, 1H).

Intermediate 281: (2S,5S)-tert-butyl 3-(2-((tert-butyldimethylsilyl)oxy)ethyl)-2-(((tert-butyldimethylsilyl)oxy)methyl)-5-hydroxy-5,6-dihydropyridine-1(2H)-carboxylate

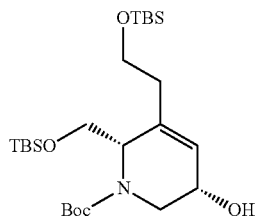 [SMILES: CC(C)(C)OC(=O)N1C[C@@H](O)C=C(CCO[Si](C)(C)C(C)(C)C)[C@H]1CO[Si](C)(C)C(C)(C)C]

The title compound was prepared from (S)-tert-butyl 3-(2-((tert-butyldimethylsilyl)oxy)ethyl)-2-(((tert-butyldimethylsilyl)oxy)methyl)-5-oxo-5,6-dihydropyridine-1(2H)-carboxylate (Intermediate 280, 8.55 g, 17.11 mmol) according to the procedure described for Intermediate 8 to afford the desired product (7.33 g, 85%) as a light yellow oil.

MS: 502 ES+ ($C_{25}H_{51}NO_5Si_2$)

$^1$H NMR (300 MHz, DMSO-d$_6$) δ 0.02 (m, 12H), 0.85 (m, 18H), 1.39 (s, 9H), 2.21 (m, 2H); 2.68 (m, 1H); 3.70 (m, 4H); 4.02 (m, 2H); 4.21 (m, 1H); 4.99 (m, 1H); 5.55 (s, 1H).

Intermediate 282: (2S,5R)-tert-butyl 5-(N-(allyloxy)-2-nitrophenylsulfonamido)-3-(2-((tert-butyldimethylsilyl)oxy)ethyl)-2-(((tert-butyldimethylsilyl)oxy)methyl)-5,6-dihydropyridine-1(2H)-carboxylate

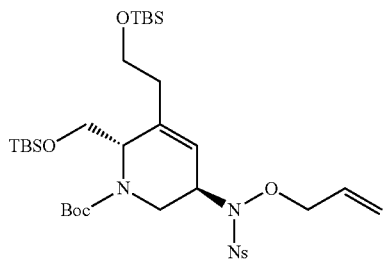

To a solution of (2S,5S)-tert-butyl 3-(2-((tert-butyldimethylsilyl)oxy)ethyl)-2-(((tert-butyldimethylsilyl)oxy)methyl)-5-hydroxy-5,6-dihydropyridine-1(2H)-carboxylate (Intermediate 281, 7.33 g, 14.61 mmol) in toluene (100 mL) at room temperature was added triphenylphosphine (4.58 g, 17.53 mmol), N-(allyloxy)-2-nitrobenzenesulfonamide (3.77 g, 14.61 mmol) and diisopropyl azodicarboxylate (3.45 mL, 17.53 mmol). The reaction mixture was stirred overnight at room temperature then concentrated. The resulting oil was triturated with hexane and filtered to remove triphenylphosphine oxide. The filtrate was concentrated onto silica gel. Silica gel chromatography (0%-20% ethyl acetate/hexanes) afforded the title compound (7.5 g, 69.2%) as a light yellow oil.

MS: 743 ES+ ($C_{34}H_{59}N_3O_9SSi_2$)

Intermediate 283: N-(allyloxy)-N-((3R,6S)-5-(2-((tert-butyldimethylsilyl)oxy)ethyl)-6-(((tert-butyldimethylsilyl)oxy)methyl)-1,2,3,6-tetrahydropyridin-3-yl)-2-nitrobenzenesulfonamide

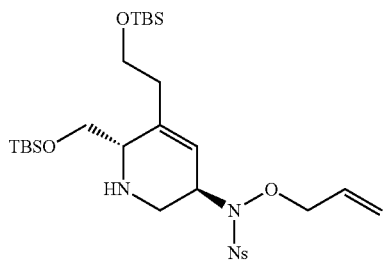

To a solution of (2S,5R)-tert-butyl 5-(N-(allyloxy)-2-nitrophenylsulfonamido)-3-(2-((tert-butyldimethylsilyl)oxy)ethyl)-2-(((tert-butyldimethylsilyl)oxy)methyl)-5,6-dihydropyridine-1(2H)-carboxylate (Intermediate 282, 7.5 g, 10.11 mmol) in DCM (100 mL) at room temperature was added zinc bromide (6.83 g, 30.32 mmol). The reaction mixture was stirred overnight at room temperature. Another equivalent of zinc bromide was added and the reaction mixture was stirred for another 24 hours. The reaction mixture was diluted with DCM and saturated sodium bicarbonate was added. The biphasic mixture was filtered through celite to remove the solids and the layers were separated. The organics were washed once with brine, dried over magnesium sulfate, filtered and concentrated to afford an orange oil (6.49 g, 100%).

MS: 642 ES+ ($C_{29}H_{51}N_3O_7SSi_2$)

Intermediate 284: O-allyl-N-((3R,6S)-5-(2-((tert-butyldimethylsilyl)oxy)ethyl)-6-(((tert-butyldimethylsilyl)oxy)methyl)-1,2,3,6-tetrahydropyridin-3-yl)hydroxylamine

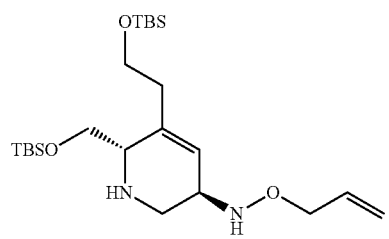 [SMILES: C=CCON[C@@H]1C=C(CCO[Si](C)(C)C(C)(C)C)[C@@H](CO[Si](C)(C)C(C)(C)C)NC1]

The title compound was prepared from N-(allyloxy)-N-((3R,6S)-5-(2-((tert-butyldimethylsilyl)oxy)ethyl)-6-(((tert-butyldimethylsilyl)oxy)methyl)-1,2,3,6-tetrahydropyridin-3-yl)-2-nitrobenzenesulfonamide (Intermediate 283, 6.49 g, 10.11 mmol) according to the procedure described for Intermediate 12. Silica gel chromatography (0%-5% methanol/dichloromethane) afforded the desired product (3.95 g, 86%) as a yellow oil.

MS: 457 ES+ ($C_{23}H_{48}N_2O_3Si_2$)

$^1$H NMR (300 MHz, DMSO-$d_6$) δ 0.03 (m, 12H), 0.85 (m, 18H), 2.15 (m, 2H), 2.65 (m, 1H); 2.89 (m, 1H); 3.20 (m, 2H); 3.61 (m, 4H); 4.08 (m, 2H); 5.15 (m, 2H); 5.44 (m, 1H); 5.88 (m, 1H); 6.16 (m, 1H).

Intermediate 285: (2S,5R)-6-(allyloxy)-3-(2-((tert-butyldimethylsilyl)oxy)ethyl)-2-(((tert-butyldimethylsilyl)oxy)methyl)-1,6-diazabicyclo[3.2.1]oct-3-en-7-one

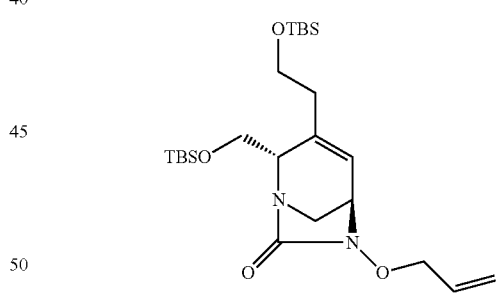

To a solution of O-allyl-N-((3R)-5-(2-((tert-butyldimethylsilyl)oxy)ethyl)-6-(((tert-butyldimethylsilyl)oxy)methyl)-1,2,3,6-tetrahydropyridin-3-yl)hydroxylamine (Intermediate 284, 3.95 g, 8.65 mmol) and diisopropylethyl amine (6.02 mL, 34.58 mmol) in acetonitrile (600 mL) at 0° C. was added triphosgene (0.871 g, 2.94 mmol) as a solution in acetonitrile (26 mL). The triphosgene solution was added at a rate of 4 mL/hour. Once addition was complete the reaction mixture was warmed to room temperature and stirred overnight. The reaction mixture was diluted with ethyl acetate, washed with saturated sodium bicarbonate and 1:1 brine:water. The organics were dried over magnesium sulfate, filtered and concentrated. Silica gel chromatography (0%-30% ethyl acetate/hexanes) afforded the title compound as a yellow oil (3.69 g, 88%). This reaction was run in two separate 1 L flasks due to the large volume and combined for work up and purification.

MS: 483 ES+ ($C_{24}H_{46}N_2O_4Si_2$)

$^1$H NMR (300 MHz, DMSO-$d_6$) δ 0.04 (m, 12H), 0.85 (m, 18H), 2.11 (m, 2H), 3.01 (m, 1H); 3.44 (m, 1H); 3.63 (m, 3H); 3.93 (m, 2H); 4.32 (m, 2H); 5.28 (m, 2H); 5.93 (m, 1H); 6.05 (m, 1H).

Intermediate 286: (2S,5R)-6-(allyloxy)-3-(2-hydroxyethyl)-2-(hydroxymethyl)-1,6-diazabicyclo[3.2.1]oct-3-en-7-one

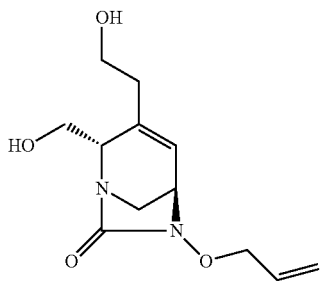 [SMILES: C=CCON1C(=O)N2C[C@H]1C=C(CCO)[C@H]2CO]

To a solution of (2S,5R)-6-(allyloxy)-3-(2-((tert-butyldimethylsilyl)oxy)ethyl)-2-(((tert-butyldimethylsilyl)oxy)methyl)-1,6-diazabicyclo[3.2.1]oct-3-en-7-one (Intermediate 285, 0.96 g, 1.99 mmol) in THF (6 mL) at 0° C. was added tetrabutylammonium fluoride (1M in THF) (5.97 mL, 5.97 mmol). The reaction mixture was stirred for ~1 hour and then concentrated onto silica gel. Silica gel chromatography (0%-10% methanol/dichloromethane) afforded the title compound (0.446 g, 88%) as a cloudy yellow oil.

MS: 255 ES+ ($C_{12}H_{18}N_2O_4$)

$^1$H NMR (300 MHz, DMSO-$d_6$) δ 2.06 (m, 2H), 2.98 (m, 1H), 3.42 (m, 3H), 3.60 (m, 1H); 3.71 (m, 2H); 3.88 (m, 1H); 4.33 (m, 2H); 4.51 (t, 1H); 4.84 (t, 1H); 5.27 (m, 2H); 5.96 (m, 2H).

Intermediate 287: (2S,5R)-6-(allyloxy)-3-(2-methoxyethyl)-2-(methoxymethyl)-1,6-diazabicyclo[3.2.1]oct-3-en-7-one

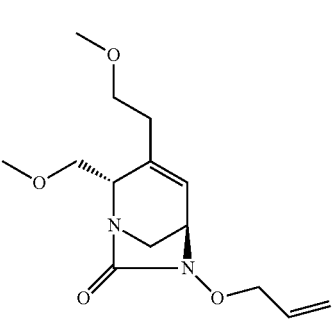 [SMILES: C=CCON1C(=O)N2C[C@H]1C=C(CCOC)[C@H]2COC]

To a solution of (2S,5R)-6-(allyloxy)-3-(2-hydroxyethyl)-2-(hydroxymethyl)-1,6-diazabicyclo[3.2.1]oct-3-en-7-one (Intermediate 286, 0.446 g, 1.75 mmol) and iodomethane (0.655 mL, 10.52 mmol) in DMF (8 mL) at 0° C. was added sodium hydride (60% in mineral oil) (0.210 g, 5.26 mmol). The reaction mixture was stirred for 10 minutes at 0° C., then quenched with water and diluted with ethyl acetate. The layers were separated and the aqueous was extracted once with DCM. The combined organics were dried over magnesium sulfate, filtered and concentrated. Silica gel chromatography (0%-50% ethyl acetate/hexanes) afforded the title compound (0.138 g, 28%) as a yellow oil.

MS: 283 ES+ ($C_{14}H_{22}N_2O_4$)

$^1$H NMR (300 MHz, DMSO-$d_6$) δ 2.12 (m, 2H), 3.02 (m, 1H), 3.21 (s, 3H); 3.27 (s, 3H); 3.35 (m, 3H); 3.66 (m, 3H); 3.90 (m, 1H); 4.33 (m, 2H); 5.27 (m, 2H); 5.96 (m, 2H).

Intermediate 288: (E)-triphenyl(prop-1-en-1-yl) phosphonium (2S,5R)-3-(2-methoxyethyl)-2-(methoxymethyl)-7-oxo-1,6-diazabicyclo[3.2.1]oct-3-en-6-yl sulfate

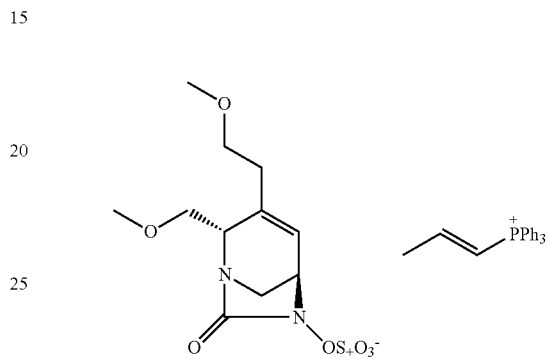

The title compound was prepared from (2S,5R)-6-(allyloxy)-3-(2-methoxyethyl)-2-(methoxymethyl)-1,6-diazabicyclo[3.2.1]oct-3-en-7-one (Intermediate 287, 0.177 g, 0.63 mmol) according to the procedure described for Intermediate 17. The desired product was obtained as a light yellow foam (0.328 g, 84%).

MS: 323, 303 ES+ ($C_{14}H_{22}N_2O_4$, $C_{21}H_{20}P$)

Example 29

(2S,5R)-2-(((1,5-dihydroxy-4-oxo-1,4-dihydropyridin-2-yl)methyl)carbamoyl)-4-methyl-7-oxo-1,6-diazabicyclo[3.2.1]oct-3-en-6-yl hydrogen sulfate sodium salt

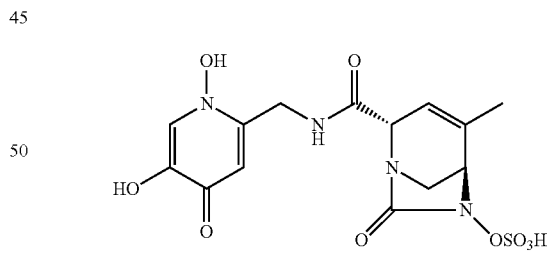

To a solution of (2S,5R)-2-(((1-(benzhydryloxy)-5-((4-methoxybenzyl)oxy)-4-oxo-1,4-dihydropyridin-2-yl)methyl)carbamoyl)-4-methyl-7-oxo-1,6-diazabicyclo[3.2.1]oct-3-en-6-yl hydrogen sulfate (Intermediate 296, 58.6 mg, 0.08 mmol) in anisole (906 μl, 8.34 mmol) at 0° C. was added trifluoroacetic acid (321 μl, 4.17 mmol). The reaction mixture was allowed to warm to room temperature and stir for 2.5 hours. The reaction mixture was diluted with DCM and water. The layers were separated and the aqueous layer was extracted once more with DCM. The aqueous layer was directly loaded onto a 5.5 g RediSep Gold C18 column and washed through with 100% water. Fractions 1 and 2 contained desired product and were combined and lyophilized to afford a light orange solid. The compound was run through another C18 column with water and collected in tubes 1 and 2. They were combined and lyophilized. HPLC purification (YMC Carotenoid C30 21.2 mm×150 mm 5 μm coupled with Synergi Polar RP 100 mm×21.2 mm 4 μm, 0%-15% acetonitrile/water) afforded the title compound as a pink solid (3.4 mg, 9.3%) after lyophilization.

MS: 417 ES+ ($C_{14}H_{16}N_4O_9S$)

$^1$H NMR (300 MHz, DMSO-$d_6$) δ: 1.93 (s, 3H); 3.31 (m, 1H); 3.61 (m, 1H); 4.22 (m, 1H); 4.49 (m, 2H); 4.61 (m, 1H); 5.69 (m, 1H); 6.49 (s, 1H); 7.64 (s, 1H).

The intermediates for Example 29 were prepared as follows:

Intermediate 289: 2-(hydroxymethyl)-5-[(4-methoxybenzyl)oxy]-4H-pyran-4-one

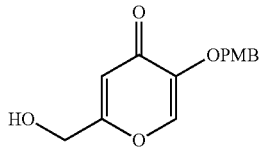

To a stirred slurry of kojic acid (500 g, 3.518 mol) in dry DMF (5 L) was added dry potassium carbonate (972 g, 7.036 mol) followed by 4-methoxy benzyl chloride (661 g, 4.221 mol) at 0° C. The reaction mixture was warmed to room temperature and then heated at 80° C. for 3 hours. After cooling to room temperature the reaction mixture was poured into ice cold water (15 L) and stirred vigorously. The precipitate was collected by filtration and dried under vacuum to afford the title compound as a pale brown solid (687 g, 75%).

$^1$H NMR (300 MHz, DMSO-$d_6$) δ 3.74 (s, 3H); 4.27 (s, 2H); 4.83 (s, 2H); 5.68 (bs, 1H); 6.29 (s, 1H); 6.93 (d, 2H); 7.33 (d, 2H); 8.12 (s, 1H).

Intermediate 290: 1-hydroxy-2-(hydroxymethyl)-5-[(4-methoxybenzyl)oxy]pyridin-4(1H)-one

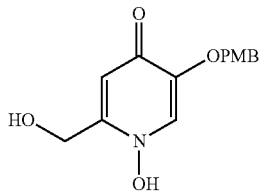

To a stirred solution of 2-(hydroxymethyl)-5-[(4-methoxybenzyl)oxy]-4H-pyran-4-one (Intermediate 289, 101.7 g, 0.388 mol) in pyridine (1.35 L) was added hydroxyl amine hydrochloride (134.7 g, 1.94 mol). The reaction mixture was heated at 85° C. for 4 hours, then evaporated to dryness and triturated with water (700 mL). The precipitate was collected by filtration and washed with water (250 mL). The solids were then stirred in isopropanol (100 mL) for 12 hours, collected by filtration and dried under vacuum to afford the title compound as a white solid (41.2 g, 38%).

$^1$H NMR (300 MHz, DMSO-$d_6$) δ 3.75 (s, 3H); 4.55 (s, 2H); 5.05 (s, 2H); 6.95 (d, 2H); 7.06 (s, 1H); 7.38 (d, 2H); 7.47 (m, 1H); 8.25 (s, 1H); 8.62 (d, 1H).

Intermediate 291: 1-(diphenylmethoxy)-2-(hydroxymethyl)-5-[(4-methoxybenzyl)oxy]pyridin-4(1H)-one

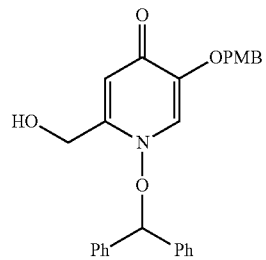

To a stirred ice cold solution of 1-hydroxy-2-(hydroxymethyl)-5-[(4-methoxybenzyl)oxy]pyridin-4(1H)-one (Intermediate 290, 45 g, 0.162 mol) was added potassium tert-butoxide (18.2 g, 0.162 mol), followed by benzyl chloride (36.14 g, 0.178 mol). The reaction mixture was stirred at room temperature for 12 hours, then poured into ice cold water (3 L) and stirred for 1 hour. The precipitate was collected by filtration and dried under vacuum to afford the title compound as a pale brown solid (70.4 g, 98%).

$^1$H NMR (300 MHz, DMSO-$d_6$) δ 3.76 (s, 3H); 4.25 (d, 2H); 4.65 (s, 2H); 5.54 (bs, 1H); 6.05 (s, 1H); 6.51 (s, 1H); 6.94 (d, 2H); 7.25 (d, 2H); 7.41 (m, 11H).

Intermediate 292: 2-((1-(benzhydryloxy)-5-((4-methoxybenzyl)oxy)-4-oxo-14-dihydropyridin-2-yl)methyl)isoindoline-1,3-dione

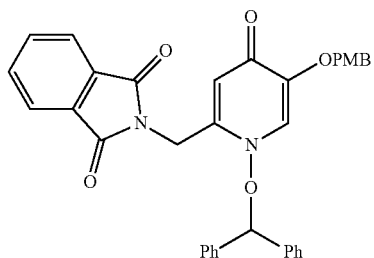

To a solution of 1-(benzhydryloxy)-2-(hydroxymethyl)-5-((4-methoxybenzyl)oxy)pyridin-4(1H)-one (Intermediate 291, 2 g, 4.51 mmol), phthalimide (0.664 g, 4.51 mmol) and triphenylphosphine (1.178 g, 4.51 mmol) in THF (20 mL) at room temperature was added diisopropyl azodicarboxylate (2.397 mL, 12.18 mmol). Reagents are insoluble. DMF (10 mL) was added. The reaction was stirred at room temperature overnight. The reaction mixture was filtered and concentrated onto silica gel. Silica gel chromatography (0%-4% methanol/dichloromethane) did not offer separation of desired product from impurities. Fractions were combined and repurified. Silica gel chromatography (0%-30% acetone/dichloromethane) afforded the title compound (1.66 g, 64.3%) as a light yellow foam.

MS: 573 ES+ ($C_{35}H_{28}N_2O_6$)

¹H NMR (300 MHz, DMSO-d₆) δ 3.76 (s, 3H); 4.51 (s, 2H); 4.70 (s, 2H); 5.71 (s, 1H); 6.63 (s, 1H); 6.94 (m, 2H); 7.26 (m, 2H); 7.45 (m, 10H); 7.62 (s, 1H); 7.88 (m, 4H).

Intermediate 293: 2-(aminomethyl)-1-(benzhydryloxy)-5-((4-methoxybenzyl)oxy)pyridin-4(1H)-one

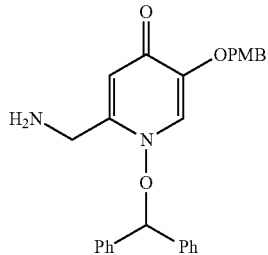

To a solution of 2-((1-(benzhydryloxy)-5-((4-methoxybenzyl)oxy)-4-oxo-1,4-dihydropyridin-2-yl)methyl)isoindoline-1,3-dione (Intermediate 292, 1.66 g, 2.90 mmol) in chloroform (20 mL) and methanol (10 mL) at room temperature was added hydrazine monohydrate (0.284 mL, 5.80 mmol). The reaction mixture was stirred overnight at room temperature. Another 1 eq of hydrazine monohydrate was added. After 3 hours still see starting material. Added another 1 eq of hydrazine monohydrate. After 2 hours the reaction mixture was filtered to remove solids. The filtrate was concentrated. The residue was triturated with MeOH and ether and the solids filtered off. This was repeated twice more. The resulting solid was triturated once with chloroform and MeOH and the solids removed by filtration. The filtrate was concentrated to afford a yellow foam (1.01 g, 79%).

MS: 443 ES+ (C₂₇H₂₆N₂O₄)
¹H NMR (300 MHz, DMSO-d₆) δ 3.76 (s, 3H); 4.25 (d, 2H); 4.65 (s, 2H); 5.54 (bs, 1H); 6.05 (s, 1H); 6.51 (s, 1H); 6.94 (d, 2H); 7.25 (d, 2H); 7.29 (s, 1H); 7.41 (m, 11H).

Intermediate 294: (2S,5R)-6-(allyloxy)-N-((1-(benzhydryloxy)-5-((4-methoxybenzyl)oxy)-4-oxo-1,4-dihydropyridin-2-yl)methyl)-4-methyl-7-oxo-1,6-diazabicyclo[3.2.1]oct-3-ene-2-carboxamide

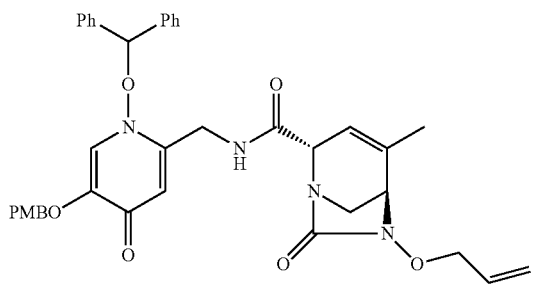

To a solution of (2R,5R)-6-(allyloxy)-4-methyl-7-oxo-1,6-diazabicyclo[3.2.1]oct-3-ene-2-carboxylic acid (Intermediate 32, 0.54 g, 2.27 mmol) in DMF (10 mL) at room temperature was added 2-(aminomethyl)-1-(benzhydryloxy)-5-((4-methoxybenzyl)oxy)pyridin-4(1H)-one (Intermediate 293, 1 g, 2.27 mmol), O-(7-azabenzotriazol-1-yl)-N,N,N',N'-tetramethyluronium hexafluorophosphate (1.724 g, 4.53 mmol) and N,N-diisopropylethylamine (1.579 mL, 9.07 mmol). After 15 minutes the reaction mixture was diluted with ethyl acetate and washed with saturated sodium bicarbonate, brine, and 1/1 brine/water twice. The organics were dried over magnesium sulfate, filtered and concentrated. Silica gel chromatography (0%-70% acetone/dichloromethane) afforded the title compound (0.704 g, 47%) as a light orange foam.

MS: 663 ES+ (C₃₈H₃₈N₄O₇)
¹H NMR (300 MHz, DMSO-d₆) δ 1.80 (m, 3H); 3.18 (m, 2H); 3.76 (s, 3H); 3.85 (m, 1H); 4.06 (m, 2H); 4.26 (m, 1H); 4.37 (m, 2H); 4.68 (s, 2H); 5.33 (m, 3H); 5.82 (s, 1H); 5.95 (m, 1H); 6.52 (s, 1H); 6.94 (m, 2H); 7.24 (m, 2H); 7.42 (m, 10H); 7.47 (s, 1H).

Intermediate 295: (E)-triphenyl(prop-1-en-1-yl)phosphonium (2S,5R)-2-(((1-(benzhydryloxy)-5-((4-methoxybenzyl)oxy)-4-oxo-1,4-dihydropyridin-2-yl)methyl)carbamoyl)-4-methyl-7-oxo-1,6-diazabicyclo[3.2.1]oct-3-en-6-yl sulfate

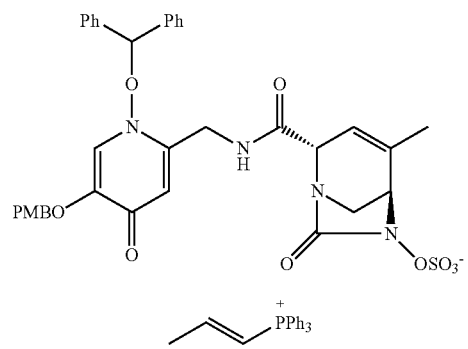

The title compound was prepared from (2S,5R)-6-(allyloxy)-N-((1-(benzhydryloxy)-5-((4-methoxybenzyl)oxy)-4-oxo-1,4-dihydropyridin-2-yl)methyl)-4-methyl-7-oxo-1,6-diazabicyclo[3.2.1]oct-3-ene-2-carboxamide (Intermediate 294, 0.704 g, 1.06 mmol) according to the procedure described for Intermediate 17. Silica gel chromatography (0%-5% methanol/dichloromethane) afforded the title compound (0.379 g, 35.5%) as a yellow foam.

MS: 703, 303 ES+ (C₃₅H₃₃N₄O₁₀S, C₂₁H₂₀P)

Intermediate 296: (2S,5R)-2-(((1-(benzhydryloxy)-5-((4-methoxybenzyl)oxy)-4-oxo-1,4-dihydropyridin-2-yl)methyl)carbamoyl)-4-methyl-7-oxo-1,6-diazabicyclo[3.2.1]oct-3-en-6-yl hydrogen sulfate sodium salt

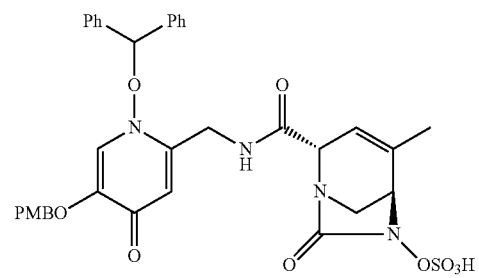

The Dowex® 50WX8-100, ion-exchange resin (35 g, 0.38 mmol) was conditioned by stirring for 2 hours in 2N sodium hydroxide (80 mL, 0.38 mmol). The resin was then loaded into column and washed with water until the pH was 7. It was then washed with (1/1) acetone/water (~100 mL), followed by water (~100 mL). (E)-triphenyl(prop-1-en-1-yl)phosphonium (2S,5R)-2-(((1-(benzhydryloxy)-5-((4-methoxybenzyl)oxy)-4-oxo-1,4-dihydropyridin-2-yl)methyl)carbamoyl)-4-methyl-7-oxo-1,6-diazabicyclo[3.2.1]oct-3-en-6-yl sulfate (Intermediate 295, 0.379 g, 0.38 mmol) was taken up in acetonitrile (~2 mL), loaded on the resin and washed through with water. The desired product mass was seen in tubes 1-2 (mixed fractions), 3-14 (clean fractions). The two mixed fractions were run through the column again. Tubes 22-23 (mixed fractions) and tubes 24-31 (clean fractions) were lyophilized. The desired product was obtained as an off-white solid (113.4 mg, 43%).

MS: 703 ES+ ($C_{35}H_{34}N_4O_{10}S$)

$^1$H NMR (300 MHz, DMSO-$d_6$) δ 1.78 (m, 3H); 3.19 (m, 2H); 3.36 (s, 2H); 3.75 (s, 3H); 4.00 (m, 2H); 4.23 (m, 1H); 4.67 (m, 2H); 5.40 (m, 1H); 5.83 (s, 1H); 6.50 (s, 1H); 6.93 (m, 2H); 7.24 (m, 2H); 7.41 (m, 10H); 7.45 (s, 1H).

Example 30

Biological Activity

Minimum Inhibitory Concentrations (MICs) were determined by the broth microdilution method in accordance with the Clinical and Laboratory Standards Institute (CLSI) guidelines. Clinical Laboratory Standards Institute: Methods for Dilution Antimicrobial Susceptibility Tests for Bacteria That Grow Aerobically ($8^{th}$ Ed. (2009)) M07-A8. In brief, organism suspensions were adjusted to a 0.5 McFarland standard and further diluted to yield a final inoculum between $3\times10^5$ and $7\times10^5$ colony-forming units (CFU)/mL. Bacterial inocula were made in sterile, cation adjusted Mueller-Hinton Broth (Beckton Dickinson) for either *Escherichia coli*, *Klebsiella pneumoniae*, or *Pseudomonas aeruginosa*. *Haemophilus influenzae* bacterial inocula were made in sterile, cation adjusted Mueller-Hinton Broth (Beckton Dickinson) containing 0.5% yeast extract (Beckton Dickinson) plus 15 μg/ml Bovine Hematin (Sigma) and 15 μg/ml β-nicotinamide adenine dinucleotide (Sigma). Bacterial inocula were made in sterile, cation adjusted Mueller-Hinton Broth (Beckton Dickinson) for *Staphylococcus aureus* or sterile, cation adjusted Mueller-Hinton Broth containing 2.5% lysed horse blood (Hema Resource & Supply Inc.) for *Streptococcus pneumoniae* and *Streptococcus pyogenes*. An inoculum volume of 100 uL was added to wells (using a Tecan EVO robot) containing 2 uL of DMSO containing 2-fold serial dilutions of drug. An inoculum volume of 100 μL was added to wells (using a Tecan EVO robot) containing 2 μL of DMSO containing 2-fold serial dilutions of drug. All inoculated microdilution trays were incubated in ambient air at 35° C. for 18-24 hours. Following incubation, the lowest concentration of the drug that prevented visible growth as read at OD600 nm was recorded as the MIC. Performance of the assay was monitored by the use of laboratory quality-control strains and commercially available control compounds with defined MIC spectrums, in accordance with CLSI guidelines.

| | MIC (μg/mL) | | | | | | | |
|---|---|---|---|---|---|---|---|---|
| Ex. # | S. pneumon. | S. pyogenes | S. aureus (MSSA) | S. aureus (MRSA) | H. influenzae | E. coli | K. pneumon. | P. aeruginosa |
| 1 | 6.25 | 3.13 | 25 | >200 | ND | 50 | 50 | 200 |
| 2 | 25 | 3.13 | 100 | 100 | 12.5 | 100 | 100 | >200 |
| 14 | 100 | 100 | 100 | >200 | 12.5 | >200 | >200 | >200 |
| 3 | 50 | 50 | >200 | >200 | 3.13 | >200 | >200 | >200 |
| 7 | >200 | >200 | >200 | >200 | >200 | >200 | >200 | >200 |
| 4 | 200 | 50 | ND | >200 | >200 | >200 | >200 | >200 |
| 5 | 100 | 50 | >200 | >200 | 100 | >200 | >200 | >200 |
| 12 | 25 | 25 | ND | >200 | 100 | 100 | 50 | >200 |
| 13 | 50 | 100 | >200 | >200 | 200 | >200 | >200 | >200 |
| 10 | 0.39 | <0.2 | 0.78 | >200 | 0.78 | 12.5 | 12.5 | 200 |
| 6 | 25 | 25 | 200 | >200 | >200 | >200 | >200 | 25 |
| 8 | ND | ND | ND | ND | ND | ND | ND | ND |
| 9 | ND | ND | ND | ND | ND | ND | ND | ND |
| 15 | ND | ND | ND | ND | ND | ND | ND | ND |
| 11 | 25 | 25 | 100 | >200 | >200 | >200 | >200 | >200 |
| 16 | 50 | 50 | 100 | >200 | 50 | 100 | 100 | >200 |

| | MIC (μg/mL) | | | |
|---|---|---|---|---|
| | Klebsiella pneumoniae KPC2 | Pseudomonas aeruginosa AmpC | Pseudomonas aeruginosa PER-1, OXA-10 | Pseudomonas aeruginosa AmpC |
| Ceftazidime | 256 | 128 | 256 | 32 |
| Ex. 13 | >16 | >16 | >16 | >16 |
| Ex. 10 | 1 | >16 | >16 | >16 |
| Ex. 6 | 0.25 | 16 | 16 | 16 |
| Ex. 4 | >64 | >64 | >64 | >64 |
| Ex. 2 | 64 | >64 | >64 | >64 |
| Ex. 1 | 8 | 64 | >64 | >64 |
| Ex. 11 | >16 | >16 | >16 | >16 |
| Ex. 12 | 64 | >64 | >64 | >64 |
| Ex. 8 | >16 | >16 | >16 | >16 |
| Ex. 16 | 8 | >16 | >16 | >16 |
| Ex. 9 | >16 | >16 | >16 | >16 |
| Ex. 5 | ND | ND | ND | ND |
| Ex. 15 | ND | ND | ND | ND |
| Ex. 7 | ND | ND | ND | ND |
| Ex. 3 | ND | ND | ND | ND |
| Ex. 14 | ND | ND | ND | ND |

Example 31

Synergy with β-lactams was assessed against several organisms producing a variety of β-lactamases belonging to different classes. Bush & Jacoby, *Updated Functional Classification of β-Lactamases*, Antimicrobial Agents and Chemotherapy, 54:969-76 (2010). In the assays, growth inhibitory activity (MIC) was measured using either two-fold dilutions of the partner β-lactam at a fixed concentration of compounds of formula (I). Compounds were prepared in DMSO, and MIC determinations using the compound of formula (I)/β-lactam combinations were done according to the CLSI guidelines. Clinical Laboratory Standards Institute: Methods for Dilution Antimicrobial Susceptability Tests for Bacteria That Grow Aerobically (8$^{th}$ Ed. (2009)) M07-A8. Synergy was defined as a four-fold or more reduction in the MIC of the β-lactam in the presence of the compound of formula (I), compared to the β-lactam alone.

| | MIC (µM) | | | |
|---|---|---|---|---|
| | Klebsiella pneumoniae KPC2 | Pseudomonas aeruginosa AmpC | Pseudomonas aeruginosa PER-1, OXA-10 | Pseudomonas aeruginosa AmpC |
| Ceftazidime | 256 | 128 | 256 | 32 |
| +Ex. 13 (4 ug/ml) | ≤0.50 | 64 | 64 | 16 |
| +Ex. 10 (4 ug/ml) | N | 2 | 2 | 1 |
| +Ex. 6 (4 ug/ml) | N | 4 | 2 | 2 |
| +Ex. 4 (4 ug/ml) | 2 | 64 | 64 | 32 |
| +Ex. 2 (4 ug/ml) | 2 | 64 | 128 | 64 |
| +Ex. 1 (4 ug/ml) | ≤0.50 | 4 | 2 | 4 |
| +Ex. 11 (4 ug/ml) | 1 | 32 | 16 | 4 |
| +Ex. 12 (4 ug/ml) | ≤0.50 | 64 | 32 | 16 |
| +Ex. 8 (4 ug/ml) | ≤0.50 | 64 | 4 | 8 |
| +Ex. 16 (4 ug/ml) | ≤0.50 | 32 | 32 | 16 |
| +Ex. 9 (4 ug/ml) | ≤0.50 | 64 | 16 | 32 |
| +Ex. 5 (4 ug/ml) | ND | ND | ND | ND |
| +Ex. 15 (4 ug/ml) | ND | ND | ND | ND |
| +Ex. 7 (4 ug/ml) | ND | ND | ND | ND |
| +Ex. 3 (4 ug/ml) | ND | ND | ND | ND |
| +Ex. 14 (4 ug/ml) | ND | ND | ND | ND |
| +Ex. 17 (4 ug/ml) | 16 | ND | ND | ND |
| +Ex. 18 (4 ug/ml) | 16 | ND | ND | ND |
| +Ex. 19 (4 ug/ml) | >32 | ND | ND | ND |
| +Ex. 20 (4 ug/ml) | 15 | ND | ND | ND |
| +Ex. 21 (4 ug/ml) | 16 | ND | ND | ND |
| +Ex. 22 (4 ug/ml) | 4 | ND | ND | ND |
| +Ex. 23 (4 ug/ml) | >256 | ND | ND | ND |
| +Ex. 24 (4 ug/ml) | 8 | ND | ND | ND |
| +Ex. 25 (4 ug/ml) | >8 | ND | ND | ND |
| +Ex. 26 (4 ug/ml) | 4 | 32 | 32 | 16 |
| +Ex. 27 (4 ug/ml) | 16 | 64 | 4 | 8 |
| +Ex. 28 (4 ug/ml) | ND | ND | ND | ND |
| +Ex. 29 (4 ug/ml) | ND | ND | ND | ND |
| piperacillin | >512 | 256 | 64 | 256 |
| +Avibactam (4 ug/ml) | 8 | 32 | 32 | 32 |
| +Ex. 1 (4 ug/ml) | N | 16 | 16 | 16 |
| ceftazidime | 256 | 128 | 256 | 32 |
| +Avibactam (4 ug/ml) | ≤0.50 | 8 | 8 | 4 |
| +Ex. 1 (4 ug/ml) | ≤0.50 | 4 | 2 | 4 |
| +Ex. 10 (4 ug/ml) | ≤0.50 | 2 | 2 | 2 |
| ampicillin | >512 | >512 | >512 | >512 |
| +Avibactam (4 ug/ml) | 16 | 512 | 512 | >512 |
| +Ex. 1 (4 ug/ml) | 128 | 512 | 512 | >512 |
| aztreonam | >512 | 64 | 128 | 32 |
| +Avibactam (4 ug/ml) | ≤0.50 | 8 | 16 | 8 |
| +Ex. 1 (4 ug/ml) | 2 | 4 | 8 | 8 |
| +Ex. 10 (4 ug/ml) | ≤0.50 | 8 | 16 | 8 |
| cefepime | 512 | 32 | 32 | 16 |
| +Avibactam (4 ug/ml) | ≤0.50 | 4 | 8 | 8 |
| +Ex. 1 (4 ug/ml) | ≤0.50 | 4 | 8 | 8 |
| Ceftaroline | >512 | 256 | 64 | 256 |
| +Avibactam (4 ug/ml) | ≤0.50 | 16 | 32 | 32 |
| +Ex. 1 (4 ug/ml) | 1 | 8 | 32 | 16 |
| ceftriaxone | >512 | >512 | 128 | 512 |
| +Avibactam (4 ug/ml) | ≤0.50 | 128 | 16 | 64 |
| +Ex. 1 (4 ug/ml) | ≤0.50 | 32 | 16 | 32 |
| meropenem | 64 | ≤0.50 | 4 | 32 |
| +Avibactam (4 ug/ml) | ≤0.50 | ≤0.50 | 4 | 16 |
| +Ex. 1 (4 ug/ml) | ≤0.50 | ≤0.50 | 4 | 8 |
| +Ex. 10 (4 ug/ml) | ≤0.50 | ≤0.25 | 4 | 8 |

The invention claimed is:

1. A method for treating a bacterial infection in a subject in need thereof, said method comprising administering to said subject an effective amount of a compound of Formula (III):

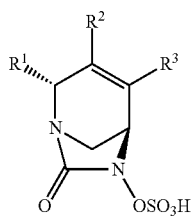

or a pharmaceutically acceptable salt thereof, wherein:
$R^1$ is —CONR'R", —CN, or an $C_1$-$C_3$ alkyl substituted with $C_1$-$C_3$ alkoxy, —OH, —CN, —NR'R", or —CONR'R";
$R^2$ and $R^3$ are independently selected from H, halo, —CN, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, —CONR'R", or $C(O)_2R'$; wherein the alkyl, alkenyl, cycloalkyl, and alkoxy represented by $R^2$ or $R^3$ are independently and optionally substituted by one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —NR'R", 5-7 membered heterocycle, —C(O)NR'R" or —NR'C(O)R"; and
each R' and R" are independently selected from hydrogen, $C_1$-$C_6$ alkyl, $C_3$-$C_6$ cycloalkyl, phenyl, 5 to 6 membered heterocyclyl or a 5 to 6 membered heteroaryl; wherein each alkyl, cycloalkyl, phenyl, heterocyclyl and heteroaryl is optionally and independently substituted with one or more halo, —CN, —OH, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, —C(O)($C_1$-$C_6$ alkyl), —C(O)($C_1$-$C_6$ alkoxy), —NH$_2$, —NH($C_1$-$C_3$ alkyl), —N($C_1$-$C_3$ alkyl)$_2$, a 5-7 membered heterocyclyl or a 5-7 membered heteroaryl;
provided that $R^2$ and $R^3$ are not both hydrogen; and when $R^1$ is —C(O)NR'R", then neither of $R^2$ or $R^3$ is —C(O)NR'R";
or a pharmaceutically acceptable salt thereof.

2. The method of claim 1, wherein, for the compound according to formula (III), or a pharmaceutically acceptable salt thereof, $R^2$ and $R^3$ are independently selected from the group consisting of H, $C_1$-$C_3$ alkyl, $C_3$-$C_6$ cycloalkyl, and —CONR'R", wherein the alkyl and cycloalkyl represented by $R^2$ and/or $R^3$ are independently and optionally substituted by one or more group selected from halo, —CN, —OH, $C_1$-$C_3$ alkyl, $C_1$-$C_3$ haloalkyl, $C_1$-$C_3$ alkoxy, $C_1$-$C_3$ haloalkoxy, —NR'R", a siderophore, —C(O)NR'R" and —NR'C(O)R".

3. The method of claim 1, wherein, for the compound according to formula (III), or a pharmaceutically acceptable salt thereof, $R^2$ is methyl, ethyl, isopropyl, or cyclopropyl, wherein each $R^2$ is optionally and independently substituted with one or more group selected from —OH and $C_1$-$C_3$ alkoxy; and $R^3$ is hydrogen.

4. The method of claim 1, wherein, for the compound according to formula (III), or a pharmaceutically acceptable salt thereof, $R^2$ is methyl and $R^3$ is hydrogen.

5. The method of claim 1, wherein, for the compound according to formula (III), or a pharmaceutically acceptable salt thereof,
$R^2$ is hydrogen;
$R^3$ is $C_1$-$C_3$ alkyl, $C_2$-$C_6$ alkenyl, $C_3$-$C_6$ cycloalkyl, or —CONR'R", each of which is optionally and independently substituted with one or more substituent selected from the group consisting of halo, —CN, —OH, $C_1$-$C_3$ alkyl, cyclopropyl, $C_1$-$C_3$ haloalkyl, $C_1$-$C_3$ alkoxy, $C_1$-$C_3$ haloalkoxy, —NR'R", a siderophore, —C(O)NR'R" and —NR'C(O)R"; and
each R' and R" is independently selected from H and $C_1$-$C_3$ alkyl.

6. The method of claim 5, wherein, for the compound according to formula (III), or a pharmaceutically acceptable salt thereof,
$R^3$ is methyl, ethyl, isopropyl, cyclopropyl, —CONH$_2$, —CONH($C_1$-$C_3$ alkyl), or —CON($C_1$-$C_3$ alkyl)$_2$, each of which is optionally and independently substituted with one or more group selected from —OH, $C_1$-$C_3$ alkyl, $C_1$-$C_3$ alkoxy, —NR'R", C(O)NR'R" and —NR'C(O)R"; and
each R' and R" is independently selected from H and $C_1$-$C_3$ alkyl.

7. The method of claim 5, wherein, for the compound according to formula (III), or a pharmaceutically acceptable salt thereof, $R^3$ is methyl, —CH$_2$OCH$_3$, or —CONH$_2$.

8. The method of claim 1, wherein, for the compound according to formula (III), or a pharmaceutically acceptable salt thereof, $R^1$ is —CONR'R", —CN, or an $C_1$-$C_3$ alkyl substituted with $C_1$-$C_3$ alkoxy or —OH; and
the R' and R" of $R^1$ are independently selected from the group consisting of H, $C_1$-$C_3$ alkyl, or a 5-7 membered heterocyclyl, wherein each alkyl and heterocyclyl of R' and R" is optionally and independently substituted with one or more —OH, $C_1$-$C_3$ alkyl, $C_1$-$C_3$ alkoxy, —NH$_2$, —NH($C_1$-$C_3$ alkyl), —N($C_1$-$C_3$ alkyl)$_2$, or a 5-7 membered heterocyclyl.

9. The method of claim 1, wherein, for the compound according to formula (III), or a pharmaceutically acceptable salt thereof,
$R^1$ is —CH$_2$OCH$_3$, —CONH(CH$_2$)-siderophore, —CONH$_2$,

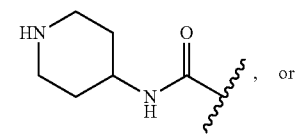, or

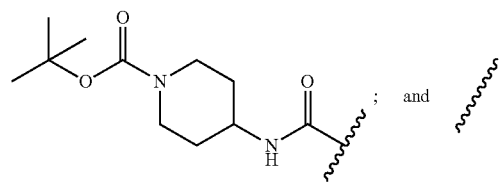; and represents the point of attachment to the bridged bicyclic core.

10. The method of claim 1, wherein, for the compound according to formula (III), or a pharmaceutically acceptable salt thereof, $R^1$ is —CH$_2$OCH$_3$ or —CONH$_2$.

11. The method of claim 1, wherein, for the compound according to formula (III), or a pharmaceutically acceptable salt thereof:
$R^1$ is —CH$_2$OCH$_3$; —CONH$_2$,

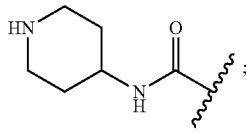 [SMILES: *C(=O)NC1CCNCC1]

$R^2$ is —H or —CH$_3$; and
$R^3$ is —H, —CH$_3$, or —CONH$_2$;
provided that R and $R^3$ are not both H; and when R is —CONH$_2$, or

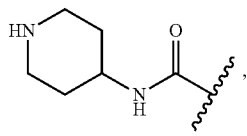

then $R^3$ is not —CONH$_2$.

12. The method of claim 1, wherein, the compound according to formula (III) is:

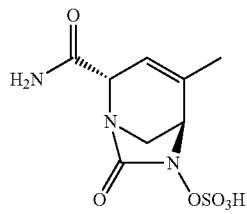

or a pharmaceutically acceptable salt thereof.

13. The method of claim 1, wherein, the compound according to formula (III) is:

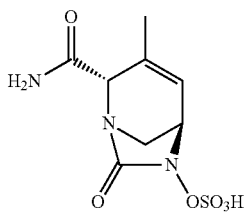

or a pharmaceutically acceptable salt thereof.

14. The method of claim 1, further comprising administering an effective amount of an additional antibiotic agent.

15. The method of claim 14, wherein the additional antibiotic compound is selected from the group consisting of penicillin, methicillin, oxacillin, nafcillin, cloxacillin, dicloxacillin, flucloxacillin, temocillin, amoxicillin, ampicillin, co-amoxiclav, azlocillin, carbenicillin, ticarcillin, mezlocillin, piperacillin, cephalexin, cephalothin, CXA-101, cefazolin, cefaclor, cefuroxime, cefamandole, cefotetan, cefoxitin, ceftriaxone, cefotaxime, cefpodoxime, cefixime, ceftazidime, ceftobiprole medocaril, cefepime, cefpirome, ceftaroline, imipenem, meropenem, ertapenem, faropenem, sulopenem, doripenem, PZ-601 (Protez Pharmaceuticals), ME1036 (Forest Labs), BAL30072, MC-1, tomopenem, tebipenemn, aztreonam, tigemonam, nocardicin A, or tabtoxinine-β-lactam.

16. The method of claim 15, wherein the second antibiotic agent is meropenem, aztreonam, or ceftazidime.

17. The method of claim 15, wherein the second antibiotic agent is imipenem.

18. The method of claim 14, wherein the bacterial infection is a Gram-negative bacterial infection.

19. The method of claim 18, wherein the Gram-negative bacterial infection is resistant to one or more antibiotics.

20. The method of claim 14, wherein the bacterial infection causes a disease selected from the group consisting of urinary tract infections, pneumonia, prostatitis, skin and soft tissue infections, sepsis, and intra-abdominal infections.

21. The method of claim 18, wherein the bacterial infection is caused by *Acinetobacter* spp.

22. The method of claim 18, wherein the bacterial infection is caused by *Pseudomonas* spp.

* * * * *

UNITED STATES PATENT AND TRADEMARK OFFICE
CERTIFICATE OF CORRECTION

PATENT NO. : 9,623,014 B2
APPLICATION NO. : 15/056090
DATED : April 18, 2017
INVENTOR(S) : Helen Mcguire et al.

It is certified that error appears in the above-identified patent and that said Letters Patent is hereby corrected as shown below:

Column 199, Claim 11, Line 7, please insert the word --or-- after "$R^1$ is $-CH_2OCH_3$; $-CONH_2$,".

Column 199, Claim 11, Line 18, please replace "provided that R and $R^3$ are not both H; and when R is" with --provided that $R^2$ and $R^3$ are not both H; and when $R^1$ is--.

Signed and Sealed this
Twenty-second Day of May, 2018

Andrei Iancu
*Director of the United States Patent and Trademark Office*